(12) United States Patent
Paramithiotis et al.

(10) Patent No.: US 10,191,063 B2
(45) Date of Patent: Jan. 29, 2019

(54) BRUCELLOSIS, Q-FEVER, AND LYME DISEASE BIOMARKERS AND USES THEREOF

(71) Applicant: CAPRION PROTEOMICS, INC., Montréal (CA)

(72) Inventors: Eustache Paramithiotis, Boucherville (CA); Pascal Croteau, Laval (CA)

(73) Assignee: Caprion Proteomics Inc., Montreal (CA)

( * ) Notice: Subject to any disclaimer, the term of this patent is extended or adjusted under 35 U.S.C. 154(b) by 95 days.

(21) Appl. No.: 14/845,399

(22) Filed: Sep. 4, 2015

(65) Prior Publication Data

US 2016/0266140 A1    Sep. 15, 2016

Related U.S. Application Data

(63) Continuation of application No. PCT/IB2014/000996, filed on Mar. 21, 2014.
(Continued)

(51) Int. Cl.
*G01N 33/68* (2006.01)
*G01N 33/573* (2006.01)

(52) U.S. Cl.
CPC ..... *G01N 33/6848* (2013.01); *G01N 33/6875* (2013.01); *G01N 33/6893* (2013.01); *G01N 33/573* (2013.01); *G01N 2333/23* (2013.01); *G01N 2560/00* (2013.01); *G01N 2570/00* (2013.01); *G01N 2800/26* (2013.01); *G01N 2800/52* (2013.01)

(58) Field of Classification Search
CPC ........... G10N 33/6848; G10N 33/6893; G10N 33/573; G10N 33/6875; G10N 2800/52; G10N 2800/26; G10N 2570/00; G10N 2560/00; G10N 2333/23
See application file for complete search history.

(56) References Cited

U.S. PATENT DOCUMENTS 6,316,197 B1    11/2001  Das et al.
7,598,080 B2    10/2009  Deirmengian
(Continued)

FOREIGN PATENT DOCUMENTS

WO    WO-1997/018790    7/1997
WO    WO-1998/008951    3/1998
(Continued)

OTHER PUBLICATIONS

Camafeita et al. (Proteomics Clin. Appl., 2009, 3:226-241) (Year: 2009).*
(Continued)

*Primary Examiner* — Jeremy C Flinders
(74) *Attorney, Agent, or Firm* — McCarter & English, LLP; Jonathan M. Sparks; Deborah L. Nagle

(57) ABSTRACT

The present invention provides biomarkers, methods and kits for diagnosing a Brucellosis, Q-Fever, and/or Lyme Disease, methods and kits for monitoring the effectiveness of treatment for Brucellosis, Q-Fever, or Lyme Disease, as well as methods for identifying a compound that can treat Brucellosis, Q-Fever, and/or Lyme Disease reduce or inhibit the development of complications associated with the disease in a subject, and methods to treat a Brucellosis, Q-Fever, and/or Lyme Disease.

12 Claims, 7 Drawing Sheets

Related U.S. Application Data

(60) Provisional application No. 61/803,857, filed on Mar. 21, 2013.

(56) References Cited

U.S. PATENT DOCUMENTS

| | | |
|---|---|---|
| 2005/0272055 A1 | 12/2005 | Das et al. |
| 2007/0031843 A1 | 2/2007 | Bentwich et al. |
| 2011/0034438 A1 | 2/2011 | Kuehne et al. |
| 2011/0177127 A1 | 7/2011 | Andrews et al. |
| 2013/0237454 A1* | 9/2013 | Schutzer .............. G01N 33/564 506/12 |

FOREIGN PATENT DOCUMENTS

| | | |
|---|---|---|
| WO | WO-1999/010536 | 11/1999 |
| WO | WO-2011/142827 | 11/2011 |
| WO | WO-2013/134786 | 9/2013 |

OTHER PUBLICATIONS

Delpino et al., Brucella-Infected Hepatocytes Mediate Potentially Tissue-Damaging Immune Responses, Journal of Hepatology, vol. 53, Issue 1, Jul. 2010, pp. 145-154.

Liu et al., Deep Sequencing-Based Expression Transcriptional Profiling Changes During Brucella Infection, Microbial Pathogenesis, vol. 52, Issue 5, May 2012, pp. 267-277.

Lowry et al., Identification of Brucella abortus Genes in Elk (Cervus elaphus) lsing in vivo-Induced Antigen Technology (IVIAT) Reveals Novel Markers of Infection, Veterinary Microbiology, vol. 142, Issues 3-4, May 19, 2010, pp. 367-372.

Zaitseva et al., Brucella abortus as a Potential Vaccine Candidate: Induction of Interleukin-12 Secretion and Enhanced B7.1 and B7.2 and Intercellular Adhesion Molecule 1 Surface Expression in Elutriated Human Monocytes Stimulated by Heatinactivated B. abortus, Infection and Immunity, 1996, 64 (8) 3109-3117.

Viadas et al., Construction and evaluation of an ORFeomebased Brucella Whole-Genome DNA Microarray, Microbial Pathogenesis 47 (2009) 189-195.

Ferrero et al., Brucella Invasion of Human Intestinal Epithelial Cells Elicits a Weak Proinflammatory Response But a Significant CCL20 Secretion, FEMS immunology and medical microbiology (England ) Oct. 2012 , 66 (1) p. 45-57.

Teixeira-Gomes et al., Identification and Characterization of Brucella ovis Immunogenic Proteins Using Two-Dimensional Electrophoresis and Immunoblotting, Electrophoresis. Aug. 1997;18(8):1491-7.

Bouhet et al., The IFN?-Induced STAT1-CBP/P300 Association, Required for a Normal Response to the Cytokine, is Disrupted in Brucella-Infected Macrophages, Microbial Pathogenesis, vol. 46, Issue 2, Feb. 2009, pp. 88-97.

Ferrero et al., Proinflammatory Response of Human Endothelial Cells to Brucella Infection, Microbes and Infection, vol. 13, Issue 10, Sep. 2011, pp. 852-861.

Kim et al., Lipid Raft Microdomains Mediate Class A Scavenger Receptor-Dependent Infection of Brucella abortus, Microbial Pathogenesis, vol. 37, Issue 1, Jul. 2004, pp. 11-19.

Sanchez-Perez et al., Methionine Adenosyltransferase as a Useful Molecular Systematics Tool Revealed by Phylogenetic and Structural Analyses, Journal of Molecular Biology, vol. 335, Issue 3, Jan. 16, 2004, pp. 693-706.

Ciocchini et al., Identification of Active Site Residues of the Inverting Glycosyltransferase Cgs Required for the Synthesis of Cyclic b-1,2-Glucan, a Brucella abortus Virulence Factor, Glycobiology vol. 16 No. 7 pp. 679-691, 2006.

Tao et al., "Comparative Proteomic Studies on Serum of Brucellosis Dairy Cows and Health Dairy Cows", Journal of Animal and Veterinary Advances, vol. 11, No. 11, (2012); pp. 1864-1867.

Hunter et al., "Protein biomarker quatification by mass spectrometry", Expert Opinion on Medical Diagnostics, Infroma Healthcare, GB, vol. 4, No. 1 (2010); pp. 11-20.

Nadarajah et al., "Serum matrix metalloproteinase-9 (MMP-9) as a biomarker for monitoring disease progression in Duchenne muscular dystrophy (DMD)", Neuromuscular Disorders, vol. 21, No. 8 (2011), pp. 569-578.

* cited by examiner

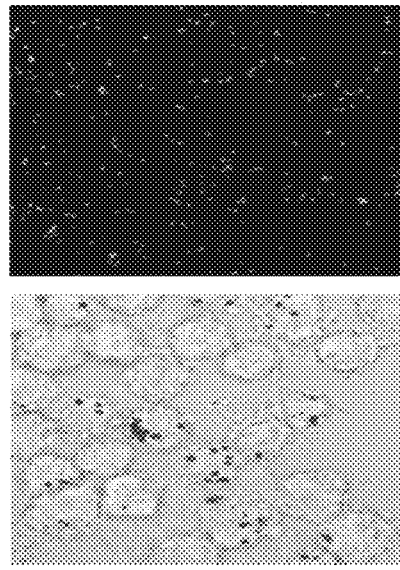
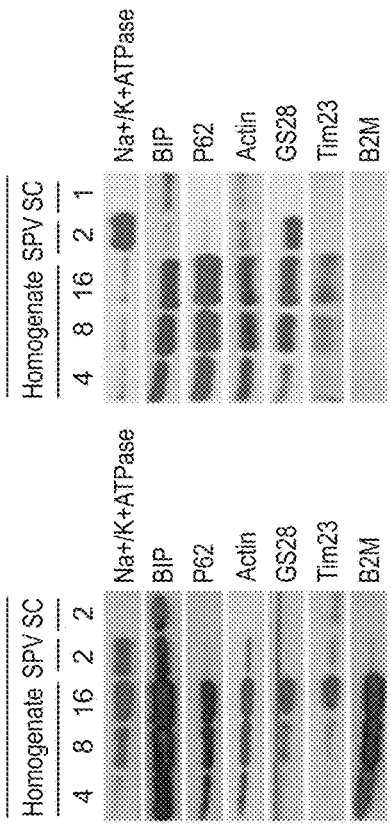
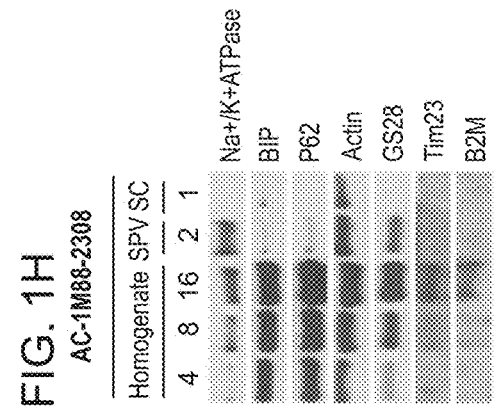
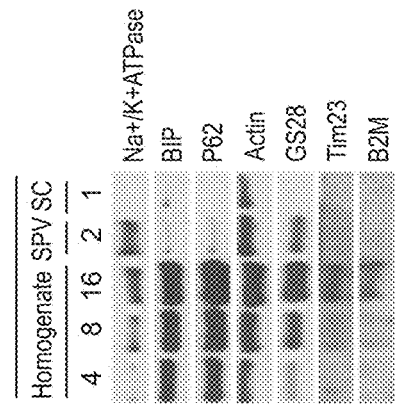
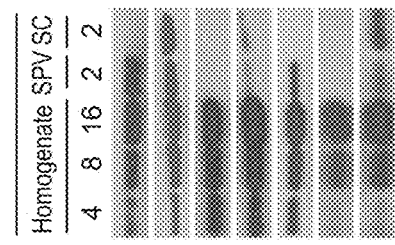
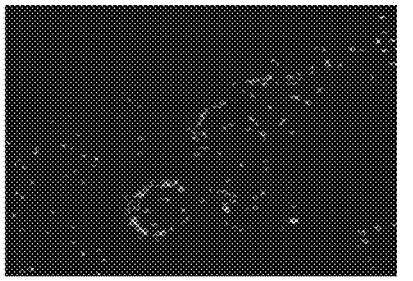
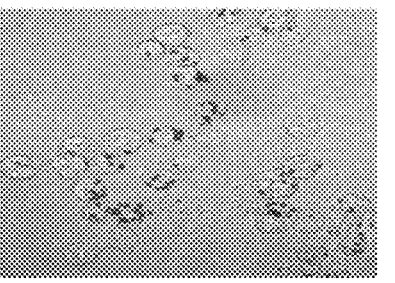
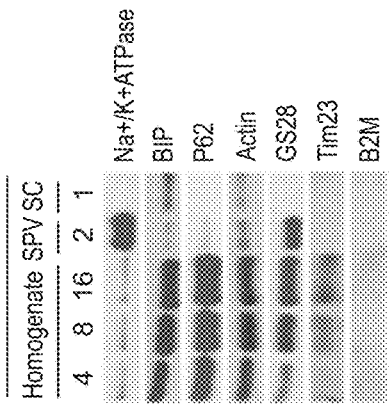

BRUCELLOSIS, Q-FEVER, AND LYME DISEASE BIOMARKERS AND USES THEREOF

RELATED APPLICATIONS

This application is a 35 U.S.C. 111(a) continuation application, which claims the benefit of priority to PCT/IB2014/000996, filed on Mar. 21, 2014 and U.S. Provisional Patent Application Ser. No. 61/803,857, filed on Mar. 21, 2013, the entire contents of each of which is incorporated herein by reference.

BACKGROUND OF THE INVENTION

A zoonosis is an infectious disease that is transmitted between species (sometimes by a vector) from animals other than humans to humans or from humans to other animals. Of the more than 1,400 pathogens known to infect humans, greater than 60% of them are zoonotic (see, e.g., Taylor et al. (2001) *Philosophical Transactions of the Royal Society B* 356(1411):983-9).

Brucellosis is a bacterial zoonosis of global magnitude. The causative agent is a gram negative alpha proteobacterium, *Brucella*, that infects a wide range of mammals, including essentially all economically important domestic mammals and many wild species. In humans, untreated brucellosis is a long lasting disease characterized by recurrent fever episodes and clinical manifestations that include spondylitis, severe headaches, joint or abdominal pain, endocarditis, and meningoencephalitis. In severe nontreated cases brucellosis can cause death (Moreno E, Moriyón I (2006). In: Dworkin M, Falkow S, Rosenberg E, Schleifer K H, Stackebrant E, editors. Vol. 5. Part 1, section 3.1. *The Prokaryotes*. New York: Springer-Verlag. pp. 315-456; Ariza J, et al. (2007) *PLOS medicine* 4:1872-1878; Pappas G, et al. (2005) *New Engl J Med.* 352:2325-2336).

Q-fever is a zoonotic disease caused by infection with *Coxiella burnetii*, an obligate intracellular pathogenic bacterium that affects humans and other animals. This organism is found in cattle, sheep, goats and other domestic mammals, including cats and dogs. The infection results from inhalation of a spore-like small cell variant, and from contact with the milk, urine, feces, vaginal mucus, or semen of infected animals; ticks may also transmit the bacteria. Although most persons with acute Q fever infection recover, others may experience serious illness with complications that may include pneumonia, granulomatous hepatitis, myocarditis (inflammation of the heart tissue), central nervous system complications, and death. Pregnant women who are infected may be at risk for pre-term delivery or miscarriage.

Lyme disease, is a zoonotic disease caused by bacteria belonging to the genus *Borrelia*. Lyme disease is transmitted to humans by the bite of infected ticks belonging to a few species of the genus *Ixodes* ("hard ticks"). If Lyme disease is not detected and treated while early symptoms are present, or if symptoms are not present, the infection may affect the skin, joints, nervous system, and heart within weeks to months after the initial infection. Late disseminated infections may occur and result in joint inflammation, numbness and tingling in the hands, feet, or back, severe fatigue, partial facial nerve paralysis, neurologic changes, including problems with memory, mood, or sleep, and sometimes problems speaking.

Detection of the zoonotic bacterium *Brucella* by culture remains the gold standard for diagnosis (Moreno E, Moriyón I (2006). In: Dworkin M, Falkow S, Rosenberg E, Schleifer K H, Stackebrant E, editors. Vol. 5. Part 1, section 3.1. *The Prokaryotes*. New York: Springer-Verlag. pp. 315-456). These methods are slow, and can require weeks to detect bacterial colonies. Further complicating this approach is that the bacteria are present in readily available body fluids intermittently at best. Diagnosis has therefore depended primarily on serology, mostly the detection of circulating immunoglobulins reactive against bacterial LPS and the closely related native hapten (NH) polysaccharides (Moreno E, Moriyón I (2006). In: Dworkin M, Falkow S, Rosenberg E, Schleifer K H, Stackebrant E, editors. Vol. 5. Part 1, section 3.1. *The Prokaryotes*. New York: Springer-Verlag. pp. 315-456; Cutler S J, et al. (2005) *J Appl Microbiol* 98:1270-1281). Early in disease, however, antibodies are not always generated or their titers may be intermittent (Baldi P C, et al. (2001) *Scand J Infect Dis* 33:200-205), hampering early diagnosis.

Furthermore, with respect to *Brucella*, antibodies against *Brucella* LPS may also cross react with the LPS of other bacteria, such as *Vibrio cholera*, and some *Yersinia* and *Salmonella* serotypes, resulting in false positives (Moreno E, Moriyón I (2006). In: Dworkin M, Falkow S, Rosenberg E, Schleifer K H, Stackebrant E, editors. Vol. 5. Part 1, section 3.1. *The Prokaryotes*. New York: Springer-Verlag. pp. 315-456; Baldi P C, et al. (2001) *Scand J Infect Dis* 33:200-205). Antibodies against alternative *Brucella* antigens have been evaluated as serological diagnostic markers but with uncertain results (Rolan H G, et al. (2008) *Clin Vaccine Immunol* 15: 208-214; Contreras-Rodriguez A, et al. (2006) *FEMS Immunol Med Microbiol* 48:252-256) since it appears that the alternative antigens tend to induce lower immunoglobulin titers than the highly immunogenic LPS. Currently none of the alternative antigens are used for diagnosis of brucellosis.

The gold standard for diagnosis of Lyme Disease is serology, detection of host antibodies reactive to *Borrelia* proteins. Antibody titers typically do not develop in the first 2 weeks of disease, neccessitating diagnosis to be done based on the non-specific clinical symptoms and the likelihood of exposure to ticks. Furthermore, the accuracy of the test is low on the order of 60% in the US, and less than that in Europe (Robertson J and al. 2000. *J Clin Microbiology*. 38(6): 2097-2102. Nelson K, Masters C. 2007. *Infectious Disease Epidemiology: Theory and Practice*. 2nd Ed. Jones and Bartlett Publishers. Chapter 25: Lyme disease. P. 1063-1086).

Serology is also the gold standard for diagnosis of Q-fever. Analysis of two samples taken 2-4 weeks apart is recommended. The reason for this is that the antibody titer for this disease also does not develop immediately after infection, and since the Q fever pathogen is endemic in most areas of the world, a significant subset of the population already has Q fever reactive antibodies from prior exposure (Fournier P E, Marrie T J, Raoult D. 1998. *J Clin Microbiol.* 36(7): 1823-1834).

PCR methods have also been evaluated as direct diagnostics (Baldi P C, et al. (2001) *Scand J Infect Dis* 33:200-205; Debeaumont C, et al. (2005) *Eur J Clin Microbiol Infect Dis* 24:842-845; Casañas M C, et al. (2001) *Eur J Clin Micribiol Infect Dis* 20:127-131; Elfaki M G, et al. (2005) *Med Sci Monit* 11:MT69-74). PCR offers considerable improvement in detection speed over culture methods, and has been used to distinguish bacterial species and strains (Baldi P C, et al. (2001) *Scand J Infect Dis* 33:200-205). Although faster, PCR is less sensitivity as a diagnostic than culture methods (Baldi P C, et al. (2001) *Scand J Infect Dis* 33:200-205; Elfaki M G, et al. (2005) *Med Sci Monit* 11:MT69-74).

The current approaches for diagnosis, therefore, rely primarily on products of the host's immune system or on the growth of viable pathogens in culture. Each approach has limitations that can translate into false negative diagnoses. Accordingly, there is a need in the art for novel biomarkers of zoonotic infections, such as *Brucella, Coxiella burnetii*, and *Borrelia* infection.

SUMMARY OF THE INVENTION

The present invention is based, at least in part, on the discovery of markers that are associated with the presence of *Brucella* infection. Accordingly, the present invention provides sensitive and facile methods and kits for determining whether a subject has Brucellosis, as well as methods for identifying a compound that can treat Brucellosis, methods of monitoring the effectiveness of a therapy for treating Brucellosis in a subject, and methods for treating a subject having Brucellosis by measuring and identifying particular markers, or particular combinations of markers.

The present invention is also based, at least in part, on the discovery of markers that are associated with the presence of Lyme Disease. Accordingly, the present invention provides sensitive and facile methods and kits for determining whether a subject has Lyme Disease, as well as methods for identifying a compound that can treat Lyme Disease, methods of monitoring the effectiveness of a therapy for treating Lyme Disease in a subject, and methods for treating a subject having Lyme Disease by measuring and identifying particular markers, or particular combinations of markers.

In addition, the present invention is based, at least in part, on the discovery of markers that are associated with the presence of Q-Fever. Accordingly, the present invention provides sensitive and facile methods and kits for determining whether a subject has Q-Fever, as well as methods for identifying a compound that can treat Q-Fever, methods of monitoring the effectiveness of a therapy for treating Q-Fever in a subject, and methods for treating a subject having Q-Fever by measuring and identifying particular markers, or particular combinations of markers.

The present invention is also based, at least in part, on the discovery of markers that can be used to determine whether a subject has Brucellosis or Q-Fever, markers that can be used to determine whether a subject has Lyme Disease or Q-Fever, markers that can be used to determine whether a subject has Brucellosis or Lyme Disease, and markers that can be used to determine whether a subject has Brucellosis or Q-Fever or Lyme Disease and provides sensitive and facile methods and kits for determining whether a subject has Brucellosis or Q-Fever or Lyme Disease.

Accordingly, in one aspect the present invention provides methods for determining whether a subject has Brucellosis. The methods include determining the level of one or more markers listed in Table 1 in a sample(s) from the subject; comparing the level of the one or more markers in the subject sample(s) with a level of the one or more markers in a control sample(s), wherein a difference in the level of the one or more markers in the subject sample(s) as compared to the level of the one or more markers in the control sample(s) indicates that the subject has Brucellosis.

In one aspect, the present invention provides methods for monitoring the effectiveness of a treatment in a subject having Brucellosis. The methods include determining the level of one or more markers listed in Table 1 in a first sample(s) from the subject prior to the initiation of the treatment; determining the level of one or more markers listed in Table 1 in a second sample(s) from the subject after at least a portion of the treatment has been administered; comparing the level of the one or more markers in the first sample(s) with a level of the one or more markers in the second sample(s), wherein a difference in the level of the one or more markers in the first sample(s) as compared to the level of the one or more markers in the second sample(s) indicates that the treatment is effective.

In one aspect, the present invention provides methods for identifying a compound that is useful for treating a subject having Brucellosis. The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or activity of the one or more markers listed in Table 1 in an aliquot as compared to the level and/or activity of the one or more markers of the invention in a control sample, thereby identifying a compound that is useful for treating a subject having Brucellosis.

In one aspect, the present invention provides methods for treating a subject having Brucellosis. The methods include administering to the subject an effective amount of an agent that modulates the level and/or activity of any one or more of the markers listed in Table 1, thereby treating the subject.

In one embodiment, the level in the subject sample(s) is determined by mass spectrometry. In one embodiment, the mass spectrometry is matrix assisted laser desorption/time of flight (MALDI/TOF) mass spectrometry, liquid chromatography quadruple ion trap electrospray (LCQ-MS), or surface enhanced laser desorption ionization/time of flight (SELDI/TOF) mass spectrometry.

In one embodiment, the level in the subject sample(s) is determined by immunoassay.

In one embodiment, the sample(s) from the subject is a fluid sample(s). In another embodiment, the sample(s) from the subject is a tissue sample(s).

In one embodiment, the level of the marker is an expression level and/or activity of the marker.

In one embodiment, the one or more markers is selected from the group consisting of LYN, MAT2A, B4GALT1, HIST3H3, ICAM1, LDHB, MDH1, CALU, CORO1A, ENO1, EPB41L3, FLNA, GSTP1, H6PD, HISTH2BE, HIST4H4, ITGAM, MMP9, PRKCSH, RPSA, TKT, and TPI1.

In one embodiment, the methods further comprise determining the level of one or more markers selected from the group consisting of SLC3A2, GOT1, GOT2, ACADVL, DBI, ACOX1, AHNAK, AIMP1, AKR1B1, ANPEP, ANXA2, ANXA5, ANXA6, AKR7A2, ARPC3, ASAH1, B4GALT1, BCAM, BLOC1S5, CALU, CAPG, CAPZB, CAPZA2, CBX1, CDC37, HSPE1, CHMP1A, CHMP1B, CHMP2A, CHMP4A, CHMP4B, CHMP5, CLIC1, CNDP2, CNPY2, COPA, COPB2, CORO1A, CORO1B, CORO1C, CPVL, C19orf10, CXorf26, CXCL10, CACYBP, DSP, HSD17B4, DLG1, DNASE2, DDT, DYNLL1, EPB41L3, EEF1A1, EEF1B2, EEF1D, EEF2, ENG, EHD1, ELAVL1, EMC2, EMR2, ENO1, ENO3, HSP90B1, ERO1L, ESYT2, EVL, ST13, F5, FKBP4, FLNA, FH, H6PD, GPI, GDI2, ARHGDIA, GGH, GBA, PRKCSH, GNS, HSPA9, HSPA5, GSTP1, GLT25D1, HIST1H1D, HIST1H1B, HIST3H2A, H2AFY, HIST2H2BE, HIST2H2BF, HIST3H3, HIST1H4A, HSD17B10, HEXA, HMGB3, HNRNPC, HNRNPD, HNRNPK, HNRNPR, HNRNPU, HSP90AA1, HSP90AB1, HSPA1A, HSPA8, ICAM1, EIF5A2, IL1B, IMPDH2, ISYNA1, ISOC1, ITGA5, ITGAM, ITPR1, KRT9, KRT7, KRT8, CAMK2D, PKM, LASP1, LDHB, LIMA1, LMNA, LMNB1, LMNB2, LRCH1, GAA, LYN, MDH1, MDH2, MESDC2, MAT2A, MYL12A, MMP9, RABIF, MYH10, MYH9, MYO1E, MYO6, PPP1R12A, NAGA, POR, NME1, NME2, NDRG1, NDUFA2, NAP1L1, NPM1, NUTF2, NCL, NUDC, OAS2, PAFAH1B2, PA2G4, PARK7, PARP1, PRCP, PDCD6IP, P4HB, PDIA5, PEBP1, PECAM1, PFDN1, PFDN2, PGAM1, PGK1, PIP4K2A, PIP5K1A, PLEKHO2, PLEC, PLOD3, LCP1, PNP, ALPP, PPIA, PPIB, PRDX1, PRDX2, PRDX3, PRDX6, PRPF19, PSMC6, PSMC3, PSMC2, PRSS8, NPEPPS, PSMA7, PSMB5, PSMD10, PSMD11, PSMD14, PSMD1, PSMD2, PSMD4, PTBP3, PAICS, ATIC, PXMP2, RAB6A, RANGAP1, RAI14, RAN, RANBP1, RBBP4, RAD23B, RPL14, RPL23A, RPL24, RPL26, RPL29, RPL3, RPL31, RPL7A, RPL8, RPLP2, MRPL39, HNRNPA1, HNRNPA2B1, RPS23, RPS8, RSAD2, RPSA, RUVBL1, RUVBL2, S100P, S100A6, S100A11, SEC61B, SEPT11, SEPT2, SEPT6, SEPT7, SEPT9, PHGDH, SF3B3, SFPQ, SIAE, SNRPD3, NAPA, SOD2, SORT1, SGSH, SPRED1, SPTBN1, SPG11, SPTAN1, SRSF3, SRSF8, STIP1, STMN1, STRAP, STX11, SUMO3, EPRS, IARS2, TAGLN2, TALDO1, TUBA4A, TUBB4B, TUBB, TBL2, CCT4, CCT8, TDRD6, VCP, TKT, TLN1, TMOD3, TPI1, TRA2B, TXNRD1, USP14, UGGT1, ATP6V1A, ATP6V1B2, ATP6V1D, ATP6V1E1, ATP6V1F, ATP6V1G1, VPS4A, XRCC6, and YBX1.

In one aspect the present invention provides methods for determining whether a subject has Brucellosis. The methods include determining the level of HISTH4 in a sample(s) from the subject; comparing the level of HISTH4 in the subject sample(s) with a level of HISTH4 in a control sample(s), wherein a difference in the level of HISTH4 in the subject sample(s) as compared to the level of HISTH4 in the control sample(s) indicates that the subject has Brucellosis.

In one aspect, the present invention provides methods for monitoring the effectiveness of a treatment in a subject having Brucellosis. The methods include determining the level of HISTH4 in a first sample(s) from the subject prior to the initiation of the treatment; determining the level of HISTH4 in a second sample(s) from the subject after at least a portion of the treatment has been administered; comparing the level of HISTH4 in the first sample(s) with a level of HISTH4 in the second sample(s), wherein a difference in the level of HISTH4 in the first sample(s) as compared to the level of HISTH4 in the second sample(s) indicates that the treatment is effective.

In one aspect, the present invention provides methods for identifying a compound that is useful for treating a subject having Brucellosis. The methods include contacting an aliquot of a sample(s) from the subject with each member of a library of compounds; determining the effect of a member of the library of compounds on the level and/or activity of HISTH4 in each of the aliquots; and selecting a member of the library of compounds which modulates the level and/or the activity of HISTH4 in an aliquot as compared to the level and/or activity of HISTH4 in a control sample, thereby identifying a compound that is useful for treating a subject having Brucellosis.

In one aspect, the present invention provides methods for treating a subject having Brucellosis. The methods include administering to the subject an effective amount of an agent that modulates the level and/or activity of HISTH4, thereby treating the subject.

In one aspect the present invention provides methods for determining whether a subject has Brucellosis. The methods include determining the level of MAT2A in a sample(s) from the subject; comparing the level of MAT2A in the subject sample(s) with a level of MAT2A in a control sample(s), wherein a difference in the level of MAT2A in the subject sample(s) as compared to the level of MAT2A in the control sample(s) indicates that the subject has Brucellosis.

In one aspect, the present invention provides methods for monitoring the effectiveness of a treatment in a subject having Brucellosis. The methods include determining the level of MAT2A in a first sample(s) from the subject prior to the initiation of the treatment; determining the level of MAT2A in a second sample(s) from the subject after at least a portion of the treatment has been administered; comparing the level of MAT2A in the first sample(s) with a level of MAT2A in the second sample(s), wherein a difference in the level of MAT2A in the first sample(s) as compared to the level of MAT2A in the second sample(s) indicates that the treatment is effective.

In one aspect, the present invention provides methods for identifying a compound that is useful for treating a subject having Brucellosis. The methods include contacting an aliquot of a sample(s) from the subject with each member of a library of compounds; determining the effect of a member of the library of compounds on the level and/or activity of MAT2A in each of the aliquots; and selecting a member of the library of compounds which modulates the level and/or the activity of MAT2A in an aliquot as compared to the level and/or activity of MAT2A in a control sample, thereby identifying a compound that is useful for treating a subject having Brucellosis.

In one aspect, the present invention provides methods for treating a subject having Brucellosis. The methods include administering to the subject an effective amount of an agent that modulates the level and/or activity of MAT2A, thereby treating the subject.

In one aspect the present invention provides methods for determining whether a subject has Brucellosis. The methods include determining the level of MDH1 in a sample(s) from the subject; comparing the level of MDH1 in the subject sample(s) with a level of MDH1 in a control sample(s), wherein a difference in the level of MDH1 in the subject sample(s) as compared to the level of MDH1 in the control sample(s) indicates that the subject has Brucellosis.

In one aspect, the present invention provides methods for monitoring the effectiveness of a treatment in a subject having Brucellosis. The methods include determining the level of MDH1 in a first sample(s) from the subject prior to the initiation of the treatment; determining the level of MDH1 in a second sample(s) from the subject after at least a portion of the treatment has been administered; comparing the level of MDH1 in the first sample(s) with a level of MDH1 in the second sample(s), wherein a difference in the level of MDH1 in the first sample(s) as compared to the level of MDH1 in the second sample(s) indicates that the treatment is effective.

In one aspect, the present invention provides methods for identifying a compound that is useful for treating a subject having Brucellosis. The methods include contacting an aliquot of a sample(s) from the subject with each member of a library of compounds; determining the effect of a member of the library of compounds on the level and/or activity of MDH1 in each of the aliquots; and selecting a member of the library of compounds which modulates the level and/or the activity of MDH1 in an aliquot as compared to the level and/or activity of MDH1 in a control sample, thereby identifying a compound that is useful for treating a subject having Brucellosis.

In one aspect, the present invention provides methods for treating a subject having Brucellosis. The methods include administering to the subject an effective amount of an agent that modulates the level and/or activity of MDH1, thereby treating the subject.

In one aspect the present invention provides methods for determining whether a subject has Brucellosis. The methods include determining the level of LYN in a sample(s) from the subject; comparing the level of LYN in the subject sample(s) with a level of LYN in a control sample(s), wherein a difference in the level of LYN in the subject sample(s) as compared to the level of LYN in the control sample(s) indicates that the subject has Brucellosis.

In one aspect, the present invention provides methods for monitoring the effectiveness of a treatment in a subject having Brucellosis. The methods include determining the level of LYN in a first sample(s) from the subject prior to the initiation of the treatment; determining the level of LYN in a second sample(s) from the subject after at least a portion of the treatment has been administered; comparing the level of LYN in the first sample(s) with a level of LYN in the second sample(s), wherein a difference in the level of LYN in the first sample(s) as compared to the level of LYN in the second sample(s) indicates that the treatment is effective.

In one aspect, the present invention provides methods for identifying a compound that is useful for treating a subject having Brucellosis. The methods include contacting an aliquot of a sample(s) from the subject with each member of a library of compounds; determining the effect of a member of the library of compounds on the level and/or activity of LYN in each of the aliquots; and selecting a member of the library of compounds which modulates the level and/or the activity of LYN in an aliquot as compared to the level and/or activity of LYN in a control sample, thereby identifying a compound that is useful for treating a subject having Brucellosis.

In one aspect, the present invention provides methods for treating a subject having Brucellosis. The methods include administering to the subject an effective amount of an agent that modulates the level and/or activity of LYN, thereby treating the subject.

In one aspect the present invention provides methods for determining whether a subject has Brucellosis. The methods include determining the level of HIST4H4 and the level of LYN in a sample(s) from the subject; comparing the level of HIST4H4 and the level of LYN in the subject sample(s) with a level of HIST4H4 and a level of LYN in a control sample(s), wherein a difference in the level of HIST4H4 and a difference in the level of LYN in the subject sample(s) as compared to the level of HIST4H4 and the level of LYN in the control sample(s) indicates that the subject has Brucelosis.

In one aspect, the present invention provides methods for monitoring the effectiveness of a treatment in a subject having Brucellosis. The methods include determining a level of HIST4H4 and a level of LYN in a first sample(s) from the subject prior to the initiation of the treatment; determining a level of HIST4H4 and a level of LYN in a second sample(s) from the subject after at least a portion of the treatment has been administered; comparing the level of HIST4H4 and the level of LYN in the first sample(s) with the level of HIST4H4 and the level of LYN in the second sample(s), wherein a difference in the level of HIST4H4 and a difference in the level of LYN in the first sample(s) as compared to the level of the HIST4H4 and the level of LYN in the second sample(s) indicates that the treatment is effective.

In one aspect, the present invention provides methods for identifying a compound that is useful for treating a subject having Brucellosis. The methods include contacting an aliquot of a sample(s) from the subject with each member of a library of compounds; determining the effect of a member of the library of compounds on the level and/or activity of HIST4H4 and the level and/or activity of LYN in each of the aliquots; and selecting a member of the library of compounds which modulates the level and/or the activity of HIST4H4 and the level and/or activity of LYN in an aliquot as compared to the level and/or activity of HIST4H4 and the level and/or activity of LYN in a control sample, thereby identifying a compound that is useful for treating a subject having Brucellosis.

In one aspect, the present invention provides methods for treating a subject having Brucellosis. The methods include administering to the subject an effective amount of an agent that modulates the level and/or activity of HIST4H4 and the level and/or activity of LYN, thereby treating the subject.

In one aspect the present invention provides methods for determining whether a subject has Brucellosis. The methods include determining the level of HIST4H4 and the level of MAT2A in a sample(s) from the subject; comparing the level of HIST4H4 and the level of MAT2A in the subject sample(s) with a level of HIST4H4 and a level of MAT2A in a control sample(s), wherein a difference in the level of HIST4H4 and a difference in the level of MAT2A in the subject sample(s) as compared to the level of HIST4H4 and the level of MAT2A in the control sample(s) indicates that the subject has Brucelosis.

In one aspect, the present invention provides methods for monitoring the effectiveness of a treatment in a subject having Brucellosis. The methods include determining a level of HIST4H4 and a level of MAT2A in a first sample(s) from the subject prior to the initiation of the treatment; determining a level of HIST4H4 and a level of MAT2A in a second sample(s) from the subject after at least a portion of the treatment has been administered; comparing the level of HIST4H4 and the level of MAT2A in the first sample(s) with the level of HIST4H4 and the level of MAT2A in the second sample(s), wherein a difference in the level of HIST4H4 and a difference in the level of MAT2A in the first sample(s) as compared to the level of the HIST4H4 and the level of MAT2A in the second sample(s) indicates that the treatment is effective.

In one aspect, the present invention provides methods for identifying a compound that is useful for treating a subject having Brucellosis. The methods include contacting an aliquot of a sample(s) from the subject with each member of a library of compounds; determining the effect of a member of the library of compounds on the level and/or activity of HIST4H4 and the level and/or activity of MAT2A in each of the aliquots; and selecting a member of the library of compounds which modulates the level and/or the activity of HIST4H4 and the level and/or activity of MAT2A in an aliquot as compared to the level and/or activity of HIST4H4 and the level and/or activity of MAT2A in a control sample, thereby identifying a compound that is useful for treating a subject having Brucellosis.

In one aspect, the present invention provides methods for treating a subject having Brucellosis. The methods include administering to the subject an effective amount of an agent that modulates the level and/or activity of HIST4H4 and the level and/or activity of MAT2A, thereby treating the subject.

In one aspect the present invention provides methods for determining whether a subject has Brucellosis. The methods include determining the level of HIST4H4 and the level of MDH1 in a sample(s) from the subject; comparing the level of HIST4H4 and the level of MDH1 in the subject sample(s) with a level of HIST4H4 and a level of MDH1 in a control sample(s), wherein a difference in the level of HIST4H4 and a difference in the level of MDH1 in the subject sample(s) as compared to the level of HIST4H4 and the level of MDH1 in the control sample(s) indicates that the subject has Brucelosis.

In one aspect, the present invention provides methods for monitoring the effectiveness of a treatment in a subject having Brucellosis. The methods include determining a level of HIST4H4 and a level of MDH1 in a first sample(s) from the subject prior to the initiation of the treatment; determining a level of HIST4H4 and a level of MDH1 in a second sample(s) from the subject after at least a portion of the treatment has been administered; comparing the level of HIST4H4 and the level of MDH1 in the first sample(s) with the level of HIST4H4 and the level of MDH1 in the second sample(s), wherein a difference in the level of HIST4H4 and a difference in the level of MDH1 in the first sample(s) as compared to the level of the HIST4H4 and the level of MDH1 in the second sample(s) indicates that the treatment is effective.

In one aspect, the present invention provides methods for identifying a compound that is useful for treating a subject having Brucellosis. The methods include contacting an aliquot of a sample(s) from the subject with each member of a library of compounds; determining the effect of a member of the library of compounds on the level and/or activity of HIST4H4 and the level and/or activity of MDH1 in each of the aliquots; and selecting a member of the library of compounds which modulates the level and/or the activity of HIST4H4 and the level and/or activity of MDH1 in an aliquot as compared to the level and/or activity of HIST4H4 and the level and/or activity of MDH1 in a control sample, thereby identifying a compound that is useful for treating a subject having Brucellosis.

In one aspect, the present invention provides methods for treating a subject having Brucellosis. The methods include administering to the subject an effective amount of an agent that modulates the level and/or activity of HIST4H4 and the level and/or activity of MDH1, thereby treating the subject.

In one aspect the present invention provides methods for determining whether a subject has Brucellosis. The methods include determining the level of LYN and the level of MAT2A in a sample(s) from the subject; comparing the level of LYN and the level of MAT2A in the subject sample(s) with a level of LYN and a level of MAT2A in a control sample(s), wherein a difference in the level of LYN and a difference in the level of MAT2A in the subject sample(s) as compared to the level of LYN and the level of MAT2A in the control sample(s) indicates that the subject has Brucelosis.

In one aspect, the present invention provides methods for monitoring the effectiveness of a treatment in a subject having Brucellosis. The methods include determining a level of LYN and a level of MAT2A in a first sample(s) from the subject prior to the initiation of the treatment; determining a level of LYN and a level of MAT2A in a second sample(s) from the subject after at least a portion of the treatment has been administered; comparing the level of LYN and the level of MAT2A in the first sample(s) with the level of LYN and the level of MAT2A in the second sample(s), wherein a difference in the level of LYN and a difference in the level of MAT2A in the first sample(s) as compared to the level of the LYN and the level of MAT2A in the second sample(s) indicates that the treatment is effective.

In one aspect, the present invention provides methods for identifying a compound that is useful for treating a subject having Brucellosis. The methods include contacting an aliquot of a sample(s) from the subject with each member of a library of compounds; determining the effect of a member of the library of compounds on the level and/or activity of LYN and the level and/or activity of MAT2A in each of the aliquots; and selecting a member of the library of compounds which modulates the level and/or the activity of LYN and the level and/or activity of MAT2A in an aliquot as compared to the level and/or activity of LYN and the level and/or activity of MAT2A in a control sample, thereby identifying a compound that is useful for treating a subject having Brucellosis.

In one aspect, the present invention provides methods for treating a subject having Brucellosis. The methods include administering to the subject an effective amount of an agent that modulates the level and/or activity of LYN and the level and/or activity of MAT2A, thereby treating the subject.

In one aspect the present invention provides methods for determining whether a subject has Brucellosis. The methods include determining the level of LYN and the level of MDH1 in a sample(s) from the subject; comparing the level of LYN and the level of MDH1 in the subject sample(s) with a level of LYN and a level of MDH1 in a control sample(s), wherein a difference in the level of LYN and a difference in the level of MDH1 in the subject sample(s) as compared to the level of LYN and the level of MDH1 in the control sample(s) indicates that the subject has Brucelosis.

In one aspect, the present invention provides methods for monitoring the effectiveness of a treatment in a subject having Brucellosis. The methods include determining a level of LYN and a level of MDH1 in a first sample(s) from the subject prior to the initiation of the treatment; determining a level of LYN and a level of MDH1 in a second sample(s) from the subject after at least a portion of the treatment has been administered; comparing the level of LYN and the level of MDH1 in the first sample(s) with the level of LYN and the level of MDH1 in the second sample(s), wherein a difference in the level of LYN and a difference in the level of MDH1 in the first sample(s) as compared to the level of the LYN and the level of MDH1 in the second sample(s) indicates that the treatment is effective.

In one aspect, the present invention provides methods for identifying a compound that is useful for treating a subject having Brucellosis. The methods include contacting an aliquot of a sample(s) from the subject with each member of a library of compounds; determining the effect of a member of the library of compounds on the level and/or activity of LYN and the level and/or activity of MDH1 in each of the aliquots; and selecting a member of the library of compounds which modulates the level and/or the activity of LYN and the level and/or activity of MDH1 in an aliquot as compared to the level and/or activity of LYN and the level and/or activity of MDH1 in a control sample, thereby identifying a compound that is useful for treating a subject having Brucellosis.

In one aspect, the present invention provides methods for treating a subject having Brucellosis. The methods include administering to the subject an effective amount of an agent that modulates the level and/or activity of LYN and the level and/or activity of MDH1, thereby treating the subject.

In one aspect the present invention provides methods for determining whether a subject has Brucellosis. The methods include determining the level of MAT2A and the level of MDH1 in a sample(s) from the subject; comparing the level of MAT2A and the level of MDH1 in the subject sample(s) with a level of MAT2A and a level of MDH1 in a control sample(s), wherein a difference in the level of MAT2A and a difference in the level of MDH1 in the subject sample(s) as compared to the level of MAT2A and the level of MDH1 in the control sample(s) indicates that the subject has Brucelosis.

In one aspect, the present invention provides methods for monitoring the effectiveness of a treatment in a subject having Brucellosis. The methods include determining a level of MAT2A and a level of MDH1 in a first sample(s) from the subject prior to the initiation of the treatment; determining a level of MAT2A and a level of MDH1 in a second sample(s) from the subject after at least a portion of the treatment has been administered; comparing the level of MAT2A and the level of MDH1 in the first sample(s) with the level of MAT2A and the level of MDH1 in the second sample(s), wherein a difference in the level of MAT2A and a difference in the level of MDH1 in the first sample(s) as compared to the level of the MAT2A and the level of MDH1 in the second sample(s) indicates that the treatment is effective.

In one aspect, the present invention provides methods for identifying a compound that is useful for treating a subject having Brucellosis. The methods include contacting an aliquot of a sample(s) from the subject with each member of a library of compounds; determining the effect of a member of the library of compounds on the level and/or activity of MAT2A and the level and/or activity of MDH1 in each of the aliquots; and selecting a member of the library of compounds which modulates the level and/or the activity of MAT2A and the level and/or activity of MDH1 in an aliquot as compared to the level and/or activity of MAT2A and the level and/or activity of MDH1 in a control sample, thereby identifying a compound that is useful for treating a subject having Brucellosis.

In one aspect, the present invention provides methods for treating a subject having Brucellosis. The methods include administering to the subject an effective amount of an agent that modulates the level and/or activity of MAT2A and the level and/or activity of MDH1, thereby treating the subject.

In one aspect the present invention provides methods for determining whether a subject has Brucellosis. The methods include determining a level of HIST4H4, a level of LYN, and a level of MAT2A in a sample(s) from the subject; comparing the level of HIST4H4, the level of LYN, and the level of MAT2A in the subject sample(s) with a level of HIST4H4, a level of LYN, and a level of MAT2A in a control sample(s), wherein a difference in the level of HIST4H4, a difference in the level of LYN, and a difference in the level of MAT2A in the subject sample(s) as compared to the level of HIST4H4, the level of LYN, and the level of MAT2A in the control sample(s) indicates that the subject has Brucellosis.

In one aspect, the present invention provides methods for monitoring the effectiveness of a treatment in a subject having Brucellosis. The methods include determining a level HIST4H4, a level of LYN, and a level of MAT2A in a first sample(s) from the subject prior to the initiation of the treatment; determining a level of HIST4H4, a level of LYN, and a level of MAT2A in a second sample(s) from the subject after at least a portion of the treatment has been administered; comparing the level of the HIST4H4, the level of LYN, and the level of MAT2A with the level of HIST4H4, the level of LYN, and the level of MAT2A in the second sample(s), wherein a difference in the level of HIST4H4, the level of LYN, and the level of MAT2A in the first sample(s) as compared to the level of HIST4H4, the level of LYN, and the level of MAT2A in the second sample(s) indicates that the treatment is effective.

In one aspect, the present invention provides methods for identifying a compound that is useful for treating a subject having Brucellosis. The methods include contacting an aliquot of a sample(s) from the subject with each member of a library of compounds; determining the effect of a member of the library of compounds on the level and/or activity of HIST4H4, the level and/or activity of LYN, and the level and/or activity of MAT2A of the invention in each of the aliquots; and selecting a member of the library of compounds which modulates the level and/or the activity of HIST4H4, the level and/or the activity of LYN, and the level and/or the activity of MAT2A in an aliquot as compared to the level and/or activity of HIST4H4, the level and/or activity of LYN, and the level and/or activity of MAT2A in a control sample, thereby identifying a compound that is useful for treating a subject having Brucellosis.

In one aspect, the present invention provides methods for treating a subject having Brucellosis. The methods include administering to the subject an effective amount of an agent that modulates the level and/or activity of HIST4H4, the level and/or activity of LYN, and the level and/or activity of MAT2A, thereby treating the subject.

In one aspect the present invention provides methods for determining whether a subject has Brucellosis. The methods include determining a level of HIST4H4, a level of LYN, and a level of MDH1 in a sample(s) from the subject; comparing the level of HIST4H4, the level of LYN, and the level of MDH1 in the subject sample(s) with a level of HIST4H4, a level of LYN, and a level of MDH1 in a control sample(s), wherein a difference in the level of HIST4H4, a difference in the level of LYN, and a difference in the level of MDH1 in the subject sample(s) as compared to the level of HIST4H4, the level of LYN, and the level of MDH1 in the control sample(s) indicates that the subject has Brucellosis.

In one aspect, the present invention provides methods for monitoring the effectiveness of a treatment in a subject having Brucellosis. The methods include determining a level HIST4H4, a level of LYN, and a level of MDH1 in a first sample(s) from the subject prior to the initiation of the treatment; determining a level of HIST4H4, a level of LYN, and a level of MDH1 in a second sample(s) from the subject after at least a portion of the treatment has been administered; comparing the level of the HIST4H4, the level of LYN, and the level of MDH1 with the level of HIST4H4, the level of LYN, and the level of MDH1 in the second sample(s), wherein a difference in the level of HIST4H4, the level of LYN, and the level of MDH1 in the first sample(s) as compared to the level of HIST4H4, the level of LYN, and the level of MDH1 in the second sample(s) indicates that the treatment is effective.

In one aspect, the present invention provides methods for identifying a compound that is useful for treating a subject having Brucellosis. The methods include contacting an aliquot of a sample(s) from the subject with each member of a library of compounds; determining the effect of a member of the library of compounds on the level and/or activity of HIST4H4, the level and/or activity of LYN, and the level and/or activity of MDH1 of the invention in each of the aliquots; and selecting a member of the library of compounds which modulates the level and/or the activity of HIST4H4, the level and/or the activity of LYN, and the level and/or the activity of MDH1 in an aliquot as compared to the level and/or activity of HIST4H4, the level and/or activity of LYN, and the level and/or activity of MDH1 in a control sample, thereby identifying a compound that is useful for treating a subject having Brucellosis.

In one aspect, the present invention provides methods for treating a subject having Brucellosis. The methods include administering to the subject an effective amount of an agent that modulates the level and/or activity of HIST4H4, the level and/or activity of LYN, and the level and/or activity of MDH1, thereby treating the subject.

In one aspect the present invention provides methods for determining whether a subject has Brucellosis. The methods include determining a level of HIST4H4, a level of MAT2A, and a level of MDH1 in a sample(s) from the subject; comparing the level of HIST4H4, the level of MAT2A, and the level of MDH1 in the subject sample(s) with a level of HIST4H4, a level of MAT2A, and a level of MDH1 in a control sample(s), wherein a difference in the level of HIST4H4, a difference in the level of MAT2A, and a difference in the level of MDH1 in the subject sample(s) as compared to the level of HIST4H4, the level of MAT2A, and the level of MDH1 in the control sample(s) indicates that the subject has Brucellosis.

In one aspect, the present invention provides methods for monitoring the effectiveness of a treatment in a subject having Brucellosis. The methods include determining a level HIST4H4, a level of MAT2A, and a level of MDH1 in a first sample(s) from the subject prior to the initiation of the treatment; determining a level of HIST4H4, a level of MAT2A, and a level of MDH1 in a second sample(s) from the subject after at least a portion of the treatment has been administered; comparing the level of the HIST4H4, the level of MAT2A, and the level of MDH1 with the level of HIST4H4, the level of MAT2A, and the level of MDH1 in the second sample(s), wherein a difference in the level of HIST4H4, the level of MAT2A, and the level of MDH1 in the first sample(s) as compared to the level of HIST4H4, the level of MAT2A, and the level of MDH1 in the second sample(s) indicates that the treatment is effective.

In one aspect, the present invention provides methods for identifying a compound that is useful for treating a subject having Brucellosis. The methods include contacting an aliquot of a sample(s) from the subject with each member of a library of compounds; determining the effect of a member of the library of compounds on the level and/or activity of HIST4H4, the level and/or activity of MAT2A, and the level and/or activity of MDH1 of the invention in each of the aliquots; and selecting a member of the library of compounds which modulates the level and/or the activity of HIST4H4, the level and/or the activity of MAT2A, and the level and/or the activity of MDH1 in an aliquot as compared to the level and/or activity of HIST4H4, the level and/or activity of MAT2A, and the level and/or activity of MDH1 in a control sample, thereby identifying a compound that is useful for treating a subject having Brucellosis.

In one aspect, the present invention provides methods for treating a subject having Brucellosis. The methods include administering to the subject an effective amount of an agent that modulates the level and/or activity of HIST4H4, the level and/or activity of MAT2A, and the level and/or activity of MDH1, thereby treating the subject.

In one aspect the present invention provides methods for determining whether a subject has Brucellosis. The methods include determining a level of LYN, a level of MAT2A, and a level of MDH1 in a sample(s) from the subject; comparing the level of LYN, the level of MAT2A, and the level of MDH1 in the subject sample(s) with a level of LYN, a level of MAT2A, and a level of MDH1 in a control sample(s), wherein a difference in the level of LYN, a difference in the level of MAT2A, and a difference in the level of MDH1 in the subject sample(s) as compared to the level of LYN, the level of MAT2A, and the level of MDH1 in the control sample(s) indicates that the subject has Brucellosis.

In one aspect, the present invention provides methods for monitoring the effectiveness of a treatment in a subject having Brucellosis. The methods include determining a level LYN, a level of MAT2A, and a level of MDH1 in a first sample(s) from the subject prior to the initiation of the treatment; determining a level of LYN, a level of MAT2A, and a level of MDH1 in a second sample(s) from the subject after at least a portion of the treatment has been administered; comparing the level of the LYN, the level of MAT2A, and the level of MDH1 with the level of LYN, the level of MAT2A, and the level of MDH1 in the second sample(s), wherein a difference in the level of LYN, the level of MAT2A, and the level of MDH1 in the first sample(s) as compared to the level of LYN, the level of MAT2A, and the level of MDH1 in the second sample(s) indicates that the treatment is effective.

In one aspect, the present invention provides methods for identifying a compound that is useful for treating a subject having Brucellosis. The methods include contacting an aliquot of a sample(s) from the subject with each member of a library of compounds; determining the effect of a member of the library of compounds on the level and/or activity of LYN, the level and/or activity of MAT2A, and the level and/or activity of MDH1 of the invention in each of the aliquots; and selecting a member of the library of compounds which modulates the level and/or the activity of LYN, the level and/or the activity of MAT2A, and the level and/or the activity of MDH1 in an aliquot as compared to the level and/or activity of LYN, the level and/or activity of MAT2A, and the level and/or activity of MDH1 in a control sample, thereby identifying a compound that is useful for treating a subject having Brucellosis.

In one aspect, the present invention provides methods for treating a subject having Brucellosis. The methods include administering to the subject an effective amount of an agent that modulates the level and/or activity of LYN, the level and/or activity of MAT2A, and the level and/or activity of MDH1, thereby treating the subject.

In one aspect the present invention provides methods for determining whether a subject has Brucellosis. The methods include determining a level of HIST4H4, a level of MAT2A, a level of MDH1, and a level of LYN in a sample(s) from the subject; comparing the level of HIST4H4, the level of MAT2A, the level of MDH1, and a level of LYN in the subject sample(s) with a level of HIST4H4, a level of MAT2A, a level of MDH1, and a level of LYN in a control sample(s), wherein a difference in the level of HIST4H4, a difference in the level of MAT2A, a difference in the level of MDH1, and a difference in the level of LYN in the subject sample(s) as compared to the level of HIST4H4, the level of MAT2A, the level of MDH1, and the level of LYN in the control sample(s) indicates that the subject has Brucellosis.

In one aspect, the present invention provides methods for monitoring the effectiveness of a treatment in a subject having Brucellosis. The methods include determining a level HIST4H4, a level of MAT2A, a level of MDH1, and a level of LYN in a first sample(s) from the subject prior to the initiation of the treatment; determining a level of HIST4H4, a level of MAT2A, a level of MDH1, and a level of LYN in a second sample(s) from the subject after at least a portion of the treatment has been administered; comparing the level of the HIST4H4, the level of MAT2A, the level of MDH1, and the level of LYN with the level of HIST4H4, the level of MAT2A, the level of MDH1, and the level of LYN in the second sample(s), wherein a difference in the level of HIST4H4, the level of MAT2A, the level of MDH1, and the level of LYN in the first sample(s) as compared to the level of HIST4H4, the level of MAT2A, the level of MDH1, and the level of LYN in the second sample(s) indicates that the treatment is effective.

In one aspect, the present invention provides methods for identifying a compound that is useful for treating a subject having Brucellosis. The methods include contacting an aliquot of a sample(s) from the subject with each member of a library of compounds; determining the effect of a member of the library of compounds on the level and/or activity of HIST4H4, the level and/or activity of MAT2A, the level and/or activity of MDH1, and the level and/or activity of LYN in each of the aliquots; and selecting a member of the library of compounds which modulates the level and/or the activity of HIST4H4, the level and/or the activity of MAT2A, the level and/or the activity of MDH1, and the level and/or activity of LYN in an aliquot as compared to the level and/or activity of HIST4H4, the level and/or activity of MAT2A, the level and/or activity of MDH1, and the level and/or activity of LYN in a control sample, thereby identifying a compound that is useful for treating a subject having Brucellosis.

In one aspect, the present invention provides methods for treating a subject having Brucellosis. The methods include administering to the subject an effective amount of an agent that modulates the level and/or activity of HIST4H4, the level and/or activity of MAT2A, the level and/or activity of MDH1, and the level and/or activity of LYN, thereby treating the subject.

In one aspect the present invention provides methods for determining whether a subject has Brucellosis or Q-Fever. The methods include determining a level of HIST4H4 in a sample(s) from the subject; comparing the level of HIST4H4 in the subject sample(s) with a level of HIST4H4 in a control sample(s), wherein a difference in the level of HIST4H4 in the subject sample(s) as compared to the level of HIST4H4 in the control sample(s) indicates that the subject has Brucellosis.

In one aspect the present invention provides methods for determining whether a subject has Brucellosis or Q-Fever. The methods include determining a level of MAT2A in a sample(s) from the subject; comparing the level of MAT2A in the subject sample(s) with a level of MAT2A in a control sample(s), wherein a difference in the level of MAT2A in the subject sample(s) as compared to the level of MAT2A in the control sample(s) indicates that the subject has Brucellosis.

In one aspect the present invention provides methods for determining whether a subject has Brucellosis or Q-Fever. The methods include determining a level of LDHB in a sample(s) from the subject; comparing the level of LDHB in the subject sample(s) with a level of LDHB in a control sample(s), wherein a difference in the level of LDHB in the subject sample(s) as compared to the level of LDHB in the control sample(s) indicates that the subject has Brucellosis.

In one aspect the present invention provides methods for determining whether a subject has Brucellosis or Q-Fever. The methods include determining a level of MDH1 in a sample(s) from the subject; comparing the level of MDH1 in the subject sample(s) with a level of MDH1 in a control sample(s), wherein a difference in the level of MDH1 in the subject sample(s) as compared to the level of MDH1 in the control sample(s) indicates that the subject has Brucellosis.

In one aspect the present invention provides methods for determining whether a subject has Brucellosis or Q-Fever. The methods include determining the level of HIST4H4 and the level of LDHB in a sample(s) from the subject; comparing the level of HIST4H4 and the level of LDHB in the subject sample(s) with a level of HIST4H4 and a level of LDHB in a control sample(s), wherein a difference in the level of HIST4H4 and a difference in the level of LDHB in the subject sample(s) as compared to the level of HIST4H4 and the level of LDHB in the control sample(s) indicates that the subject has Brucelosis.

In one aspect the present invention provides methods for determining whether a subject has Brucellosis or Q-Fever. The methods include determining the level of HIST4H4 and the level of MAT2A in a sample(s) from the subject; comparing the level of HIST4H4 and the level of MAT2A in the subject sample(s) with a level of HIST4H4 and a level of MAT2A in a control sample(s), wherein a difference in the level of HIST4H4 and a difference in the level of MAT2A in the subject sample(s) as compared to the level of HIST4H4 and the level of MAT2A in the control sample(s) indicates that the subject has Brucelosis.

In one aspect the present invention provides methods for determining whether a subject has Brucellosis or Q-Fever. The methods include determining the level of HIST4H4 and the level of MDH1 in a sample(s) from the subject; comparing the level of HIST4H4 and the level of MDH1 in the subject sample(s) with a level of HIST4H4 and a level of MDH1 in a control sample(s), wherein a difference in the level of HIST4H4 and a difference in the level of MDH1 in the subject sample(s) as compared to the level of HIST4H4 and the level of MDH1 in the control sample(s) indicates that the subject has Brucelosis.

In one aspect the present invention provides methods for determining whether a subject has Brucellosis or Q-Fever. The methods include determining the level of LDHB and the level of MAT2A in a sample(s) from the subject; comparing the level of LDHB and the level of MAT2A in the subject sample(s) with a level of LDHB and a level of MAT2A in a control sample(s), wherein a difference in the level of LDHB and a difference in the level of MAT2A in the subject sample(s) as compared to the level of LDHB and the level of MAT2A in the control sample(s) indicates that the subject has Brucellosis.

In one aspect the present invention provides methods for determining whether a subject has Brucellosis or Q-Fever. The methods include determining the level of LDHB and the level of MDH1 in a sample(s) from the subject; comparing the level of LDHB and the level of MDH1 in the subject sample(s) with a level of LDHB and a level of MDH1 in a control sample(s), wherein a difference in the level of LDHB and a difference in the level of MDH1 in the subject sample(s) as compared to the level of LDHB and the level of MDH1 in the control sample(s) indicates that the subject has Brucelosis.

In one aspect the present invention provides methods for determining whether a subject has Brucellosis or Q-Fever. The methods include determining the level of MAT2A and the level of MDH1 in a sample(s) from the subject; comparing the level of MAT2A and the level of MDH1 in the subject sample(s) with a level of MAT2A and a level of MDH1 in a control sample(s), wherein a difference in the level of MAT2A and a difference in the level of MDH1 in the subject sample(s) as compared to the level of MAT2A and the level of MDH1 in the control sample(s) indicates that the subject has Brucelosis.

In one aspect the present invention provides methods for determining whether a subject has Brucellosis or Q-Fever. The methods include determining a level of HIST4H4, a level of LDHB, and a level of MAT2A in a sample(s) from the subject; comparing the level of HIST4H4, the level of LDHB, and the level of MAT2A in the subject sample(s) with a level of HIST4H4, a level of LDHB, and a level of MAT2A in a control sample(s), wherein a difference in the level of HIST4H4, a difference in the level of LDHB, and a difference in the level of MAT2A in the subject sample(s) as compared to the level of HIST4H4, the level of LDHB, and the level of MAT2A in the control sample(s) indicates that the subject has Brucellosis.

In one aspect the present invention provides methods for determining whether a subject has Brucellosis or Q-Fever. The methods include determining a level of HIST4H4, a level of LDHB, and a level of MDH1 in a sample(s) from the subject; comparing the level of HIST4H4, the level of LDHB, and the level of MDH1 in the subject sample(s) with a level of HIST4H4, a level of LDHB, and a level of MDH1 in a control sample(s), wherein a difference in the level of HIST4H4, a difference in the level of LDHB, and a difference in the level of MDH1 in the subject sample(s) as compared to the level of HIST4H4, the level of LDHB, and the level of MDH1 in the control sample(s) indicates that the subject has Brucellosis.

In one aspect the present invention provides methods for determining whether a subject has Brucellosis or Q-Fever. The methods include determining a level of HIST4H4, a level of MAT2A, and a level of MDH1 in a sample(s) from the subject; comparing the level of HIST4H4, the level of MAT2A, and the level of MDH1 in the subject sample(s) with a level of HIST4H4, a level of MAT2A, and a level of MDH1 in a control sample(s), wherein a difference in the level of HIST4H4, a difference in the level of MAT2A, and a difference in the level of MDH1 in the subject sample(s) as compared to the level of HIST4H4, the level of MAT2A, and the level of MDH1 in the control sample(s) indicates that the subject has Brucellosis.

In one aspect the present invention provides methods for determining whether a subject has Brucellosis or Q-Fever. The methods include determining a level of LDHB, a level of MAT2A, and a level of MDH1 in a sample(s) from the subject; comparing the level of LDHB, the level of MAT2A, and the level of MDH1 in the subject sample(s) with a level of LDHB, a level of MAT2A, and a level of MDH1 in a control sample(s), wherein a difference in the level of LDHB, a difference in the level of MAT2A, and a difference in the level of MDH1 in the subject sample(s) as compared to the level of LDHB, the level of MAT2A, and the level of MDH1 in the control sample(s) indicates that the subject has Brucellosis.

In one aspect the present invention provides methods for determining whether a subject has Brucellosis or Lyme Disease. The methods include determining a level of HIST4H4 in a sample(s) from the subject; comparing the level of HIST4H4 in the subject sample(s) with a level of HIST4H4 in a control sample(s), wherein a difference in the level of HIST4H4 in the subject sample(s) as compared to the level of HIST4H4 in the control sample(s) indicates that the subject has Brucellosis.

In one aspect the present invention provides methods for determining whether a subject has Brucellosis or Lyme Disease. The methods include determining a level of MMP9 in a sample(s) from the subject; comparing the level of MMP9 in the subject sample(s) with a level of MMP9 in a control sample(s), wherein a difference in the level of MMP9 in the subject sample(s) as compared to the level of MMP9 in the control sample(s) indicates that the subject has Brucellosis.

In one aspect the present invention provides methods for determining whether a subject has Brucellosis or Lyme Disease. The methods include determining a level of LYN in a sample(s) from the subject; comparing the level of LYN in the subject sample(s) with a level of LYN in a control sample(s), wherein a difference in the level of LYN in the subject sample(s) as compared to the level of LYN in the control sample(s) indicates that the subject has Brucellosis.

In one aspect the present invention provides methods for determining whether a subject has Brucellosis or Lyme Disease. The methods include determining a level of ICAM1 in a sample(s) from the subject; comparing the level of ICAM1 in the subject sample(s) with a level of ICAM1 in a control sample(s), wherein a difference in the level of ICAM1 in the subject sample(s) as compared to the level of ICAM1 in the control sample(s) indicates that the subject has Brucellosis.

In one aspect the present invention provides methods for determining whether a subject has Brucellosis or Lyme Disease. The methods include determining the level of HIST4H4 and the level of ICAM1 in a sample(s) from the subject; comparing the level of HIST4H4 and the level of ICAM1 in the subject sample(s) with a level of HIST4H4 and a level of ICAM1 in a control sample(s), wherein a difference in the level of HIST4H4 and a difference in the level of ICAM1 in the subject sample(s) as compared to the level of HIST4H4 and the level of ICAM1 in the control sample(s) indicates that the subject has Brucelosis.

In one aspect the present invention provides methods for determining whether a subject has Brucellosis or Lyme Disease. The methods include determining the level of HIST4H4 and the level of LYN in a sample(s) from the subject; comparing the level of HIST4H4 and the level of LYN in the subject sample(s) with a level of HIST4H4 and a level of LYN in a control sample(s), wherein a difference in the level of HIST4H4 and a difference in the level of LYN in the subject sample(s) as compared to the level of HIST4H4 and the level of LYN in the control sample(s) indicates that the subject has Brucelosis.

In one aspect the present invention provides methods for determining whether a subject has Brucellosis or Lyme Disease. The methods include determining the level of HIST4H4 and the level of MMP9 in a sample(s) from the subject; comparing the level of HIST4H4 and the level of MMP9 in the subject sample(s) with a level of HIST4H4 and a level of MMP9 in a control sample(s), wherein a difference in the level of HIST4H4 and a difference in the level of MMP9 in the subject sample(s) as compared to the level of HIST4H4 and the level of MMP9 in the control sample(s) indicates that the subject has Brucelosis.

In one aspect the present invention provides methods for determining whether a subject has Brucellosis or Lyme Disease. The methods include determining the level of ICAM1 and the level of LYN in a sample(s) from the subject; comparing the level of ICAM1 and the level of LYN in the subject sample(s) with a level of ICAM1 and a level of LYN in a control sample(s), wherein a difference in the level of ICAM1 and a difference in the level of LYN in the subject sample(s) as compared to the level of ICAM1 and the level of LYN in the control sample(s) indicates that the subject has Brucelosis.

In one aspect the present invention provides methods for determining whether a subject has Brucellosis or Lyme Disease. The methods include determining the level of ICAM1 and the level of MMP9 in a sample(s) from the subject; comparing the level of ICAM1 and the level of MMP9 in the subject sample(s) with a level of ICAM1 and a level of MMP9 in a control sample(s), wherein a difference in the level of ICAM1 and a difference in the level of MMP9 in the subject sample(s) as compared to the level of ICAM1 and the level of MMP9 in the control sample(s) indicates that the subject has Brucelosis.

In one aspect the present invention provides methods for determining whether a subject has Brucellosis or Lyme Disease. The methods include determining the level of LYN and the level of MMP9 in a sample(s) from the subject; comparing the level of LYN and the level of MMP9 in the subject sample(s) with a level of LYN and a level of MMP9 in a control sample(s), wherein a difference in the level of LYN and a difference in the level of MMP9 in the subject sample(s) as compared to the level of LYN and the level of MMP9 in the control sample(s) indicates that the subject has Brucelosis.

In one aspect the present invention provides methods for determining whether a subject has Brucellosis or Lyme Disease. The methods include determining a level of HIST4H4, a level of ICAM1, and a level of LYN in a sample(s) from the subject; comparing the level of HIST4H4, the level of ICAM1, and the level of LYN in the subject sample(s) with a level of HIST4H4, a level of ICAM1, and a level of LYN in a control sample(s), wherein a difference in the level of HIST4H4, a difference in the level of ICAM1, and a difference in the level of LYN in the subject sample(s) as compared to the level of HIST4H4, the level of ICAM1, and the level of LYN in the control sample(s) indicates that the subject has Brucellosis.

In one aspect the present invention provides methods for determining whether a subject has Brucellosis or Lyme Disease. The methods include determining a level of HIST4H4, a level of ICAM1, and a level of MMP9 in a sample(s) from the subject; comparing the level of HIST4H4, the level of ICAM1, and the level of MMP9 in the subject sample(s) with a level of HIST4H4, a level of ICAM1, and a level of MMP9 in a control sample(s), wherein a difference in the level of HIST4H4, a difference in the level of ICAM1, and a difference in the level of MMP9 in the subject sample(s) as compared to the level of HIST4H4, the level of ICAM1, and the level of MMP9 in the control sample(s) indicates that the subject has Brucellosis.

In one aspect the present invention provides methods for determining whether a subject has Brucellosis or Lyme Disease. The methods include determining a level of HIST4H4, a level of LYN, and a level of MMP9 in a sample(s) from the subject; comparing the level of HIST4H4, the level of LYN, and the level of MMP9 in the subject sample(s) with a level of HIST4H4, a level of LYN, and a level of MMP9 in a control sample(s), wherein a difference in the level of HIST4H4, a difference in the level of LYN, and a difference in the level of MMP9 in the subject sample(s) as compared to the level of HIST4H4, the level of LYN, and the level of MMP9 in the control sample(s) indicates that the subject has Brucellosis.

In one aspect the present invention provides methods for determining whether a subject has Brucellosis or Lyme Disease. The methods include determining a level of ICAM1, a level of LYN, and a level of MMP9 in a sample(s) from the subject; comparing the level of ICAM1, the level of LYN, and the level of MMP9 in the subject sample(s) with a level of ICAM1, a level of LYN, and a level of MMP9 in a control sample(s), wherein a difference in the level of ICAM1, a difference in the level of LYN, and a difference in the level of MMP9 in the subject sample(s) as compared to the level of ICAM1, the level of LYN, and the level of MMP9 in the control sample(s) indicates that the subject has Brucellosis.

In one embodiment, the methods further comprise determining the level of one or more additional markers listed in Table 1.

In another embodiment, the methods further comprise determining the level of one or more additional markers selected from the group consisting of LYN, MAT2A, B4GALT1, HIST3H3, ICAM1, LDHB, MDH1, CALU, CORO1A, ENO1, EPB41L3, FLNA, GSTP1, H6PD, HISTH2BE, HIST4H4, ITGAM, MMP9, PRKCSH, RPSA, TKT, and TPI1.

In one embodiment, the level of the marker is an expression level and/or activity of the marker.

In one embodiment, the level in the subject sample(s) is determined by mass spectrometry. In one embodiment, the mass spectrometry is matrix assisted laser desorption/time of flight (MALDI/TOF) mass spectrometry, liquid chromatography quadruple ion trap electrospray (LCQ-MS), or surface enhanced laser desorption ionization/time of flight (SELDI/TOF) mass spectrometry.

In one embodiment, the level in the subject sample(s) is determined by immunoassay.

In one embodiment, the sample(s) from the subject is a fluid sample(s). In another embodiment, the sample(s) from the subject is a tissue sample(s).

In one aspect, the present invention provides kits for determining whether a subject has Brucellosis. The kits include reagents for determining the level of one or more markers listed in Table 1 in a subject sample(s) and instructions for use of the kit to determine whether the subject has Brucellosis.

In one aspect, the present invention provides kits for monitoring the effectiveness of a treatment in a subject having Brucellosis. The kits include reagents for determining the level of one or more markers listed in Table 1 in a subject sample(s) and instructions for use of the kit to monitor the effectiveness of the treatment.

In one aspect, the present invention provides kits for determining whether a subject has Brucellosis. The kits include reagents for determining the level of HISTH4 in a subject sample(s) and instructions for use of the kit to determine whether the subject has Brucellosis.

In one aspect, the present invention provides kits for monitoring the effectiveness of a treatment in a subject having Brucellosis. The kits include reagents for determining the level of HISTH4 in a subject sample(s) and instructions for use of the kit to monitor the effectiveness of the treatment.

In one aspect, the present invention provides kits for determining whether a subject has Brucellosis. The kits include reagents for determining the level of MAT2A in a subject sample(s) and instructions for use of the kit to determine whether the subject has Brucellosis.

In one aspect, the present invention provides kits for monitoring the effectiveness of a treatment in a subject having Brucellosis. The kits include reagents for determining the level of MAT2A in a subject sample(s) and instructions for use of the kit to monitor the effectiveness of the treatment.

In one aspect, the present invention provides kits for determining whether a subject has Brucellosis. The kits include reagents determining the level of MDH1 in a subject sample(s) and instructions for use of the kit to determine whether the subject has Brucellosis.

In one aspect, the present invention provides kits for monitoring the effectiveness of a treatment in a subject having Brucellosis. The kits include reagents for determining the level of MDH1 in a subject sample(s) and instructions for use of the kit to monitor the effectiveness of the treatment.

In one aspect, the present invention provides kits for determining whether a subject has Brucellosis. The kits include reagents for determining the level of LYN in a subject sample(s) and instructions for use of the kit to determine whether the subject has Brucellosis.

In one aspect, the present invention provides kits for monitoring the effectiveness of a treatment in a subject having Brucellosis. The kits include reagents for determining the level of LYN in a subject sample(s) and instructions for use of the kit to monitor the effectiveness of the treatment.

In one aspect, the present invention provides kits for determining whether a subject has Brucellosis. The kits include reagents for determining the level of HIST4H4 and the level of LYN in a subject sample(s) and instructions for use of the kit to determine whether the subject has Brucellosis.

In one aspect, the present invention provides kits for monitoring the effectiveness of a treatment in a subject having Brucellosis. The kits include reagents for determining the level of HIST4H4 and the level of LYN in a subject sample(s) and instructions for use of the kit to monitor the effectiveness of the treatment.

In one aspect, the present invention provides kits for determining whether a subject has Brucellosis. The kits include reagents for determining the level of HIST4H4 and the level of MAT2A in a subject sample(s) and instructions for use of the kit to determine whether the subject has Brucellosis.

In one aspect, the present invention provides kits for monitoring the effectiveness of a treatment in a subject having Brucellosis. The kits include reagents for determining the level of HIST4H4 and the level of MAT2A in a subject sample(s) and instructions for use of the kit to monitor the effectiveness of the treatment.

In one aspect, the present invention provides kits for determining whether a subject has Brucellosis. The kits include reagents for determining the level of HIST4H4 and the level of MDH1 in a subject sample(s) and instructions for use of the kit to determine whether the subject has Brucellosis.

In one aspect, the present invention provides kits for monitoring the effectiveness of a treatment in a subject having Brucellosis. The kits include reagents for determining the level of HIST4H4 and the level of MDH1 in a subject sample(s) and instructions for use of the kit to monitor the effectiveness of the treatment.

In one aspect, the present invention provides kits for determining whether a subject has Brucellosis. The kits include reagents for determining the level of LYN and the level of MAT2A in a subject sample(s) and instructions for use of the kit to determine whether the subject has Brucellosis.

In one aspect, the present invention provides kits for monitoring the effectiveness of a treatment in a subject having Brucellosis. The kits include reagents for determining the level of LYN and the level of MAT2A in a subject sample(s) and instructions for use of the kit to monitor the effectiveness of the treatment.

In one aspect, the present invention provides kits for determining whether a subject has Brucellosis. The kits include reagents for determining the level of LYN and the level of MDH1 in a subject sample(s) and instructions for use of the kit to determine whether the subject has Brucellosis.

In one aspect, the present invention provides kits for monitoring the effectiveness of a treatment in a subject having Brucellosis. The kits include reagents for determining the level of LYN and the level of MDH1 in a subject sample(s) and instructions for use of the kit to monitor the effectiveness of the treatment.

In one aspect, the present invention provides kits for determining whether a subject has Brucellosis. The kits include reagents for determining the level of MAT2A and the level of MDH1 in a subject sample(s) and instructions for use of the kit to determine whether the subject has Brucellosis.

In one aspect, the present invention provides kits for monitoring the effectiveness of a treatment in a subject having Brucellosis. The kits include reagents for determining the level of MAT2A and the level of MDH1 in a subject sample(s) and instructions for use of the kit to monitor the effectiveness of the treatment.

In one aspect, the present invention provides kits for determining whether a subject has Brucellosis. The kits include reagents for determining a level of HIST4H4, a level of LYN, and a level of MAT2A in a subject sample(s) and instructions for use of the kit to determine whether the subject has Brucellosis.

In one aspect, the present invention provides kits for monitoring the effectiveness of a treatment in a subject having Brucellosis. The kits include reagents for determining the level of HIST4H4, a level of LYN, and a level of MAT2A in a subject sample(s) and instructions for use of the kit to monitor the effectiveness of the treatment.

In one aspect, the present invention provides kits for determining whether a subject has Brucellosis. The kits include reagents for determining a level of HIST4H4, a level of LYN, and a level of MDH1 in a subject sample(s) and instructions for use of the kit to determine whether the subject has Brucellosis.

In one aspect, the present invention provides kits for monitoring the effectiveness of a treatment in a subject having Brucellosis. The kits include reagents for determining the level of HIST4H4, a level of LYN, and a level of MDH1 in a subject sample(s) and instructions for use of the kit to monitor the effectiveness of the treatment.

In one aspect, the present invention provides kits for determining whether a subject has Brucellosis. The kits include reagents for determining a level of HIST4H4, a level of MAT2A, and a level of MDH1 in a subject sample(s) and instructions for use of the kit to determine whether the subject has Brucellosis.

In one aspect, the present invention provides kits for monitoring the effectiveness of a treatment in a subject having Brucellosis. The kits include reagents for determining the level of HIST4H4, a level of MAT2A, and a level of MDH1 in a subject sample(s) and instructions for use of the kit to monitor the effectiveness of the treatment.

In one aspect, the present invention provides kits for determining whether a subject has Brucellosis. The kits include reagents for determining a level of LYN, a level of MAT2A, and a level of MDH1 in a subject sample(s) and instructions for use of the kit to determine whether the subject has Brucellosis.

In one aspect, the present invention provides kits for monitoring the effectiveness of a treatment in a subject having Brucellosis. The kits include reagents for determining the level of LYN, a level of MAT2A, and a level of MDH1 in a subject sample(s) and instructions for use of the kit to monitor the effectiveness of the treatment.

In one aspect, the present invention provides kits for determining whether a subject has Brucellosis. The kits include reagents for determining a level of HIST4H4, a level of MAT2A, a level of MDH1 in a subject sample(s) and instructions for use of the kit to determine whether the subject has Brucellosis.

In one aspect, the present invention provides kits for monitoring the effectiveness of a treatment in a subject having Brucellosis. The kits include reagents for determining the level of HIST4H4, a level of MAT2A, and a level of MDH1 in a subject sample(s) and instructions for use of the kit to monitor the effectiveness of the treatment.

In one aspect, the present invention provides kits for determining whether a subject has Brucellosis or Q-fever. The kits include reagents for determining a level of HIST4H4 in a subject sample(s) and instructions for use of the kit to determine whether the subject has Brucellosis or Q-Fever.

In one aspect, the present invention provides kits for determining whether a subject has Brucellosis or Q-fever. The kits include reagents for determining a level of MAT2A in a subject sample(s) and instructions for use of the kit to determine whether the subject has Brucellosis or Q-Fever.

In one aspect, the present invention provides kits for determining whether a subject has Brucellosis or Q-fever. The kits include reagents for determining a level of LDHB in a subject sample(s) and instructions for use of the kit to determine whether the subject has Brucellosis or Q-Fever.

In one aspect, the present invention provides kits for determining whether a subject has Brucellosis or Q-fever. The kits include reagents for determining a level of MDH1 in a subject sample(s) and instructions for use of the kit to determine whether the subject has Brucellosis or Q-Fever.

In one aspect, the present invention provides kits for determining whether a subject has Brucellosis or Q-fever. The kits include reagents for determining the level of HIST4H4 and the level of LDHB in a subject sample(s) and instructions for use of the kit to determine whether the subject has Brucellosis or Q-Fever.

In one aspect, the present invention provides kits for determining whether a subject has Brucellosis or Q-fever. The kits include reagents for determining the level of HIST4H4 and the level of MAT2A in a subject sample(s) and instructions for use of the kit to determine whether the subject has Brucellosis or Q-Fever.

In one aspect, the present invention provides kits for determining whether a subject has Brucellosis or Q-fever. The kits include reagents for determining the level of HIST4H4 and the level of MDH1 in a subject sample(s) and instructions for use of the kit to determine whether the subject has Brucellosis or Q-Fever.

In one aspect, the present invention provides kits for determining whether a subject has Brucellosis or Q-fever. The kits include reagents for determining the level of LDHB and the level of MAT2A in a subject sample(s) and instructions for use of the kit to determine whether the subject has Brucellosis or Q-Fever.

In one aspect, the present invention provides kits for determining whether a subject has Brucellosis or Q-fever. The kits include reagents for determining the level of LDHB and the level of MDH1 in a subject sample(s) and instructions for use of the kit to determine whether the subject has Brucellosis or Q-Fever.

In one aspect, the present invention provides kits for determining whether a subject has Brucellosis or Q-fever. The kits include reagents for determining the level of MAT2A and the level of MDH1 in a subject sample(s) and instructions for use of the kit to determine whether the subject has Brucellosis or Q-Fever.

In one aspect, the present invention provides kits for determining whether a subject has Brucellosis or Q-fever. The kits include reagents for determining a level of HIST4H4, a level of LDHB, and a level of MAT2A in a subject sample(s) and instructions for use of the kit to determine whether the subject has Brucellosis or Q-Fever.

In one aspect, the present invention provides kits for determining whether a subject has Brucellosis or Q-fever. The kits include reagents for determining a level of HIST4H4, a level of LDHB, and a level of MDH1 in a subject sample(s) and instructions for use of the kit to determine whether the subject has Brucellosis or Q-Fever.

In one aspect, the present invention provides kits for determining whether a subject has Brucellosis or Q-fever. The kits include reagents for determining a level of HIST4H4, a level of MAT2A, and a level of MDH1 in a subject sample(s) and instructions for use of the kit to determine whether the subject has Brucellosis or Q-Fever.

In one aspect, the present invention provides kits for determining whether a subject has Brucellosis or Q-fever. The kits include reagents for determining a level of LDHB, a level of MAT2A, and a level of MDH1 in a subject sample(s) and instructions for use of the kit to determine whether the subject has Brucellosis or Q-Fever.

In one aspect, the present invention provides kits for determining whether a subject has Brucellosis or Lyme Disease. The kits include reagents for determining a level of HIST4H4 in a subject sample(s) and instructions for use of the kit to determine whether the subject has Brucellosis or Lyme Disease.

In one aspect, the present invention provides kits for determining whether a subject has Brucellosis or Lyme Disease. The kits include reagents for determining a level of MMP9 in a subject sample(s) and instructions for use of the kit to determine whether the subject has Brucellosis or Lyme Disease.

In one aspect, the present invention provides kits for determining whether a subject has Brucellosis or Lyme Disease. The kits include reagents for determining a level of LYN in a subject sample(s) and instructions for use of the kit to determine whether the subject has Brucellosis or Lyme Disease.

In one aspect, the present invention provides kits for determining whether a subject has Brucellosis or Lyme Disease. The kits include reagents for determining a level of ICAM1 in a subject sample(s) and instructions for use of the kit to determine whether the subject has Brucellosis or Lyme Disease.

In one aspect, the present invention provides kits for determining whether a subject has Brucellosis or Lyme Disease. The kits include reagents for determining the level of HIST4H4 and the level of ICAM1 in a subject sample(s) and instructions for use of the kit to determine whether the subject has Brucellosis or Lyme Disease.

In one aspect, the present invention provides kits for determining whether a subject has Brucellosis or Lyme Disease. The kits include reagents for determining the level of HIST4H4 and the level of LYN in a subject sample(s) and instructions for use of the kit to determine whether the subject has Brucellosis or Lyme Disease.

In one aspect, the present invention provides kits for determining whether a subject has Brucellosis or Lyme Disease. The kits include reagents for determining the level of HIST4H4 and the level of MMP9 in a subject sample(s) and instructions for use of the kit to determine whether the subject has Brucellosis or Lyme Disease.

In one aspect, the present invention provides kits for determining whether a subject has Brucellosis or Lyme Disease. The kits include reagents for determining the level of ICAM1 and the level of LYN in a subject sample(s) and instructions for use of the kit to determine whether the subject has Brucellosis or Lyme Disease.

In one aspect, the present invention provides kits for determining whether a subject has Brucellosis or Lyme Disease. The kits include reagents for determining the level of ICAM1 and the level of MMP9 in a subject sample(s) and instructions for use of the kit to determine whether the subject has Brucellosis or Lyme Disease.

In one aspect, the present invention provides kits for determining whether a subject has Brucellosis or Lyme Disease. The kits include reagents for determining the level of LYN and the level of MMP9 in a subject sample(s) and instructions for use of the kit to determine whether the subject has Brucellosis or Lyme Disease.

In one aspect, the present invention provides kits for determining whether a subject has Brucellosis or Lyme Disease. The kits include reagents for determining a level of HIST4H4, a level of ICAM1, and a level of LYN in a subject sample(s) and instructions for use of the kit to determine whether the subject has Brucellosis or Lyme Disease.

In one aspect, the present invention provides kits for determining whether a subject has Brucellosis or Lyme Disease. The kits include reagents for determining a level of HIST4H4, a level of ICAM1, and a level of MMP9 in a subject sample(s) and instructions for use of the kit to determine whether the subject has Brucellosis or Lyme Disease.

In one aspect, the present invention provides kits for determining whether a subject has Brucellosis or Lyme Disease. The kits include reagents for determining a level of HIST4H4, a level of LYN, and a level of MMP9 in a subject sample(s) and instructions for use of the kit to determine whether the subject has Brucellosis or Lyme Disease.

In one aspect, the present invention provides kits for determining whether a subject has Brucellosis or Lyme Disease. The kits include reagents for determining a level of ICAM1, a level of LYN, and a level of MMP in a subject sample(s) and instructions for use of the kit to determine whether the subject has Brucellosis or Lyme Disease.

In one embodiment, the kits further include reagents for determining the level of any one or more of the markers listed in Table 1 in a sample(s) from the subject.

In another embodiment, the kits further include reagents for determining the level of one or more additional markers selected from the group consisting of LYN, MAT2A, B4GALT1, HIST3H3, ICAM1, LDHB, MDH1, CALU, CORO1A, ENO1, EPB41L3, FLNA, GSTP1, H6PD, HISTH2BE, HIST4H4, ITGAM, MMP9, PRKCSH, RPSA, TKT, and TPI1.

In one aspect, the present invention provides methods for identifying a Brucellosis marker. The methods include identifying proteins differentially expressed in a cell that is not infected with Brucella and a cell that is infected with Brucella, thereby generating a provisional list of markers, determining the level of one or more of the provisional markers in a control sample; and determining the level of the one or more provisional markers in a test sample, wherein a difference in the level of a marker in the control sample as compared to the level in the test sample identifies the marker as a Brucellosis marker.

In one aspect, the present invention provides methods for determining whether a subject has Q-Fever or Lyme Disease. The methods include determining a level of B4GALT1 in a sample(s) from the subject; comparing the level of B4GALT1 in the subject sample(s) with a level of B4GALT1 in a control sample(s), wherein a difference in the level of B4GALT1 in the subject sample(s) as compared to the level of B4GALT1 in the control sample(s) indicates that the subject has Q-Fever.

In one aspect, the present invention provides methods for determining whether a subject has Q-Fever or Lyme Disease. The methods include determining a level of CALU in a sample(s) from the subject; comparing the level of CALU in the subject sample(s) with a level of CALU in a control sample(s), wherein a difference in the level of CALU in the subject sample(s) as compared to the level of CALU in the control sample(s) indicates that the subject has Q-Fever.

In one aspect, the present invention provides methods for determining whether a subject has Q-Fever or Lyme Disease. The methods include determining a level of LYN in a sample(s) from the subject; comparing the level of LYN in the subject sample(s) with a level of LYN in a control sample(s), wherein a difference in the level of LYN in the subject sample(s) as compared to the level of LYN in the control sample(s) indicates that the subject has Q-Fever.

In one aspect, the present invention provides methods for determining whether a subject has Q-Fever or Lyme Disease. The methods include determining a level of TPI1 in a sample(s) from the subject; comparing the level of TPI1 in the subject sample(s) with a level of TPI1 in a control sample(s), wherein a difference in the level of TPI1 in the subject sample(s) as compared to the level of TPI1 in the control sample(s) indicates that the subject has Q-Fever.

In one aspect, the present invention provides methods for determining whether a subject has Q-Fever or Lyme Disease. The methods include determining a level of B4GALT1 and the level of CALU in a sample(s) from the subject; comparing the level of B4GALT1 and the level of CALU in the subject sample(s) with a level of B4GALT1 and a level of CALU in a control sample(s), wherein a difference in the level of B4GALT1 and a difference in the level of CALU in the subject sample(s) as compared to the level of B4GALT1 and the level of CALU in the control sample(s) indicates that the subject has Q-Fever.

In one aspect, the present invention provides methods for determining whether a subject has Q-Fever or Lyme Disease. The methods include determining the level of B4GALT1 and the level of LYN in a sample(s) from the subject; comparing the level of B4GALT1 and the level of LYN in the subject sample(s) with a level of B4GALT1 and a level of LYN in a control sample(s), wherein a difference in the level of B4GALT1 and a difference in the level of LYN in the subject sample(s) as compared to the level of B4GALT1 and the level of LYN in the control sample(s) indicates that the subject has Q-Fever.

In one aspect, the present invention provides methods for determining whether a subject has Q-Fever or Lyme Disease. The methods include determining the level of B4GALT1 and the level of TPI1 in a sample(s) from the subject; comparing the level of B4GALT1 and the level of TPI1 in the subject sample(s) with a level of B4GALT1 and a level of TPI1 in a control sample(s), wherein a difference in the level of B4GALT1 and a difference in the level of TPI1 in the subject sample(s) as compared to the level of B4GALT1 and the level of TPI1 in the control sample(s) indicates that the subject has Q-Fever.

In one aspect, the present invention provides methods for determining whether a subject has Q-Fever or Lyme Disease. The methods include determining a level of B4GALT1, a level of CALU, and a level of LYN in a sample(s) from the subject; comparing the level of B4GALT1, the level of CALU, and the level of LYN in the subject sample(s) with a level of B4GALT1, a level of CALU, and a level of LYN in a control sample(s), wherein a difference in the level of B4GALT1, a difference in the level of CALU, and a difference in the level of LYN in the subject sample(s) as compared to the level of B4GALT1, the level of CALU, and the level of LYN in the control sample(s) indicates that the subject has Q-Fever.

In one aspect, the present invention provides methods for determining whether a subject has Q-Fever or Lyme Disease. The methods include determining a level of B4GALT1, a level of CALU, and a level of TPI1 in a sample(s) from the subject; comparing the level of B4GALT1, the level of CALU, and the level of TPI1 in the subject sample(s) with a level of B4GALT1, a level of CALU, and a level of TPI1 in a control sample(s), wherein a difference in the level of B4GALT1, a difference in the level of CALU, and a difference in the level of TPI1 in the subject sample(s) as compared to the level of B4GALT1, the level of CALU, and the level of TPI1 in the control sample(s) indicates that the subject has Q-Fever.

In one aspect, the present invention provides methods for determining whether a subject has Q-Fever or Lyme Disease. The methods include determining a level of B4GALT1, a level of LYN, and a level of TPI1 in a sample(s) from the subject; comparing the level of B4GALT1, the level of LYN, and the level of TPI1 in the subject sample(s) with a level of B4GALT1, a level of LYN, and a level of TPI1 in a control sample(s), wherein a difference in the level of B4GALT1, a difference in the level of LYN, and a difference in the level of TPI1 in the subject sample(s) as compared to the level of B4GALT1, the level of LYN, and the level of TPI1 in the control sample(s) indicates that the subject has Q-Fever.

In one aspect, the present invention provides methods for determining whether a subject has Q-Fever or Lyme Disease. The methods include determining a level of B4GALT1, a level of LYN, a level of CALU, and a level of TPI1 in a sample(s) from the subject; comparing the level of B4GALT1, the level of LYN, the level of CALU, and the level of TPI1 in the subject sample(s) with a level of B4GALT1, a level of LYN, the level of CALU, and a level of TPI1 in a control sample(s), wherein a difference in the level of B4GALT1, a difference in the level of LYN, a difference in the level of CALU, and a difference in the level of TPI1 in the subject sample(s) as compared to the level of B4GALT1, the level of LYN, the level of CALU, and the level of TPI1 in the control sample(s) indicates that the subject has Q-Fever.

In one aspect, the present invention provides methods for determining whether a subject has Q-Fever or Lyme Disease. The methods include determining the level of CALU and the level of LYN in a sample(s) from the subject; comparing the level of CALU and the level of LYN in the subject sample(s) with a level of CALU and a level of LYN in a control sample(s), wherein a difference in the level of CALU and a difference in the level of LYN in the subject sample(s) as compared to the level of CALU and the level of LYN in the control sample(s) indicates that the subject has Q-Fever.

In one aspect, the present invention provides methods for determining whether a subject has Q-Fever or Lyme Disease. The methods include determining the level of CALU and the level of TPI1 in a sample(s) from the subject; comparing the level of CALU and the level of TPI1 in the subject sample(s) with a level of CALU and a level of TPI1 in a control sample(s), wherein a difference in the level of CALU and a difference in the level of TPI1 in the subject sample(s) as compared to the level of CALU and the level of TPI1 in the control sample(s) indicates that the subject has Q-Fever.

In one aspect, the present invention provides methods for determining whether a subject has Q-Fever or Lyme Disease. The methods include determining the level of LYN and the level of TPI1 in a sample(s) from the subject; comparing the level of LYN and the level of TPI1 in the subject sample(s) with a level of LYN and a level of TPI1 in a control sample(s), wherein a difference in the level of LYN and a difference in the level of TPI1 in the subject sample(s) as compared to the level of LYN and the level of TPI1 in the control sample(s) indicates that the subject has Q-Fever.

In one aspect, the present invention provides methods for determining whether a subject has Q-Fever or Lyme Disease. The methods include determining a level of CALU, a level of LYN, and a level of TPI1 in a sample(s) from the subject; comparing the level of CALU, the level of LYN, and the level of TPI1 in the subject sample(s) with a level of CALU, a level of LYN, and a level of TPI1 in a control sample(s), wherein a difference in the level of CALU, a difference in the level of LYN, and a difference in the level of TPI1 in the subject sample(s) as compared to the level of CALU, the level of LYN, and the level of TPI1 in the control sample(s) indicates that the subject has Q-Fever.

In one embodiment, the methods further comprise determining the level of one or more additional markers listed in Table 1.

In another embodiment, the methods further comprise determining the level of one or more additional markers selected from the group consisting of LYN, MAT2A, B4GALT1, HIST3H3, ICAM1, LDHB, MDH1, CALU, CORO1A, ENO1, EPB41L3, FLNA, GSTP1, H6PD, HISTH2BE, HIST4H4, ITGAM, MMP9, PRKCSH, RPSA, TKT, and TPI1.

In one embodiment, the level of the marker is an expression level and/or activity of the marker.

In one embodiment, the level in the subject sample(s) is determined by mass spectrometry. In one embodiment, the mass spectrometry is matrix assisted laser desorption/time of flight (MALDI/TOF) mass spectrometry, liquid chromatography quadruple ion trap electrospray (LCQ-MS), or surface enhanced laser desorption ionization/time of flight (SELDI/TOF) mass spectrometry.

In one embodiment, the level in the subject sample(s) is determined by immunoassay.

In one embodiment, the sample(s) from the subject is a fluid sample(s). In another embodiment, the sample(s) from the subject is a tissue sample(s).

In one aspect, the present invention provides kits for determining whether a subject has Q-Fever or Lyme Disease. The kits include reagents for determining a level of B4GALT1 in a subject sample(s) and instructions for use of the kit to determine whether the subject has Q-Fever or Lyme Disease.

In one aspect, the present invention provides kits for determining whether a subject has Q-Fever or Lyme Disease. The kits include reagents for determining a level of CALU in a subject sample(s) and instructions for use of the kit to determine whether the subject has Q-Fever or Lyme Disease.

In one aspect, the present invention provides kits for determining whether a subject has Q-Fever or Lyme Disease. The kits include agents for determining a level of LYN in a subject sample(s) and instructions for use of the kit to determine whether the subject has Q-Fever or Lyme Disease.

In one aspect, the present invention provides kits for determining whether a subject has Q-Fever or Lyme Disease. The kits include reagents for determining a level of TPI1 in a subject sample(s) and instructions for use of the kit to determine whether the subject has Q-Fever or Lyme Disease.

In one aspect, the present invention provides kits for determining whether a subject has Q-Fever or Lyme Disease. The kits include reagents for determining the level of B4GALT1 and the level of CALU in a subject sample(s) and instructions for use of the kit to determine whether the subject has Q-Fever or Lyme Disease.

In one aspect, the present invention provides kits for determining whether a subject has Q-Fever or Lyme Disease. The kits include reagents for determining the level of B4GALT1 and the level of LYN in a subject sample(s) and instructions for use of the kit to determine whether the subject has Q-Fever or Lyme Disease.

In one aspect, the present invention provides kits for determining whether a subject has Q-Fever or Lyme Disease. The kits include reagents for determining the level of B4GALT1 and the level of TPI1 in a subject sample(s) and instructions for use of the kit to determine whether the subject has Q-Fever or Lyme Disease.

In one aspect, the present invention provides kits for determining whether a subject has Q-Fever or Lyme Disease. The kits include reagents for determining a level of B4GALT1, a level of CALU, and a level of LYN in a subject sample(s) and instructions for use of the kit to determine whether the subject has Q-Fever or Lyme Disease.

In one aspect, the present invention provides kits for determining whether a subject has Q-Fever or Lyme Disease. The kits include reagents for determining a level of B4GALT1, a level of LYN, and a level of TPI1 in a subject sample(s) and instructions for use of the kit to determine whether the subject has Q-Fever or Lyme Disease.

In one aspect, the present invention provides kits for determining whether a subject has Q-Fever or Lyme Disease. The kits include reagents for determining a level of B4GALT1, a level of CALU, and a level of TPI1 in a subject sample(s) and instructions for use of the kit to determine whether the subject has Q-Fever or Lyme Disease.

In one aspect, the present invention provides kits for determining whether a subject has Q-Fever or Lyme Disease. The kits include reagents for determining a level of B4GALT1, a level of CALU, a level of LYN, and a level of TPI1 in a subject sample(s) and instructions for use of the kit to determine whether the subject has Q-Fever or Lyme Disease.

In one aspect, the present invention provides kits for determining whether a subject has Q-Fever or Lyme Disease. The kits include reagents for determining the level of CALU and the level of LYN in a subject sample(s) and instructions for use of the kit to determine whether the subject has Q-Fever or Lyme Disease.

In one aspect, the present invention provides kits for determining whether a subject has Q-Fever or Lyme Disease. The kits include reagents for determining the level of CALU and the level of TPI1 in a subject sample(s) and instructions for use of the kit to determine whether the subject has Q-Fever or Lyme Disease.

In one aspect, the present invention provides kits for determining whether a subject has Q-Fever or Lyme Disease. The kits include reagents for determining a level of CALU, a level of LYN, and a level of TPI1 in a subject sample(s) and instructions for use of the kit to determine whether the subject has Q-Fever or Lyme Disease.

In one aspect, the present invention provides kits for determining whether a subject has Q-Fever or Lyme Disease. The kits include reagents for determining the level of LYN and the level of TPI1 in a subject sample(s) and instructions for use of the kit to determine whether the subject has Q-Fever or Lyme Disease.

In one embodiment, the kits further include reagents for determining the level of any one or more of the markers listed in Table 1 in a sample(s) from the subject.

In another embodiment, the kits further include reagents for determining the level of one or more additional markers selected from the group consisting of LYN, MAT2A, B4GALT1, HIST3H3, ICAM1, LDHB, MDH1, CALU, CORO1A, ENO1, EPB41L3, FLNA, GSTP1, H6PD, HISTH2BE, HIST4H4, ITGAM, MMP9, PRKCSH, RPSA, TKT, and TPI1.

In one aspect, the present invention provides methods for determining whether a subject has Brucellosis or Q-Fever or Lyme Disease. The methods include determining a level of HIST4H4, a level of LYN, a level of MAT2A, a level of MMP9, a level of CALU, a level of LDHB, and a level of B4GALT1 in a sample(s) from the subject; comparing the level of HIST4H4, the level of LYN, the level of MAT2A, the level of MMP9, the level of CALU, the level of LDHB, and the level of B4GALT1 in a control sample(s), wherein a higher level of HIST4H4, a higher level of LYN, a higher level of MAT2A, a higher level of MMP9, a higher level of CALU, a higher level of LDHB, and a higher level of B4GALT1 in a sample(s) from the subject as compared to the level of HIST4H4, the level of LYN, the level of MAT2A, the level of MMP9, the level of CALU, the level of LDHB, and the level of B4GALT1 in the control sample(s) indicates that the subject has Brucellosis, wherein a lower level of HIST4H4, a higher level of LYN, a higher level of MAT2A, a lower level of MMP9, a lower level of CALU, a lower level of LDHB, and a lower level of B4GALT1 in a sample(s) from the subject as compared to the level of HIST4H4, the level of LYN, the level of MAT2A, the level of MMP9, the level of CALU, the level of LDHB, and the level of B4GALT1 in the control sample(s) indicates that the subject has Q-Fever, and wherein a lower level of HIST4H4, a higher level of LYN, a higher level of MAT2A, a higher level of MMP9, a higher level of CALU, a lower level of LDHB, and a lower level of B4GALT1 in a sample(s) from the subject as compared to the level of HIST4H4, the level of LYN, the level of MAT2A, the level of MMP9, the level of CALU, the level of LDHB, and the level of B4GALT1 in the control sample(s) indicates that the subject has Lyme Disease.

In one aspect, the present invention provides methods for determining whether a subject has Lyme Disease. The methods include determining the level of MMP9 in a sample(s) from the subject; comparing the level of MMP9 in the subject sample(s) with a level of MMP9 in a control sample(s), wherein a difference in the level of MMP9 in the subject sample(s) as compared to the level of MMP9 in the control sample(s) indicates that the subject has Lyme Disease.

In one aspect, the present invention provides methods for monitoring the effectiveness of a treatment in a subject having Lyme Disease. The methods include determining the level of MMP9 in a first sample(s) from the subject prior to the initiation of the treatment; determining the level of MMP9 in a second sample(s) from the subject after at least a portion of the treatment has been administered; comparing the level of MMP9 in the first sample(s) with a level of MMP9 in the second sample(s), wherein a difference in the level of MMP9 in the first sample(s) as compared to the level of MMP9 in the second sample(s) indicates that the treatment is effective.

In one aspect, the present invention provides methods for identifying a compound that is useful for treating a subject having Lyme Disease. The methods include contacting an aliquot of a sample(s) from the subject with each member of a library of compounds; determining the effect of a member of the library of compounds on the level and/or activity of MMP9 in each of the aliquots; and selecting a member of the library of compounds which modulates the level and/or the activity of MMP9 in an aliquot as compared to the level and/or activity of MMP9 in a control sample, thereby identifying a compound that is useful for treating a subject having Lyme Disease.

In one aspect, the present invention provides methods for treating a subject having Lyme Disease. The methods include administering to the subject an effective amount of an agent that modulates the level and/or activity of MMP9, thereby treating the subject.

In one aspect, the present invention provides methods for determining whether a subject has Lyme Disease. The methods include determining the level of MMP9 and the level of MDH1 in a sample(s) from the subject; comparing the level of MMP9 and the level of MDH1 in the subject sample(s) with a level of MMP9 and a level of MDH1 in a control sample(s), wherein a difference in the level of MMP9 and a difference in the level of MDH1 in the subject sample(s) as compared to the level of MMP9 and the level of MDH1 in the control sample(s) indicates that the subject has Lyme Disease.

In one aspect, the present invention provides methods for monitoring the effectiveness of a treatment in a subject having Lyme Disease. The methods include determining the level of MMP9 and the level of MDH1 in a first sample(s) from the subject prior to the initiation of the treatment; determining the level of MMP9 and the level of MDH1 in a second sample(s) from the subject after at least a portion of the treatment has been administered; comparing the level of MMP9 and the level of MDH1 in the first sample(s) with the level of MMP9 and the level of MDH1 in the second sample(s), wherein a difference in the level of MMP9 and a difference in the level of MDH1 in the first sample(s) as compared to the level of MMP9 and the level of MDH1 in the second sample(s) indicates that the treatment is effective.

In one aspect, the present invention provides methods for identifying a compound that is useful for treating a subject having Lyme Disease. The methods include contacting an aliquot of a sample(s) from the subject with each member of a library of compounds; determining the effect of a member of the library of compounds on the level and/or activity of MMP9 and the level and/or activity of MDH1 in each of the aliquots; and selecting a member of the library of compounds which modulates the level and/or the activity of MMP9 and the level and/or activity of MDH1 in an aliquot as compared to the level and/or activity of MMP9 and the level and/or activity of MDH1 in a control sample, thereby identifying a compound that is useful for treating a subject having Lyme Disease.

In one aspect, the present invention provides methods for treating a subject having Lyme Disease. The methods include administering to the subject an effective amount of an agent that modulates the level and/or activity of MMP9 and the level and/or activity of MDH1, thereby treating the subject.

In one aspect, the present invention provides methods for determining whether a subject has Q-Fever. The methods include determining the level of LYN and the level of LDHB in a sample(s) from the subject; comparing the level of LYN and the level of LDHB in the subject sample(s) with a level of LYN and a level of LDHB in a control sample(s), wherein a difference in the level of LYN and a difference in the level of LDHB in the subject sample(s) as compared to the level of LYN and the level of LDHB in the control sample(s) indicates that the subject has Q-Fever.

In one aspect, the present invention provides methods for monitoring the effectiveness of a treatment in a subject having Q-Fever. The methods include determining the level of LYN and the level of LDHB in a first sample(s) from the subject prior to the initiation of the treatment; determining the level of LYN and the level of LDHB in a second sample(s) from the subject after at least a portion of the treatment has been administered; comparing the level of LYN and the level of LDHB in the first sample(s) with the level of LYN and the level of LDHB in the second sample(s), wherein a difference in the level of LYN and a difference in the level of LDHB in the first sample(s) as compared to the level of LYN and the level of LDHB in the second sample(s) indicates that the treatment is effective.

In one aspect, the present invention provides methods for identifying a compound that is useful for treating a subject having Q-Fever. The methods include contacting an aliquot of a sample(s) from the subject with each member of a library of compounds; determining the effect of a member of the library of compounds on the level and/or activity of LYN and the level and/or activity of LDHB in each of the aliquots; and selecting a member of the library of compounds which modulates the level and/or the activity of LYN and the level and/or activity of LDHB in an aliquot as compared to the level and/or activity of LYN and the level and/or activity of LDHB in a control sample, thereby identifying a compound that is useful for treating a subject having Q-Fever.

In one aspect, the present invention provides methods for treating a subject having Q-Fever. The methods include administering to the subject an effective amount of an agent that modulates the level and/or activity of LYN and the level and/or activity of LDHB, thereby treating the subject.

In one embodiment, the methods further include determining the level of one or more additional markers listed in Table 1.

In another embodiment, the methods further include determining the level of one or more additional markers selected from the group consisting of LYN, MAT2A, B4GALT1, HIST3H3, ICAM1, LDHB, MDH1, CALU, CORO1A, ENO1, EPB41L3, FLNA, GSTP1, H6PD, HIST2BE, HIST4H4, ITGAM, MMP9, PRKCSH, RPSA, TKT, and TPI1.

In one embodiment, the level of the marker is an expression level and/or activity of the marker.

In one embodiment, the level in the subject sample(s) is determined by mass spectrometry. In one embodiment, the mass spectrometry is matrix assisted laser desorption/time of flight (MALDI/TOF) mass spectrometry, liquid chromatography quadruple ion trap electrospray (LCQ-MS), or surface enhanced laser desorption ionization/time of flight (SELDI/TOF) mass spectrometry.

In one embodiment, the level in the subject sample(s) is determined by immunoassay.

In one embodiment, the sample(s) from the subject is a fluid sample(s). In another embodiment, the sample(s) from the subject is a tissue sample(s).

In one aspect, the present invention provides kits for determining whether a subject has Brucellosis or Q-Fever or Lyme Disease. The kits include reagents for determining level of HIST4H4, a level of LYN, a level of MAT2A, a level of MMP9, a level of CALU, a level of LDHB, and a level of B4GALT1 in a sample(s) from the subject and instructions for use of the kit to determine whether the subject has Brucellosis or Q-Fever or Lyme Disease.

In one aspect, the present invention provides kits for determining whether a subject has Lyme Disease. The kits include reagents for determining the level of MMP9 in a subject sample(s) and instructions for use of the kit to determine whether the subject has Lyme Disease.

In one aspect, the present invention provides kits monitoring the effectiveness of a treatment in a subject having Lyme Disease. The kits include reagents for determining the level of MMP9 in a subject sample(s) and instructions for use of the kit to monitor the effectiveness of the treatment.

In one aspect, the present invention provides kits for determining whether a subject has Lyme Disease. The kits include reagents for determining the level of MMP9 and the level of MDH1 in a subject sample(s) and instructions for use of the kit to determine whether the subject has Lyme Disease.

In one aspect, the present invention provides kits monitoring the effectiveness of a treatment in a subject having Lyme Disease. The kits include reagents for determining the level of MMP9 and the level of MDH1 in a subject sample(s) and instructions for use of the kit to monitor the effectiveness of the treatment.

In one aspect, the present invention provides kits for determining whether a subject has Q-Fever. The kits include for determining the level of LYN and the level of LDHB in a subject sample(s) and instructions for use of the kit to determine whether the subject has Q-Fever.

In one aspect, the present invention provides kits monitoring the effectiveness of a treatment in a subject having Q-Fever. The kits include reagents for determining the level of LYN and the level of LDHB in a subject sample(s) and instructions for use of the kit to monitor the effectiveness of the treatment.

In one embodiment, the kits further include reagents for determining the level of any one or more of the markers listed in Table 1 in a sample(s) from the subject.

In another embodiment, the kits further include reagents for determining the level of one or more additional markers selected from the group consisting of LYN, MAT2A, B4GALT1, HIST3H3, ICAM1, LDHB, MDH1, CALU, CORO1A, ENO1, EPB41L3, FLNA, GSTP1, H6PD, HISTH2BE, HIST4H4, ITGAM, MMP9, PRKCSH, RPSA, TKT, and TPI1.

BRIEF DESCRIPTION OF THE DRAWINGS

FIG. 1A depicts the immunofluorescence microscopy of THP-1 host cell subcellular fractions 24 hours after infection with B. abortus 2308. Dark gray dots represent intracellular bacteria.

FIG. 1B depicts the immunofluorescence microscopy of THP-1 host cell subcellular fractions 24 hours after infection with B. abortus 544. Dark gray dots represent intracellular bacteria.

FIG. 1C depicts the immunofluorescence microscopy of JAr trophoblast host cell subcellular fractions 24 hours after infection with B. abortus 2308. Dark gray dots represent intracellular bacteria.

FIG. 1D depicts immunofluorescence microscopy of AC-1M88 trophoblast host cell subcellular fractions 24 hours after infection with B. abortus 2308. Dark gray dots represent intracellular bacteria.

FIG. 1E is a Western blot analysis depicting the preparation of host cell subcellular fractions by comparing increasing amounts of starting material (homogenate; μg) to secretory vesicle preparations (SPV) and secretory vesicle contents (SC) of THP-1 host cells 24 hours following B. abortus 2308 infection using markers of specific subcellular compartments. Na+/K+ ATPase reactivity was used a marker of plasma membrane, BIP and B2M as soluble potentially secreted proteins, P62, GS28, TIM23 as markers of nuclear, Golgi, and mitochondrial membranes, respectively, and actin as a marker of the cytoskeleton.

FIG. 1F is a Western blot analysis depicting the preparation of host cell subcellular fractions by comparing increasing amounts of starting material (homogenate; μg) to secretory vesicle preparations (SPV) and secretory vesicle contents (SC) of THP-1 host cells 24 hours following B. abortus 544 infection using markers of specific subcellular compartments. Na+/K+ ATPase reactivity was used a marker of plasma membrane, BIP and B2M as soluble potentially secreted proteins, P62, GS28, TIM23 as markers of nuclear, Golgi, and mitochondrial membranes, respectively, and actin as a marker of the cytoskeleton.

FIG. 1G is a Western blot analysis depicting the preparation of host cell subcellular fractions by comparing increasing amounts of starting material (homogenate; μg) to secretory vesicle preparations (SPV) and secretory vesicle contents (SC) of JAr host cells 24 hours following B. abortus 2308 infection using markers of specific subcellular compartments. Na+/K+ ATPase reactivity was used a marker of plasma membrane, BIP and B2M as soluble potentially secreted proteins, P62, GS28, TIM23 as markers of nuclear, Golgi, and mitochondrial membranes, respectively, and actin as a marker of the cytoskeleton.

FIG. 1H is a Western blot analysis depicting the preparation of host cell subcellular fractions by comparing increasing amounts of starting material (homogenate; μg) to secretory vesicle preparations (SPV) and secretory vesicle contents (SC) of AC-1M88 host cells 24 hours following B. abortus 2308 infection using markers of specific subcellular compartments. Na+/K+ ATPase reactivity was used a marker of plasma membrane, BIP and B2M as soluble potentially secreted proteins, P62, GS28, TIM23 as markers of nuclear, Golgi, and mitochondrial membranes, respectively, and actin as a marker of the cytoskeleton.

Figure 4:
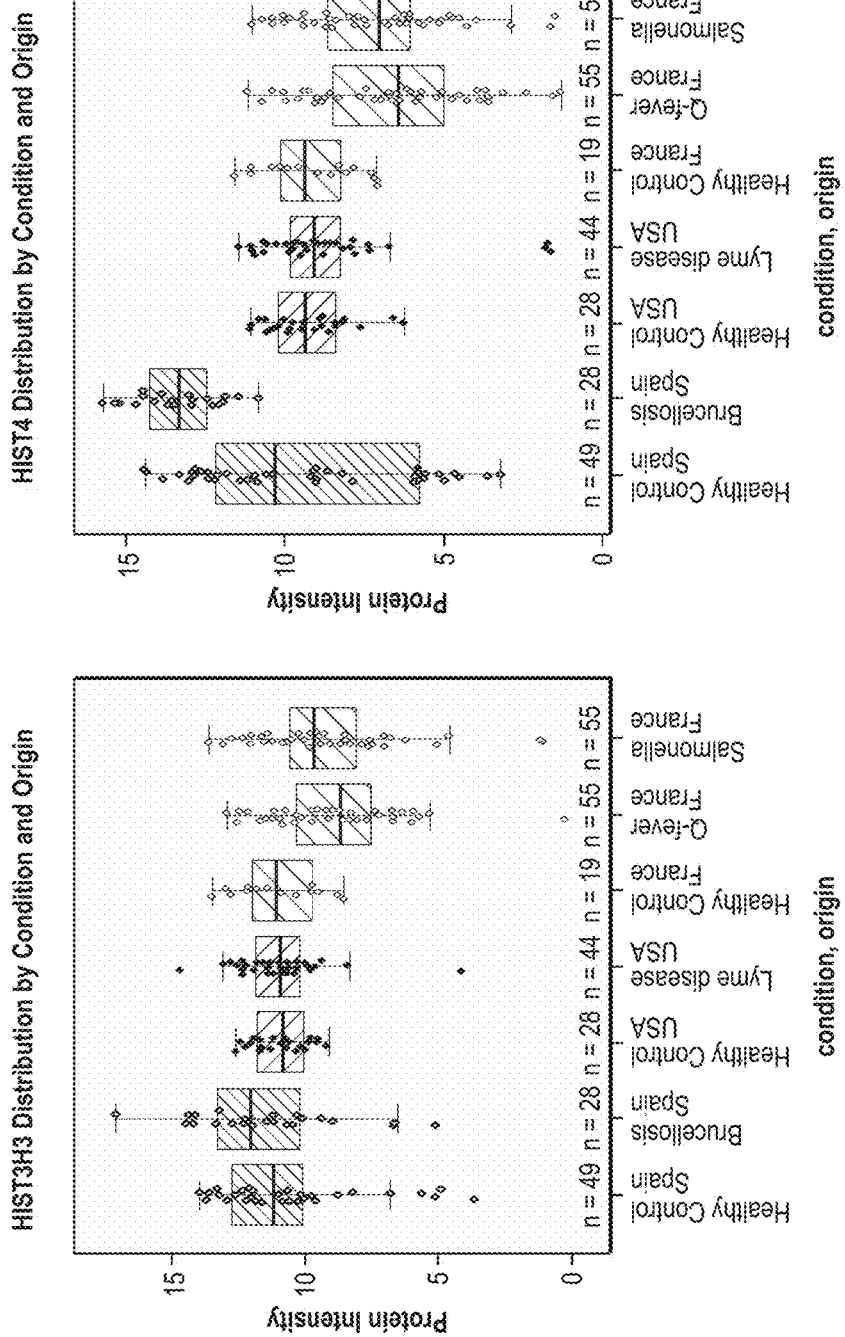

FIG. 4 is a boxplot of the normalized protein intensity of an exemplary biomarker of the invention (HIST3H3). In each boxplot, each subject is represented by a dot. The median protein concentration is indicated by a bold line, the 50% range by filed rectangles, and the 95% range by hatched lines. Size and description of each group is indicated on the x-axis, normalized protein intensity on the y-axis.

Figure 3:
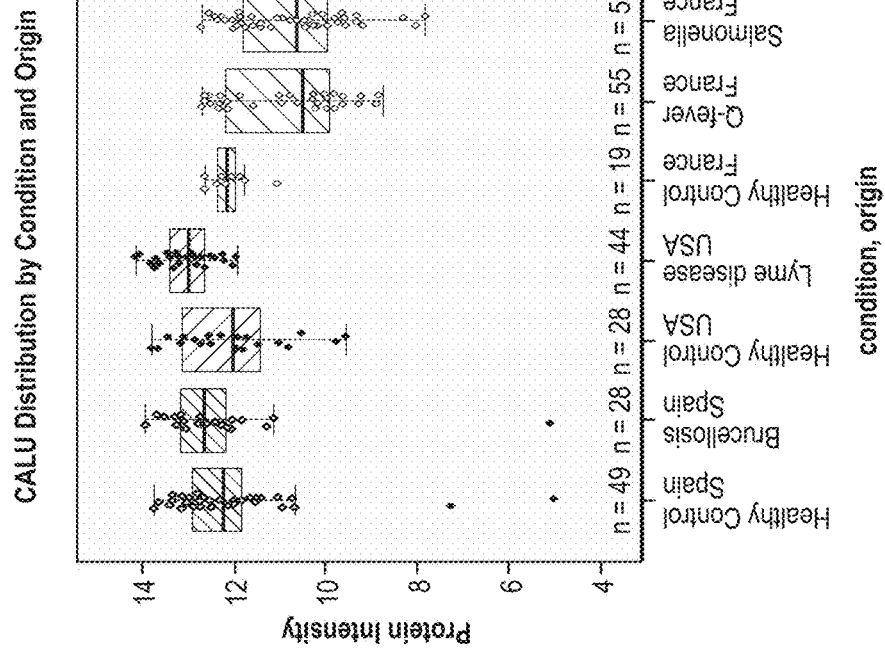
FIG. 3 is a boxplot of the normalized protein intensity of an exemplary biomarker of the invention (CALU). In each boxplot, each subject is represented by a dot. The median protein concentration is indicated by a bold line, the 50% range by filed rectangles, and the 95% range by hatched lines. Size and description of each group is indicated on the x-axis, normalized protein intensity on the y-axis.
Figure 2:
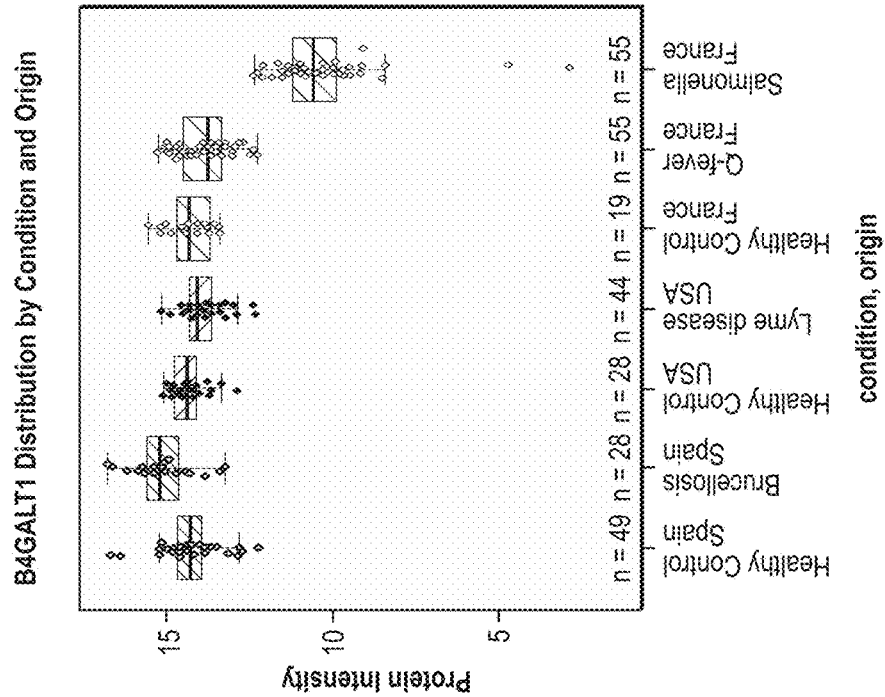
FIG. 2 is a boxplot of the normalized protein intensity of an exemplary biomarker of the invention (B4GALT1). In each boxplot, each subject is represented by a dot. The median protein concentration is indicated by a bold line, the 50% range by filed rectanges, and the 95% range by hatched lines. Size and description of each group is indicated on the x-axis, normalized protein intensity on the y-axis.
Figure 5:
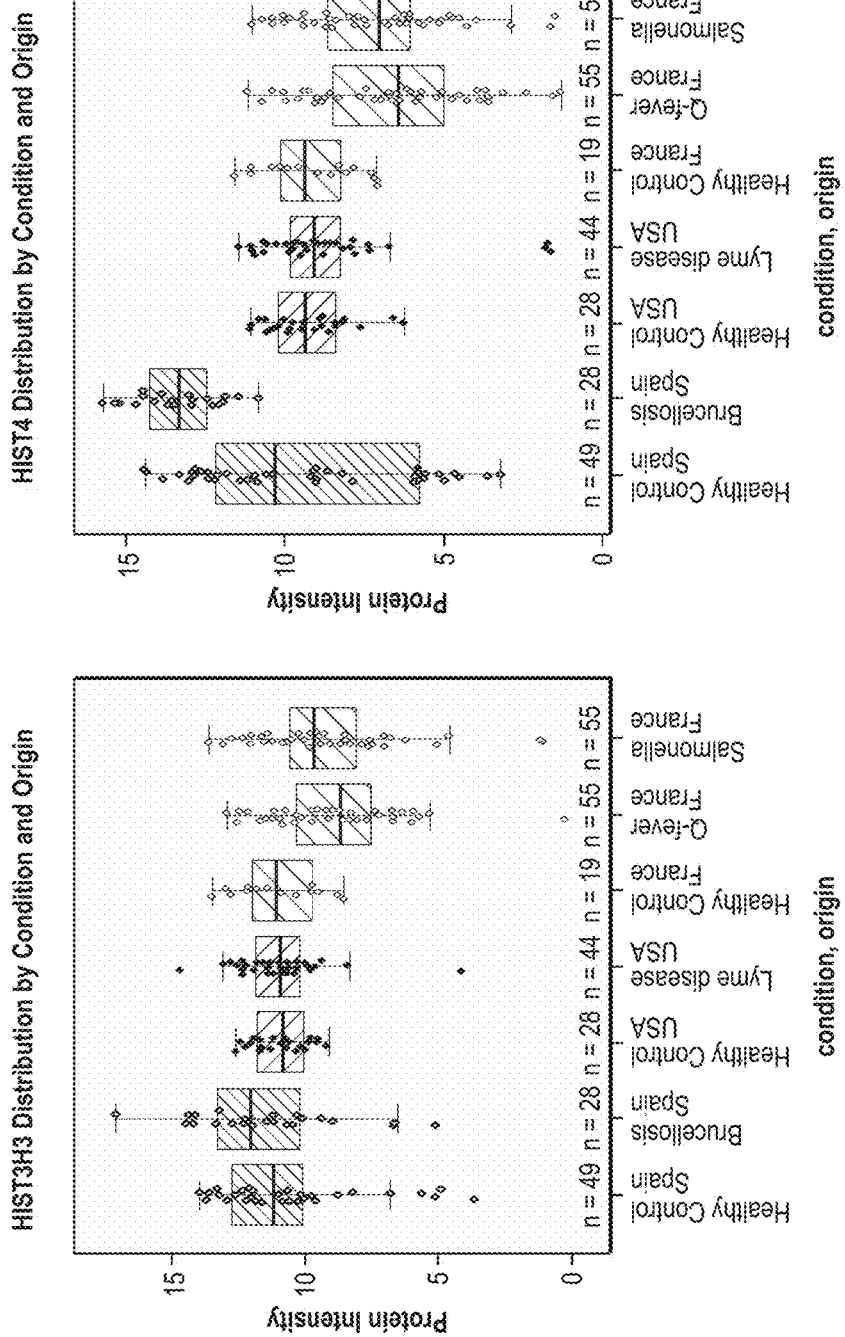

FIG. 5 is a boxplot of the normalized protein intensity of an exemplary biomarker of the invention (HIST4). In each boxplot, each subject is represented by a dot. The median protein concentration is indicated by a bold line, the 50% range by filed rectangles, and the 95% range by hatched lines. Size and description of each group is indicated on the x-axis, normalized protein intensity on the y-axis.

Figure 6:
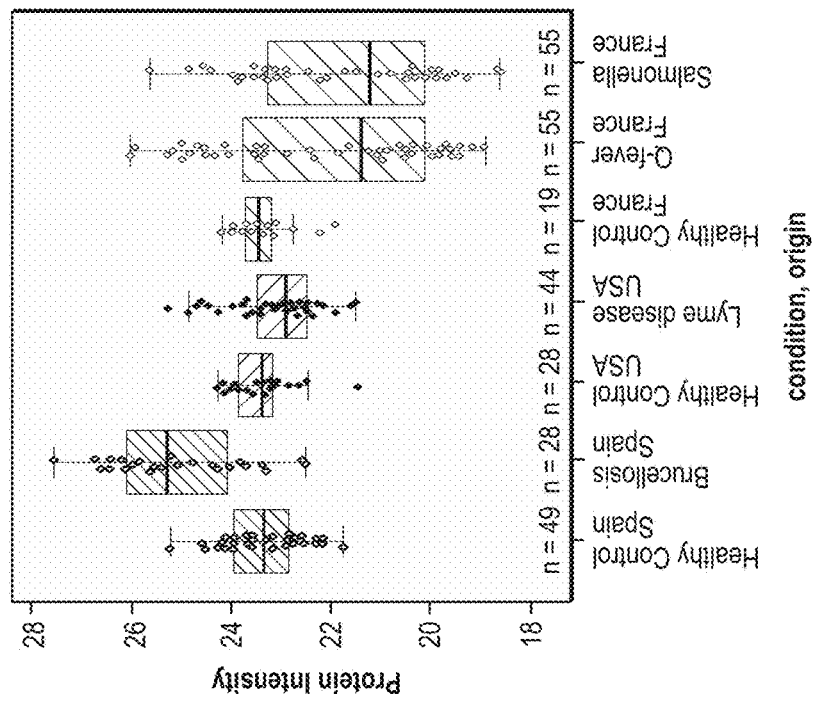

FIG. 6 is a boxplot of the normalized protein intensity of an exemplary biomarker of the invention (ICAM1). In each boxplot, each subject is represented by a dot. The median protein concentration is indicated by a bold line, the 50% range by filed rectangles, and the 95% range by hatched lines. Size and description of each group is indicated on the x-axis, normalized protein intensity on the y-axis.

Figure 7:
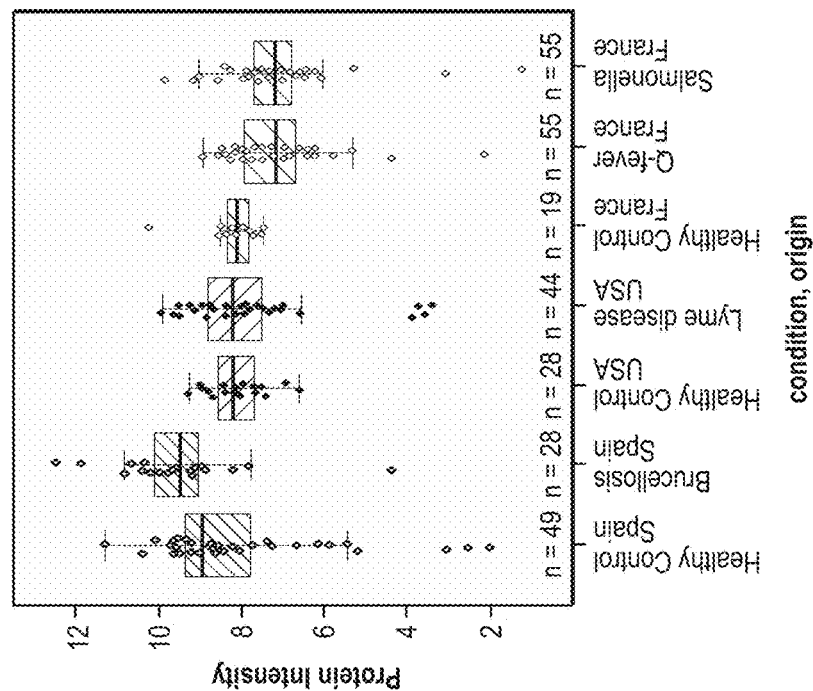

FIG. 7 is a boxplot of the normalized protein intensity of an exemplary biomarker of the invention (LDHB). In each boxplot, each subject is represented by a dot. The median protein concentration is indicated by a bold line, the 50% range by filed rectangles, and the 95% range by hatched lines. Size and description of each group is indicated on the x-axis, normalized protein intensity on the y-axis.

Figure 8:
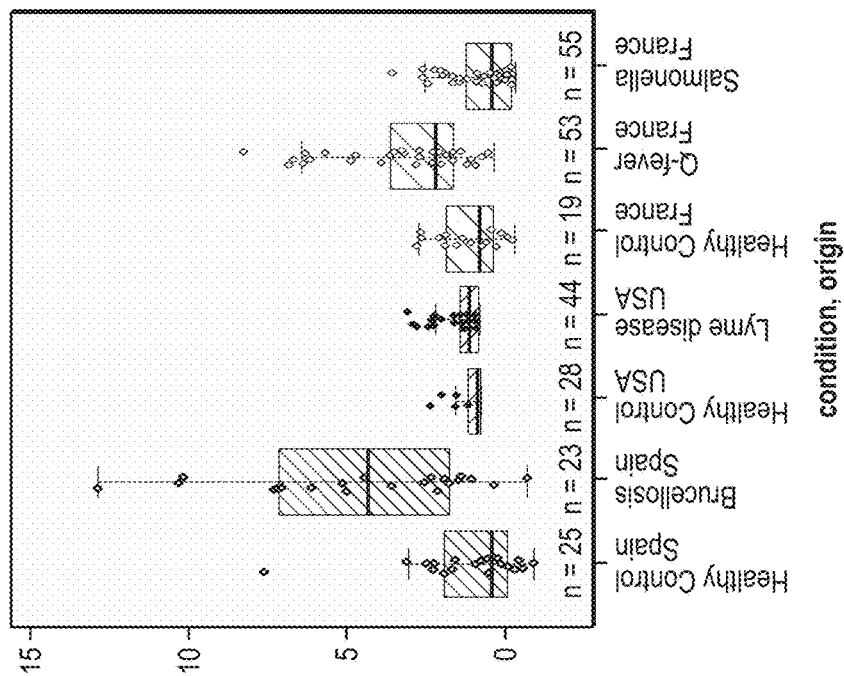

FIG. 8 is a boxplot of the normalized protein intensity of an exemplary biomarker of the invention (LYN). In each boxplot, each subject is represented by a dot. The median protein concentration is indicated by a bold line, the 50% range by filed rectangles, and the 95% range by hatched lines. Size and description of each group is indicated on the x-axis, normalized protein intensity on the y-axis.

Figure 9:
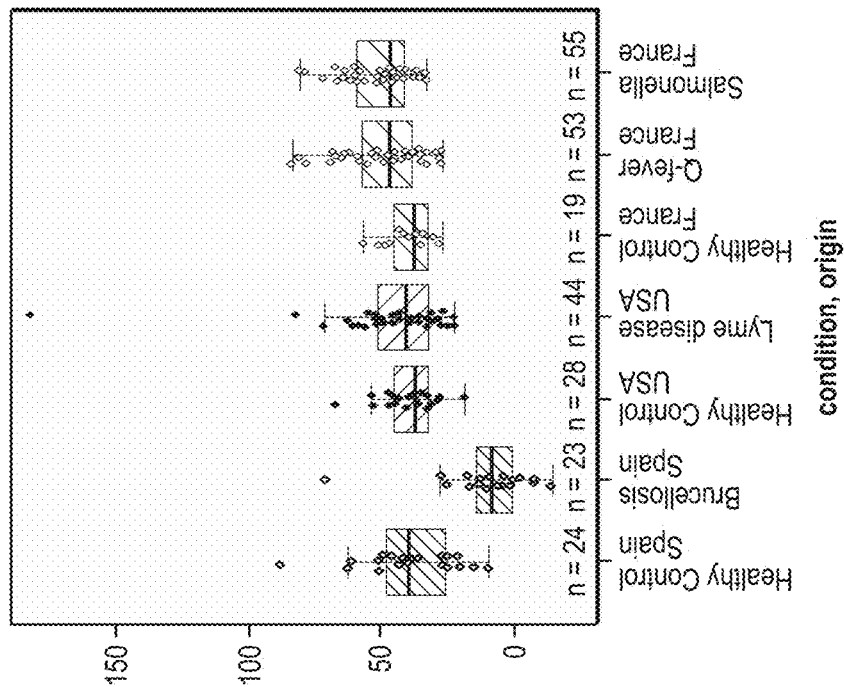

FIG. 9 is a boxplot of the normalized protein intensity of an exemplary biomarker of the invention (MAT2A). In each boxplot, each subject is represented by a dot. The median protein concentration is indicated by a bold line, the 50% range by filed rectangles, and the 95% range by hatched lines. Size and description of each group is indicated on the x-axis, normalized protein intensity on the y-axis.

Figure 10:
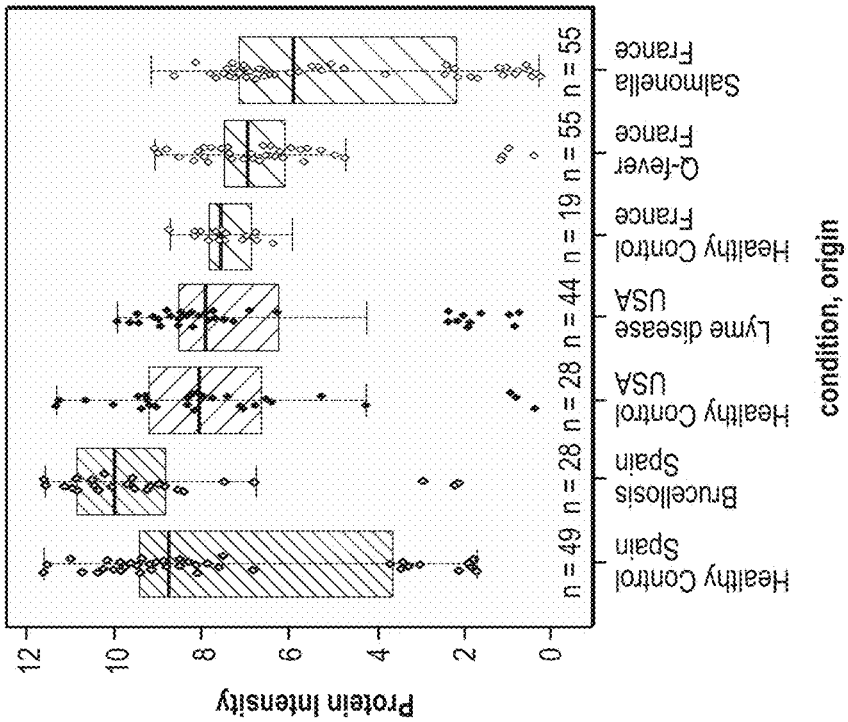

FIG. 10 is a boxplot of the normalized protein intensity of an exemplary biomarker of the invention (MDH1). In each boxplot, each subject is represented by a dot. The median protein concentration is indicated by a bold line, the 50% range by filed rectangles, and the 95% range by hatched lines. Size and description of each group is indicated on the x-axis, normalized protein intensity on the y-axis.

Figure 11:
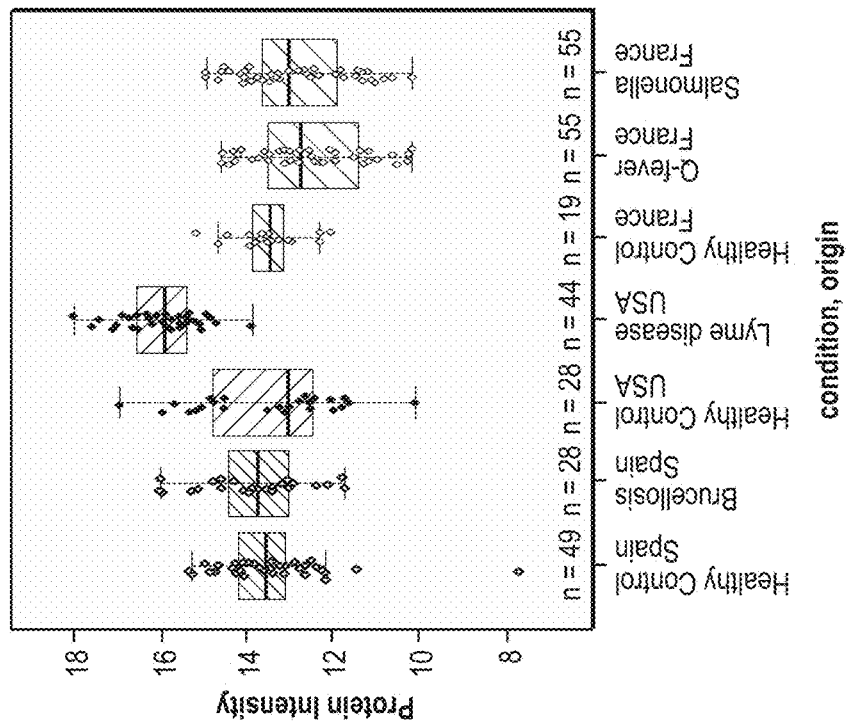

FIG. 11 is a boxplot of the normalized protein intensity of an exemplary biomarker of the invention (MMP9). In each boxplot, each subject is represented by a dot. The median protein concentration is indicated by a bold line, the 50% range by filed rectangles, and the 95% range by hatched lines. Size and description of each group is indicated on the x-axis, normalized protein intensity on the y-axis.

Figure 12:
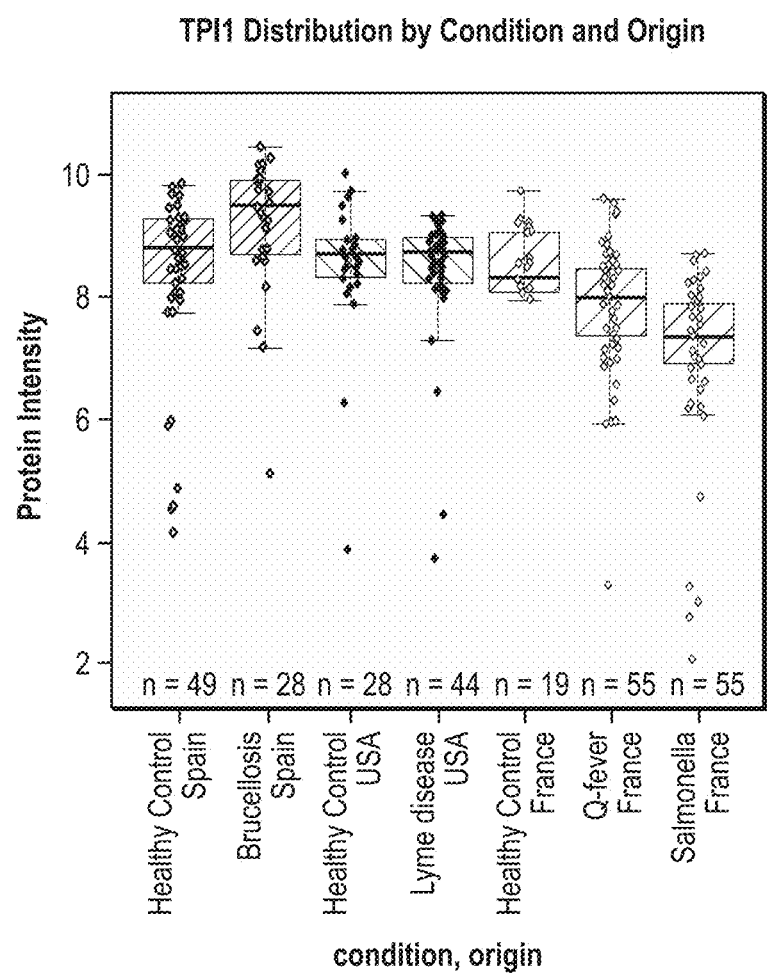

FIG. 12 is a boxplot of the normalized protein intensity of an exemplary biomarker of the invention (TPI1). In each boxplot, each subject is represented by a dot. The median protein concentration is indicated by a bold line, the 50% range by filed rectangles, and the 95% range by hatched lines. Size and description of each group is indicated on the x-axis, normalized protein intensity on the y-axis.

DETAILED DESCRIPTION OF THE INVENTION

The present invention is based, at least in part, on the discovery of markers that are associated with Brucellosis. In particular, biomarkers associated with Brucellosis have been discovered, prioritized, and validated in relevant in vitro experimental systems. The markers were identified as being expressed, e.g., essentially specifically expressed, in samples from subjects having Brucellosis as compared to healthy control subjects, subjects having Q Fever, and subjects having Lyme Disease.

Accordingly, the present invention provides sensitive and facile methods and kits for determining whether a subject has Brucellosis, methods and kits for determining whether a subject has Brucellosis or Q Fever, methods and kits for determining whether a subject has Brucellosis or Lyme Disease, methods for identifying a compound that is useful for treating Brucellosis, methods and kits for monitoring the effectiveness of a therapy for resting a subject having Brucellosis, and methods for treating a subject having Brucellosis by measuring and identifying particular markers, or particular combinations of markers.

Various aspects of the invention are described in further detail in the following subsections:

I. Definitions

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

A "marker" or "biomarker" is an organic biomolecule which is differentially present in a sample taken from a subject of one phenotypic status (e.g., having a disease) as compared with another phenotypic status (e.g., not having the disease). A biomarker is differentially present between different phenotypic statuses if the mean or median level, e.g., expression level, of the biomarker in the different groups is calculated to be statistically significant. Common tests for statistical significance include, among others, t-test, ANOVA, Kruskal-Wallis, Wilcoxon, Mann-Whitney and odds ratio. Biomarkers, alone or in combination, provide measures of relative risk that a subject belongs to one phenotypic status or another. As such, they are useful as markers for, e.g., disease (prognostics and diagnostics), therapeutic effectiveness of a drug (theranostics) and of drug toxicity.

In some embodiments, the accuracy of a marker(s) useful in the compositions and methods of the present invention may be characterized by a Receiver Operating Characteristic curve ("ROC curve"). An ROC is a plot of the true positive rate against the false positive rate for the different possible cutpoints of a diagnostic marker(s). An ROC curve shows the relationship between sensitivity and specificity. That is, an increase in sensitivity will be accompanied by a decrease in specificity. The closer the curve follows the left axis and then the top edge of the ROC space, the more accurate the marker(s). Conversely, the closer the curve comes to the 45-degree diagonal of the ROC graph, the less accurate the marker(s). The area under the ROC is a measure of a marker(s) accuracy. The accuracy of the marker(s) depends on how well the marker(s) separates the group being tested into those with and without the disease in question. An area under the curve (referred to as "AUC") of 1 represents a perfect marker(s), while an area of 0.5 represents a less useful marker(s). Thus, in some embodiments, biomarkers and methods of the present invention have an AUC greater than about 0.50, an AUC greater than about 0.60, or an AUC greater than about 0.70.

A "zoonosis" is an infectious disease that is transmitted between species (sometimes by a vector) from animals other than humans to humans or from humans to other animals, such as Brucellosis, Q-Fever, and Lyme Disease.

"Brucellosis", also called Bang's disease, Crimean fever, Gibraltar fever, Malta fever, Maltese fever, Mediterranean fever, rock fever, or undulant fever, is a worldwide zoonosis caused by infection with the bacterial genus *Brucella*. These organisms, which are small aerobic intracellular coccobacilli, localize in the reproductive organs of host animals, causing abortions and sterility. They are shed in large numbers in the animal's urine, milk, placental fluid, and other fluids. Exposure to infected animals and animal products causes Brucellosis in humans Transmission from human to human is rare but possible. There are seven currently recognized *Brucella* species: *B. melitensis, B abortus, B suis, B. canis, B. ovis* Sheep, *B. neotomae*, and *B. pinnipediae* and *B. cetaceae*, four of which are known to cause disease in humans (*B. abortus, B. melitensis, B. canis, B. suis*). *B. pinnipediae* and *B. cetaceae* are distinctive species that typically affect marine animals; however, these strains were recently described to cause disease in humans.

The most common symptoms of Brucellosis are like those associated with many other febrile diseases and may include muscular pain and sweating. The duration of the disease can vary from a few weeks to many months or even years. In the first stage of the disease, septicaemia occurs and leads to the classic triad of undulant fevers, sweating, and migratory arthralgia and myalgia.

"Q fever" is a zonnoses caused by infection with *Coxiella burnetii*, an obligate gram-negative intracellular bacterium. This organism may be found in cattle, sheep, goats and other domestic mammals, including cats and dogs. The infection results from inhalation of a spore-like small cell variant, and from contact with the milk, urine, feces, vaginal mucus, or semen of infected animals. These products contain large numbers of bacteria that become aerosolized after drying.

The most common manifestation is mild flu-like symptoms with abrupt onset of fever, malaise, profuse perspiration, severe headache, myalgia (muscle pain), joint pain, loss of appetite, upper respiratory problems, dry cough, pleuritic pain, chills, confusion and gastrointestinal symptoms, such as nausea, vomiting and diarrhea. The fever typically lasts seven to 14 days.

"Lyme Disease" is a zonnoses caused by infection with the spirochete, *Borrelia*. There are at least three species of bacteria belonging to the genus *Borrelia* that cause infection in humans: *Borrelia burgdorferi* sensu stricto, *Borrelia afzelii*, and *Borrelia garinii*. The bacteria are inoculated into the skin by a tick bite, from ticks of the genus *Ixodes*.

The manifestations of Lyme disease have been divided into 3 stages: localized, disseminated, and persistent. However, in individual patients, no rigid cutoffs exist between stages. The first 2 stages are part of the early infection, whereas persistent disease is considered late infection. Stage 3 disease may occur within 1 year of infection, not many years later.

In some instances, subjects with early localized Lyme disease develop erythema migrans, a rash characteristic of Lyme Disease. However, since many subjects do not develop erythema migrans or because erythema migrans was not recognized by the patient or correctly diagnosed by the physician, and/or the subject was unaware that they have been bitten by a tick, the main presentation of subjects having Lyme Disease is undifferentiated febrile illness.

A "level of a marker" or "the level of a biomarker" refers to an amount of a marker present in a sample being tested. A level of a marker may be either in absolute level or amount (e.g., µg/ml) or a relative level or amount (e.g., relative intensity of signals).

A "higher level" or an "increase in the level" of marker refers to a level of a marker in a test sample that is greater than the standard error of the assay employed to assess the level of the marker, and is preferably at least twice, and more preferably three, four, five, six, seven, eight, nine, or ten or more times the level of marker in a control sample (e.g., a sample from a healthy subject, a subject having Q-Fever, a subject having Lyme Disease, and/or, the average level of the marker in several control samples).

A "lower level" or a "decrease in the level" of a marker refers to a level of the marker in a test sample that is less than the standard error of the assay employed to assess the level of the marker, and preferably at least twice, and more preferably three, four, five, six, seven, eight, nine, or ten or more times less than the level of the marker in a control sample (e.g., a sample from a healthy subject, a subject having Q-Fever, a subject having Lyme Disease, and/or, the average level of the marker in several control samples).

The term "known standard level" or "control level" refers to an accepted or pre-determined level of a marker which is used to compare the level of the marker in a sample derived from a subject. In one embodiment, the control level of a marker is based the level of the marker in a sample(s) from a healthy subject(s), and/or, the average level of the marker in several control samples. In another embodiment, the control level of a marker is based the level of the marker in a sample(s) from a subject(s) having Brucellosis, and/or, the average level of the marker in several control samples. In another embodiment, the control level of a marker is based the level of the marker in a sample(s) from a subject(s) having Q-Fever, and/or, the average level of the marker in several control samples. In another embodiment, the control level of a marker is based the level of the marker in a sample(s) from a subject(s) having Lyme Disease, and/or, the average level of the marker in several control samples. In another embodiment, the control level of a marker is based the level of the marker in a sample(s) from a subject(s) having *Salmonellosis* (i.e., infection with a gram-negative motile bacilli from the genus *Salmonella*), and/or, the average level of the marker in several control samples. In one embodiment, the control level of a marker in a sample from a subject is a level of the marker previously determined in a sample(s) from the subject. In yet another embodiment, the control level of a marker is based on the level of the marker in a sample from a subject(s) prior to the administration of a therapy for Brucellosis. In another embodiment, the control level of a marker is based on the level of the marker in a sample from a subject(s) prior to the administration of a therapy for Q-Fever. In another embodiment, the control level of a marker is based on the level of the marker in a sample from a subject(s) prior to the administration of a therapy for Lyme Disease. In another embodiment, the control level of a marker is based on the level of the marker in a sample(s) from a subject(s) having Brucellosis that is not contacted with a test compound. In another embodiment, the control level of a marker is based on the level of the marker in a sample(s) from a subject(s) having Q-Fever that is not contacted with a test compound. In another embodiment, the control level of a marker is based on the level of the marker in a sample(s) from a subject(s) having Lyme Disease that is not contacted with a test compound. In another embodiment, the control level of a marker is based on the level of the marker in a sample(s) from a subject(s) having Brucellosis that is contacted with a test compound. In another embodiment, the control level of a marker is based on the level of the marker in a sample(s) from a subject(s) having Q-Fever that is contacted with a test compound. In another embodiment, the control level of a marker is based on the level of the marker in a sample(s) from a subject(s) having Lyme Diease that is contacted with a test compound. In one embodiment, the control level of a marker is based on the level of the marker in a sample(s) from an in vitro model of Brucellosis infection. In one embodiment, the control level of a marker is based on the level of the marker in a sample(s) from an animal model of Brucellosis, a cell, or a cell line derived from the animal model of Brucellosis. In another embodiment, the control level of a marker is based on the level of the marker in a sample(s) from an animal model of Q-Fever, a cell, or a cell line derived from the animal model of Q-Fever. In another embodiment, the control level of a marker is based on the level of the marker in a sample(s) from an animal model of Lyme Disease, a cell, or a cell line derived from the animal model of Lyme Disease.

Alternatively, and particularly as further information becomes available as a result of routine performance of the methods described herein, population-average values for "control" level of expression of a marker may be used. In other embodiments, the "control" level of a marker may be determined by determining the level of a marker in a subject sample obtained from a subject before infection with *Brucella, Coxiella burnetii,* and/or Burrelia from archived subject samples, and the like.

As used herein, the terms "patient" or "subject" refer to human and non-human animals, e.g., veterinary patients. The term "non-human animal" includes all vertebrates, e.g., mammals and non-mammals, such as non-human primates, mice, rabbits, sheep, dog, cat, horse, cow, chickens, amphibians, and reptiles. In one embodiment, the subject is a human.

The term "sample" as used herein refers to a collection of similar cells or tissue isolated from a subject, as well as tissues, cells and fluids present within a subject. The term "sample" includes any body fluid (e.g., blood fluids, lymph, gynecological fluids, cystic fluid, urine, ocular fluids and fluids collected by bronchial lavage and/or peritoneal rinsing), or a cell from a subject. In one embodiment, the tissue or cell is removed from the subject. In another embodiment, the tissue or cell is present within the subject. Other subject samples, include tear drops, serum, cerebrospinal fluid, feces, sputum and cell extracts. In one embodiment the sample is a blood sample. In another embodiment, the sample is a serum sample. In one embodiment, the biological sample contains protein molecules from the test subject. In another embodiment, the biological sample may contain mRNA molecules from the test subject or genomic DNA molecules from the test subject.

The term "determining" means methods which include detecting the presence or absence of marker(s) in the sample, quantifying the amount of marker(s) in the sample, and/or qualifying the type of biomarker. Measuring can be accomplished by methods known in the art and those further described herein.

As used herein, the various forms of the term "modulate" are intended to include stimulation (e.g., increasing or upregulating a particular response or activity) and inhibition (e.g., decreasing or downregulating a particular response or activity).

A kit is any manufacture (e.g. a package or container) comprising at least one reagent, e.g. a probe, a primer, or an antibody, for specifically detecting a marker of the invention, the manufacture being promoted, distributed, or sold as a unit for performing the methods of the present invention. In certain embodiments, a lit may include a substrate, e.g., a substrate comprising a capture reagent for one or more markers of the invention and/or a capture reagent bound to one or more markers of the invention. In some embodiments, such kits comprise instructions for determining the level of a marker(s) using mass spectrometry.

II. Markers of the Invention

The present invention is based upon the discovery of markers that are essentially specifically expressed in samples from subjects having a zoonosis, such as Brucellosis, Q-Fever, or Lyme Disease (Table 1). The markers in Table 1 have been shown to be differentially present in samples of subjects having Brucellosis and control subjects, samples from subjects having Q-Fever and control subjects, and/or samples from subjects having Lyme Disease and control subjects.

The present invention is also based upon the discovery of markers that are essentially specifically expressed in samples from subjects having Brucellosis (Table 1) and can distinguish a disorder presenting as a fever of unknown origin, i.e., Brucellosis, from other diseases presenting as fever of unknown origin, such as, for example, Q-fever and/or Lyme Disease. These markers have been shown to be differentially present in samples of subjects having Brucellosis and subjects having Q-fever and/or Lyme Disease.

Accordingly, the level of any one marker or any combination of markers listed in Table 1 and found in a test sample compared to a control, or the presence or absence of one marker or combination of markers listed in Table 1 in the test sample may be used in the methods and kits of the present invention.

The markers of the invention are listed in Table 1. The nucleotide and amino acid sequences of the markers are known in the art and may be found in, for example, the GenBank Accession numbers listed in Table 1, the entire contents of which are incorporated herein by reference.

TABLE 1

| | | Markers of the Invention. | | |
|---|---|---|---|---|
| Marker Name | Protein Description | UNIPROT_ID | UNIPROT ACCESSION | GENBANK ACCESSION |
| SLC3A2 | 4F2 cell-surface antigen heavy | 4F2_HUMAN | P08195 | NP_001012680.1 NP_001012682.1 |

TABLE 1-continued

Markers of the Invention.

| Marker Name | Protein Description | UNIPROT_ID | UNIPROT ACCESSION | GENBANK ACCESSION |
|---|---|---|---|---|
| | chain | | | NP_001013269.1 |
| | | | | NP_002385.3 |
| | | | | NM_001012662.2 |
| | | | | NM_001012664.2 |
| | | | | NM_001013251.2 |
| | | | | NM_002394.5 |
| GOT1 | Aspartate aminotransferase, cytoplasmic | AATC_HUMAN | P17174 | NP_002070.1 |
| | | | | NM_002079.2 |
| GOT2 | Aspartate aminotransferase, mitochondrial precursor | AATM_HUMAN | P00505 | NP_002071.2 |
| | | | | NM_002080.2 |
| ACADVL | Very long-chain specific acyl-CoA dehydrogenase, mitochondrial precursor | ACADV_HUMAN | P49748 | NP_000009.1 |
| | | | | NP_001029031.1 |
| | | | | NP_001257376.1 |
| | | | | NM_000018.3 |
| | | | | NM_001033859.2 |
| | | | | NM_001270447.1 |
| DBI | Acyl-CoA-binding protein | ACBP_HUMAN | P07108 | NP_001073331.1 |
| | | | | NP_001073332.1 |
| | | | | NP_001171488.1 |
| | | | | NP_001171512.1 |
| | | | | NP_001171513.1 |
| | | | | NP_001171514.1 |
| | | | | NP_065438.1 |
| | | | | NM_001079862.1 |
| | | | | NM_001079863.1 |
| | | | | NM_001178017.1 |
| | | | | NM_001178041.1 |
| | | | | NM_001178042.1 |
| | | | | NM_001178043.1 |
| | | | | NM_020548.6 |
| ACOX1 | Peroxisomal acyl-coenzyme A oxidase 1 | ACOX1_HUMAN | Q15067 | NP_001171968.1 |
| | | | | NP_004026.2 |
| | | | | NP_009223.2 |
| | | | | NM_001185039.1 |
| | | | | NM_004035.6 |
| | | | | NM_007292.5 |
| AHNAK | Neuroblast differentiation-associated protein AHNAK | AHNK_HUMAN | Q09666 | NP_001611.1 |
| | | | | NP_076965.2 |
| | | | | NM_001620.2 |
| | | | | NM_024060.3 |
| AIMP1 | Aminoacyl tRNA synthase complex-interacting multifunctional protein 1 | AIMP1_HUMAN | Q12904 | NP_001135887.1 |
| | | | | NP_001135888.1 |
| | | | | NP_004748.2 |
| | | | | NM_001142415.1 |
| | | | | NM_001142416.1 |
| | | | | NM_004757.3 |
| AKR1B1 | Aldose reductase | ALDR_HUMAN | P15121 | NP_001619.1 |
| | | | | NM_001628.2 |
| ANPEP | Aminopeptidase N | AMPN_HUMAN | P15144 | NP_001141.2 |
| | | | | NM_001150.2 |
| ANXA2 | Annexin A2 | ANXA2_HUMAN | P07355 | NP_001002857.1 |
| | | | | NP_001002858.1 |
| | | | | NP_001129487.1 |
| | | | | NP_004030.1 |
| | | | | NM_001002857.1 |
| | | | | NM_001002858.2 |
| | | | | NM_001136015.2 |
| | | | | NM_004039.2 |
| ANXA5 | Annexin A5 | ANXA5_HUMAN | P08758 | NP_001145.1 |
| | | | | NM_001154.3 |
| ANXA6 | Annexin A6 | ANXA6_HUMAN | P08133 | NP_001146.2 |
| | | | | NP_001180473.1 |
| | | | | NM_001155.4 |
| | | | | NM_001193544.1 |
| AKR7A2 | Aflatoxin B1 aldehyde reductase member 2 | ARK72_HUMAN | O43488 | NP_003680.2 |
| | | | | NM_003689.3 |
| ARPC3 | Actin-related protein 2/3 complex subunit 3 | ARPC3_HUMAN | O15145 | NP_005710.1 |
| | | | | NM_005719.2 |

TABLE 1-continued

Markers of the Invention.

| Marker Name | Protein Description | UNIPROT_ID | UNIPROT ACCESSION | GENBANK ACCESSION |
|---|---|---|---|---|
| ASAH1 | Acid ceramidase precursor | ASAH1_HUMAN | Q13510 | NP_001120977.1<br>NP_004306.3<br>NP_808592.2<br>NM_001127505.1<br>NM_004315.4<br>NM_177924.3 |
| B4GALT1 | Beta-1,4-galactosyltransferase 1 | B4GT1_HUMAN | P15291 | NP_001488.2<br>NM_001497.3 |
| BCAM | Basal cell adhesion molecule precursor | BCAM_HUMAN | P50895 | NP_001013275.1<br>NP_005572.2<br>NM_001013257.2<br>NM_005581.4 |
| BLOC1S5 | Biogenesis of lysosome-related organelles complex 1 subunit 5 | BL1S5_HUMAN | Q8TDH9 | NP_958437.1<br>NM_201280.2 |
| CALU | Calumenin precursor | CALU_HUMAN | O43852 | NP_001124146.1<br>NP_001186600.1<br>NP_001186601.1<br>NP_001186602.1<br>NP_001186603.1<br>NP_001210.1<br>NM_001130674.2<br>NM_001199671.1<br>NM_001199672.1<br>NM_001199673.1<br>NM_001199674.1<br>NM_001219.4 |
| CAPG | Macrophage-capping protein | CAPG_HUMAN | P40121 | NP_001243068.1<br>NP_001738.2<br>NM_001256139.1<br>NM_001747.3 |
| CAPZB | F-actin-capping protein subunit beta | CAPZB_HUMAN | P47756 | NP_001193469.1<br>NP_004921.1<br>NM_001206540.1<br>NM_004930.3 |
| CAPZA2 | F-actin-capping protein subunit alpha-2 | CAZA2_HUMAN | P47755 | NP_006127.1<br>NM_006136.2 |
| CBX1 | Chromobox protein homolog 1 | CBX1_HUMAN | P83916 | NP_001120700.1<br>NP_006798.1<br>NM_001127228.1<br>NM_006807.4 |
| CDC37 | Hsp90 co-chaperone Cdc37 | CDC37_HUMAN | Q16543 | NP_008996.1<br>NM_007065.3 |
| HSPE1 | 10 kDa heat shock protein, mitochondrial | CH10_HUMAN | P61604 | NP_002148.1<br>NM_002157.2 |
| CHMP1A | Charged multivesicular body protein 1a | CHM1A_HUMAN | Q9HD42 | NP_002759.2<br>NM_002768.3 |
| CHMP1B | Charged multivesicular body protein 1b | CHM1B_HUMAN | Q7LBR1 | NP_065145.2<br>NM_020412.4 |
| CHMP2A | Charged multivesicular body protein 2a | CHM2A_HUMAN | O43633 | NP_055268.1<br>NP_940818.1<br>NM_014453.2<br>NM_198426.1 |
| CHMP4A | Charged multivesicular body protein 4a | CHM4A_HUMAN | Q9BY43 | NP_054888.2<br>NM_014169.3 |
| CHMP4B | Charged multivesicular body protein 4b | CHM4B_HUMAN | Q9H444 | NP_789782.1<br>NM_176812.4 |
| CHMP5 | Charged multivesicular body protein 5 | CHMP5_HUMAN | Q9NZZ3 | NP_001182465.1<br>NP_057494.3<br>NM_001195536.1<br>NM_016410.5 |

TABLE 1-continued

Markers of the Invention.

| Marker Name | Protein Description | UNIPROT_ID | UNIPROT ACCESSION | GENBANK ACCESSION |
|---|---|---|---|---|
| CLIC1 | Chloride intracellular channel protein 1 | CLIC1_HUMAN | O00299 | NP_001279.2<br>NM_001288.4 |
| CNDP2 | Cytosolic non-specific dipeptidase | CNDP2_HUMAN | Q96KP4 | NP_001161971.1<br>NP_060705.2<br>NM_001168499.1<br>NM_018235.2 |
| CNPY2 | Protein canopy homolog 2 precursor | CNPY2_HUMAN | Q9Y2B0 | NP_001177920.1<br>NP_055070.1<br>NM_001190991.1<br>NM_014255.5 |
| COPA | Coatomer subunit alpha | COPA_HUMAN | P53621 | NP_001091868.1<br>NP_004362.2<br>NM_001098398.1<br>NM_004371.3 |
| COPB2 | Coatomer subunit beta' | COPB2_HUMAN | P35606 | NP_004757.1<br>NM_004766.2 |
| CORO1A | Coronin-1A | COR1A_HUMAN | P31146 | NP_001180262.1<br>NP_009005.1<br>NM_001193333.2<br>NM_007074.3 |
| CORO1B | Coronin-1B | COR1B_HUMAN | Q9BR76 | NP_001018080.1<br>NP_065174.1<br>NM_001018070.2<br>NM_020441.2 |
| CORO1C | Coronin-1C | COR1C_HUMAN | Q9ULV4 | NP_055140.1<br>NM_014325.2 |
| CPVL | Probable serine carboxypeptidase CPVL precursor | CPVL_HUMAN | Q9H3G5 | NP_061902.2<br>NP_112601.3<br>NM_019029.2<br>NM_031311.3 |
| C19orf10 | UPF0556 protein C19orf10 precursor | CS010_HUMAN | Q969H8 | NP_061980.1<br>NM_019107.3 |
| CXorf26 | UPF0368 protein Cxorf26 | CX026_HUMAN | Q9BVG4 | NP_057584.2<br>NM_016500.3 |
| CXCL10 | C-X-C motif chemokine 10 precursor | CXL10_HUMAN | P02778 | NP_001556.2<br>NM_001565.3 |
| CACYBP | Calcyclin-binding protein | CYBP_HUMAN | Q9HB71 | NP_001007215.1<br>NP_055227.1<br>NM_001007214.1<br>NM_014412.2 |
| DSP | Desmoplakin | DESP_HUMAN | P15924 | NP_001008844.1<br>NP_004406.2<br>NM_001008844.1<br>NM_004415.2 |
| HSD17B4 | Peroxisomal multifunctional enzyme type 2 | DHB4_HUMAN | P51659 | NP_000405.1<br>NP_001186220.1<br>NP_001186221.1<br>NM_000414.3<br>NM_001199291.1<br>NM_001199292.1 |
| DLG1 | Disks large homolog 1 | DLG1_HUMAN | Q12959 | NP_001091894.1<br>NP_001191315.1<br>NP_001191316.1<br>NP_001191317.1<br>NP_004078.2<br>NM_001098424.1<br>NM_001204386.1<br>NM_001204387.1<br>NM_001204388.1<br>NM_004087.2 |
| DNASE2 | Deoxyribonuclease-2-alpha precursor | DNS2A_HUMAN_ | O00115 | NP_001366.1<br>NM_001375.2 |
| DDT | D-dopachrome decarboxylase | DOPD_HUMAN | P30046 | NP_001077861.1<br>NP_001346.1<br>NM_001084392.1<br>NM_001355.3 |
| DYNLL1 | Dynein light chain 1, cytoplasmic | DYL1_HUMAN | P63167 | NP_001032583.1<br>NP_001032584.1<br>NP_003737.1<br>NM_001037494.1 |

TABLE 1-continued

Markers of the Invention.

| Marker Name | Protein Description | UNIPROT_ID | UNIPROT ACCESSION | GENBANK ACCESSION |
|---|---|---|---|---|
| EPB41L3 | Band 4.1-like protein 3 | E41L3_HUMAN | Q9Y2J2 | NM_001037495.1<br>NM_003746.2<br>NP_036439.2<br>NM_012307.2 |
| EEF1A1 | Elongation factor 1-alpha 1 | EF1A1_HUMAN | P68104 | NP_001393.1<br>NM_001402.5 |
| EEF1B2 | Elongation factor 1-beta | EF1B_HUMAN | P24534 | NP_001032752.1<br>NP_001950.1<br>NP_066944.1<br>NM_001037663.1<br>NM_001959.3<br>NM_021121.3 |
| EEF1D | Elongation factor 1-delta | EF1D_HUMAN | P29692 | NP_001123525.2<br>NP_001123527.1<br>NP_001123528.1<br>NP_001123529.1<br>NP_001951.2<br>NP_115754.3<br>NM_001130053.2<br>NM_001130055.2<br>NM_001130056.2<br>NM_001130057.2<br>NM_001960.4<br>NM_032378.4 |
| EEF2 | Elongation factor 2 | EF2_HUMAN | P13639 | NP_001952.1<br>NM_001961.3 |
| ENG | Endoglin precursor | EGLN_HUMAN | P17813 | NP_000109.1<br>NP_001108225.1<br>NM_000118.2<br>NM_001114753.1 |
| EHD1 | EH domain-containing protein 1 | EHD1_HUMAN | Q9H4M9 | NP_006786.2<br>NM_006795.2 |
| ELAVL1 | ELAV-like protein 1 | ELAV1_HUMAN | Q15717 | NP_001410.2<br>NM_001419.2 |
| EMC2 | ER membrane protein complex subunit 2 | EMC2_HUMAN | Q15006 | NP_055488.1<br>NM_014673.3 |
| EMR2 | EGF-like module-containing mucin-like hormone receptor-like 2 precursor | EMR2_HUMAN | Q9UHX3 | NP_038475.2<br>NM_013447.3 |
| ENO1 | Alpha-enolase | ENOA_HUMAN | P06733 | NP_001188412.1<br>NP_001419.1<br>NM_001201483.1<br>NM_001428.3 |
| ENO3 | Beta-enolase | ENOB_HUMAN | P13929 | NP_001180432.1<br>NP_001967.3<br>NP_443739.3<br>NM_001193503.1<br>NM_001976.4<br>NM_053013.3 |
| HSP90B1 | Endoplasmin precursor | ENPL_HUMAN | P14625 | NP_003290.1<br>NM_003299.2 |
| ERO1L | ERO1-like protein alpha precursor | ERO1A_HUMAN | Q96HE7 | NP_055399.1<br>NM_014584.1 |
| ESYT2 | Extended synaptotagmin-2 | ESYT2_HUMAN | A0FGR8 | NP_065779.1<br>NM_020728.2 |
| EVL | Ena/VASP-like protein | EVL_HUMAN | Q9UI08 | NP_057421.1<br>NM_016337.2 |
| ST13 | Hsc70-interacting protein | F10A1_HUMAN | P50502 | NP_003923.2<br>NM_003932.3 |
| F5 | Coagulation factor V precursor | FA5_HUMAN | P12259 | NP_000121.2<br>NM_000130.4 |
| FKBP4 | Peptidyl-prolyl cis-trans isomerase FKBP4 | FKBP4_HUMAN | Q02790 | NP_002005.1<br>NM_002014.3 |

TABLE 1-continued

Markers of the Invention.

| Marker Name | Protein Description | UNIPROT_ID | UNIPROT ACCESSION | GENBANK ACCESSION |
|---|---|---|---|---|
| FLNA | Filamin-A | FLNA_HUMAN | P21333 | NP_001104026.1<br>NP_001447.2<br>NM_001110556.1<br>NM_001456.3 |
| FH | Fumarate hydratase, mitochondrial precursor | FUMH_HUMAN | P07954 | NP_000134.2<br>NM_000143.3 |
| H6PD | GDH/6PGL endoplasmic bifunctional protein precursor | G6PE_HUMAN | O95479 | NP_004276.2<br>NM_004285.3 |
| GPI | Glucose-6-phosphate isomerase | G6PI_HUMAN | P06744 | NP_000166.2<br>NP_001171651.1<br>NM_000175.3<br>NM_001184722.1 |
| GDI2 | Rab GDP dissociation inhibitor beta | GDIB_HUMAN | P50395 | NP_001108628.1<br>NP_001485.2<br>NM_001115156.1<br>NM_001494.3 |
| ARHGDIA | Rho GDP-dissociation inhibitor 1 | GDIR1_HUMAN | P52565 | NP_001172006.1<br>NP_001172007.1<br>NP_004300.1<br>NM_001185077.1<br>NM_001185078.1<br>NM_004309.4 |
| GGH | Gamma-glutamyl hydrolase precursor | GGH_HUMAN | Q92820 | NP_003869.1<br>NM_003878.2 |
| GBA | Glucosylceramidase precursor | GLCM_HUMAN | P04062 | NP_000148.2<br>NP_001005741.1<br>NP_001005742.1<br>NM_000157.3<br>NM_001005741.2<br>NM_001005742.2 |
| PRKCSH | Glucosidase 2 subunit beta precursor | GLU2B_HUMAN | P14314 | NP_001001329.1<br>NP_002734.2<br>NM_001001329.1<br>NM_002743.2 |
| GNS | N-acetylglucosamine-6-sulfatase precursor | GNS_HUMAN | P15586 | NP_002067.1<br>NM_002076.3 |
| HSPA9 | Stress-70 protein, mitochondrial precursor | GRP75_HUMAN | P38646 | NP_004125.3<br>NM_004134.6 |
| HSPA5 | 78 kDa glucose-regulated protein precursor | GRP78_HUMAN | P11021 | NP_005338.1<br>NM_005347.4 |
| GSTP1 | Glutathione S-transferase P | GSTP1_HUMAN | P09211 | NP_000843.1<br>NM_000852.3 |
| GLT25D1 | Procollagen galactosyltransferase 1 precursor | GT251_HUMAN | Q8NBJ5 | NP_078932.2<br>NM_024656.2 |
| HIST1H1D | Histone H1.3 | H13_HUMAN | P16402 | NP_005311.1<br>NM_005320.2 |
| HIST1H1B | Histone H1.5 | H15_HUMAN | P16401 | NP_005313.1<br>NM_005322.2 |
| HIST3H2A | Histone H2A type 3 | H2A3_HUMAN | Q7L7L0 | NP_254280.1<br>NM_033445.2 |
| H2AFY | Core histone macro-H2A.1 | H2AY_HUMAN | O75367 | NP_001035248.1<br>NP_004884.1<br>NP_613075.1<br>NP_613258.2<br>NM_001040158.1<br>NM_004893.2<br>NM_138609.2<br>NM_138610.2 |
| HIST2H2BE | Histone H2B type 2-E | H2B2E_HUMAN | Q16778 | NP_003519.1<br>NM_003528.2 |

TABLE 1-continued

Markers of the Invention.

| Marker Name | Protein Description | UNIPROT_ID | UNIPROT ACCESSION | GENBANK ACCESSION |
|---|---|---|---|---|
| HIST2H2BF | Histone H2B type 2-F | H2B2F_HUMAN | Q5QNW6 | NP_001019770.1<br>NP_001154806.1<br>NM_001024599.3<br>NM_001161334.1 |
| HIST3H3 | Histone H3.1t | H31T_HUMAN | Q16695 | NP_003484.1<br>NM_003493.2 |
| HIST1H4A | Histone H4 | H4_HUMAN | P62805 | NP_001029249.1<br>NP_003486.1<br>NP_003529.1<br>NP_003530.1<br>NP_003531.1<br>NP_003532.1<br>NP_003533.1<br>NP_003534.1<br>NP_003535.1<br>NP_003536.1<br>NP_003537.1<br>NP_003539.1<br>NP_068803.1<br>NP_778224.1<br>NM_001034077.4<br>NM_003495.2<br>NM_003538.3<br>NM_003539.3<br>NM_003540.3<br>NM_003541.2<br>NM_003542.3<br>NM_003543.3<br>NM_003544.2<br>NM_003545.3<br>NM_003546.2<br>NM_003548.2<br>NM_021968.3<br>NM_175054.2 |
| HSD17B10 | 3-hydroxyacyl-CoA dehydrogenase type-2 | HCD2_HUMAN | Q99714 | NP_001032900.1<br>NP_004484.1<br>NM_001037811.2<br>NM_004493.2 |
| HEXA | Beta-hexosaminidase subunit alpha precursor | HEXA_HUMAN | P06865 | NP_000511.2<br>NM_000520.4 |
| HMGB3 | High mobility group protein B3 | HMGB3_HUMAN | O15347 | NP_005333.2<br>NM_005342.2 |
| HNRNPC | Heterogeneous nuclear ribonucleoproteins C1/C2 | HNRPC_HUMAN | P07910 | NP_001070910.1<br>NP_001070911.1<br>NP_004491.2<br>NP_112604.2<br>NM_001077442.1<br>NM_001077443.1<br>NM_004500.3<br>NM_031314.2 |
| HNRNPD | Heterogeneous nuclear ribonucleoprotein D0 | HNRPD_HUMAN | Q14103 | NP_001003810.1<br>NP_002129.2<br>NP_112737.1<br>NP_112738.1<br>NM_001003810.1<br>NM_002138.3<br>NM_031369.2<br>NM_031370.2 |
| HNRNPK | Heterogeneous nuclear ribonucleoprotein K | HNRPK_HUMAN | P61978 | NP_002131.2<br>NP_112552.1<br>NP_112553.1<br>NM_002140.3<br>NM_031262.2<br>NM_031263.2 |
| HNRNPR | Heterogeneous nuclear ribonucleoprotein R | HNRPR_HUMAN | O43390 | NP_001095867.1<br>NP_001095868.1<br>NP_005817.1<br>NM_001102397.1<br>NM_001102398.1<br>NM_005826.3 |
| HNRNPU | Heterogeneous nuclear | HNRPU_HUMAN | Q00839 | NP_004492.2<br>NP_114032.2 |

TABLE 1-continued

Markers of the Invention.

| Marker Name | Protein Description | UNIPROT_ID | UNIPROT ACCESSION | GENBANK ACCESSION |
|---|---|---|---|---|
| | ribonucleoprotein U | | | NM_004501.3 NM_031844.2 |
| HSP90AA1 | Heat shock protein HSP 90-alpha | HS90A_HUMAN | P07900 | NP_001017963.2 NP_005339.3 NM_001017963.2 NM_005348.3 |
| HSP90AB1 | Heat shock protein HSP 90-beta | HS90B_HUMAN | P08238 | NP_031381.2 NM_007355.2 |
| HSPA1A | Heat shock 70 kDa protein 1A/1B | HSP71_HUMAN | P08107 | NP_005336.3 NP_005337.2 NM_005345.5 NM_005346.4 |
| HSPA8 | Heat shock cognate 71 kDa protein | HSP7C_HUMAN | P11142 | NP_006588.1 NP_694881.1 NM_006597.4 NM_153201.2 |
| ICAM1 | Intercellular adhesion molecule 1 precursor | ICAM1_HUMAN | P05362 | NP_000192.2 NM_000201.2 |
| EIF5A2 | Eukaryotic translation initiation factor 5A-2 | IF5A2_HUMAN | Q9GZV4 | NP_065123.1 NM_020390.5 |
| IL1B | Interleukin-1 beta precursor | IL1B_HUMAN | P01584 | NP_000567.1 NM_000576.2 |
| IMPDH2 | Inosine-5'-monophosphate dehydrogenase 2 | IMDH2_HUMAN | P12268 | NP_000875.2 NM_000884.2 |
| ISYNA1 | Inositol-3-phosphate synthase 1 | INO1_HUMAN | Q9NPH2 | NP_001164409.1 NP_001240318.1 NP_057452.1 NM_001170938.1 NM_001253389.1 NM_016368.4 |
| ISOC1 | Isochorismatase domain-containing protein 1 | ISOC1_HUMAN | Q96CN7 | NP_057132.2 NM_016048.2 |
| ITGA5 | Integrin alpha-5 precursor | ITA5_HUMAN | P08648 | NP_002196.2 NM_002205.2 |
| ITGAM | Integrin alpha-M precursor | ITAM_HUMAN | P11215 | NP_000623.2 NP_001139280.1 NM_000632.3 NM_001145808.1 |
| ITPR1 | Inositol 1,4,5-trisphosphate receptor type 1 | ITPR1_HUMAN | Q14643 | NP_001093422.2 NP_002213.5 NM_001099952.2 NM_002222.5 |
| KRT9 | Keratin, type I cytoskeletal 9 | K1C9_HUMAN | P35527 | NP_000217.2 NM_000226.3 |
| KRT7 | Keratin, type II cytoskeletal 7 | K2C7_HUMAN | P08729 | NP_005547.3 NM_005556.3 |
| KRT8 | Keratin, type II cytoskeletal 8 | K2C8_HUMAN | P05787 | NP_001243222.1 NP_002264.1 NM_001256293.1 NM_002273.3 |
| CAMK2D | Calcium/calmodulin-dependent protein kinase type II subunit delta | KCC2D_HUMAN | Q13557 | NP_001212.2 NP_742112.1 NP_742113.1 NP_742125.1 NP_742126.1 NP_742127.1 NM_001221.3 NM_172114.1 NM_172115.2 NM_172127.2 NM_172128.2 NM_172129.1 |
| PKM | Pyruvate kinase isozymes M1/M2 | KPYM_HUMAN | P14618 | NP_001193725.1 NP_001193726.1 NP_001193727.1 NP_001193728.1 |

TABLE 1-continued

Markers of the Invention.

| Marker Name | Protein Description | UNIPROT_ID | UNIPROT ACCESSION | GENBANK ACCESSION |
|---|---|---|---|---|
| | | | | NP_002645.3 |
| | | | | NP_872270.1 |
| | | | | NP_872271.1 |
| | | | | NM_001206796.1 |
| | | | | NM_001206797.1 |
| | | | | NM_001206798.1 |
| | | | | NM_001206799.1 |
| | | | | NM_002654.4 |
| | | | | NM_182470.2 |
| | | | | NM_182471.2 |
| LASP1 | LIM and SH3 domain protein 1 | LASP1_HUMAN | Q14847 | NP_001258537.1 NP_006139.1 NM_001271608.1 NM_006148.3 |
| LDHB | L-lactate dehydrogenase B chain | LDHB_HUMAN | P07195 | NP_001167568.1 NP_002291.1 NM_001174097.1 NM_002300.6 |
| LIMA1 | LIM domain and actin-binding protein 1 | LIMA1_HUMAN | Q9UHB6 | NP_001107018.1 NP_001107019.1 NP_001230704.1 NP_057441.1 NM_001113546.1 NM_001113547.1 NM_001243775.1 NM_016357.4 |
| LMNA | Prelamin-A/C precursor | LMNA_HUMAN | P02545 | NP_005563.1 NP_733821.1 NP_733822.1 NM_005572.3 NM_170707.3 NM_170708.3 |
| LMNB1 | Lamin-B1 precursor | LMNB1_HUMAN | P20700 | NP_005564.1 NM_005573.3 |
| LMNB2 | Lamin-B2 precursor | LMNB2_HUMAN | Q03252 | NP_116126.3 NM_032737.3 |
| LRCH1 | Leucine-rich repeat and calponin homology domain-containing protein 1 | LRCH1_HUMAN | Q9Y2L9 | NP_001157683.1 NP_001157685.1 NP_055931.1 NM_001164211.1 NM_001164213.1 NM_015116.2 |
| GAA | Lysosomal alpha-glucosidase precursor | LYAG_HUMAN | P10253 | NP_000143.2 NP_001073271.1 NP_001073272.1 NM_000152.3 NM_001079803.1 NM_001079804.1 |
| LYN | Tyrosine-protein kinase Lyn | LYN_HUMAN | P07948 | NP_001104567.1 NP_002341.1 NM_001111097.2 NM_002350.3 |
| MDH1 | Malate dehydrogenase, cytoplasmic | MDHC_HUMAN | P40925 | NP_001186040.1 NP_001186041.1 NP_005908.1 NM_001199111.1 NM_001199112.1 NM_005917.3 |
| MDH2 | Malate dehydrogenase, mitochondrial precursor | MDHM_HUMAN | P40926 | NP_005909.2 NM_005918.2 |
| MESDC2 | LDLR chaperone MESD precursor | MESD_HUMAN | Q14696 | NP_055969.1 NM_015154.1 |
| MAT2A | S-adenosylmethionine synthase isoform type-2 | METK2_HUMAN | P31153 | NP_005902.1 NM_005911.5 |
| MYL12A | Myosin regulatory light chain 12A | ML12A_HUMAN | P19105 | NP_006462.1 NM_006471.2 |
| MMP9 | Matrix metalloproteinase-9 precursor | MMP9_HUMAN | P14780 | NP_004985.2 NM_004994.2 |

TABLE 1-continued

Markers of the Invention.

| Marker Name | Protein Description | UNIPROT_ID | UNIPROT ACCESSION | GENBANK ACCESSION |
|---|---|---|---|---|
| RABIF | Guanine nucleotide exchange factor MSS4 | MSS4_HUMAN | P47224 | NP_002862.2<br>NM_002871.4 |
| MYH10 | Myosin-10 | MYH10_HUMAN | P35580 | NP_001242941.1<br>NP_005955.3<br>NM_001256012.1<br>NM_005964.3 |
| MYH9 | Myosin-9 | MYH9_HUMAN | P35579 | NP_002464.1<br>NM_002473.4 |
| MYO1E | Unconventional myosin-Ie | MYO1E_HUMAN | Q12965 | NP_004989.2<br>NM_004998.3 |
| MYO6 | Unconventional myosin-VI | MYO6_HUMAN | Q9UM54 | NP_004990.3<br>NM_004999.3 |
| PPP1R12A | Protein phosphatase 1 regulatory subunit 12A | MYPT1_HUMAN | O14974 | NP_001137357.1<br>NP_001137358.1<br>NP_001231919.1<br>NP_001231921.1<br>NP_002471.1<br>NM_001143885.1<br>NM_001143886.1<br>NM_001244990.1<br>NM_001244992.1<br>NM_002480.2 |
| NAGA | Alpha-N-acetylgalactosaminidase precursor | NAGAB_HUMAN | P17050 | NP_000253.1<br>NM_000262.2 |
| POR | NADPH--cytochrome P450 reductase | NCPR_HUMAN | P16435 | NP_000932.3<br>NM_000941.2 |
| NME1 | Nucleoside diphosphate kinase A | NDKA_HUMAN | P15531 | NP_000260.1<br>NP_937818.1<br>NM_000269.2<br>NM_198175.1 |
| NME2 | Nucleoside diphosphate kinase B | NDKB_HUMAN | P22392 | NP_001018146.1<br>NP_001018147.1<br>NP_001018148.1<br>NP_001018149.1<br>NP_002503.1<br>NM_001018136.2<br>NM_001018137.2<br>NM_001018138.1<br>NM_001018139.2<br>NM_002512.3 |
| NDRG1 | Protein NDRG1 | NDRG1_HUMAN | Q92597 | NP_001128714.1<br>NP_001245361.1<br>NP_001245362.1<br>NP_006087.2<br>NM_001135242.1<br>NM_001258432.1<br>NM_001258433.1<br>NM_006096.3 |
| NDUFA2 | NADH dehydrogenase [ubiquinone] 1 alpha subcomplex subunit 2 | NDUA2_HUMAN | O43678 | NP_002479.1<br>NM_002488.4 |
| NAP1L1 | Nucleosome assembly protein 1-like 1 precursor | NP1L1_HUMAN | P55209 | NP_004528.1<br>NP_631946.1<br>NM_004537.4<br>NM_139207.2 |
| NPM1 | Nucleophosmin | NPM_HUMAN | P06748 | NP_001032827.1<br>NP_002511.1<br>NP_954654.1<br>NM_001037738.2<br>NM_002520.6<br>NM_199185.3 |
| NUTF2 | Nuclear transport factor 2 | NTF2_HUMAN | P61970 | NP_005787.1<br>NM_005796.1 |
| NCL | Nucleolin | NUCL_HUMAN | P19338 | NP_005372.2<br>NM_005381.2 |

TABLE 1-continued

Markers of the Invention.

| Marker Name | Protein Description | UNIPROT_ID | UNIPROT ACCESSION | GENBANK ACCESSION |
|---|---|---|---|---|
| NUDC | Nuclear migration protein nudC | NUDC_HUMAN | Q9Y266 | NP_006591.1<br>NM_006600.3 |
| OAS2 | 2'-5'-oligoadenylate synthase 2 | OAS2_HUMAN | P29728 | NP_001027903.1<br>NP_002526.2<br>NP_058197.2<br>NM_001032731.1<br>NM_002535.2<br>NM_016817.2 |
| PAFAH1B2 | Platelet-activating factor acetylhydrolase IB subunit beta | PA1B2_HUMAN | P68402 | NP_001171675.1<br>NP_001171676.1<br>NP_001171677.1<br>NP_002563.1<br>NM_001184746.1<br>NM_001184747.1<br>NM_001184748.1<br>NM_002572.3 |
| PA2G4 | Proliferation-associated protein 2G4 | PA2G4_HUMAN | Q9UQ80 | NP_006182.2<br>NM_006191.2 |
| PARK7 | Protein DJ-1 precursor | PARK7_HUMAN | Q99497 | NP_001116849.1<br>NP_009193.2<br>NM_001123377.1<br>NM_007262.4 |
| PARP1 | Poly [ADP-ribose] polymerase 1 | PARP1_HUMAN | P09874 | NP_001609.2<br>NM_001618.3 |
| PRCP | Lysosomal Pro-X carboxypeptidase precursor | PCP_HUMAN | P42785 | NP_005031.1<br>NP_955450.2<br>NM_005040.2<br>NM_199418.2 |
| PDCD6IP | Programmed cell death 6-interacting protein | PDC6I_HUMAN | Q8WUM4 | NP_001155901.1<br>NP_037506.2<br>NM_001162429.2<br>NM_013374.5 |
| P4HB | Protein disulfide-isomerase precursor | PDIA1_HUMAN | P07237 | NP_000909.2<br>NM_000918.3 |
| PDIA5 | Protein disulfide-isomerase A5 precursor | PDIA5_HUMAN | Q14554 | NP_006801.1<br>NM_006810.3 |
| PEBP1 | Phosphatidylethanolamine-binding protein 1 | PEBP1_HUMAN | P30086 | NP_002558.1<br>NM_002567.2 |
| PECAM1 | Platelet endothelial cell adhesion molecule precursor | PECA1_HUMAN | P16284 | NP_000433.4<br>NM_000442.4 |
| PFDN1 | Prefoldin subunit 1 | PFD1_HUMAN | O60925 | NP_002613.2<br>NM_002622.4 |
| PFDN2 | Prefoldin subunit 2 | PFD2_HUMAN | Q9UHV9 | NP_036526.2<br>NM_012394.3 |
| PGAM1 | Phosphoglycerate mutase 1 | PGAM1_HUMAN | P18669 | NP_002620.1<br>NM_002629.2 |
| PGK1 | Phosphoglycerate kinase 1 | PGK1_HUMAN | P00558 | NP_000282.1<br>NM_000291.3 |
| PIP4K2A | Phosphatidylinositol 5-phosphate 4-kinase type-2 alpha | PI42A_HUMAN | P48426 | NP_005019.2<br>NM_005028.4 |
| PIP5K1A | Phosphatidylinositol 4-phosphate 5-kinase type-1 alpha | PI51A_HUMAN | Q99755 | NP_001129108.1<br>NP_001129109.1<br>NP_001129110.1<br>NP_003548.1<br>NM_001135636.1<br>NM_001135637.1<br>NM_001135638.1<br>NM_003557.2 |
| PLEKHO2 | Pleckstrin homology domain-containing | PKHO2_HUMAN | Q8TD55 | NP_001181988.1<br>NP_079477.2<br>NM_001195059.1<br>NM_025201.4 |

TABLE 1-continued

Markers of the Invention.

| Marker Name | Protein Description | UNIPROT_ID | UNIPROT ACCESSION | GENBANK ACCESSION |
|---|---|---|---|---|
| | family O member 2 | | | |
| PLEC | Plectin | PLEC_HUMAN | Q15149 | NP_000436.2 |
| | | | | NP_958780.1 |
| | | | | NP_958781.1 |
| | | | | NP_958782.1 |
| | | | | NP_958783.1 |
| | | | | NP_958784.1 |
| | | | | NP_958785.1 |
| | | | | NP_958786.1 |
| | | | | NM_000445.3 |
| | | | | NM_201378.2 |
| | | | | NM_201379.1 |
| | | | | NM_201380.2 |
| | | | | NM_201381.1 |
| | | | | NM_201382.2 |
| | | | | NM_201383.1 |
| | | | | NM_201384.1 |
| PLOD3 | Procollagen-lysine, 2-oxoglutarate 5-dioxygenase 3 precursor | PLOD3_HUMAN | O60568 | NP_001075.1 |
| | | | | NM_001084.4 |
| LCP1 | Plastin-2 | PLSL_HUMAN | P13796 | NP_002289.2 |
| | | | | NM_002298.4 |
| PNP | Purine nucleoside phosphorylase | PNPH_HUMAN | P00491 | NP_000261.2 |
| | | | | NM_000270.3 |
| ALPP | Alkaline phosphatase, placental type precursor | PPB1_HUMAN | P05187 | NP_001623.3 |
| | | | | NM_001632.3 |
| PPIA | Peptidyl-prolyl cis-trans isomerase A | PPIA_HUMAN | P62937 | NP_066953.1 |
| | | | | NM_021130.3 |
| PPIB | Peptidyl-prolyl cis-trans isomerase B precursor | PPIB_HUMAN | P23284 | NP_000933.1 |
| | | | | NM_000942.4 |
| PRDX1 | Peroxiredoxin-1 | PRDX1_HUMAN | Q06830 | NP_001189360.1 |
| | | | | NP_002565.1 |
| | | | | NP_859047.1 |
| | | | | NP_859048.1 |
| | | | | NM_001202431.1 |
| | | | | NM_002574.3 |
| | | | | NM_181696.2 |
| | | | | NM_181697.2 |
| PRDX2 | Peroxiredoxin-2 | PRDX2_HUMAN | P32119 | NP_005800.3 |
| | | | | NP_859428.1 |
| | | | | NM_005809.4 |
| | | | | NM_181738.1 |
| PRDX3 | Thioredoxin-dependent peroxide reductase, mitochondrial precursor | PRDX3_HUMAN | P30048 | NP_006784.1 |
| | | | | NP_054817.2 |
| | | | | NM_006793.2 |
| | | | | NM_014098.2 |
| PRDX6 | Peroxiredoxin-6 | PRDX6_HUMAN | P30041 | NP_004896.1 |
| | | | | NM_004905.2 |
| PRPF19 | Pre-mRNA-processing factor 19 | PRP19_HUMAN | Q9UMS4 | NP_055317.1 |
| | | | | NM_014502.4 |
| PSMC6 | 26S protease regulatory subunit 10B | PRS10_HUMAN | P62333 | NP_002797.3 |
| | | | | NM_002806.3 |
| PSMC3 | 26S protease regulatory subunit 6A | PRS6A_HUMAN | P17980 | NP_002795.2 |
| | | | | NM_002804.4 |
| PSMC2 | 26S protease regulatory subunit 7 | PRS7_HUMAN | P35998 | NP_001191382.1 |
| | | | | NP_002794.1 |
| | | | | NM_001204453.1 |
| | | | | NM_002803.3 |
| PRSS8 | Prostasin precursor | PRSS8_HUMAN | Q16651 | NP_002764.1 |
| | | | | NM_002773.3 |

TABLE 1-continued

Markers of the Invention.

| Marker Name | Protein Description | UNIPROT_ID | UNIPROT ACCESSION | GENBANK ACCESSION |
|---|---|---|---|---|
| NPEPPS | Puromycin-sensitive aminopeptidase | PSA_HUMAN | P55786 | NP_006301.3<br>NM_006310.3 |
| PSMA7 | Proteasome subunit alpha type-7 | PSA7_HUMAN | O14818 | NP_002783.1<br>NM_002792.3 |
| PSMB5 | Proteasome subunit beta type-5 precursor | PSB5_HUMAN | P28074 | NP_001124197.1<br>NP_001138404.1<br>NP_002788.1<br>NM_001130725.1<br>NM_001144932.1<br>NM_002797.3 |
| PSMD10 | 26S proteasome non-ATPase regulatory subunit 10 | PSD10_HUMAN | O75832 | NP_002805.1<br>NP_736606.1<br>NM_002814.3<br>NM_170750.2 |
| PSMD11 | 26S proteasome non-ATPase regulatory subunit 11 | PSD11_HUMAN | O00231 | NP_001257411.1<br>NP_002806.2<br>NM_001270482.1<br>NM_002815.3 |
| PSMD14 | 26S proteasome non-ATPase regulatory subunit 14 | PSDE_HUMAN | O00487 | NP_005796.1<br>NM_005805.5 |
| PSMD1 | 26S proteasome non-ATPase regulatory subunit 1 | PSMD1_HUMAN | Q99460 | NP_001177966.1<br>NP_002798.2<br>NM_001191037.1<br>NM_002807.3 |
| PSMD2 | 26S proteasome non-ATPase regulatory subunit 2 | PSMD2_HUMAN | Q13200 | NP_002799.3<br>NM_002808.3 |
| PSMD4 | 26S proteasome non-ATPase regulatory subunit 4 | PSMD4_HUMAN | P55036 | NP_002801.1<br>NM_002810.2 |
| PTBP3 | Polypyrimidine tract-binding protein 3 | PTBP3_HUMAN | O95758 | NP_001157260.1<br>NP_001157262.1<br>NP_001231826.1<br>NP_001231827.1<br>NP_005147.3<br>NM_001163788.2<br>NM_001163790.2<br>NM_001244897.1<br>NM_001244898.1<br>NM_005156.6 |
| PAICS | Multifunctional protein ADE2 | PUR6_HUMAN | P22234 | NP_001072992.1<br>NP_001072993.1<br>NP_006443.1<br>NM_001079524.1<br>NM_001079525.1<br>NM_006452.3 |
| ATIC | Bifunctional purine biosynthesis protein PURH | PUR9_HUMAN | P31939 | NP_004035.2<br>NM_004044.6 |
| PXMP2 | Peroxisomal membrane protein 2 | PXMP2_HUMAN | Q9NR77 | NP_061133.1<br>NM_018663.1 |
| RAB6A | Ras-related protein Rab-6A | RAB6A_HUMAN | P20340 | NP_002860.2<br>NP_942599.1<br>NM_002869.4<br>NM_198896.1 |
| RANGAP1 | Ran GTPase-activating protein 1 | RAGP1_HUMAN | P46060 | NP_002874.1<br>NM_002883.2 |
| RAI14 | Ankycorbin | RAI14_HUMAN | Q9P0K7 | NP_001138992.1<br>NP_001138993.1<br>NP_001138994.1<br>NP_001138995.1<br>NP_001138997.1<br>NP_056392.2<br>NM_001145520.1<br>NM_001145521.1<br>NM_001145522.1 |

TABLE 1-continued

Markers of the Invention.

| Marker Name | Protein Description | UNIPROT_ID | UNIPROT ACCESSION | GENBANK ACCESSION |
|---|---|---|---|---|
| | | | | NM_001145523.1 |
| | | | | NM_001145525.1 |
| | | | | NM_015577.2 |
| RAN | GTP-binding nuclear protein Ran | RAN_HUMAN | P62826 | NP_006316.1 |
| | | | | NM_006325.3 |
| RANBP1 | Ran-specific GTPase-activating protein | RANG_HUMAN | P43487 | NP_002873.1 |
| | | | | NM_002882.2 |
| RBBP4 | Histone-binding protein RBBP4 | RBBP4_HUMAN | Q09028 | NP_001128727.1 |
| | | | | NP_001128728.1 |
| | | | | NP_005601.1 |
| | | | | NM_001135255.1 |
| | | | | NM_001135256.1 |
| | | | | NM_005610.2 |
| RAD23B | UV excision repair protein RAD23 homolog B | RD23B_HUMAN | P54727 | NP_002865.1 |
| | | | | NM_002874.4 |
| RPL14 | 60S ribosomal protein L14 | RL14_HUMAN | P50914 | NP_001030168.1 |
| | | | | NP_003964.3 |
| | | | | NM_001034996.2 |
| | | | | NM_003973.4 |
| RPL23A | 60S ribosomal protein L23a | RL23A_HUMAN | P62750 | NP_000975.2 |
| | | | | NM_000984.5 |
| RPL24 | 60S ribosomal protein L24 | RL24_HUMAN | P83731 | NP_000977.1 |
| | | | | NM_000986.3 |
| RPL26 | 60S ribosomal protein L26 | RL26_HUMAN | P61254 | NP_000978.1 |
| | | | | NM_000987.3 |
| RPL29 | 60S ribosomal protein L29 | RL29_HUMAN | P47914 | NP_000983.1 |
| | | | | NM_000992.2 |
| RPL3 | 60S ribosomal protein L3 | RL3_HUMAN | P39023 | NP_000958.1 |
| | | | | NM_000967.3 |
| RPL31 | 60S ribosomal protein L31 | RL31_HUMAN | P62899 | NP_000984.1 |
| | | | | NP_001092047.1 |
| | | | | NP_001093163.1 |
| | | | | NM_000993.4 |
| | | | | NM_001098577.2 |
| | | | | NM_001099693.1 |
| RPL7A | 60S ribosomal protein L7a | RL7A_HUMAN | P62424 | NP_000963.1 |
| | | | | NM_000972.2 |
| RPL8 | 60S ribosomal protein L8 | RL8_HUMAN | P62917 | NP_000964.1 |
| | | | | NP_150644.1 |
| | | | | NM_000973.3 |
| | | | | NM_033301.1 |
| RPLP2 | 60S acidic ribosomal protein P2 | RLA2_HUMAN | P05387 | NP_000995.1 |
| | | | | NM_001004.3 |
| MRPL39 | 39S ribosomal protein L39, mitochondrial | RM39_HUMAN | Q9NYK5 | NP_059142.2 |
| | | | | NP_542984.2 |
| | | | | NM_017446.3 |
| | | | | NM_080794.3 |
| HNRNPA1 | Heterogeneous nuclear ribonucleoprotein A1 | ROA1_HUMAN | P09651 | NP_002127.1 |
| | | | | NP_112420.1 |
| | | | | NM_002136.2 |
| | | | | NM_031157.2 |
| HNRNPA2B1 | Heterogeneous nuclear ribonucleoproteins A2/B1 | ROA2_HUMAN | P22626 | NP_002128.1 |
| | | | | NP_112533.1 |
| | | | | NM_002137.3 |
| | | | | NM_031243.2 |
| RPS23 | 40S ribosomal protein S23 | RS23_HUMAN | P62266 | NP_001016.1 |
| | | | | NM_001025.4 |
| RPS8 | 40S ribosomal protein S8 | RS8_HUMAN | P62241 | NP_001003.1 |
| | | | | NM_001012.1 |
| RSAD2 | Radical S-adenosyl methionine domain-containing protein 2 | RSAD2_HUMAN | Q8WXG1 | NP_542388.2 |
| | | | | NM_080657.4 |
| RPSA | 40S ribosomal protein SA | RSSA_HUMAN | P08865 | NP_001012321.1 |
| | | | | NP_002286.2 |
| | | | | NM_001012321.1 |
| | | | | NM_002295.4 |

TABLE 1-continued

Markers of the Invention.

| Marker Name | Protein Description | UNIPROT_ID | UNIPROT ACCESSION | GENBANK ACCESSION |
|---|---|---|---|---|
| RUVBL1 | RuvB-like 1 | RUVB1_HUMAN | Q9Y265 | NP_003698.1<br>NM_003707.2 |
| RUVBL2 | RuvB-like 2 | RUVB2_HUMAN | Q9Y230 | NP_006657.1<br>NM_006666.1 |
| S100P | Protein S100-P | S100P_HUMAN | P25815 | NP_005971.1<br>NM_005980.2 |
| S100A6 | Protein S100-A6 | S10A6_HUMAN | P06703 | NP_055439.1<br>NM_014624.3 |
| S100A11 | Protein S100-A11 | S10AB_HUMAN | P31949 | NP_005611.1<br>NM_005620.1 |
| SEC61B | Protein transport protein Sec61 subunit beta | SC61B_HUMAN | P60468 | NP_006799.1<br>NM_006808.2 |
| SEPT11 | Septin-11 | SEP11_HUMAN | Q9NVA2 | NP_060713.1<br>NM_018243.2 |
| SEPT2 | Septin-2 | SEPT2_HUMAN | Q15019 | NP_001008491.1<br>NP_001008492.1<br>NP_004395.1<br>NP_006146.1<br>NM_001008491.1<br>NM_001008492.1<br>NM_004404.3<br>NM_006155.1 |
| SEPT6 | Septin-6 | SEPT6_HUMAN | Q14141 | NP_055944.2<br>NP_665798.1<br>NP_665799.1<br>NP_665801.1<br>NM_015129.5<br>NM_145799.3<br>NM_145800.3<br>NM_145802.3 |
| SEPT7 | Septin-7 | SEPT7_HUMAN | Q16181 | NP_001779.3<br>NM_001788.5 |
| SEPT9 | Septin-9 | SEPT9_HUMAN | Q9UHD8 | NP_001106963.1<br>NP_001106964.1<br>NP_001106965.1<br>NP_001106966.1<br>NP_001106967.1<br>NP_001106968.1<br>NP_006631.2<br>NM_001113491.1<br>NM_001113492.1<br>NM_001113493.1<br>NM_001113494.1<br>NM_001113495.1<br>NM_001113496.1<br>NM_006640.4 |
| PHGDH | D-3-phosphoglycerate dehydrogenase | SERA_HUMAN | O43175 | NP_006614.2<br>NM_006623.3 |
| SF3B3 | Splicing factor 3B subunit 3 | SF3B3_HUMAN | Q15393 | NP_036558.3<br>NM_012426.4 |
| SFPQ | Splicing factor, proline- and glutamine-rich | SFPQ_HUMAN | P23246 | NP_005057.1<br>NM_005066.2 |
| SIAE | Sialate O-acetylesterase precursor | SIAE_HUMAN | Q9HAT2 | NP_001186851.1<br>NP_733746.1<br>NM_001199922.1<br>NM_170601.4 |
| SNRPD3 | Small nuclear ribonucleoprotein Sm D3 | SMD3_HUMAN | P62318 | NP_004166.1<br>NM_004175.3 |
| NAPA | Alpha-soluble NSF attachment protein | SNAA_HUMAN | P54920 | NP_003818.2<br>NM_003827.3 |
| SOD2 | Superoxide dismutase [Mn], mitochondrial precursor | SODM_HUMAN | P04179 | NP_000627.2<br>NP_001019636.1<br>NP_001019637.1<br>NM_000636.2<br>NM_001024465.1<br>NM_001024466.1 |

TABLE 1-continued

Markers of the Invention.

| Marker Name | Protein Description | UNIPROT_ID | UNIPROT ACCESSION | GENBANK ACCESSION |
|---|---|---|---|---|
| SORT1 | Sortilin precursor | SORT_HUMAN | Q99523 | NP_001192157.1<br>NP_002950.3<br>NM_001205228.1<br>NM_002959.5 |
| SGSH | N-sulphoglucosamine sulphohydrolase precursor | SPHM_HUMAN | P51688 | NP_000190.1<br>NM_000199.3 |
| SPRED1 | Sprouty-related, EVH1 domain-containing protein 1 | SPRE1_HUMAN | Q72699 | NP_689807.1<br>NM_152594.2 |
| SPTBN1 | Spectrin beta chain, non-erythrocytic 1 | SPTB2_HUMAN | Q01082 | NP_003119.2<br>NP_842565.2<br>NM_003128.2<br>NM_178313.2 |
| SPG11 | Spatacsin | SPTCS_HUMAN | Q96JI7 | NP_001153699.1<br>NP_079413.3<br>NM_001160227.1<br>NM_025137.3 |
| SPTAN1 | Spectrin alpha chain, non-erythrocytic 1 | SPTN1_HUMAN | Q13813 | NP_001123910.1<br>NP_001182461.1<br>NP_003118.2<br>NM_001130438.2<br>NM_001195532.1<br>NM_003127.3 |
| SRSF3 | Serine/arginine-rich splicing factor 3 | SRSF3_HUMAN | P84103 | NP_003008.1<br>NM_003017.4 |
| SRSF8 | Serine/arginine-rich splicing factor 8 | SRSF8_HUMAN | Q9BRL6 | NP_115285.1<br>NM_032102.2 |
| STIP1 | Stress-induced-phosphoprotein 1 | STIP1_HUMAN | P31948 | NP_006810.1<br>NM_006819.2 |
| STMN1 | Stathmin | STMN1_HUMAN | P16949 | NP_001138926.1<br>NP_005554.1<br>NP_981944.1<br>NP_981946.1<br>NM_001145454.1<br>NM_005563.3<br>NM_203399.1<br>NM_203401.1 |
| STRAP | Serine-threonine kinase receptor-associated protein | STRAP_HUMAN | Q9Y3F4 | NP_009109.3<br>NM_007178.3 |
| STX11 | Syntaxin-11 | STX11_HUMAN | O75558 | NP_003755.2<br>NM_003764.3 |
| SUMO3 | Small ubiquitin-related modifier 3 precursor | SUMO3_HUMAN | P55854 | NP_008867.2<br>NM_006936.2 |
| EPRS | Bifunctional glutamate/proline--tRNA ligase | SYEP_HUMAN | P07814 | NP_004437.2<br>NM_004446.2 |
| IARS2 | Isoleucine--tRNA ligase, mitochondrial precursor | SYIM_HUMAN | Q9NSE4 | NP_060530.3<br>NM_018060.3 |
| TAGLN2 | Transgelin-2 | TAGL2_HUMAN | P37802 | NP_003555.1<br>NM_003564.1 |
| TALDO1 | Transaldolase | TALDO_HUMAN | P37837 | NP_006746.1<br>NM_006755.1 |
| TUBA4A | Tubulin alpha-4A chain | TBA4A_HUMAN | P68366 | NP_005991.1<br>NM_006000.1 |
| TUBB4B | Tubulin beta-4B chain | TBB4B_HUMAN | P68371 | NP_006079.1<br>NM_006088.5 |
| TUBB | Tubulin beta chain | TBB5_HUMAN | P07437 | NP_821133.1<br>NM_178014.2 |
| TBL2 | Transducin beta-like protein 2 | TBL2_HUMAN | Q9Y4P3 | NP_036585.1<br>NM_012453.2 |
| CCT4 | T-complex protein 1 subunit delta | TCPD_HUMAN | P50991 | NP_006421.2<br>NM_006430.3 |

TABLE 1-continued

Markers of the Invention.

| Marker Name | Protein Description | UNIPROT_ID | UNIPROT ACCESSION | GENBANK ACCESSION |
|---|---|---|---|---|
| CCT8 | T-complex protein 1 subunit theta | TCPQ_HUMAN | P50990 | NP_006576.2<br>NM_006585.2 |
| TDRD6 | Tudor domain-containing protein 6 | TDRD6_HUMAN | O60522 | NP_001010870.1<br>NP_001161831.1<br>NM_001010870.2<br>NM_001168359.1 |
| VCP | Transitional endoplasmic reticulum ATPase | TERA_HUMAN | P55072 | NP_009057.1<br>NM_007126.3 |
| TKT | Transketolase | TKT_HUMAN | P29401 | NP_001055.1<br>NP_001128527.1<br>NP_001244957.1<br>NM_001064.3<br>NM_001135055.2<br>NM_001258028.1 |
| TLN1 | Talin-1 | TLN1_HUMAN | Q9Y490 | NP_006280.3<br>NM_006289.3 |
| TMOD3 | Tropomodulin-3 | TMOD3_HUMAN | Q9NYL9 | NP_055362.1<br>NM_014547.4 |
| TPI1 | Triosephosphate isomerase | TPIS_HUMAN | P60174 | NP_000356.1<br>NP_001152759.1<br>NM_000365.5<br>NM_001159287.1 |
| TRA2B | Transformer-2 protein homolog beta | TRA2B_HUMAN | P62995 | NP_001230808.1<br>NP_004584.1<br>NM_001243879.1<br>NM_004593.2 |
| TXNRD1 | Thioredoxin reductase 1, cytoplasmic | TRXR1_HUMAN | Q16881 | NP_001087240.1<br>NP_001248374.1<br>NP_001248375.1<br>NP_003321.3<br>NP_877393.1<br>NP_877419.1<br>NP_877420.1<br>NM_001093771.2<br>NM_001261445.1<br>NM_001261446.1<br>NM_003330.3<br>NM_182729.2<br>NM_182742.2<br>NM_182743.2 |
| USP14 | Ubiquitin carboxyl-terminal hydrolase 14 | UBP14_HUMAN | P54578 | NP_001032411.1<br>NP_005142.1<br>NM_001037334.1<br>NM_005151.3 |
| UGGT1 | UDP-glucose:glycoprotein glucosyltransferase 1 precursor | UGGG1_HUMAN | Q9NYU2 | NP_064505.1<br>NM_020120.3 |
| ATP6V1A | V-type proton ATPase catalytic subunit A | VATA_HUMAN | P38606 | NP_001681.2<br>NM_001690.3 |
| ATP6V1B2 | V-type proton ATPase subunit B, brain isoform | VATB2_HUMAN | P21281 | NP_001684.2<br>NM_001693.3 |
| ATP6V1D | V-type proton ATPase subunit D | VATD_HUMAN | Q9Y5K8 | NP_057078.1<br>NM_015994.3 |
| ATP6V1E1 | V-type proton ATPase subunit E 1 | VATE1_HUMAN | P36543 | NP_001034455.1<br>NP_001034456.1<br>NP_001687.1<br>NM_001039366.1<br>NM_001039367.1<br>NM_001696.3 |
| ATP6V1F | V-type proton ATPase subunit F | VATF_HUMAN | Q16864 | NP_001185838.1<br>NP_004222.2<br>NM_001198909.1<br>NM_004231.3 |
| ATP6V1G1 | V-type proton ATPase subunit G 1 | VATG1_HUMAN | O75348 | NP_004879.1<br>NM_004888.3 |
| VPS4A | Vacuolar protein sorting- | VPS4A_HUMAN | Q9UN37 | NP_037377.1<br>NM_013245.2 |

TABLE 1-continued

Markers of the Invention.

| Marker Name | Protein Description | UNIPROT_ID | UNIPROT ACCESSION | GENBANK ACCESSION |
|---|---|---|---|---|
| XRCC6 | associated protein 4A X-ray repair cross-complementing protein 6 | XRCC6_HUMAN | P12956 | NP_001460.1 NM_001469.3 |
| YBX1 | Nuclease-sensitive element-binding protein 1 | YBOX1_HUMAN | P67809 | NP_004550.2 NM_004559.3 |

In certain aspects of the invention, a single marker (e.g., any one of the markers listed in Table 1) may be used in the methods and compositions of the invention. For example, in one embodiment, the marker for use in the methods and compositions of the invention is LYN. In one embodiment, the marker is MAT2A. In one embodiment, the marker is B4GALT1. In one embodiment, the marker is HIST3H3. In one embodiment, the marker is ICAM1. In one embodiment, the marker is LDHB. In one embodiment, the marker is MDH1. In one embodiment, the marker is CALU. In one embodiment, the marker is CORO1A. In one embodiment, the marker is ENO1. In one embodiment, the marker is EPB41L3. In one embodiment, the marker is FLNA. In one embodiment, the marker is GSTP1. In one embodiment, the marker is H6PD. In one embodiment, the marker is HISTH2BE. In one embodiment, the marker is HIST4H4. In one embodiment, the marker is ITGAM. In one embodiment, the marker is MMP9. In one embodiment, the marker is PRKCSH. In one embodiment, the marker is RPSA. In one embodiment, the marker is TKT. In one embodiment, the marker is TPI1. In some embodiments, the methods (and kits) may further comprise determining the level of a marker selected from the group consisting of the markers listed in Table 1. In other embodiments, the methods may further comprise determining the level of one or more markers selected from the group consisting of SLC3A2, GOT1, GOT2, ACADVL, DBI, ACOX1, AHNAK, AIMP1, AKR1B1, ANPEP, ANXA2, ANXA5, ANXA6, AKR7A2, ARPC3, ASAH1, B4GALT1, BCAM, BLOC1S5, CALU, CAPG, CAPZB, CAPZA2, CBX1, CDC37, HSPE1, CHMP1A, CHMP1B, CHMP2A, CHMP4A, CHMP4B, CHMP5, CLIC1, CNDP2, CNPY2, COPA, COPB2, CORO1A, CORO1B, CORO1C, CPVL, C19orf10, CXorf26, CXCL10, CACYBP, DSP, HSD17B4, DLG1, DNASE2, DDT, DYNLL1, EPB41L3, EEF1A1, EEF1B2, EEF1D, EEF2, ENG, EHD1, ELAVL1, EMC2, EMR2, ENO1, ENO3, HSP90B1, ERO1L, ESYT2, EVL, ST13, F5, FKBP4, FLNA, FH, H6PD, GPI, GDI2, ARHGDIA, GGH, GBA, PRKCSH, GNS, HSPA9, HSPA5, GSTP1, GLT25D1, HIST1H1D, HIST1H1B, HIST3H2A, H2AFY, HIST2H2BE, HIST2H2BF, HIST3H3, HIST1H4A, HSD17B10, HEXA, HMGB3, HNRNPC, HNRNPD, HNRNPK, HNRNPR, HNRNPU, HSP90AA1, HSP90AB1, HSPA1A, HSPA8, ICAM1, EIF5A2, IL1B, IMPDH2, ISYNA1, ISOC1, ITGA5, ITGAM, ITPR1, KRT9, KRT7, KRT8, CAMK2D, PKM, LASP1, LDHB, LIMA1, LMNA, LMNB1, LMNB2, LRCH1, GAA, LYN, MDH1, MDH2, MESDC2, MAT2A, MYL12A, MMP9, RABIF, MYH10, MYH9, MYO1E, MYO6, PPP1R12A, NAGA, POR, NME1, NME2, NDRG1, NDUFA2, NAP1L1, NPM1, NUTF2, NCL, NUDC, OAS2, PAFAH1B2, PA2G4, PARK7, PARP1, PRCP, PDCD6IP, P4HB, PDIA5, PEBP1, PECAM1, PFDN1, PFDN2, PGAM1, PGK1, PIP4K2A, PIP5K1A, PLEKHO2, PLEC, PLOD3, LCP1, PNP, ALPP, PPIA, PPIB, PRDX1, PRDX2, PRDX3, PRDX6, PRPF19, PSMC6, PSMC3, PSMC2, PRSS8, NPEPPS, PSMA7, PSMB5, PSMD10, PSMD11, PSMD14, PSMD1, PSMD2, PSMD4, PTBP3, PAICS, ATIC, PXMP2, RAB6A, RANGAP1, RAI14, RAN, RANBP1, RBBP4, RAD23B, RPL14, RPL23A, RPL24, RPL26, RPL29, RPL3, RPL31, RPL7A, RPL8, RPLP2, MRPL39, HNRNPA1, HNRNPA2B1, RPS23, RPS8, RSAD2, RPSA, RUVBL1, RUVBL2, S100P, S100A6, S100A11, SEC61B, SEPT11, SEPT2, SEPT6, SEPT7, SEPT9, PHGDH, SF3B3, SFPQ, SIAE, SNRPD3, NAPA, SOD2, SORT1, SGSH, SPRED1, SPTBN1, SPG11, SPTAN1, SRSF3, SRSF8, STIP1, STMN1, STRAP, STX11, SUMO3, EPRS, IARS2, TAGLN2, TALDO1, TUBA4A, TUBB4B, TUBB, TBL2, CCT4, CCT8, TDRD6, VCP, TKT, TLN1, TMOD3, TPI1, TRA2B, TXNRD1, USP14, UGGT1, ATP6V1A, ATP6V1B2, ATP6V1D, ATP6V1E1, ATP6V1F, ATP6V1G1, VPS4A, XRCC6, and YBX1.

In other aspects of the invention, more than one marker, e.g., a plurality of markers, e.g., two, three, four, five, six, seven, eight, nine, ten, eleven, or more markers, may be used in the methods and compositions of the invention. For example, in one embodiment, the markers for use in the methods and compositions of the invention include HIST4H4 and LYN. In one embodiment, the markers include HIST4H4 and MAT2A. In one embodiment, the markers include HIST4H4 and MDH1. In one embodiment, the markers include HIST4H4, LYN, and MAT2A. In one embodiment, the markers include HIST4H4, LYN, and MDH1. In one embodiment, the markers include HIST4H4, MAT2A, and MDH1. In one embodiment, the markers include LYN and MAT2A. In one embodiment, the markers include LYN and MDH1. In one embodiment, the markers include LYN, AMY2A, and MDH1. In one embodiment, the markers include MAT2A, and MDH1. In one embodiment, the markers include HIST4H4, MDH1, MAT2A, and LYN. In one embodiment, the markers include HIST4H4 and LDHB. In one embodiment, the markers include HIST4H4 and MAT2A. In one embodiment, the markers include HIST4H4 and MDH1. In one embodiment, the markers include HIST4H4, LDHB, and MAT2A. In one embodiment, the markers include HIST4H4, LDHB, and MDH1. In one embodiment, the markers include HIST4H4, MAT2A, and MDH1. In one embodiment, the markers include LDHB and MDH1. In one embodiment, the markers include LDHB, MAT2A, and MDH1. In one embodiment, the markers include HIST4H4 and ICAM1. In one embodiment, the markers include HIST4H4 and MMP9. In one embodiment, the markers include HIST4H4, ICAM1, and LYN. In one embodiment, the markers include HIST4H4, ICAM1, and MMP9. In one embodiment, the markers include HIST4H4, LYN and MMP9. In one embodiment, the markers include ICAM1 and LYN. In one embodiment, the markers include ICAM1 and MMP9. In one embodiment, the markers include ICAM1, LYN, and MMP9. In one embodiment, the markers include LYN and MMP9. In one embodiment, the markers include B4GALT1 and CALU. In one embodiment, the markers include B4GALT1 and LYN. In one embodiment, the markers include B4GALT1 and TPI1. In one embodiment, the markers include B4GALT1, CALU, and LYN. In one embodiment, the markers include B4GALT1, CALU, and TPI1. In one embodiment, the markers include B4GALT1, LYN, and TPI1. In one embodiment, the markers include B4GALT1, LYN, CALU, and TPI1. In one embodiment, the markers include CALU and LYN. In one embodiment, the markers include CALU and TPI1. In one embodiment, the markers include LYN and TPI1. In one embodiment, the markers include CALU, LYN, and TPI1. In one embodiment, the markers include HIST4H4, LYN, MAT2A, MMP9, CALU, LDHB, and B4GALT1. In one embodiment, the markers include MMP9 and MDH1. In one embodiment, the markers include LYN and LDHB.

In some embodiments, the methods may further comprise determining the level of a marker selected from the group consisting of the markers listed in Table 1. In other embodiments, the methods may further comprise determining the level of one or more markers selected from the group consisting of B4GALT1, HIST3H3, CALU, CORO1A, ENO1, EPB41L3, FLNA, GSTP1, H6PD, ITGAM, PRKCSH, RPSA, TKT, and TPI1.

III. Methods of the Invention

A. Diagnostic Methods

In certain aspects, the present invention provides diagnostic methods. For example, in one aspect, the present invention provides methods for determining whether a subject has Brucellosis. The methods include determining the level of one or more markers of the invention in a sample(s) from the subject with a level of the one or more markers in a control sample(s). A difference in the level (e.g., higher or lower) of the one or more markers in the sample(s) from the subject as compared to the level of the one or more markers in the control sample indicates that the subject has Brucellosis.

In another aspect, the present invention provides methods for determining whether a subject has Q-fever. The methods include determining the level of one or more markers of the invention in a sample(s) from the subject with a level of the one or more markers in a control sample(s). A difference in the level (e.g., higher or lower) of the one or more markers in the sample(s) from the subject as compared to the level of the one or more markers in the control sample indicates that the subject has Q-Fever.

In another aspect, the present invention provides methods for determining whether a subject has Lyme Disease. The methods include determining the level of one or more markers of the invention in a sample(s) from the subject with a level of the one or more markers in a control sample(s). A difference in the level (e.g., higher or lower) of the one or more markers in the sample(s) from the subject as compared to the level of the one or more markers in the control sample indicates that the subject has Lyme Disease.

In another aspect, the present invention provides methods for determining whether a subject has Brucellosis or Q-fever. The methods include determining the level of one or more markers of the invention in a sample(s) from the subject with a level of the one or more markers in a control sample(s). A difference in the level (e.g., higher or lower) of the one or more markers in the sample(s) from the subject as compared to the level of the one or more markers in the control sample indicates that the subject has Brucellosis.

In another aspect, the present invention provides methods for determining whether a subject has Brucellosis or Lyme Disease. The methods include determining the level of one or more markers of the invention in a sample(s) from the subject with a level of the one or more markers in a control sample(s). A difference in the level (e.g., higher or lower) of the one or more markers in the sample(s) from the subject as compared to the level of the one or more markers in the control sample indicates that the subject has Brucellosis.

In another aspect, the present invention provides methods for determining whether a subject has Q-Fever or Lyme Disease. The methods include determining the level of one or more markers of the invention in a sample(s) from the subject with a level of the one or more markers in a control sample(s). A difference in the level (e.g., higher or lower) of the one or more markers in the sample(s) from the subject as compared to the level of the one or more markers in the control sample indicates that the subject has Q-Fever.

In another aspect, the present invention provides methods for determining whether a subject has Brucellosis or Q-Fever or Lyme Disease. The methods include determining the level of one or more markers of the invention in a sample(s) from the subject with a level of the one or more markers in a control sample(s). A difference in the level (e.g., higher or lower) of the one or more markers in the sample(s) from the subject as compared to the level of the one or more markers in the control sample indicates wherther the subject has Brucellosis or Q-Fever or Lyme Disease.

The methods of the present invention can be practiced in conjunction with any other method(s) used by the skilled practitioner to diagnose, prognose, and/or monitor Brucellosis, Q-Fever, and/or Lyme Disease. For example, the methods of the invention may be performed in conjunction with any clinical measurement of Brucellosis, Q-Fever, and/or Lyme Disease known in the art including serological, cytological, radiological, and/or detection (and quantification, if appropriate) of other molecular markers.

In any of the methods (and kits) of the invention, the level of a marker(s) of the invention in a sample obtained from a subject may be determined by any of a wide variety of well-known techniques and methods, which transform a marker of the invention within the sample into a moiety that can be detected and quantified. Non-limiting examples of such methods include analyzing the sample using immunological methods for detection of proteins, protein purification methods, protein function or activity assays, nucleic acid hybridization methods, nucleic acid reverse transcription methods, and nucleic acid amplification methods, immunoblotting, Western blotting, Northern blotting, electron microscopy, mass spectrometry, e.g., MALDI-TOF and SELDI-TOF, immunoprecipitations, immunofluorescence, immunohistochemistry, enzyme linked immunosorbent assays (ELISAs), e.g., amplified ELISA, quantitative blood based assays, e.g., serum ELISA, quantitative urine based assays, flow cytometry, Southern hybridizations, array analysis, and the like, and combinations or sub-combinations thereof.

For example, an mRNA sample may be obtained from the sample from the subject (e.g., blood, serum, bronchial lavage, mouth swab, biopsy, or peripheral blood mononuclear cells, by standard methods) and expression of mRNA(s) encoding a marker of the invention in the sample may be detected and/or determined using standard molecular biology techniques, such as PCR analysis. A preferred method of PCR analysis is reverse transcriptase-polymerase chain reaction (RT-PCR). Other suitable systems for mRNA sample analysis include microarray analysis (e.g., using Affymetrix's microarray system or Illumina's BeadArray Technology).

It will be readily understood by the ordinarily skilled artisan that essentially any technical means established in the art for detecting the level a marker of the invention at either the nucleic acid or protein level, can be used to determine the level a marker of the invention as discussed herein.

In one embodiment, the level of a marker of the invention in a sample is determined by detecting a transcribed polynucleotide, or portion thereof, e.g., mRNA, or cDNA, of a marker of the invention gene. RNA may be extracted from cells using RNA extraction techniques including, for example, using acid phenol/guanidine isothiocyanate extraction (RNAzol B; Biogenesis), RNeasy RNA preparation kits (Qiagen) or PAXgene (PreAnalytix, Switzerland). Typical assay formats utilizing ribonucleic acid hybridization include nuclear run-on assays, RT-PCR, RNase protection assays (Melton et al., *Nuc. Acids Res.* 12:7035), Northern blotting, in situ hybridization, and microarray analysis.

In one embodiment, the level of a marker of the invention is determined using a nucleic acid probe. The term "probe", as used herein, refers to any molecule that is capable of selectively binding to a specific marker of the invention. Probes can be synthesized by one of skill in the art, or derived from appropriate biological preparations. Probes may be specifically designed to be labeled. Examples of molecules that can be utilized as probes include, but are not limited to, RNA, DNA, proteins, antibodies, and organic molecules.

Isolated mRNA can be used in hybridization or amplification assays that include, but are not limited to, Southern or Northern analyses, polymerase chain reaction (PCR) analyses and probe arrays. One method for the determination of mRNA levels involves contacting the isolated mRNA with a nucleic acid molecule (probe) that can hybridize to a marker mRNA. The nucleic acid probe can be, for example, a full-length cDNA, or a portion thereof, such as an oligonucleotide of at least about 7, 10, 15, 20, 25, 30, 35, 40, 45, 50, 100, 250 or about 500 nucleotides in length and sufficient to specifically hybridize under stringent conditions to marker genomic DNA.

In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface and the mRNA is contacted with the probe(s), for example, in an Affymetrix gene chip array. A skilled artisan can readily adapt known mRNA detection methods for use in determining the level of a marker of the invention mRNA.

An alternative method for determining the level of a marker of the invention in a sample involves the process of nucleic acid amplification and/or reverse transcriptase (to prepare cDNA) of for example mRNA in the sample, e.g., by RT-PCR (the experimental embodiment set forth in Mullis, 1987, U.S. Pat. No. 4,683,202), ligase chain reaction (Barany (1991) *Proc. Natl. Acad. Sci. USA* 88:189-193), self-sustained sequence replication (Guatelli et al. (1990) *Proc. Natl. Acad. Sci. USA* 87:1874-1878), transcriptional amplification system (Kwoh et al. (1989) *Proc. Natl. Acad. Sci. USA* 86:1173-1177), Q-Beta Replicase (Lizardi et al. (1988) *Bio/Technology* 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. In particular aspects of the invention, the level of expression of a marker of the invention is determined by quantitative fluorogenic RT-PCR (i.e., the TaqMan™ System). Such methods typically utilize pairs of oligonucleotide primers that are specific for a marker of the invention. Methods for designing oligonucleotide primers specific for a known sequence are well known in the art.

The level of a marker of the invention mRNA may be monitored using a membrane blot (such as used in hybridization analysis such as Northern, Southern, dot, and the like), or microwells, sample tubes, gels, beads or fibers (or any solid support comprising bound nucleic acids). See U.S. Pat. Nos. 5,770,722, 5,874,219, 5,744,305, 5,677,195 and 5,445,934, which are incorporated herein by reference. The determination of a level of a marker of the invention may also comprise using nucleic acid probes in solution.

In one embodiment of the invention, microarrays are used to detect the level of a marker of the invention. Microarrays are particularly well suited for this purpose because of the reproducibility between different experiments. DNA microarrays provide one method for the simultaneous measurement of the levels of large numbers of genes. Each array consists of a reproducible pattern of capture probes attached to a solid support. Labeled RNA or DNA is hybridized to complementary probes on the array and then detected by laser scanning. Hybridization intensities for each probe on the array are determined and converted to a quantitative value representing relative gene expression levels. See, e.g., U.S. Pat. Nos. 6,040,138, 5,800,992 and 6,020,135, 6,033, 860, and 6,344,316, which are incorporated herein by reference. High-density oligonucleotide arrays are particularly useful for determining the gene expression profile for a large number of RNA's in a sample.

In certain situations it may be possible to assay for the level of a marker of the invention at the protein level, using a detection reagent that detects the protein product encoded by the mRNA of a marker of the invention. For example, if an antibody reagent is available that binds specifically to a marker of the invention protein product to be detected, and not to other proteins, then such an antibody reagent can be used to detect the expression of a marker of the invention in a cellular sample from the subject, or a preparation derived from the cellular sample, using standard antibody-based techniques known in the art, such as FACS analysis, and the like.

Other known methods for detecting a marker of the invention at the protein level include methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immuno-electrophoresis, radioimmunoassay (RIA), enzyme-linked immunosorbent assays (ELISAs), immunofluorescent assays, and Western blotting.

Proteins from samples can be isolated using techniques that are well known to those of skill in the art. The protein isolation methods employed can, for example, be those described in Harlow and Lane (Harlow and Lane, 1988, Antibodies: A Laboratory Manual, Cold Spring Harbor Laboratory Press, Cold Spring Harbor, N.Y.).

In one embodiment, antibodies, or antibody fragments, are used in methods such as Western blots or immunofluorescence techniques to detect the expressed proteins. Antibodies for determining the expression of a marker of the invention are commercially available and one of ordinary skill in the art can readily identify appropriate antibodies for use in the methods of the invention.

It is generally preferable to immobilize either the antibody or proteins on a solid support for Western blots and immunofluorescence techniques. Suitable solid phase supports or carriers include any support capable of binding an antigen or an antibody. Well-known supports or carriers include glass, polystyrene, polypropylene, polyethylene, dextran, nylon, amylases, natural and modified celluloses, polyacrylamides, gabbros, and magnetite.

One skilled in the art will know many other suitable carriers for binding antibody or antigen, and will be able to adapt such support for use with the present invention. For example, protein isolated from cells can be run on a polyacrylamide gel electrophoresis and immobilized onto a solid phase support such as nitrocellulose. The support can then be washed with suitable buffers followed by treatment with the detectably labeled antibody. The solid phase support can then be washed with the buffer a second time to remove unbound antibody. The amount of bound label on the solid support can then be detected by conventional means. Means of detecting proteins using electrophoretic techniques are well known to those of skill in the art (see generally, R. Scopes (1982) *Protein Purification*, Springer-Verlag, N.Y.; Deutscher, (1990) *Methods in Enzymology* Vol. 182: *Guide to Protein Purification*, Academic Press, Inc., N.Y.).

Other standard methods include immunoassay techniques which are well known to one of ordinary skill in the art and may be found in Principles And Practice Of Immunoassay, 2nd Edition, Price and Newman, eds., MacMillan (1997) and Antibodies, A Laboratory Manual, Harlow and Lane, eds., Cold Spring Harbor Laboratory, Ch. 9 (1988), each of which is incorporated herein by reference in its entirety.

Antibodies used in immunoassays to determine the level of a marker of the invention, may be labeled with a detectable label. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

In one embodiment, the antibody is labeled, e.g. a radiolabeled, chromophore-labeled, fluorophore-labeled, or enzyme-labeled antibody. In another embodiment, an antibody derivative (e.g. an antibody conjugated with a substrate or with the protein or ligand of a protein-ligand pair {e.g. biotin-streptavidin}), or an antibody fragment (e.g. a single-chain antibody, an isolated antibody hypervariable domain, etc.) which binds specifically with a marker of the invention.

In one embodiment of the invention, proteomic methods, e.g., mass spectrometry, are used. Mass spectrometry is an analytical technique that consists of ionizing chemical compounds to generate charged molecules (or fragments thereof) and measuring their mass-to-charge ratios. In a typical mass spectrometry procedure, a sample is obtained from a subject, loaded onto the mass spectrometry, and its components (e.g., a marker of the invention) are ionized by different methods (e.g., by impacting them with an electron beam), resulting in the formation of charged particles (ions). The mass-to-charge ratio of the particles is then calculated from the motion of the ions as they transit through electromagnetic fields.

For example, matrix-associated laser desorption/ionization time-of-flight mass spectrometry (MALDI-TOF MS) or surface-enhanced laser desorption/ionization time-of-flight mass spectrometry (SELDI-TOF MS) which involves the application of a biological sample, such as serum, to a protein-binding chip (Wright, G. L., Jr., et al. (2002) *Expert Rev Mol Diagn* 2:549; Li, J., et al. (2002) *Clin Chem* 48:1296; Laronga, C., et al. (2003) *Dis Markers* 19:229; Petricoin, E. F., et al. (2002) 359:572; Adam, B. L., et al. (2002) *Cancer Res* 62:3609; Tolson, J., et al. (2004) *Lab Invest* 84:845; Xiao, Z., et al. (2001) *Cancer Res* 61:6029) can be used to determine the level of a marker of the invention.

Furthermore, in vivo techniques for determination of the level of a marker of the invention include introducing into a subject a labeled antibody directed against a marker of the invention, which binds to and transforms a marker of the invention into a detectable molecule. As discussed above, the presence, level, or even location of the detectable marker of the invention in a subject may be detected determined by standard imaging techniques.

In general, it is preferable that the difference between the level of a marker of the invention in a sample from a subject and the amount of a marker of the invention in a control sample, is as great as possible. Although this difference can be as small as the limit of detection of the method for determining the level of a marker it is preferred that the difference be at least greater than the standard error of the assessment method, and preferably a difference of at least 2-, 3-, 4-, 5-, 6-, 7-, 8-, 9-, 10-, 15-, 20-, 25-, 100-, 500-, 1000-fold or greater than the standard error of the assessment method.

B. Methods for Monitoring the Effectiveness of a Treatment

The present invention also provides methods for monitoring the effectiveness of a therapy or treatment regimen or any other therapeutic approach useful for treating a subject having a zoonosis, e.g., Brucellosis and/or inhibiting relapse of the zoonosis, e.g., Brucellosis, inhibiting chronic zoonotic infection, e.g., *Brucella* infection, the progression of the zoonosis, e.g., Brucellosis to other organs (or a complication associated with involvement of other organ systems (e.g., sacroiliitis, spondylitis, osteomyelitis, endocarditis (a primary cause of death), myocarditis, pericarditis, infections of the central nervous system, such as meningitis, encepahlitis, and meningoencephalitis, hepatitis, hepatic abscess, colitis, spontaneous peritonitis, orchitis, epididymo-orchitis, heaptomegaly, pneumonia, optic neuritis, and uveitis)) in a subject having Brucellosis.

The present invention also provides methods for monitoring the effectiveness of a therapy or treatment regimen or any other therapeutic approach useful for treating a subject having Q-Fever and/or inhibiting relapse of Q-Fever, inhibiting chronic *Coxiella burnetii* infection, the progression of Q-Fever to other organs (or a complication associated with involvement of other organ systems (e.g., endocarditis, chronic hepatitis without endocarditis, osteomyelitis, osteoarthritis, and pneumonitis) in a subject having Q-Fever.

The present invention also provides methods for monitoring the effectiveness of a therapy or treatment regimen or any other therapeutic approach useful for treating a subject having Q-Fever and/or inhibiting relapse of Lyme Disease, inhibiting chronic Borrelia infection, the progression of Lyme Disease to other organs (or a complication associated with involvement of other organ systems (e.g., paralysis of the facial nerves, recurring headaches or fainting, poor memory and reduced ability to concentrate, conjunctivitis, heart palpitations, endocarditis.

Inflammation of the joints, numbness and tingling in the hands, feet, or back, severe fatigue. Partial facial nerve paralysis, which usually occurs within the first few months after the tick bite, neurologic changes, including problems with memory, mood, or sleep, and sometimes problems speaking) in a subject having Lyme Disease.

In these methods the level of one or more markers of the invention in a pair of samples (a first sample not subjected to the treatment regimen and a second sample subjected to at least a portion of the treatment regimen) is assessed. A modulation in the level of expression of the one or more markers in the first sample, relative to the second sample, is an indication that the therapy is effective for treating a subject having the zoonosis and/or inhibiting relapse of the zoonosis, inhibiting chronic zoonotic infection, the progression of the zoonosis to other organs (or a complication thereof) in a subject having the zoonosis.

C. Screening Methods

Using the methods described herein, a variety of molecules, particularly molecules sufficiently small to be able to cross the cell membrane, may be screened in order to identify molecules which modulate, e.g., decrease or increase, the level and/or activity of a marker(s) of the invention. Compounds so identified can be administered to a subject in order to for treating a subject having a zoonosis, e.g., Brucellosis, Q-Fever, or Lyme Disease, and/or inhibiting relapse of the zoonosis, inhibiting chronic zoonotic infection, the progression of the zoonosis to other organs (or a complication associated with involvement of other organ systems in a subject having the zoonosis.

Accordingly, in one embodiment, the invention provides methods for identifying modulators, i.e., candidate or test compounds or agents (e.g., enzymes, peptides, peptidomimetics, small molecules, ribozymes, or marker antisense molecules) which bind to a marker polypeptide; have a stimulatory or inhibitory effect on a marker expression; marker processing; marker post-translational modification (e.g., glycosylation, ubiquitinization, or phosphorylation); marker activity; and/or have a stimulatory or inhibitory effect on the expression, processing or activity of a marker target molecule.

Methods for identifying a compound that can modulate the level and/or activity of a marker in a cell (in vitro and/or in vivo), for treating a subject having a zoonosis and/or inhibiting relapse of the zoonosis, inhibiting chronic zoonotic infection, the progression of the zoonosis to other organs (or a complication associated with involvement of other organ systems) (also referred to herein as screening assays) include separately contacting an aliquot of a sample (e.g., a sample from the subject) with each member of a library of compounds; determining the effect of a member of the library of compounds on the level of one or more marker(s) of the invention (or the activity of one or more marker(s) of the invention) in each of the aliquots; and selecting a member of the library of compounds which modulates the level of and/or the activity of the one or more marker(s) of the invention in an aliquot as compared to the level and/or activity of the one or more marker(s) of the invention in a control sample, thereby identifying a compound that can modulate the level and/or activity of a marker in a cell, for treating a subject having the zoonosis and/or inhibiting relapse of the zoonosis, inhibiting chronic zoonotic infection, the progression of the zoonosis to other organs (or a complication associated with involvement of other organ systems).

As used interchangeably herein, the terms "marker activity" and "biological activity of a marker" include activities exerted by a marker(s) protein on marker responsive cell or tissue, or on marker(s) nucleic acid molecule or protein target molecule, as determined in vivo, and/or in vitro, according to standard techniques. A marker(s) activity can be a direct activity, such as an association with a marker-target molecule. Alternatively, marker(s) activity is an indirect activity, such as a downstream biological event mediated by interaction of the marker(s) protein with a marker-target molecule or other molecule in a signal-transduction pathway involving the marker(s). The biological activities of the markers of the invention are known in the art and can be found at, for example, www.uniprot.org. The Uniprot Accession Numbers for each of the markers of the invention are provided in Table 1. The entire contents of each of these Uniprot records are hereby incorporated by reference. Methods for determining the effect of a compound on the level and/or activity of marker are known in the art and/or described herein.

A variety of test compounds can be evaluated using the screening assays described herein. The term "test compound" includes any reagent or test agent which is employed in the assays of the invention and assayed for its ability to influence the expression and/or activity of a marker. More than one compound, e.g., a plurality of compounds, can be tested at the same time for their ability to modulate the expression and/or activity of a marker in a screening assay. The term "screening assay" preferably refers to assays which test the ability of a plurality of compounds to influence the readout of choice rather than to tests which test the ability of one compound to influence a readout. Preferably, the subject assays identify compounds not previously known to have the effect that is being screened for. In one embodiment, high throughput screening can be used to assay for the activity of a compound.

Candidate/test compounds include, for example, 1) peptides such as soluble peptides, including Ig-tailed fusion peptides and members of random peptide libraries (see, e.g., Lam, K. S. et al. (1991) *Nature* 354:82-84; Houghten, R. et al. (1991) *Nature* 354:84-86) and combinatorial chemistry-derived molecular libraries made of D- and/or L-configuration amino acids; 2) phosphopeptides (e.g., members of random and partially degenerate, directed phosphopeptide libraries, see, e.g., Songyang, Z. et al. (1993) *Cell* 72:767-778); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); 4) small organic and inorganic molecules (e.g., molecules obtained from combinatorial and natural product libraries); 5) enzymes (e.g., endoribonucleases, hydrolases, nucleases, proteases, synthatases, isomerases, polymerases, kinases, phosphatases, oxido-reductases and ATPases), 6) mutant forms of marker(s) molecules, e.g., dominant negative mutant forms of the molecules, 7) nucleic acids, 8) carbohydrates, and 9) natural product extract compounds.

Test compounds can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994) *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds can be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner USP '409), plasmids (Cull et al. (1992) *Proc Natl Acad Sci USA* 89:1865-1869) or phage (Scott and Smith (1990) *Science* 249:386-390; Devlin (1990) *Science* 249: 404-406; Cwirla et al. (1990) *Proc. Natl. Acad. Sci.* 87:6378-6382; Felici (1991) *J. Mol. Biol.* 222:301-310; Ladner supra.).

Compounds identified in the screening assays can be used in methods of modulating one or more of the biological responses regulated by a marker. It will be understood that it may be desirable to formulate such compound(s) as pharmaceutical compositions prior to contacting them with cells.

Once a test compound is identified by one of the variety of methods described hereinbefore, the selected test compound (or "compound of interest") can then be further evaluated for its effect on cells, for example by contacting the compound of interest with cells either in vivo (e.g., by administering the compound of interest to a subject or animal model) or ex vivo (e.g., by isolating cells from the subject or animal model and contacting the isolated cells with the compound of interest or, alternatively, by contacting the compound of interest with a cell line) and determining the effect of the compound of interest on the cells, as compared to an appropriate control (such as untreated cells or cells treated with a control compound, or carrier, that does not modulate the biological response).

Computer-based analysis of a marker with a known structure can also be used to identify molecules which will bind to a marker of the invention. Such methods rank molecules based on their shape complementary to a receptor site. For example, using a 3-D database, a program such as DOCK can be used to identify molecules which will bind. See DesJarlias et al. (1988) *J. Med. Chem.* 31:722; Meng et al. (1992) *J. Computer Chem.* 13:505; Meng et al. (1993) *Proteins* 17:266; Shoichet et al. (1993) *Science* 259:1445. In addition, the electronic complementarity of a molecule to a marker can be analyzed to identify molecules which bind to the marker. This can be determined using, for example, a molecular mechanics force field as described in Meng et al. (1992) *J. Computer Chem.* 13:505 and Meng et al. (1993) *Proteins* 17:266. Other programs which can be used include CLIX which uses a GRID force field in docking of putative ligands. See Lawrence et al. (1992) *Proteins* 12:31; Goodford et al. (1985) *J. Med. Chem.* 28:849; Boobbyer et al. (1989) *J. Med. Chem.* 32:1083.

The instant invention also pertains to compounds identified using the foregoing screening assays.

D. Methods for Modulating the Expression and/or Activity of a Biomarker of the Invention Yet another aspect of the invention pertains to methods of modulating expression and/or activity of a marker in a cell. The modulatory methods of the invention involve contacting the cell with an agent that modulates the expression and/or activity of a marker such that the expression and/or activity of a marker in the cell is modulated. In order for the expression and/or activity of a marker to be modulated in a cell, the cell is contacted with a modulatory agent in an amount sufficient to modulate the expression and/or activity of a marker.

A "modulator" or "modulatory agent" is a compound or molecule that modulates, and may be, e.g., an agonist, antagonist, activator, stimulator, suppressor, or inhibitor. As used herein, the term "modulator" refers to any moiety which modulates activity of a marker(s), including moieties which modulates marker(s) expression or modulates marker(s) function. The modulator may act by modulating the activity of a marker polypeptide in the cell, (e.g., by contacting a cell with an agent that, e.g., interfers with the binding of a marker(s) to a molecule with which it interacts, changes the binding specificity of a marker(s), or post-translationally modifies a marker(s) or the expression of a marker(s), (e.g., by modulating transcription of the marker gene or translation of the marker mRNA). Accordingly, the invention features methods for modulating one or more biological responses regulated by a marker(s) by contacting the cells with a modulator of the expression and/or activity the marker(s) such that the biological response is modulated.

Representative modulators are described below and include, but are not limited to, proteins, nucleic acid molecules, antibodies, nucleic acids (e.g., antisense molecules, such as ribozymes and RNA interfering agents), immunoconjugates (e.g., an antibody conjugated to a therapeutic agent), small molecules, fusion proteins, adnectins, aptamers, anticalins, lipocalins, and marker-derived peptidic compounds.

As used herein, the term "contacting" (e.g., contacting a cell with a modulator) is intended to include incubating the modulator and the cell together in vitro (e.g., adding the modulator to cells in culture) or administering the modulator to a subject such that the modulator and cells of the subject are contacted in vivo. The term "contacting" is not intended to include exposure of cells to an agent that may occur naturally in a subject (i.e., exposure that may occur as a result of a natural physiological process).

In one embodiment, the modulatory methods of the invention are performed in vitro. In another embodiment, the modulatory methods of the invention are performed in vivo, e.g., in a subject, e.g., having a zoonis, e.g., Brucellosis, Q-Fever, or Lyme Disease, that would benefit from modulation of the expression and/or activity of a marker of the invention.

Accordingly, the present invention also provides methods for reducing or inhibiting the development of complications associated with the disease in a subject The methods of "inhibiting", "slowing", and/or "treating" include administration of a marker modulator to a subject in order to cure or to prolong the health or survival of a subject beyond that expected in the absence of such treatment.

The terms "patient" or "subject" as used herein is intended to include human and veterinary patients. In a particular embodiment, the subject is a human. The term "non-human animal" includes all vertebrates, e.g., mammals and non-mammals, such as non-human primates, mice, rabbits, sheep, dog, cow, chickens, amphibians, and reptiles.

The methods of the invention also contemplate the use of marker(s) modulators in combination with other therapies, including surgery and/or life-style changes. Thus, in addition to the use of marker(s) modulators, the methods of the invention may also include administering to the subject one or more "standard" therapies. For example, the modulators can be administered in combination with (i.e., together with or linked to (i.e., an immunoconjugate)) cytotoxins, antibiotics, e.g., streptomycin, gentamicin, doxycycline, cotrimoxazole, azithromycin, ciprofloxacin, chloramphenicol, trimethoprim-sulfamethoxazole, rifampin, minocycline, co-trimoxazole, and members of the tetracycline and quinolone classes of compounds, or combinations thereof.

Marker(s) modulators and the co-therapeutic agent or co-therapy can be administered in the same formulation or separately. In the case of separate administration, the marker(s) modulators can be administered before, after or concurrently with the co-therapeutic or co-therapy. One agent may precede or follow administration of the other agent by intervals ranging from minutes to weeks. In embodiments where two or more different kinds of therapeutic agents are applied separately to a subject, one would generally ensure that a significant period of time did not expire between the time of each delivery, such that these different kinds of agents would still be able to exert an advantageously combined effect on the target tissues or cells.

In one embodiment, the marker(s) modulators (e.g., an anti-marker(s) antibody) may be linked to a second binding molecule, such as an antibody (i.e., thereby forming a bispecific molecule) or other binding agent that, for example, binds to a different target or a different epitope on the marker(s).

The term "effective amount" as used herein, refers to that amount of marker(s) modulators, which is sufficient to inhibit the progression of fibrosis in a subject when administered to a subject. An effective amount will vary depending upon the subject and the severity of the disease and age of the subject, the manner of administration and the like, which can readily be determined by one of ordinary skill in the art. Marker(s) modulators dosages for administration can range from, for example, about 1 ng to about 10,000 mg, about 5 ng to about 9,500 mg, about 10 ng to about 9,000 mg, about 20 ng to about 8,500 mg, about 30 ng to about 7,500 mg, about 40 ng to about 7,000 mg, about 50 ng to about 6,500 mg, about 100 ng to about 6,000 mg, about 200 ng to about 5,500 mg, about 300 ng to about 5,000 mg, about 400 ng to about 4,500 mg, about 500 ng to about 4,000 mg, about 1 μg to about 3,500 mg, about 5 μg to about 3,000 mg, about 10 μg to about 2,600 mg, about 20 μg to about 2,575 mg, about 30 μg to about 2,550 mg, about 40 μg to about 2,500 mg, about 50 μg to about 2,475 mg, about 100 μg to about 2,450 mg, about 200 μg to about 2,425 mg, about 300 μg to about 2,000, about 400 μg to about 1,175 mg, about 500 μg to about 1,150 mg, about 0.5 mg to about 1,125 mg, about 1 mg to about 1,100 mg, about 1.25 mg to about 1,075 mg, about 1.5 mg to about 1,050 mg, about 2.0 mg to about 1,025 mg, about 2.5 mg to about 1,000 mg, about 3.0 mg to about 975 mg, about 3.5 mg to about 950 mg, about 4.0 mg to about 925 mg, about 4.5 mg to about 900 mg, about 5 mg to about 875 mg, about 10 mg to about 850 mg, about 20 mg to about 825 mg, about 30 mg to about 800 mg, about 40 mg to about 775 mg, about 50 mg to about 750 mg, about 100 mg to about 725 mg, about 200 mg to about 700 mg, about 300 mg to about 675 mg, about 400 mg to about 650 mg, about 500 mg, or about 525 mg to about 625 mg, of a marker(s) modulator. Dosage regimens may be adjusted to provide the optimum therapeutic response. An effective amount is also one in which any toxic or detrimental effects (i.e., side effects) of a marker(s) modulator are minimized and/or outweighed by the beneficial effects.

Actual dosage levels of the marker(s) modulators used in the methods of the present invention may be varied so as to obtain an amount of the active ingredient which is effective to achieve the desired response, e.g., inhibiting the progression of diabetes, for a particular patient, composition, and mode of administration, without being toxic to the patient. The selected dosage level will depend upon a variety of pharmacokinetic factors including the activity of the particular marker(s) modulator employed, or the ester, salt or amide thereof, the route of administration, the time of administration, the rate of excretion of the particular modulator being employed, the duration of the treatment, other drugs, compounds and/or materials used in combination with the particular modulator employed, the age, sex, weight, condition, general health and prior medical history of the patient being treated, and like factors well known in the medical arts. A physician or veterinarian having ordinary skill in the art can readily determine and prescribe the effective amount of the modulator required. For example, the physician or veterinarian could start doses of the modulator at levels lower than that required in order to achieve the desired therapeutic effect and gradually increase the dosage until the desired effect is achieved. In general, a suitable daily dose of a marker(s) modulator will be that amount which is the lowest dose effective to produce a therapeutic effect. Such an effective dose will generally depend upon the factors described above. It is preferred that administration be intravenous, intramuscular, intraperitoneal, or subcutaneous, preferably administered proximal to the site of the target. If desired, the effective daily dose of a marker(s) modulator may be administered as two, three, four, five, six or more sub-doses administered separately at appropriate intervals throughout the day, optionally, in unit dosage forms. While it is possible for a marker(s) modulator of the present invention to be administered alone, it is preferable to administer the modulator as a pharmaceutical formulation (composition).

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. For example, the marker(s) modulators used in the methods of the present invention may be administered once or twice weekly by subcutaneous injection or once or twice monthly by subcutaneous injection.

To administer a marker(s) modulator used in the methods of the present invention by certain routes of administration, it may be necessary to include the modulator in a formulation suitable for preventing its inactivation. For example, the marker(s) modulator may be administered to a subject in an appropriate carrier, for example, liposomes, or a diluent. Pharmaceutically acceptable diluents include saline and aqueous buffer solutions. Liposomes include water-in-oil-in-water CGF emulsions, as well as conventional liposomes (Strejan et al. (1984) *J. Neuroimmunol.* 7:27).

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active marker(s) modulator, use thereof in pharmaceutical compositions is contemplated. Supplementary active compounds can also be incorporated with the marker(s) modulator.

Marker(s) modulators used in the methods of the invention typically must be sterile and stable under the conditions of manufacture and storage. The modulator can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including an agent that delays absorption, for example, monostearate salts and gelatin.

Sterile injectable solutions can be prepared by incorporating the active modulator in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Marker(s) modulators that can be used in the methods of the present invention include those suitable for oral, nasal, topical (including buccal and sublingual), rectal, vaginal and/or parenteral administration. The formulations may conveniently be presented in unit dosage form and may be prepared by any methods known in the art of pharmacy. The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the modulator which produces a therapeutic effect. Generally, out of one hundred percent, this amount will range from about 0.001% to about 90% of active ingredient, preferably from about 0.005% to about 70%, most preferably from about 0.01% to about 30%.

The phrases "parenteral administration" and "administered parenterally", as used herein, means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Examples of suitable aqueous and non-aqueous carriers which may be employed along with the marker(s) modulators utilized in the methods of the present invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Marker(s) modulatos may also be administered with adjuvants such as preservatives, wetting agents, emulsifying agents and dispersing agents. Prevention of presence of microorganisms may be ensured both by sterilization procedures and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

When marker(s) modulators used in the methods of the present invention are administered to humans and animals, they can be given alone or as a pharmaceutical modulator containing, for example, 0.001 to 90% (more preferably, 0.005 to 70%, such as 0.01 to 30%) of active ingredient in combination with a pharmaceutically acceptable carrier.

Marker(s) modulators can be administered with medical devices known in the art. For example, in a preferred embodiment, a modulator can be administered with a needleless hypodermic injection device, such as the devices disclosed in U.S. Pat. No. 5,399,163, 5,383,851, 5,312,335, 5,064,413, 4,941,880, 4,790,824, or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medications through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multichamber compartments; and U.S. Pat. No. 4,475,196, which discloses an osmotic drug delivery system. Many other such implants, delivery systems, and modules are known to those skilled in the art.

1. Inhibitory Agents

According to a modulatory method of the invention, the expression and/or activity of a marker(s) is inhibited in a cell or subject by contacting the cell with (or administering to a subject) an inhibitory agent Inhibitory agents of the invention can be, for example, molecules that act to decrease or inhibit the expression and/or activity of the marker(s).

In one embodiment of the invention, the modulatory, e.g., therapeutic, and diagnostic methods described herein employ an antibody that binds, e.g., directly to or indirectly to, and inhibits marker(s) activity and/or down-modulates marker(s) expression.

The term "antibody" or "immunoglobulin," as used interchangeably herein, includes whole antibodies and any antigen binding fragment (i.e., "antigen-binding portion") or single chains thereof. An "antibody" comprises at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or simply "antibody portion"), as used herein, refers to one or more fragments of an antibody that retain the ability to specifically bind to an antigen (e.g., a marker). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, CL and CH1 domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb including VH and VL domains; (vi) a dAb fragment (Ward et al. (1989) Nature 341, 544-546), which consists of a $V_H$ domain; (vii) a dAb which consists of a VH or a VL domain; and (viii) an isolated complementarity determining region (CDR) or (ix) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242, 423-426; and Huston et al. (1988) Proc. Natl. Acad. Sci. USA 85, 5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

The term "antibody", as used herein, includes polyclonal antibodies, monoclonal antibodies, chimeric antibodies, humanized antibodies, and human antibodies, and those that occur naturally or are recombinantly produced according to methods well known in the art.

In one embodiment, an antibody for use in the methods of the invention is a bispecific antibody. A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, (1990) Clin. Exp. Immunol. 79, 315-321; Kostelny et al. (1992) J. Immunol. 148, 1547-1553.

In another embodiment, an antibody for use in the methods of the invention is a camelid antibody as described in, for example, PCT Publication WO 94/04678, the entire contents of which are incorporated herein by reference.

A region of the camelid antibody that is the small, single variable domain identified as $V_{HH}$ can be obtained by genetic engineering to yield a small protein having high affinity for a target, resulting in a low molecular weight, antibody-derived protein known as a "camelid nanobody". See U.S. Pat. No. 5,759,808; see also Stijlemans et al., 2004 J. Biol. Chem. 279: 1256-1261; Dumoulin et al., 2003 Nature 424: 783-788; Pleschberger et al., 2003 Bioconjugate Chem. 14: 440-448; Cortez-Retamozo et al., 2002 Int. J. Cancer 89: 456-62; and Lauwereys, et al., 1998 EMBO J. 17: 3512-3520. Engineered libraries of camelid antibodies and antibody fragments are commercially available, for example, from Ablynx, Ghent, Belgium. Accordingly, a feature of the present invention is a camelid nanobody having high affinity for a marker.

In other embodiments of the invention, an antibody for use in the methods of the invention is a diabody, a single chain diabody, or a di-diabody.

Diabodies are bivalent, bispecific molecules in which $V_H$ and $V_L$ domains are expressed on a single polypeptide chain, connected by a linker that is too short to allow for pairing between the two domains on the same chain. The $V_H$ and $V_L$ domains pair with complementary domains of another chain, thereby creating two antigen binding sites (see e.g., Holliger et al., 1993 Proc. Natl. Acad. Sci. USA 90:6444-6448; Poljak et al., 1994 Structure 2:1121-1123). Diabodies can be produced by expressing two polypeptide chains with either the structure $V_{HA}$-$V_{LB}$ and $V_{HB}$-$V_{LA}$ ($V_H$-$V_L$ configuration), or $V_{LA}$-$V_{HB}$ and $V_{LB}$-$V_{HA}$ ($V_L$-$V_H$ configuration) within the same cell. Most of them can be expressed in soluble form in bacteria.

Single chain diabodies (scDb) are produced by connecting the two diabody-forming polypeptide chains with linker of approximately 15 amino acid residues (see Holliger and Winter, 1997 Cancer Immunol. Immunother., 45(3-4):128-30; Wu et al., 1996 Immunotechnology, 2(1):21-36). scDb can be expressed in bacteria in soluble, active monomeric form (see Holliger and Winter, 1997 Cancer Immunol. Immunother., 45(34): 128-30; Wu et al., 1996 Immunotechnology, 2(1):21-36; Pluckthun and Pack, 1997 Immunotechnology, 3(2): 83-105; Ridgway et al., 1996 Protein Eng., 9(7):617-21).

A diabody can be fused to Fc to generate a "di-diabody" (see Lu et al., 2004 J. Biol. Chem., 279(4):2856-65).

Marker binding molecules that exhibit functional properties of antibodies but derive their framework and antigen binding portions from other polypeptides (e.g., polypeptides other than those encoded by antibody genes or generated by the recombination of antibody genes in vivo) may also be used in the methods of the present invention. The antigen binding domains (e.g., marker binding domains) of these binding molecules are generated through a directed evolution process. See U.S. Pat. No. 7,115,396. Molecules that have an overall fold similar to that of a variable domain of an antibody (an "immunoglobulin-like" fold) are appropriate scaffold proteins. Scaffold proteins suitable for deriving antigen binding molecules include fibronectin or a fibronectin dimer, tenascin, N-cadherin, E-cadherin, ICAM, titin, GCSF-receptor, cytokine receptor, glycosidase inhibitor, antibiotic chromoprotein, myelin membrane adhesion molecule P0, CD8, CD4, CD2, class I MHC, T-cell antigen receptor, CD1, C2 and I-set domains of VCAM-1, I-set immunoglobulin domain of myosin-binding protein C, I-set immunoglobulin domain of myosin-binding protein H, I-set immunoglobulin domain of telokin, NCAM, twitchin, neuroglian, growth hormone receptor, erythropoietin receptor, prolactin receptor, interferon-gamma receptor, β-galactosidase/glucuronidase, β-glucuronidase, transglutaminase, T-cell antigen receptor, superoxide dismutase, tissue factor domain, cytochrome F, green fluorescent protein, GroEL, and thaumatin.

To generate non-antibody binding molecules, a library of clones is created in which sequences in regions of the scaffold protein that form antigen binding surfaces (e.g., regions analogous in position and structure to CDRs of an antibody variable domain immunoglobulin fold) are randomized Library clones are tested for specific binding to the antigen of interest (e.g., a marker(s) of the invention) and for other functions (e.g., inhibition of biological activity of a marker(s) of the invention). Selected clones can be used as the basis for further randomization and selection to produce derivatives of higher affinity for the antigen.

High affinity binding molecules are generated, for example, using the tenth module of fibronectin III ($^{10}$Fn3) as the scaffold, described in U.S. Pat. Nos. 6,818,418 and 7,115,396; Roberts and Szostak, 1997 *Proc. Natl. Acad. Sci USA* 94:12297; U.S. Pat. No. 6,261,804; U.S. Pat. No. 6,258,558; and Szostak et al. WO98/31700, the entire contents of each of which are incorporated herein by reference.

Non-antibody binding molecules can be produced as dimers or multimers to increase avidity for the target antigen. For example, the antigen binding domain is expressed as a fusion with a constant region (Fc) of an antibody that forms Fc-Fc dimers. See, e.g., U.S. Pat. No. 7,115,396, the entire contents of which are incorporated herein by reference.

The therapeutic methods of the invention also may be practiced through the use of antibody fragments and antibody mimetics. As detailed below, a wide variety of antibody fragment and antibody mimetic technologies have now been developed and are widely known in the art. While a number of these technologies, such as domain antibodies, Nanobodies, and UniBodies make use of fragments of, or other modifications to, traditional antibody structures, there are also alternative technologies, such as Adnectins, Affibodies, DARPins, Anticalins, Avimers, and Versabodies that employ binding structures that, while they mimic traditional antibody binding, are generated from and function via distinct mechanisms. Some of these alternative structures are reviewed in Gill and Damle (2006) 17: 653-658.

Domain Antibodies (dAbs) are the smallest functional binding units of antibodies, corresponding to the variable regions of either the heavy (VH) or light (VL) chains of human antibodies. Domantis has developed a series of large and highly functional libraries of fully human VH and VL dAbs (more than ten billion different sequences in each library), and uses these libraries to select dAbs that are specific to therapeutic targets. In contrast to many conventional antibodies, domain antibodies are well expressed in bacterial, yeast, and mammalian cell systems. Further details of domain antibodies and methods of production thereof may be obtained by reference to U.S. Pat. Nos. 6,291,158; 6,582,915; 6,593,081; 6,172,197; 6,696,245; U.S. Serial No. 2004/0110941; European patent application No. 1433846 and European Patents 0368684 & 0616640; WO05/035572, WO04/101790, WO04/081026, WO04/058821, WO04/003019 and WO03/002609, the contents of each of which is herein incorporated by reference in its entirety.

Nanobodies are antibody-derived therapeutic proteins that contain the unique structural and functional properties of naturally-occurring heavy-chain antibodies. These heavy-chain antibodies contain a single variable domain (VHH) and two constant domains (CH2 and CH3) Importantly, the cloned and isolated VHH domain is a perfectly stable polypeptide harboring the full antigen-binding capacity of the original heavy-chain antibody. Nanobodies have a high homology with the VH domains of human antibodies and can be further humanized without any loss of activity.

Nanobodies are encoded by single genes and are efficiently produced in almost all prokaryotic and eukaryotic hosts, e.g., *E. coli* (see, e.g., U.S. Pat. No. 6,765,087, which is herein incorporated by reference in its entirety), molds (for example *Aspergillus* or *Trichoderma*) and yeast (for example *Saccharomyces, Kluyveromyces, Hansenula* or *Pichia*) (see, e.g., U.S. Pat. No. 6,838,254, which is herein incorporated by reference in its entirety). The production process is scalable and multi-kilogram quantities of Nanobodies have been produced. Because Nanobodies exhibit a superior stability compared with conventional antibodies, they can be formulated as a long shelf-life, ready-to-use solution.

The Nanoclone method (see, e.g., WO 06/079372, which is herein incorporated by reference in its entirety) is a proprietary method for generating Nanobodies against a desired target, based on automated high-throughout selection of B-cells and could be used in the context of the instant invention.

UniBodies are another antibody fragment technology, however this one is based upon the removal of the hinge region of IgG4 antibodies. The deletion of the hinge region results in a molecule that is essentially half the size of traditional IgG4 antibodies and has a univalent binding region rather than the bivalent binding region of IgG4 antibodies. It is also well known that IgG4 antibodies are inert and thus do not interact with the immune system, which may be advantageous for the treatment of diseases where an immune response is not desired, and this advantage is passed onto UniBodies. Further details of UniBodies may be obtained by reference to patent application WO2007/059782, which is herein incorporated by reference in its entirety.

Adnectin molecules are engineered binding proteins derived from one or more domains of the fibronectin protein. In one embodiment, adnectin molecules are derived from the fibronectin type 21 domain by altering the native protein which is composed of multiple beta strands distributed between two beta sheets. Depending on the originating tissue, fibronectin may contain multiple type 21 domains which may be denoted, e.g., $^{1}$Fn3, $^{2}$Fn3, $^{3}$Fn3, etc. Adnectin molecules may also be derived from polymers of $^{10}$Fn3 related molecules rather than a simple monomeric $^{10}$Fn3 structure.

Although the native $^{10}$Fn3 domain typically binds to integrin, $^{10}$Fn3 proteins adapted to become adnectin molecules are altered so to bind antigens of interest, e.g., a marker(s). In one embodiment, the alteration to the $^{10}$Fn3 molecule comprises at least one mutation to a beta strand. In a preferred embodiment, the loop regions which connect the beta strands of the $^{10}$Fn3 molecule are altered to bind to an antigen of interest, e.g., a marker(s). The alterations in the $^{10}$Fn3 may be made by any method known in the art including, but not limited to, error prone PCR, site-directed mutagenesis, DNA shuffling, or other types of recombinational mutagenesis which have been referenced herein. In one example, variants of the DNA encoding the $^{10}$Fn3 sequence may be directly synthesized in vitro, and later transcribed and translated in vitro or in vivo. Alternatively, a natural $^{10}$Fn3 sequence may be isolated or cloned from the genome using standard methods (as performed, e.g., in U.S. Pat. Application No. 20070082365), and then mutated using mutagenesis methods known in the art.

An aptamer is another type of antibody-mimetic which may be used in the methods of the present invention. Aptamers are typically small nucleotide polymers that bind to specific molecular targets. Aptamers may be single or double stranded nucleic acid molecules (DNA or RNA), although DNA based aptamers are most commonly double stranded. There is no defined length for an aptamer nucleic acid; however, aptamer molecules are most commonly between 15 and 40 nucleotides long.

Aptamers may be generated using a variety of techniques, but were originally developed using in vitro selection (Ellington and Szostak. (1990) *Nature.* 346(6287):818-22) and the SELEX method (systematic evolution of ligands by exponential enrichment) (Schneider et al. 1992. *J Mol Biol.* 228(3):862-9) the contents of which are incorporated herein by reference. Other methods to make and uses of aptamers have been published including Klussmann. The Aptamer Handbook: Functional Oligonucleotides and Their Applications. ISBN: 978-3-527-31059-3; Ulrich et al. 2006. *Comb Chem High Throughput Screen* 9(8):619-32; Cerchia and de Franciscis. 2007. *Methods Mol Biol.* 361:187-200; Ireson and Kelland. 2006. *Mol Cancer Ther.* 2006 5(12):2957-62; U.S. Pat. Nos. 5,582,981; 5,840,867; 5,756,291; 6,261,783; 6,458,559; 5,792,613; 6,111,095; and U.S. patent application Ser. Nos. 11/482,671; 11/102,428; 11/291,610; and 10/627,543 which are all incorporated herein by reference.

Aptamer molecules made from peptides instead of nucleotides may also be used in the methods of the invention. Peptide aptamers share many properties with nucleotide aptamers (e.g, small size and ability to bind target molecules with high affinity) and they may be generated by selection methods that have similar principles to those used to generate nucleotide aptamers, for example Baines and Colas. 2006. *Drug Discov Today.* 11(7-8):334-41; and Bickle et al. 2006. *Nat Protoc.* 1(3):1066-91 which are incorporated herein by reference.

Affibody molecules represent a class of affinity proteins based on a 58-amino acid residue protein domain, derived from one of the IgG-binding domains of staphylococcal protein A. This three helix bundle domain has been used as a scaffold for the construction of combinatorial phagemid libraries, from which Affibody variants that target the desired molecules can be selected using phage display technology (Nord K, et al. *Nat Biotechnol* 1997; 15:772-7. Ronmark J, et al., *Eur J Biochem* 2002; 269:2647-55). Further details of Affibodies and methods of production thereof may be obtained by reference to U.S. Pat. No. 5,831,012 which is herein incorporated by reference in its entirety.

DARPins (Designed Ankyrin Repeat Proteins) are one example of an antibody mimetic DRP (Designed Repeat Protein) technology that has been developed to exploit the binding abilities of non-antibody polypeptides. Repeat proteins such as ankyrin or leucine-rich repeat proteins, are ubiquitous binding molecules, which occur, unlike antibodies, intra- and extracellularly. Their unique modular architecture features repeating structural units (repeats), which stack together to form elongated repeat domains displaying variable and modular target-binding surfaces. Based on this modularity, combinatorial libraries of polypeptides with highly diversified binding specificities can be generated. This strategy includes the consensus design of self-compatible repeats displaying variable surface residues and their random assembly into repeat domains.

Additional information regarding DARPins and other DRP technologies can be found in U.S. Patent Application Publication No. 2004/0132028 and International Patent Application Publication No. WO 02/20565, both of which are hereby incorporated by reference in their entirety.

Anticalins are an additional antibody mimetic technology, however in this case the binding specificity is derived from lipocalins, a family of low molecular weight proteins that are naturally and abundantly expressed in human tissues and body fluids. Lipocalins have evolved to perform a range of functions in vivo associated with the physiological transport and storage of chemically sensitive or insoluble compounds. Lipocalins have a robust intrinsic structure comprising a highly conserved β-barrel which supports four loops at one terminus of the protein. These loops form the entrance to a binding pocket and conformational differences in this part of the molecule account for the variation in binding specificity between individual lipocalins.

Lipocalins are cloned and their loops are subjected to engineering in order to create Anticalins. Libraries of structurally diverse Anticalins have been generated and Anticalin display allows the selection and screening of binding function, followed by the expression and production of soluble protein for further analysis in prokaryotic or eukaryotic systems. Studies have successfully demonstrated that Anticalins can be developed that are specific for virtually any human target protein can be isolated and binding affinities in the nanomolar or higher range can be obtained.

Anticalins can also be formatted as dual targeting proteins, so-called Duocalins. A Duocalin binds two separate therapeutic targets in one easily produced monomeric protein using standard manufacturing processes while retaining target specificity and affinity regardless of the structural orientation of its two binding domains.

Additional information regarding Anticalins can be found in U.S. Pat. No. 7,250,297 and International Patent Application Publication No. WO 99/16873, both of which are hereby incorporated by reference in their entirety.

Another antibody mimetic technology useful in the context of the instant invention are Avimers. Avimers are evolved from a large family of human extracellular receptor domains by in vitro exon shuffling and phage display, generating multidomain proteins with binding and inhibitory properties. Linking multiple independent binding domains has been shown to create avidity and results in improved affinity and specificity compared with conventional single-epitope binding proteins. Other potential advantages include simple and efficient production of multitarget-specific molecules in *Escherichia coli*, improved thermostability and resistance to proteases. Avimers with sub-nanomolar affinities have been obtained against a variety of targets.

Additional information regarding Avimers can be found in U.S. Patent Application Publication Nos. 2006/0286603, 2006/0234299, 2006/0223114, 2006/0177831, 2006/0008844, 2005/0221384, 2005/0164301, 2005/0089932, 2005/0053973, 2005/0048512, 2004/0175756, all of which are hereby incorporated by reference in their entirety.

Versabodies are another antibody mimetic technology that could be used in the context of the instant invention. Versabodies are small proteins of 3-5 kDa with >15% cysteines, which form a high disulfide density scaffold, replacing the hydrophobic core that typical proteins have. The replacement of a large number of hydrophobic amino acids, comprising the hydrophobic core, with a small number of disulfides results in a protein that is smaller, more hydrophilic (less aggregation and non-specific binding), more resistant to proteases and heat, and has a lower density of T-cell epitopes, because the residues that contribute most to MHC presentation are hydrophobic. All four of these properties are well-known to affect immunogenicity, and together they are expected to cause a large decrease in immunogenicity.

Additional information regarding Versabodies can be found in U.S. Patent Application Publication No. 2007/0191272 which is hereby incorporated by reference in its entirety.

SMIPs™ (Small Modular ImmunoPharmaceuticals-Trubion Pharmaceuticals) engineered to maintain and optimize target binding, effector functions, in vivo half-life, and expression levels. SMIPS consist of three distinct modular domains. First they contain a binding domain which may consist of any protein which confers specificity (e.g., cell surface receptors, single chain antibodies, soluble proteins, etc). Secondly, they contain a hinge domain which serves as a flexible linker between the binding domain and the effector domain, and also helps control multimerization of the SMIP drug. Finally, SMIPS contain an effector domain which may be derived from a variety of molecules including Fc domains or other specially designed proteins. The modularity of the design, which allows the simple construction of SMIPs with a variety of different binding, hinge, and effector domains, provides for rapid and customizable drug design.

More information on SMIPs, including examples of how to design them, may be found in Zhao et al. (2007) Blood 110:2569-77 and the following U.S. Pat. App. Nos. 20050238646; 20050202534; 20050202028; 20050202023; 20050202012; 20050186216; 20050180970; and 20050175614.

In another aspect, the methods of the present invention employ immunoconjugate agents that target a marker(s) and which inhibit or down-modulate the marker(s). Agents that can be targeted to a marker(s) include, but are not limited to, cytotoxic agents, anti-inflammatory agents, e.g., a steroidal or nonsteroidal inflammatory agent, or a cytotoxin antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

In another embodiment, marker(s) modulator employed in the methods of the invention are small molecules. As used herein, the term "small molecule" is a term of the art and includes molecules that are less than about 7500, less than about 5000, less than about 1000 molecular weight or less than about 500 molecular weight, and inhibit marker(s) activity. Exemplary small molecules include, but are not limited to, small organic molecules (e.g., Cane et al. 1998. Science 282:63), and natural product extract libraries. In another embodiment, the compounds are small, organic non-peptidic compounds. Like antibodies, these small molecule inhibitors indirectly or directly inhibit the activity of a marker(s).

In another embodiment, the marker(s) modulator employed in the methods of the present invention is an antisense nucleic acid molecule that is complementary to a gene encoding a marker(s) or to a portion of that gene, or a recombinant expression vector encoding the antisense nucleic acid molecule. As used herein, an "antisense" nucleic acid comprises a nucleotide sequence which is complementary to a "sense" nucleic acid encoding a protein, e.g., complementary to the coding strand of a double-stranded cDNA molecule, complementary to an mRNA sequence or complementary to the coding strand of a gene. Accordingly, an antisense nucleic acid can hydrogen bond to a sense nucleic acid.

The use of antisense nucleic acids to down-modulate the expression of a particular protein in a cell is well known in the art (see e.g., Weintraub, H. et al., Antisense RNA as a molecular tool for genetic analysis, *Reviews—Trends in Genetics*, Vol. 1(1) 1986; Askari, F. K. and McDonnell, W. M. (1996) *N. Eng. J. Med.* 334:316-318; Bennett, M. R. and Schwartz, S. M. (1995) *Circulation* 92:1981-1993; Mercola, D. and Cohen, J. S. (1995) *Cancer Gene Ther.* 2:47-59; Rossi, J. J. (1995) *Br. Med. Bull.* 51:217-225; Wagner, R. W. (1994) *Nature* 372:333-335). An antisense nucleic acid molecule comprises a nucleotide sequence that is complementary to the coding strand of another nucleic acid molecule (e.g., an mRNA sequence) and accordingly is capable of hydrogen bonding to the coding strand of the other nucleic acid molecule. Antisense sequences complementary to a sequence of an mRNA can be complementary to a sequence found in the coding region of the mRNA, the 5' or 3' untranslated region of the mRNA or a region bridging the coding region and an untranslated region (e.g., at the junction of the 5' untranslated region and the coding region). Furthermore, an antisense nucleic acid can be complementary in sequence to a regulatory region of the gene encoding the mRNA, for instance a transcription initiation sequence or regulatory element. Preferably, an antisense nucleic acid is designed so as to be complementary to a region preceding or spanning the initiation codon on the coding strand or in the 3' untranslated region of an mRNA.

Antisense nucleic acids can be designed according to the rules of Watson and Crick base pairing. The antisense nucleic acid molecule can be complementary to the entire coding region of marker(s) mRNA, but more preferably is an oligonucleotide which is antisense to only a portion of the coding or noncoding region of marker(s) mRNA. For example, the antisense oligonucleotide can be complementary to the region surrounding the translation start site of marker(s) mRNA. An antisense oligonucleotide can be, for example, about 5, 10, 15, 20, 25, 30, 35, 40, 45 or 50 nucleotides in length.

An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules that can be utilized in the methods of the present invention are typically administered to a subject or generated in situ such that they hybridize with or bind to cellular mRNA and/or genomic DNA encoding a marker(s) to thereby inhibit expression by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using vectors well known in the art and described in, for example, US20070111230 the entire contents of which are incorporated herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule employed by the methods of the present invention can include an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215:327-330).

In another embodiment, an antisense nucleic acid used in the methods of the present invention is a compound that mediates RNAi. RNA interfering agents include, but are not limited to, nucleic acid molecules including RNA molecules which are homologous to a marker(s) or a fragment thereof, "short interfering RNA" (siRNA), "short hairpin" or "small hairpin RNA" (shRNA), and small molecules which interfere with or inhibit expression of a target gene by RNA interference (RNAi). RNA interference is a post-transcriptional, targeted gene-silencing technique that uses double-stranded RNA (dsRNA) to degrade messenger RNA (mRNA) containing the same sequence as the dsRNA (Sharp, P. A. and Zamore, P. D. 287, 2431-2432 (2000); Zamore, P. D., et al. *Cell* 101, 25-33 (2000). Tuschl, T. et al. *Genes Dev.* 13, 3191-3197 (1999)). The process occurs when an endogenous ribonuclease cleaves the longer dsRNA into shorter, 21- or 22-nucleotide-long RNAs, termed small interfering RNAs or siRNAs. The smaller RNA segments then mediate the degradation of the target mRNA. Kits for synthesis of RNAi are commercially available from, e.g., New England Biolabs and Ambion. In one embodiment one or more of the chemistries described above for use in antisense RNA can be employed.

In still another embodiment, an antisense nucleic acid is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach, 1988, *Nature* 334:585-591) can be used to catalytically cleave marker(s) mRNA transcripts to thereby inhibit translation of the marker(s) mRNA.

Alternatively, gene expression can be inhibited by targeting nucleotide sequences complementary to the regulatory region of a marker(s) (e.g., the promoter and/or enhancers) to form triple helical structures that prevent transcription of the marker(s) gene. See generally, Helene, C., 1991, *Anticancer Drug Des.* 6(6):569-84; Helene, C. et al., 1992, *Ann. N.Y. Acad. Sci.* 660:27-36; and Maher, L. J., 1992, *Bioassays* 14(12):807-15.

In another embodiment, the marker(s) modulator used in the methods of the present invention is a fusion protein or peptidic compound derived from the marker(s) amino acid sequence. In particular, the inhibitory compound comprises a fusion protein or a portion of a marker(s) (or a mimetic thereof) that mediates interaction of the marker(s) with a target molecule such that contact of the marker(s) with this fusion protein or peptidic compound competitively inhibits the interaction of the marker(s) with the target molecule. Such fusion proteins and peptidic compounds can be made using standard techniques known in the art. For example, peptidic compounds can be made by chemical synthesis using standard peptide synthesis techniques and then introduced into cells by a variety of means known in the art for introducing peptides into cells (e.g., liposome and the like).

The in vivo half-life of the fusion protein or peptidic compounds of the invention can be improved by making peptide modifications, such as the addition of N-linked glycosylation sites into the marker(s) or conjugating the marker(s) to poly(ethylene glycol) (PEG; pegylation), e.g., via lysine-monopegylation. Such techniques have proven to be beneficial in prolonging the half-life of therapeutic protein drugs. It is expected that pegylation of marker(s) polypeptides of the invention may result in similar pharmaceutical advantages.

In addition, pegylation can be achieved in any part of a polypeptide of the invention by the introduction of a nonnatural amino acid. Certain nonnatural amino acids can be introduced by the technology described in Deiters et al., *J Am Chem Soc* 125:11782-11783, 2003; Wang and Schultz, *Science* 301:964-967, 2003; Wang et al., *Science* 292:498-500, 2001; Zhang et al., *Science* 303:371-373, 2004 or in U.S. Pat. No. 7,083,970. Briefly, some of these expression systems involve site-directed mutagenesis to introduce a nonsense codon, such as an amber TAG, into the open reading frame encoding a polypeptide of the invention. Such expression vectors are then introduced into a host that can utilize a tRNA specific for the introduced nonsense codon and charged with the nonnatural amino acid of choice. Particular nonnatural amino acids that are beneficial for purpose of conjugating moieties to the polypeptides of the invention include those with acetylene and azido side chains. Marker(s) polypeptides containing these novel amino acids can then be pegylated at these chosen sites in the protein.

2. Stimulatory Agents

According to a modulatory method of the invention, the expression and/or activity of a marker(s) is stimulated in a cell or subject by contacting the cell with (or administering to a subject) a stimulatory agent. Stimulatory agents of the invention can be, for example, molecules that act to stimulate or increase the expression and/or activity of the marker(s).

Examples of such stimulatory agents include active marker(s) polypeptide and nucleic acid molecules encoding the marker(s) that are introduced into the cell to increase expression and/or activity of the marker in the cell. A preferred stimulatory agent is a nucleic acid molecule encoding a marker(s) polypeptide, wherein the nucleic acid molecule is introduced into the cell in a form suitable for expression of the active marker(s) polypeptide in the cell. To express a marker(s) polypeptide in a cell, typically a marker(s)-encoding cDNA (full length or partial cDNA sequence) is first introduced into a recombinant expression vector using standard molecular biology techniques, and the vector may be transfected into cells using standard molecular biology techniques. A cDNA can be obtained, for example, by amplification using the polymerase chain reaction (PCR), using primers based on the marker(s) nucleotide sequence or by screening an appropriate cDNA library.

The nucleic acids for use in the methods of the invention can also be prepared, e.g., by standard recombinant DNA techniques. A nucleic acid of the invention can also be chemically synthesized using standard techniques. Various methods of chemically synthesizing polydeoxynucleotides are known, including solid-phase synthesis which has been automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071, incorporated by reference herein).

In one embodiment, a nucleic acid molecule encoding a marker(s) may be present in an inducible construct. In another embodiment, a nucleic acid molecule encoding marker(s) may be present in a construct which leads to constitutive expression. In one embodiment, a nucleic acid molecule encoding marker(s) may be delivered to cells, or to subjects, in the absence of a vector.

A nucleic acid molecule encoding marker(s) may be delivered to cells or to subjects using a viral vector, preferably one whose use for gene therapy is well known in the art. Techniques for the formation of vectors or virions are generally described in "Working Toward Human Gene Therapy," Chapter 28 in Recombinant DNA, 2nd Ed., Watson, J. D. et al., eds., New York: Scientific American Books, pp. 567-581 (1992). An overview of suitable viral vectors or virions is provided in Wilson, J. M., Clin. Exp. Immunol. 107(Suppl. 1):31-32 (1997), as well as Nakanishi, M., Crit. Rev. Therapeu. Drug Carrier Systems 12:263-310 (1995); Robbins, P. D., et al., Trends Biotechnol. 16:35-40 (1998); Zhang, J., et al., Cancer Metastasis Rev. 15:385-401 (1996); and Kramm, C. M., et al., Brain Pathology 5:345-381 (1995). Such vectors may be derived from viruses that contain RNA (Vile, R. G., et al., Br. Med Bull. 51:12-30 (1995)) or DNA (Ali M., et al., Gene Ther. 1:367-384 (1994)).

Examples of viral vector systems utilized in the gene therapy art and, thus, suitable for use in the present invention, include the following: retroviruses (Vile, R. G., supra; U.S. Pat. Nos. 5,741,486 and 5,763,242); adenoviruses (Brody, S. L., et al., Ann. N.Y. Acad. Sci. 716: 90-101 (1994); Heise, C. et al., Nat. Med. 3:639-645 (1997)); adenoviral/retroviral chimeras (Bilbao, G., et al., FASEB J. 11:624-634 (1997); Feng, M., et al., Nat. Biotechnol. 15:866-870 (1997)); adeno-associated viruses (Flotte, T. R. and Carter, B. J., Gene Ther. 2:357-362 (1995); U.S. Pat. No. 5,756,283); herpes simplex virus I or II (Latchman, D. S., Mol. Biotechnol. 2:179-195 (1994); U.S. Pat. No. 5,763,217; Chase, M., et al., Nature Biotechnol. 16:444-448 (1998)); parvovirus (Shaughnessy, E., et al., Semin Oncol. 23:159-171 (1996)); reticuloendotheliosis virus (Donburg, R., Gene Therap. 2:301-310 (1995)). Extrachromosomal replicating vectors may also be used in the gene therapy methods of the present invention. Such vectors are described in, for example, Calos, M. P. (1996) Trends Genet. 12:463-466, the entire contents of which are incorporated herein by reference. Other viruses that can be used as vectors for gene delivery include poliovirus, papillomavirus, vaccinia virus, lentivirus, as well as hybrid or chimeric vectors incorporating favorable aspects of two or more viruses (Nakanishi, M. (1995) Crit. Rev. Therapeu. Drug Carrier Systems 12:263-310; Zhang, J., et al. (1996) Cancer Metastasis Rev. 15:385-401; Jacoby, D. R., et al. (1997) Gene Therapy 4:1281-1283).

The term "AAV vector" refers to a vector derived from an adeno-associated virus serotype, including without limitation, AAV-1, AAV-2, AAV-3, AAV-4, AAV-5, or AAVX7. "rAAV vector" refers to a vector that includes AAV nucleotide sequences as well as heterologous nucleotide sequences. rAAV vectors require only the 145 base terminal repeats in cis to generate virus. All other viral sequences are dispensable and may be supplied in trans (Muzyczka (1992) Curr. Topics Microbiol. Immunol. 158:97). Typically, the rAAV vector genome will only retain the inverted terminal repeat (ITR) sequences so as to maximize the size of the transgene that can be efficiently packaged by the vector. The ITRs need not be the wild-type nucleotide sequences, and may be altered, e.g., by the insertion, deletion or substitution of nucleotides, as long as the sequences provide for functional rescue, replication and packaging. In particular embodiments, the AAV vector is an AAV2/5 or AAV2/8 vector. Suitable AAV vectors are described in, for example, U.S. Pat. No. 7,056,502 and Yan et al. (2002) J. Virology 76(5): 2043-2053, the entire contents of which are incorporated herein by reference.

As used herein, the term "lentivirus" refers to a group (or genus) of retroviruses that give rise to slowly developing disease. Viruses included within this group include HIV (human immunodeficiency virus; including but not limited to HIV type 1 and HIV type 2), the etiologic agent of the human acquired immunodeficiency syndrome (AIDS); visna-maedi, which causes encephalitis (visna) or pneumonia (maedi) in sheep; the caprine arthritis-encephalitis virus, which causes immune deficiency, arthritis, and encephalopathy in goats; equine infectious anemia virus (EIAV), which causes autoimmune hemolytic anemia, and encephalopathy in horses; feline immunodeficiency virus (FIV), which causes immune deficiency in cats; bovine immune deficiency virus (BIV), which causes lymphadenopathy, lymphocytosis, and possibly central nervous system infection in cattle; and simian immunodeficiency virus (SIV), which cause immune deficiency and encephalopathy in sub-human primates. Diseases caused by these viruses are characterized by a long incubation period and protracted course. Usually, the viruses latently infect monocytes and macrophages, from which they spread to other cells. HIV, FIV, and SIV also readily infect T lymphocytes (i.e., T-cells). In one embodiment of the invention, the lentivirus is not HIV.

As used herein, the term "adenovirus" ("Ad") refers to a group of double-stranded DNA viruses with a linear genome of about 36 kb. See, e.g., Berkner et al., Curr. Top. Microbiol. Immunol., 158: 39-61 (1992). In some embodiments, the adenovirus-based vector is an Ad-2 or Ad-5 based vector. See, e.g., Muzyczka, Curr. Top. Microbiol. Immunol., 158: 97-123, 1992; Ali et al., 1994 Gene Therapy 1: 367-384; U.S. Pat. Nos. 4,797,368, and 5,399,346. Suitable adenovirus vectors derived from the adenovirus strain Ad type 5 d1324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types. Additionally, introduced adenovirus DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenovirus genome for foreign DNA is large (up to 8 kilobases) relative to other gene delivery vectors (Haj-Ahmand et al. J. Virol. 57, 267-273 [1986]).

In one embodiment, an adenovirus is a replication defective adenovirus. Most replication-defective adenoviral vectors currently in use have all or parts of the viral E1 and E3 genes deleted but retain as much as 80% of the adenovirus genetic material. Adenovirus vectors deleted for all viral coding regions are also described by Kochanek et al. and Chamberlain et al. (U.S. Pat. No. 5,985,846 and U.S. Pat. No. 6,083,750). Such viruses are unable to replicate as viruses in the absence of viral products provided by a second virus, referred to as a "helper" virus.

In one embodiment, an adenoviral vector is a "gutless" vector. Such vectors contain a minimal amount of adenovirus DNA and are incapable of expressing any adenovirus antigens (hence the term "gutless"). The gutless replication defective Ad vectors provide the significant advantage of accommodating large inserts of foreign DNA while completely eliminating the problem of expressing adenoviral genes that result in an immunological response to viral proteins when a gutless replication defective Ad vector is used in gene therapy. Methods for producing gutless replication defective Ad vectors have been described, for example, in U.S. Pat. No. 5,981,225 to Kochanek et al., and U.S. Pat. Nos. 6,063,622 and 6,451,596 to Chamberlain et al; Parks et al., PNAS 93:13565 (1996) and Lieber et al., J. Virol. 70:8944-8960 (1996).

In another embodiment, an adenoviral vector is a "conditionally replicative adenovirus" ("CRAds"). CRAds are genetically modified to preferentially replicate in specific cells by either (i) replacing viral promoters with tissue specific promoters or (ii) deletion of viral genes important for replication that are compensated for by the target cells only. The skilled artisan would be able to identify epithelial cell specific promoters.

Other art known adenoviral vectors may be used in the methods of the invention. Examples include Ad vectors with recombinant fiber proteins for modified tropism (as described in, e.g., van Beusechem et al., 2000 Gene Ther. 7: 1940-1946), protease pre-treated viral vectors (as described in, e.g., Kuriyama et al., 2000 Hum. Gene Ther. 11: 2219-2230), E2a temperature sensitive mutant Ad vectors (as described in, e.g., Engelhardt et al., 1994 Hum. Gene Ther. 5: 1217-1229), and "gutless" Ad vectors (as described in, e.g., Armentano et al., 1997 J. Virol. 71: 2408-2416; Chen et al., 1997 Proc. Nat. Acad. Sci. USA 94: 1645-1650; Schieder et al., 1998 Nature Genetics 18: 180-183).

The vector will include one or more promoters or enhancers, the selection of which will be known to those skilled in the art. Suitable promoters include, but are not limited to, the retroviral long terminal repeat (LTR), the SV40 promoter, the human cytomegalovirus (CMV) promoter, and other viral and eukaryotic cellular promoters known to the skilled artisan.

Guidance in the construction of gene therapy vectors and the introduction thereof into affected subjects for therapeutic purposes may be obtained in the above-referenced publications, as well as in U.S. Pat. Nos. 5,631,236, 5,688,773, 5,691,177, 5,670,488, 5,529,774, 5,601,818, and PCT Publication No. WO 95/06486, the entire contents of which are incorporated herein by reference.

Generally, methods are known in the art for viral infection of the cells of interest. The virus can be placed in contact with the cell of interest or alternatively, can be injected into a subject suffering from a retinal disorder, for example, as described in U.S. Provisional Patent Application No. 61/169,835 and PCT Application No. PCT/US09/053730, the contents of each of which are incorporated by reference.

Gene therapy vectors comprising a nucleic acid molecule encoding a marker(s) can be delivered to a subject or a cell by any suitable method in the art, for example, intravenous injection, local administration, e.g., application of the nucleic acid in a gel, oil, or cream, (see, e.g., U.S. Pat. No. 5,328,470), stereotactic injection (see, e.g., Chen et al. (1994) Proc. Natl. Acad. Sci. U.S.A. 91:3054), gene gun, or by electroporation (see, e.g., Matsuda and Cepko (2007) Proc. Natl. Acad. Sci. U.S.A. 104:1027), using lipid-based transfection reagents, or by any other suitable transfection method.

As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection (e.g., using commercially available reagents such as, for example, LIPOFECTIN® (Invitrogen Corp., San Diego, Calif.), LIPOFECTAMINE® (Invitrogen), FUGENE® (Roche Applied Science, Basel, Switzerland), JETPEI™ (Polyplus-transfection Inc., New York, N.Y.), EFFECTENE® (Qiagen, Valencia, Calif.), DREAMFECT™ (OZ Biosciences, France) and the like), or electroporation (e.g., in vivo electroporation). Suitable methods for transforming or transfecting host cells can be found in Sambrook, et al. (Molecular Cloning: A Laboratory Manual. 2nd, ed., Cold Spring harbor Laboratory, Cold Spring Harbor Laboratory Press, Cold Spring Harbor, N.Y., 1989), and other laboratory manuals.

In one embodiment, a marker(s) is delivered to a subject or cells in the form of a peptide or protein. In order to produce such peptides or proteins, recombinant expression vectors of the invention can be designed for expression of one or more marker(s) proteins, and/or portion(s) thereof in prokaryotic or eukaryotic cells. For example, one or more marker proteins and/or portion(s) thereof can be expressed in bacterial cells such as *E. coli*, insect cells (using baculovirus expression vectors) yeast cells or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

In one embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include retinal cell-type-specific promoters (e.g., rhodopsin regulatory sequences, Cabp5, Cralbp, Nrl, Crx, Ndrg4, clusterin, Rax, Hest and the like (Matsuda and Cepko, supra)), the albumin promoter (liver-specific, Pinkert et al. (1987) Genes Dev. 1:268), neuron-specific promoters (e.g., the neurofilament promoter; Byrne and Ruddle (1989) Proc. Natl. Acad. Sci. U.S.A. 86:5473). Developmentally-regulated promoters are also encompassed, for example the α-fetoprotein promoter (Campes and Tilghman (1989) Genes Dev. 3:537).

Application of the methods of the invention for the treatment and/or prevention of a retinal disorder can result in curing the disorder, decreasing at least one symptom associated with the disorder, either in the long term or short term or simply a transient beneficial effect to the subject. Accordingly, as used herein, the terms "treat," "treatment" and "treating" include the application or administration of agents, as described herein, to a subject who is suffering from Brucellosis, or who is susceptible to such conditions with the purpose of curing, healing, alleviating, relieving, altering, remedying, ameliorating, improving or affecting such conditions or at least one symptom of such conditions. As used herein, the condition is also "treated" if recurrence of the condition is reduced, slowed, delayed or prevented.

A modulatory agent, such as a chemical compound, can be administered to a subject as a pharmaceutical composition. Such compositions typically comprise the modulatory agent and a pharmaceutically acceptable carrier. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. Pharmaceutical compositions can be prepared as described above.

E. Methods of Identifying Brucellosis Biomarkers

The present invention further provides methods for identifying biomarkers useful as markers for, e.g., disease (prognostics and diagnostics), therapeutic effectiveness of a drug (theranostics) and of drug toxicity. For example, as described above, the markers described herein and the markers identified using the methods for biomarker discovery are useful for, e.g., determining whether a subject has Brucellosis; determining whether a subject has Brucellosis or Q-fever; determining whether a subject has Brucellosis or Lyme Disease; monitoring the effectiveness of a therapy for treating Brucellosis, reducing or slowing down the progression of Bruceelosis, and/or reducing or inhibiting the development of complications associated with Brucellosis in a subject; in screening assays to identify molecules which modulate, e.g., decrease or increase, the level and/or activity of a marker(s) of the invention for e.g., use as therapeutics.

Methods for identifying a Brucellosis marker are described in the working examples and include identifying proteins differentially expressed in cells that are not infected with *Brucella* and cells infected with *Brucella*, thereby generating a provisional list of markers, determining the level of a marker in a sample form a control subject, e.g., a healthy subject, a subject having Q-fever, a subject having Lyme Disease, a subject having *Salmonellosis*, and determining the level of the marker in a test sample from a subject, e.g., a subject having Brucellosis. A difference in the level of a marker in the control sample as compared to the level in the test sample, e.g., a statistically significant level, identifies the marker as a Brucellosis marker.

IV. Kits of the Invention

The invention also provides kits for determining whether a subject has Brucellosis, Lyme Disease, or Q-Fever. Kits for monitoring the effectiveness of a treatment for Brucellosis, Q-Fever, or Lyme Disease, kits for determining whether a subject has Brucellosis or Q-Fever, kits for determining whether a subject has Brucellosis or Lyme Disease, lits for determining whether a subject has Q-Fever or Lyme Disease, and kits for determining whether a subject has Brucellosis or Q-Fever or Lyme Disease are also provided.

These kits include means for determining the level of one or more markers of the invention and instructions for use of the kit.

The kits of the invention may optionally comprise additional components useful for performing the methods of the invention. By way of example, the kits may comprise reagents for obtaining a biological sample from a subject, a control sample, one or more sample compartments, a diabetic therapeutic, and instructional material which describes performance of a method of the invention and tissue specific controls/standards.

The reagents for determining the level of one or more marker(s) can include, for example, buffers or other reagents for use in an assay for evaluating the level of one or more markers, e.g., expression level (e.g., at either the mRNA or protein level). The instructions can be, for example, printed instructions for performing the assay for evaluating the level of one or more marker(s) of the invention.

The reagents for isolating a biological sample from a subject can comprise one or more reagents that can be used to obtain a fluid or tissue from a subject, such as means for obtaining a saliva or blood.

The kits of the invention may further comprise reagents for culturing a sample obtained from a subject.

Preferably, the kits are designed for use with a human subject.

The present invention is further illustrated by the following examples which should not be construed as further limiting. The contents of all references, patents and published patent applications cited throughout this application, as well as the Figures, are expressly incorporated herein by reference in their entirety.

EXAMPLES

Example I. Biomarker Identification

Materials and Methods
Infection Conditions.

THP-1 cells were obtained from ATCC (#TIB-202) and routinely maintained in RPMI 1640 media containing 10% heat-inactivated fetal bovine serum. THP-1 cells were differentiated using Phorbol 12-Myristate 13-acetate (PMA) (Sigma, P-8139) at a final concentration of $10^{-7}$M 24 hours before use in infection experiments. AC-1M88 (#ACC-457) and JAR (#ACC-462) cells were obtained from DSMZ and maintained in Hams-F12+10% FBS and RPMI-1640+10% FBS, respectively.

All experiments involving live *B. abortus* were conducted under Biosafety Level 3 (BSL3) conditions. Bacterial cultures were prepared as described (Lamontagne J, et al. (2009) *J Proteome Res* 8:1594-1609). *B. abortus* strains 2308 and 544 were used to infect human THP-1 macrophages at a multiplicity of infection (MOI) of 250, as described (Lamontagne J, et al. (2009) *J Proteome Res* 8:1594-1609). Bacteria were incubated with the host macrophages for 30 minutes, the extracellular bacteria were then removed, and the infection allowed to continue for 24 hours. The same bacterial culture protocols were used to prepare *B. abortus* 2308 for infection of the JAr and AC-1M88 human trophoblast cell lines. Bacteria were incubated with the host trophoblasts at an multiplicity of infection (MOI) of 250 for 24 hrs before the extracellular bacteria were removed and the infection allowed to continue for an additional 24 hrs. Lengthening the incubation period reliably allowed 85-100% of the trophoblasts per culture to be infected.

Immunofluorescence

THP-1 macrophages were seeded on microscope coverslips and infected with *B. abortus* 2308 or 544 as described above. Cells were then washed with phosphate-buffered saline and incubated with anti-LPS primary antibody for 30 minutes. This step was used to stain the extracellular bacteria. The cells were washed, fixed with cold 4% paraformaldehyde (Merck) for 20 min on ice, washed, incubated for 2 min with PBS-1% Triton X-100 (ACE Chemicals, #T935050), washed, and incubated with blocking buffer (5% Goat Serum, 5% Glycerol; 0.04% Na Azide in D-PBS) for 2 minutes. The cells were then incubated with anti-bovine-Rhodamine conjugated antibody (Jackson Immuno Research, #101-025-165) diluted 1/500) for 20 minutes, washed, incubated with blocking buffer for 30 min, washed, and incubated with the anti-LPS primary antibody for 30 min. This latter step was to allow staining of intracellular bacteria. The cells were washed, incubated with blocking buffer for 30 minutes, washed, and incubated with anti-bovine-FITC (KPL, #02-12-06) for 20 min. The coverslips were washed with PBS, mounted using Prolong anti-fade kit (Molecular Probes, #P7481), and analyzed by fluorescence microscopy. Counts of green and red intracellular fluorescent bacteria were performed in at least 100 infected cells and expressed as a mean of green-red/red fluorescent bacteria per cell. The same protocol was used to determine *B. abortus* infectivity in the trophoblast cell lines, except that 2-well chamber slides (Fisher Scientific, #FSSP9772261) were used instead of the microscope coverslips.

Light Membrane Sample Preparation

Six to eight independent replicates of infected and non-infected cultures for each cell line were independently prepared and processed. Secretory vesicle isolation was done in batches using the cell homogenization and density centrifugation methods modified from a previous study (Sicar K, et al, (2006) *Clin Cancer Res* 12:4178-4184). Briefly, cells were harvested by scraping, centrifuged and resuspended in homogenization buffer. They were homogenized using 15 strokes with a stainless steel dounce homogenizer (Wheaton Science, Millville N.J.). The homogenate was adjusted to 1.4M sucrose. A 14 ml SW40Ti ultra-clear centrifuge tube (Beckman Coulter #344060) was layered with homogenate followed by 4 ml of 1.2M sucrose and topped with 0.8M sucrose. The samples were centrifuged for 2 hrs at 155,000×g at 40 C and vesicles were harvested from the 0.8-1.2M interface. The vesicles were washed in 0.5M KCl followed by incubation in ammonium carbonate pH11. Vesicle content was separated from the vesicle membranes by centrifugation at 112,000 g. Protein yields were measured using the BCA Protein Assay (Pierce #23227). Secretory vesicle content yield from infected THP-1 macrophages was 0.85 μg per 10 million cells, and from uninfected macrophages it was 1.9 μg per 10 million cells. Infected AC-1M88 cells yielded 12.9 μg per 10 million cells, whereas uninfected cells yielded 7.8 μg per 10 million cells. Infected JAr cells yielded 20 μg per 10 million cells whereas uninfected JAr cells yielded and 17.8 μg per million cells. Western blot characterization of the starting cell line homogenates and secretory protein final products were done using antibodies against Na+ K+ ATPase (Upstate, #05-369), BIP (BD #610979), Nucleoporin p62 (BD #610498, PAN Actin (Neomarkers, #MS-1295P), GS-28 (BD #G83820), Tom20 (BD #612278), Beta-2-microglobulin (Abcam #Ab6608), and *Brucella* LPS (Hyperomics Farma #Ba05-0001).

Tandem Mass Spectrometry Analysis

All samples were digested with trypsin. The resulting peptides were then separated by SCX into three fractions. Each of the three fractions per sample was analyzed by reversed phase liquid chromatography, coupled by electrospray to a Waters QTOF mass spectrometer (LC-MS). Components were detected and matched across all samples and compared for relative peak intensity. Peak intensity was normalized to account for small differences in protein concentration between samples. ANOVA was then applied to identify peptides that were differentially expressed between the groups of interest. High stringency thresholds were used to ensure the statistical significance of the identified peptides. All intensity values were log (base e) transformed with values <0 replaced by 0. A subset of the samples was used to create an average sample (i.e. the Reference sample) against which all samples were then normalized. The normalization factors were chosen so that the median of log ratios between each sample and the Reference sample over all the peptides was adjusted to zero. For the macrophage analysis, a one-way ANOVA (infection status) was used to find the differentially expressed peptides. For the trophoblast analysis, a two-factor ANOVA (cell line, infection status, and the interaction between the two) was used. FDR (false detection rate) and q-value were calculated, based on the p-values obtained from the ANOVA, using Storey's method to make multiple testing adjustments (implemented in MATLAB). 'Post hoc' contrast analyses were conducted using Tukey's hsd method to calculate p-values associated with each pair wise comparison (Hochberg Y, Tamhane A C (1987) Multiple Comparison Procedures. Canada: Wiley & Sons). For the macrophage analysis, peptides meeting q-value ≤0.05, Tukey's hsd p-value ≤0.05, fold-change ≥2.0; peptide intensity ≥70 in at least 6 samples were selected. For the trophoblast analysis, peptides meeting q-value (either for the factor 'infection status' or for the interaction)<0.05, Tukey's hsd p-value <0.05, fold-change ≥2.0 were selected. Protein identification was accomplished by the analysis of replicate samples by tandem mass spectrometry (LC-MS/MS). Differentially expressed peptides were targeted for sequencing, and the resulting fragmentation patterns were matched to the corresponding peptide sequences found in a custom protein database using Mascot (Matrix Science) software. For the macrophages, the database was composed of the IPI (International Protein Index) human protein sequences and the NCBI protein sequences from *Brucella* species which infect humans (NCBI taxonomy ID 235, 29459, 29461, 36855, 120576 and 120577). Several strains of *Brucella* were included in the database, because the strain 544 had not yet been sequenced. For the trophoblasts, since only the sequenced strain 2308 was used the database was composed of the IPI (International Protein Index) human protein sequences and the NCBI protein sequences from *Brucella melitensis* biovar abortus 2308 species only (NCBI taxonomy ID 359391).

Biomarker Candidate Selection

Biomarker candidates were drawn from the proteins upregulated in the infected host secretomes. They were further evaluated using the Meng importance score (Lamontagne J, et al. (2009) *J Proteome Res* 8:1594-1609), which ranked each peptide by their ability to separate the infected from non-infected samples, and a detailed literature review. The literature review focused on the known roles of each protein, association with brucellosis with other infectious diseases, or association with other relevant conditions which has been associated with aberrant trophoblast function, such as spontaneous abortion. The combination of the Meng scores and the literature annotation was used to produce a ranking of the biomarker candidates.

Enzyme-Linked Immunosorbent Assay (ELISA)

Twenty-three candidates for which commercially ELISA kits were available, were evaluated (from manufacturer Uscn Life Science Inc.: IL-25 (#E91694Hu), CALU (#E91854Hu), SEPT6 (#E95866Hu), S100A11 (#E90568Hu), MYH10 (#E93423Hu), MAT2A (#E96469Hu), S100P (#E92054Hu), GPI (#E90725Hu), RPL23A (#E83643Hu), ANXA2 (#E91944Hu), RSAD2 (#E81762Hu), LYN (#E96523Hu), EVL (#E84820Hu), HNRNPU (#E95128Hu), ARHGDIA (#E94329Hu), SFRS2 (#E95102Hu), PFDN1 (#E92722Hu), and GSTP1 (#E91090Hu); from other manufacturers: ANXA5 (US Biological, #A2296-15 or Uscn Life Science Inc., #E90259Hu), PKM2 (ScheBo Biotech, #08), IL1B (Abcam, #ab46052 and Thermo Scientific, #EH2IL1B), and HSPA8 (StressMarq, #SKT-106). All ELISAs were performed according to manufacturer's instructions. An initial small scale analysis used 28 serum samples from subjects with acute, non-complicated brucellosis along with 28 age and gender matched healthy controls and 24 age and gender matched samples from subjects infected with Lyme disease (ProMedDx, Norton, Mass., USA). Four biomarker candidates (ANXA5, MAT2A, RPL23A, and LYN) were further evaluated using 278 serum samples as described in Table 1.

Multiple Reaction Monitoring Mass Spectrometry

One MRM assay for the macrophage model of infection and one for the trophoblast model of infection was developed. The macrophage MRM assay contained 70 proteins upregulated after infection, represented by 149 peptides and the trophoblast MRM assay contained 123 proteins upregulated after infection represented by 254 peptides. Peptides were synthesized by JPT Peptide Technologies (Berlin, Germany) The synthesized peptides were resolubilized in 72/25 water/DMSO, pooled and diluted with water+0.2% formic acid to a final concentration of 2 nmol/mL. 5 uL of this solution was analyzed on a QTRAP 4000 mass spectrometer (ABSciex, Canada) using a 320 um×150 mm, Sum particle size, Thermo Biobasic C18 column. A linear gradient of 10-40% acetonitrile (0.2% formic acid) in 30 minutes was used for peptide separation. MS/MS spectra of the synthetic peptides were acquired using selected reaction monitoring (SRM)-triggered MS/MS allowing the identification of peptide and peptide fragments (transitions). The two most intense fragment ions (b or y fragment ions only) in the MS/MS spectrum and its elution time were determined for each acquired peptide. The collision energy was then optimized for each of the chosen transitions. The CE values evaluated were the empirical calculated CE value and the empirical CE value −3 and +3. Study samples were then subjected to immunodepletion of high and medium abundance proteins using a Human IgY-14/SuperMix depletion column (Sigma, USA). Depleted samples were digested with trypsin overnight (Trypsin to protein ratio 1:10) and desalted by solid phase extraction using a 3M Empore C18 desalting plate. Samples were after analyzed by the MRM assay.

Expression Analysis on MRM Results

Expression analysis on MRM results was performed using essentially the same principles as for the tandem MS analysis described above, with the following adaptations for MRM analysis. All the statistical analyses were performed using R version 2.12.0, platform i386-pc-mingw32/i386 (32-bit). The calculation of q-values was done using function "qvalue" from Storey's package "qvalue" version 1.24.0 (Storey, John D. (2002). *Journal of the Royal Statistical Society, Series B (Methodological)* 64(3):479-498; Storey, John D. (2003). *Annals of Statistics* 31(6):2013-2035; R Development Core Team (2010). R Foundation for Statistical Computing, Vienna, Austria. ISBN 3-900051-07-0). A limit of quantification (LOQ) (defined as an intensity value below which the measure is deemed unreliable) was determined empirically according to the instrument that was used for the study (QTrap), and was set to 10000, pre-normalization. The detection rate (DR), defined for each group that needed to be compared, was defined as the proportion of samples with a raw (i.e. pre-normalized) intensity value at least equal to the LOQ. Prior expression analysis, an outlier and pattern detection analysis was performed using a standard Principal Component Analysis (PCA) that was applied to the transformed intensities in order to visually assess any pattern in the data that are likely to be unrelated to sample condition. (The PCA was performed as follow. If L is the matrix of transformed intensities with samples as rows and transitions as intensities, then we define L* as the matrix of intensities doubly centered. Double centering means that each cell of the matrix has both its column and row mean subtracted from it, to which we also add back the grand mean—i.e. the mean of all intensity values. This is done to remove principal component dependencies to systematic shifts in intensity levels (i.e. transitions that are over all samples less or more intense than other transitions, or samples that are, over all transitions, more or less intense than other samples). The SVD L*=UDVT was performed, with U containing the components for samples. This analysis identified a clustering of samples, based on their region of origin (data not shown). Therefore, samples were always compared to their corresponding regional controls. Differential intensity ratios (DI) were then calculated for each transition, for two-group comparisons (disease vs corresponding regional controls), as the ratio of the median normalized intensities of each group. Prior to calculating the DI, all intensity values that were below the LOQ quantity in the raw (i.e. prior to normalization) data were replaced by the half-LOQ value. ANOVA or t-test with gender as covariate were used.

Normalization and Box Plots Generation

Samples were normalized, using the regional non-infected controls as reference. The actual normalization was based on two regression models predicting intensity level:

$$M1: I_i = \mu_1 + \gamma S_i + \varepsilon_i, \hat{I}_{i1} = \mu_1 + \gamma S_i$$

$$M2: I_i = \mu_2 + \varepsilon_i, \hat{I}_{i2} = \mu_2$$

In each model, I and S are respectively intensity value (or ELISA value) and Sample Source (i.e. France, Spain, USA). The parameters were estimated using the control samples only, and the following normalization was applied on all samples: $I_{it} = I_i - (\hat{I}_{i1} - \hat{I}_{i2}) = I_i - \hat{I}_{i1} + \hat{I}_{i2}$, applied to each transition/ELISA. This was done independently for MRM and ELISA. For each protein, normalized intensities for each sample, grouped by condition, were then plotted as box plots, using XYZ software.

Panel Definition

Area under the ROC curve (AUC) was computed from bootstrap. Boostrap samples (n) were selected with replacement i.e. take a sample at random, then a second—with the first selected sample being possibly selected again, and so on. Some samples, called out-of-bag, were left out by design. The panel was built on the bootstrap samples and evaluated on the out-of-bag samples by calculating AUC. The process was repeated 100 times. The reported AUC was the average of the 100 AUCs. Each protein was represented by a single MRM transition. Transitions with a DR lower than 80% and transitions that did not trend according to the protein DI were filtered out. The transition selected for a protein was the one with the highest DR. Logistic Regression models were built with the secretome proteins as explanatory variables. All combinations of 1 to 6 proteins were systematically fitted into such logistic models. These combinations were either used as is to build the models, or with the addition of either or both of the proteins measured by ELISA that were found to have appropriate performance. The proteins were ranked by their propensity to be a good team player. For k from 1 to 6, combinations were ranked by their AUC, and for each protein, the mean rank of the combinations they appear in, for a given k, was calculated. Within each k, the protein rank was calculated as the rank of the average rank. The final rank was taken as the weighted average over k of the ranks. The protein ranking was done for classifying brucellosis vs. controls, brucellosis vs. Lyme and brucellosis vs. Q-fever.

Results

Protein Biomarker Discovery

The infection models used were selected to reflect *Brucella* cell tropism In particular, the well characterized human THP-1 macrophage cell line was used for the macrophage infection experiments (Auwerx J (1991) *Experientia* 47: 22-31), and selected trophoblast cell lines that have been used as models of first trimester pregnancy (Anderson T D, et al. (1986) *Vet Pathol* 23: 227-239; Anderson T D, et al. (1986) *Vet Pathol* 23: 219-226), a time period where trophoblasts can be prone to *Brucella* infection were also used. Two different trophoblast cell lines, JAr and ACM188 were used. The choriocarcinoma cell line (JAr) was derived from a human trophoblastic tumor of the placenta (Hochberg A, et al. (1992) *Cancer Research* 52: 3713-3717) whereas the trophoblastic hybridoma cell line AC-1M88 was a fusion of primary extravillous trophoblast from term placenta with a choriocarcinoma cell line (Gellersen B, et al. (2010) *Hum Reprod* 25: 862-873).

THP-1 macrophages were infected with either *B. abortus* 2308 or 544. Seven independent replicates of *B. abortus* 2308-infected as well as 8 independent replicates of *B. abortus* 544-infected cultures were produced, matched by an equal number of non-infected cultures, respectively. Twenty four hours after infection approximately 70% of the macrophages had become infected, typically with 1-3 bacteria per cell (FIGS. 1A-1D). Infecting the THP-1 macrophages with two virulent *B. abortus* strains was done to determine if any of the protein expression changes observed were strain-specific. As will be illustrated in more detail below, 90% of the significantly differentially expressed proteins identified were common to both infections. Therefore, only *B. abortus* 2308 was used to infect the trophoblast cell lines. The macrophage cultures were homogenized and light density membrane vesicles were prepared as described in the methods section. The preparations appeared to be enriched for secreted proteins by western blot (FIGS. 1E-1H).

Eight independent replicate cultures of infected and non-infected cells of each of the 2 trophoblast cell lines were produced and evaluated as described above (FIG. 1). The two trophoblast cell lines displayed different growth characteristics and infection patterns. The AC-1M88 cell line formed monolayers, and the cultures became infected with a pattern consistent with in vivo trophoblast tissue infections (Carvalho Neta A V, et al. (2008) *Infect Immun* 76: 1897-1907). The trophoblasts on the outer part of the monolayer contained typically 50-100 bacteria per cell, whereas the trophoblasts in the inner part of the monolayer contained much fewer bacteria per cell, on the order of 8-10. In contrast, the JAr cell line did not have contact inhibition, and the cells of those cultures became uniformly infected with 8-10 bacteria per cell. Thus while the AC-1M88 cell line became infected in a manner consistent with in vivo infections, its cultures had cells with both heavy and comparably lighter bacterial burdens. The JAr cell line was far more uniformly infected, although too uniform compared to in vivo infections. Analysis of the results from both trophoblast cell lines thus allows insights that would not be possible from one cell line alone.

Expression analysis of the mass spectrometry data acquired identified 3917 components differentially expressed between infected and non-infected macrophages. Targeted sequencing of the differentially expressed peptides resulted in the identification of 184 candidate protein biomarkers (Table 2). There was a 90% overlap of the differentially expressed proteins identified after THP-1 macrophage infection with either bacterial strain. Moreover the proteins in common had the same expression profiles in both infection conditions. The two macrophage datasets have therefore been merged and will not consider them separately. Of the 184 differentially expressed proteins identified in the secretory vesicle contents of infected cells, 77 (41%) were over-expressed by infected cells and 107 (59%) were under-expressed by infected cells compared to non-infected cells.

Expression analysis of the mass spectrometry data acquired identified 812 components differentially expressed between the non-infected and the infected AC-1M88 cultures, and 2295 components differentially expressed between the non-infected and the infected JAr cultures. Targeted sequencing of the differentially expressed peptides resulted in the identification of 143 (Table 2) candidate biomarkers proteins from the AC-1M88 cell infections, and 287 from the JAr cell infections. Only 25% of the differentially expressed proteins identified were common to both cell lines. Since the two trophoblast datasets are mostly dissimilar, they were not merged but rather considered independently. For the secretory vesicle content dataset derived from the JAr trophoblasts, 66% (189 proteins) were upregulated in the infected cells, and 42% (61 proteins) were upregulated in the AC-1M88 cells.

The differentially expressed proteins identified in each infection model modestly overlapped with each other.

The differentially expressed proteins identified and the DI (Differential Intensity) values of the proteins are shown in Table 2. If the DI value is above 1, the level of the protein is upregulated. If the DI value is less than 1, the level of the marker is downregulated.

TABLE 2

| Protein | Macrophages (combined) | Trophoblasts Jar | Trophoblasts AC-1M88 |
|---|---|---|---|
| MCCC2 | 0.16 | | |
| GLS | 0.28 | | |
| GATM | 0.29 | | |
| SHMT2 | 0.30 | | |
| IVD | 0.33 | | |
| ALDH4A1 | 0.38 | | |
| GLUD1 | 0.39 | | |
| HSD17B10 | 0.43 | 2.51 | |
| DLD | 0.45 | | |
| GOT2 | 0.46 | 2.22 | |
| LRPPRC | 0.26 | | |
| PHB2 | 0.30 | 0.47 | 0.50 |
| POLDIP2 | 0.34 | | |
| PNPT1 | 0.50 | | |
| HIST1H1D | 2.52 | | |
| PARP1 | 2.59 | | |
| HIST1H1B | 2.68 | 4.48 | 2.47 |
| HIST2H2BF | 2.99 | | |
| HIST1H4 | 3.77 | | |
| IDH2 | 0.18 | | |
| MTHFD1L | 0.22 | | |
| NNT | 0.23 | | |
| SUCLG2 | 0.27 | | |
| ALDH2 | 0.27 | | |
| DLAT | 0.28 | | 0.41 |
| IDH3A | 0.28 | | |
| ACO2 | 0.29 | | |
| PDHB | 0.31 | | |
| CS | 0.35 | | |
| FH | 0.44 | 2.17 | |
| AKR7A2 | 0.46 | 7.93 | |
| ME2 | 0.47 | | |
| DLST; DLSTP | 0.47 | | |
| MTHFD2 | 0.51 | | |
| MDH2 | 1.32 | | 0.08 |
| H6PD | 2.04 | | |
| PLD4 | 0.04 | | |
| OXCT1 | 0.16 | | |
| HADHA | 0.22 | | |
| ACAT1 | 0.29 | | |
| ECHS1 | 0.31 | | |
| CPT1A | 0.33 | | |
| CPT2 | 0.33 | | |
| ECH1 | 0.33 | | |
| HADHB | 0.34 | | |
| PCCA | 0.37 | | |
| HADH | 0.42 | | 0.35 |
| ACAA2 | 0.43 | | |
| DCI | 0.43 | | |
| HSD17B4 | 2.00 | 2.09 | |
| AARS2 | 0.09 | | |
| TUFM | 0.26 | | |
| DARS2 | 0.29 | | |
| GFM1 | 0.29 | | |
| HARS | 0.31 | | |
| SARS2 | 0.32 | | |
| RPN1 | 0.42 | | |
| GATC | 0.44 | | |
| ICT1 | 0.51 | | |
| P4HB | 1.92 | | |
| RPL14 | 1.99 | | |
| IARS2 | 2.07 | | |
| RPLP2 | 2.07 | | 3.04 |
| IL4I1 | 0.17 | | |
| LONP1 | 0.23 | | |
| PMPCB | 0.27 | | |
| PMPCA | 0.29 | | |
| CPVL | 0.38 | 2.40 | |
| CLPP | 0.38 | | |
| PPT1 | 0.46 | | |
| GLB1 | 0.48 | | 0.44 |
| ANPEP | 1.94 | | |
| ASAH1 | 2.01 | | |
| MMP9 | 3.19 | | |
| SGSH | 4.00 | | |
| CLPX | 0.22 | | |
| TRAP1 | 0.29 | | |
| HSPD1 | 0.31 | | 0.05 |
| DNAJA3 | 0.37 | | |
| HSP90B1 | 0.38 | 1.56 | 0.48 |
| HSPA9 | 0.39 | | 4.00 |
| ERP29 | 0.47 | | |
| SQRDL | 0.50 | | |
| PLOD3 | 1.24 | | |
| HSPA5 | 1.90 | 2.10 | 1.09 |
| CNPY2 | 1.94 | | |
| PPIB | 1.94 | | |
| UGGT1 | 1.96 | | |
| CALU | 2.12 | | |
| ERO1L | 2.68 | | |
| PRDX1 | 2.69 | | |
| CLEC11A | 0.32 | | |
| OPA1 | 0.36 | | |
| SPRED1 | 1.90 | | |
| S100A6 | 1.90 | | |
| PIP4K2A | 2.02 | | |
| TBL2 | 2.03 | | |
| PIP5K1A | 2.19 | | |
| CAMK2D | 2.20 | | |
| ITPR1 | 2.24 | | |
| LYN | 2.33 | | |
| ESYT2 | 2.80 | | |
| ITGB2 | 0.39 | | |
| PECAM1 | 1.82 | | |
| ARPC3 | 2.01 | | |
| EMR2 | 2.03 | | |
| YBX1 | 2.09 | | 2.01 |
| ENG | 2.09 | | |
| AHNAK | 2.11 | | 0.22 |
| LCP1 | 2.11 | 2.15 | |
| ICAM1 | 2.11 | | |
| ITGAM | 2.36 | | |
| EVL | 2.59 | | |
| ITGA5 | 2.78 | | |
| STOML2 | 0.24 | | |
| PHB | 0.32 | 0.42 | 0.60 |
| IMMT | 0.36 | 0.46 | |
| C5orf33 | 0.37 | | |
| TUBA1A | 0.48 | | |
| TUBB2C | 0.62 | 2.21 | |
| TUBB | 0.69 | 2.30 | |
| LASP1 | 1.74 | 0.49 | |
| LRCH1 | 1.94 | | |
| SEPT2 | 1.97 | 0.43 | |
| CAPZB | 2.06 | | |
| CORO1B | 2.07 | | |
| TLN1 | 2.15 | 0.48 | 0.61 |
| PLEKHO2 | 2.21 | | |
| ANXA2 | 2.25 | 0.39 | 0.17 |
| CORO1C | 2.29 | 0.48 | |
| SEPT7 | 2.34 | | |
| CLIC1 | 2.40 | | |
| SEPT6 | 2.43 | | |
| S100A11 | 2.54 | 1.20 | 0.85 |
| SEPT9 | 2.76 | | 2.09 |
| EPB41L3 | 2.90 | 0.47 | |
| GBAS | 0.40 | | |
| GLG1 | 0.44 | | |
| RAB7A | 0.50 | | |
| RAB6A | 2.06 | | |
| MYO6 | 2.13 | | |
| ANXA6 | 2.25 | | 0.42 |
| EHD1 | 2.39 | | |

TABLE 2-continued

Differetially Expressed Proteins

| Protein | Macrophages (combined) | Trophoblasts Jar | Trophoblasts AC-1M88 |
|---|---|---|---|
| CORO1A | 2.46 | | |
| NAPA | 2.51 | 2.68 | |
| MYO1E | 2.60 | | |
| STX11 | 2.69 | | |
| C19orf10 | 1.98 | 2.50 | |
| CXCL10 | 2.10 | | |
| PRKCSH | 2.13 | | |
| IL1B | 2.89 | | |
| F5 | 3.21 | | |
| OAS2 | 4.60 | | |
| ANXA5 | 6.19 | 8.82 | |
| RSAD2 | 16.29 | | |
| PPA2 | 0.47 | | |
| SOD2 | 2.56 | | |
| MRPL37 | 0.23 | | |
| MRPS28 | 0.26 | | |
| MRPS22 | 0.29 | | |
| MRPS27 | 0.30 | | |
| MRPS7 | 0.31 | | |
| MRPL46 | 0.36 | | |
| ACADM | 0.20 | | |
| ACADVL | 0.42 | 2.10 | |
| ACADS | 0.45 | | |
| UQCRC2 | 0.20 | 0.31 | |
| ATP5A1 | 0.31 | | |
| UQCRC1 | 0.32 | 0.47 | |
| ETFA | 0.32 | | |
| NDUFS7 | 0.33 | | |
| ETFB | 0.34 | | |
| NDUFV1 | 0.37 | | |
| TIMM13 | 0.43 | | |
| ATP5O | 0.44 | | |
| NDUFS1 | 0.44 | 0.42 | 0.26 |
| ATP5B | 0.44 | 0.37 | 0.20 |
| NDUFS3 | 0.46 | | |
| COX5A | 0.46 | | 0.35 |
| NDUFA5 | 0.50 | | |
| POR | 1.46 | | |
| TIMM44 | 0.25 | | |
| VDAC1 | 0.34 | 0.34 | |
| C14orf159 | 0.30 | | |
| PHGDH | | 2.15 | |
| MAT2A | | 4.74 | |
| GOT1 | | 8.74 | |
| DNASE2 | | 2.18 | |
| ATIC | | 2.19 | |
| TRA2B | | 2.39 | |
| HNRNPK | | 2.42 | 3.79 |
| HNRNPD | | 2.54 | |
| SF3B3 | | 2.79 | |
| HNRNPA1 | | 3.04 | |
| HNRNPC | | 3.20 | 1.43 |
| HNRNPU | | 3.62 | 2.24 |
| HNRNPR | | 3.66 | |
| PAICS | | 3.76 | |
| PNP | | 3.91 | |
| SFPQ | | 3.97 | |
| HNRNPA2B1 | | 4.31 | |
| SFRS2B | | 4.75 | 4.46 |
| STRAP | | 5.32 | |
| SNRPD3 | | 6.94 | |
| GPD2 | | 0.38 | 0.37 |
| TKT | | 2.13 | |
| GNS | | 2.15 | 1.69 |
| TALDO1 | | 2.16 | |
| NAGA | | 2.28 | |
| ENO3 | | 2.46 | 1.46 |
| PKM2 | | 2.49 | |
| PGK1 | | 2.64 | |
| ENO1 | | 2.67 | 1.40 |
| GAA | | 2.91 | |
| DDT | | 2.94 | |
| GLT25D1 | | 3.07 | |
| GGH | | 3.13 | 0.52 |
| HEXA | | 3.68 | |
| GPI | | 3.73 | |
| MDH1 | | 4.05 | |
| LDHB | | 4.29 | |
| AKR1B1 | | 4.71 | |
| PGAM1 | | 4.78 | |
| TPI1 | | 6.15 | 2.73 |
| APOE | | 0.37 | |
| ACSL4 | | 0.50 | 0.53 |
| GBA | | 2.74 | 0.30 |
| PRDX6 | | 2.80 | |
| PAFAH1B2 | | 2.93 | |
| ISYNA1 | | 3.23 | |
| ACOX1 | | 3.88 | |
| PDIA3 | | 0.12 | |
| PDIA4 | | 0.28 | 0.24 |
| MAN2A1 | | 0.59 | 0.36 |
| C1GALT1 | | 0.76 | 0.46 |
| RPL8 | | 1.82 | 2.64 |
| PDIA5 | | 1.94 | 1.71 |
| RPSA | | 1.97 | 1.97 |
| FKBP4 | | 2.05 | |
| EEF1A1 | | 2.12 | |
| AIMP1 | | 2.14 | |
| EEF1B2 | | 2.35 | |
| STIP1 | | 2.35 | |
| EEF2 | | 2.45 | |
| PA2G4 | | 2.46 | |
| EEF1D | | 2.51 | 1.91 |
| RPS23 | | 2.54 | |
| ELAVL1 | | 2.55 | |
| EPRS | | 3.37 | |
| EIF5A2 | | 5.30 | |
| B4GALT1 | | 5.39 | 0.08 |
| CTSL2 | | 0.21 | 0.37 |
| CTSL1 | | 0.22 | |
| CTSC | | 0.49 | |
| CTSB | | 0.72 | 0.64 |
| PSMA7 | | 2.01 | |
| USP14 | | 2.06 | |
| NPEPPS | | 2.31 | |
| PSMC2 | | 2.38 | |
| PSMB5 | | 2.42 | |
| PRCP | | 2.57 | |
| PSMD11 | | 2.76 | |
| SIAE | | 2.80 | |
| PSMC6 | | 3.01 | |
| PSMC3 | | 3.18 | |
| CNDP2 | | 3.21 | |
| SUMO3 | | 3.31 | |
| PSMD4 | | 3.34 | |
| PSMD14 | | 3.72 | |
| PSMD10 | | 6.03 | 0.49 |
| PSMD2 | | 13.69 | |
| PSMD1 | | 14.29 | |
| HBA1; HBA2 | | 0.38 | 0.39 |
| CACYBP | | 1.92 | 2.28 |
| MESDC2 | | 2.03 | |
| HSPA1A; HSPA1B | | 2.03 | 1.54 |
| CCT8 | | 2.11 | 2.35 |
| NPM1 | | 2.22 | 2.42 |
| PRDX2 | | 2.25 | |
| HSPA8 | | 2.25 | 1.26 |
| CDC37 | | 2.27 | |
| PFDN2 | | 2.35 | |
| HSP90AB1 | | 2.44 | 1.29 |
| ST13 | | 2.48 | |
| PARK7 | | 2.49 | |
| HSP90AA1 | | 2.52 | 1.26 |
| PPIA | | 2.53 | |
| NDRG1 | | 2.54 | |
| CCT4 | | 2.68 | |
| PFDN1 | | 3.09 | |

TABLE 2-continued

Differetially Expressed Proteins

| Protein | Macrophages (combined) | Trophoblasts Jar | AC-1M88 |
|---|---|---|---|
| GSTP1 | | 3.49 | |
| ILK | | 0.29 | |
| PTPN11 | | 0.36 | 0.54 |
| AKAP2 | | 0.37 | |
| MPP6 | | 0.38 | |
| IQGAP1 | | 0.44 | 0.89 |
| CTNNA1 | | 0.47 | 0.18 |
| CTNNB1 | | 0.47 | 0.76 |
| MPP1 | | 0.48 | 0.90 |
| RANGAP1 | | 3.65 | |
| ARHGDIA | | 4.36 | 3.96 |
| RANBP1 | | 4.50 | |
| THBS1 | | 0.20 | |
| CTNND1 | | 0.24 | 0.69 |
| ITGA6 | | 0.25 | |
| FN1 | | 0.29 | 0.47 |
| FBLN1 | | 0.29 | 0.41 |
| FAT2 | | 0.36 | 0.50 |
| PTPRJ | | 0.36 | |
| PARVA | | 0.38 | |
| ZYX | | 0.39 | |
| LIMS1 | | 0.41 | |
| PTPRF | | 0.42 | |
| MPDZ | | 0.46 | |
| DAG1 | | 0.47 | |
| CDH3 | | 0.48 | |
| MLLT4 | | 0.54 | 0.44 |
| DSP | | 1.10 | 2.25 |
| MMP2 | | 0.18 | 0.14 |
| CSRP2 | | 0.22 | |
| NEBL | | 0.25 | |
| DMD | | 0.29 | |
| BAIAP2 | | 0.30 | |
| FLNB | | 0.31 | 0.28 |
| FMNL2 | | 0.31 | |
| NUCB1 | | 0.32 | 0.62 |
| SEPT10 | | 0.34 | |
| CNN2 | | 0.38 | |
| PALLD | | 0.40 | |
| CALD1 | | 0.40 | |
| NUCB2 | | 0.40 | |
| CNN3 | | 0.41 | |
| CSRP1 | | 0.42 | |
| SLC9A3R1 | | 0.42 | |
| EPB41L2 | | 0.42 | |
| EPB41 | | 0.43 | |
| MYO1B | | 0.44 | |
| FLNA | | 0.44 | 1.34 |
| EZR | | 0.45 | 0.64 |
| RDX | | 0.46 | 0.57 |
| MYO1C | | 0.46 | |
| ACTB | | 0.47 | 0.17 |
| CNP | | 0.49 | 0.48 |
| ATP6V1A | | 1.82 | 1.86 |
| ATP6V1F | | 2.01 | |
| PLEC | | 2.06 | 1.66 |
| CAPZA2 | | 2.08 | |
| TUBA1 | | 2.14 | |
| MYH10 | | 2.18 | |
| KRT8 | | 2.20 | |
| ISOC1 | | 2.23 | |
| MYH9 | | 2.26 | |
| SPTAN1 | | 2.30 | |
| SPTBN1 | | 2.32 | |
| ALPP | | 2.34 | |
| KRT7 | | 2.34 | |
| ATP6V1D | | 2.40 | |
| MYL12A | | 2.40 | 1.25 |
| ATP6V1B2 | | 2.49 | |
| ATP6V1E1 | | 2.51 | |
| KRT9 | | 2.54 | |
| TMOD3 | | 2.62 | |
| TDRD6 | | 2.74 | |
| ATP6V1G1 | | 2.78 | |
| PEBP1 | | 2.93 | |
| STMN1 | | 3.48 | 1.55 |
| ROD1 | | 3.62 | |
| CAPG | | 4.28 | |
| S100P | | 7.42 | |
| GOLGA4 | | 0.25 | 0.50 |
| GOLGA2 | | 0.25 | |
| TMED10 | | 0.26 | 0.53 |
| GOLGA1 | | 0.31 | 0.51 |
| SDF4 | | 0.36 | 0.55 |
| OCIAD1 | | 0.39 | |
| TRIP11 | | 0.43 | 0.65 |
| SCFD1 | | 0.49 | 0.47 |
| LRP1 | | 0.50 | |
| GOLGB1 | | 0.54 | 0.52 |
| VPS4A | | 2.07 | |
| VCP | | 2.21 | |
| DYNLL1 | | 2.58 | |
| COPA | | 2.58 | |
| MUTED | | 2.62 | |
| SORT1 | | 2.75 | |
| PDCD6IP | | 2.81 | |
| COPB2 | | 4.00 | |
| B2M | | 0.39 | |
| PIP4K2C | | 0.42 | |
| YES1 | | 0.43 | |
| CBX1 | | 2.10 | |
| NCL | | 2.17 | |
| NUDC | | 2.28 | |
| RAD23B | | 2.53 | |
| NAP1L1 | | 2.65 | |
| PRPF19 | | 2.76 | 6.49 |
| NME1-NME2 | | 2.80 | |
| LMNA | | 2.81 | |
| HMGB3 | | 2.92 | |
| LMNB2 | | 3.35 | |
| LMNB1 | | 3.43 | |
| RBBP4 | | 3.56 | |
| HIST1H1 | | 4.27 | 2.11 |
| RUVBL2 | | 4.34 | |
| RUVBL1 | | 4.46 | 2.12 |
| IMPDH2 | | 5.27 | |
| HIST2H2B | | 5.63 | 1.82 |
| H2AFY | | 8.29 | |
| HIST3H3 | | 9.80 | 2.38 |
| HIST4 | | 10.63 | 2.52 |
| HIST3H2A | | 10.92 | |
| ATP5J2 | | 0.16 | |
| ATP5I | | 0.29 | |
| ATP5F1 | | 0.34 | |
| ATP5H | | 0.44 | |
| MRPL39 | | 2.06 | |
| VDAC2 | | 0.21 | 0.20 |
| SLC25A6 | | 0.29 | 0.38 |
| SLC25A5 | | 0.29 | 0.37 |
| CLIC4 | | 0.40 | |
| SFXN1 | | 0.52 | 0.36 |
| SLC25A13 | | 0.60 | 0.30 |
| PXMP2 | | 2.17 | |
| RAN | | 2.20 | |
| SEC61B | | 2.49 | 2.89 |
| GDI2 | | 2.80 | |
| NUTF2 | | 2.90 | |
| RABIF | | 3.08 | |
| CHMP4B | | 4.29 | |
| CHMP1A | | 4.30 | |
| TXNRD1 | | 4.40 | |
| CHMP5 | | 4.44 | |
| DBI | | 4.66 | |
| CHMP2A | | 4.82 | 0.46 |
| CHMP1B | | 5.80 | |
| CHMP4A | | 18.56 | |
| SPG11 | | 2.79 | |
| TTC35 | | 3.64 | |

TABLE 2-continued

Differetially Expressed Proteins

| Protein | Macrophages (combined) | Trophoblasts Jar | AC-1M88 |
|---|---|---|---|
| CXorf26 | 6.47 | | |
| SLC3A2 | | | 2.32 |
| SFRS3 | | | 2.03 |
| GAPDH | | | 0.18 |
| GLA | | | 0.45 |
| HEXB | | | 0.48 |
| GM2A | | | 0.45 |
| MGAT3 | | | 0.28 |
| PDIA6 | | | 0.30 |
| DDOST | | | 0.35 |
| RPL24 | | | 2.07 |
| RPL7A | | | 2.10 |
| RPL26 | | | 2.15 |
| RPL23A | | | 2.36 |
| RPS8 | | | 2.38 |
| RPL3 | | | 2.70 |
| RPL29 | | | 2.84 |
| RPL31 | | | 3.53 |
| PSMA5 | | | 0.49 |
| PRSS8 | | | 2.07 |
| HMOX1 | | | 0.33 |
| HSPE1 | | | 2.19 |
| PRDX3 | | | 3.83 |
| C11orf59 | | | 0.46 |
| RAB2A | | | 0.50 |
| PPP1R12A | | | 2.15 |
| DLG1 | | | 2.23 |
| L1CAM | | | 0.41 |
| BCAM | | | 2.01 |
| LAMP2 | | | 0.09 |
| MYL6B | | | 0.28 |
| TAGLN2 | | | 2.05 |
| RAI14 | | | 2.08 |
| SEPT11 | | | 2.11 |
| LIMA1 | | | 2.14 |
| GOLGA7 | | | 0.24 |
| GCC2 | | | 0.26 |
| GOSR1 | | | 0.45 |
| UXS1 | | | 0.43 |
| XRCC6 | | | 2.26 |
| ATP5L | | | 0.18 |
| NDUFB10 | | | 0.37 |
| COX5B | | | 0.43 |
| NDUFA2 | | | 2.45 |
| SLC25A11 | | | 0.12 |
| PGRMC1 | | | 0.37 |
| CYB5A | | | 0.38 |

Protein Biomarker Selection and MRM Assay Development

The proteomics analysis was focused on host compartments associated with secretion in order to enrich for proteins that were likely to be eventually found in the circulation. Both upregulated and down regulated proteins were identified following infection, and that combined dataset was useful for deriving insights into the host-pathogen interactions. However, for selection of biomarker candidates of infection, the secretory proteins that appear to become up-regulated in the host cell secretomes after infection were focused on.

A multiplex MRM assay was developed for 169 proteins that were upregulated in infected macrophages and trophoblasts, represented by 331 peptides. The proteins were selected from all the biological processes identified to be affected by the infection. A relatively small number of the upregulated candidate biomarker proteins identified were excluded from the multiplex MRM assay. That number included those candidates for which protein-specific peptides meeting the selection criteria described in the Materials and Methods could not be identified, as well as those where the selected peptides failed to produce an appropriate signal during MRM method development.

Biomarker Verification by ELISA and MRM

The majority of the candidate biomarkers in the MRM assay did not have known concentrations in plasma or serum. Although sera depleted of multiple high abundance proteins was used, it remained a distinct possibility that many of the biomarker candidates included in the multiplex MRM assay would be beneath its limit of detection. For a few of the secreted proteins that became upregulated after infection, such as IL-1b, serum concentrations were expected to be beneath the level of detection of the MRM assay. However, for the vast majority of the other biomarker candidates there was insufficient information to make that assessment. Twenty-two commercially available ELISA kits against a selection of biomarker candidates were obtained, 20 of which were also included in the MRM assay. A two-stage evaluation was used. Initially, each ELISA kit was used to measure the candidate biomarker levels in sera of 28 brucellosis patients, an equal number of age and gender matched controls, and 24 samples from subjects with Lyme disease. The biomarker candidates that were able to discriminate the brucellosis samples from the combination of controls and other infectious disease samples were selected for more extensive evaluation. Four candidate biomarkers were thus selected, LYN, MAT2A, ANXA5, and RPL32A.

A total of 254 serum samples were used for the second stage ELISA-based evaluation. These samples represented subjects with acute brucellosis, healthy controls, as well as subjects with Lyme disease, Q-fever, and *salmonellosis* (Table 1). Brucellosis presents clinically as recurring fever typically with joint and abdominal pain. Lyme disease has a similar clinical presentation and epidemiology as brucellosis, but a dissimilar infection mechanism. Q-fever also has a similar presentation and epidemiology as brucellosis, and a similar infection mechanism. *Salmonellosis*, in contrast, has a dissimilar clinical presentation and epidemiology as brucellosis but also a similar infection mechanism. These three additional diseases, therefore, were useful in assessing the specificity of the candidate biomarkers as well as their physiological relevance. All the serum samples were age and gender matched to the brucellosis cohort (Table 3). The disease samples were all archival and obtained from different regions. To control for regional differences in immune profiles and site to site sample handling, healthy control samples from the same regions, matching site and geography were also obtained.

TABLE 3

Clinical samples used in biomarker candidate verification.

| Condition | Country | Number | Male/Female ratio (%) | Age (mean +/− standard deviation) |
|---|---|---|---|---|
| Healthy | Spain | 49* | 73/27 | 27.02 +/− 12.25 |
| Brucellosis | Spain | 28 | 82/18 | 25.11 +/− 12.60 |
| Healthy | USA | 28 | 86/14 | 28.29 +/− 18.09 |
| Lyme disease | USA | 44 | 77/23 | 31.41 +/− 16.47 |
| Healthy | France | 19 | 68/32 | 33.63 +/− 3.24 |
| Q-fever | France | 55 | 60/40 | 32.55 +/− 15.93 |
| Salmonellosis | France | 55 | 53/47 | 30.11 +/− 15.37 |

*For the ELISAs 25 samples were used (Male/Female ratio (%): 68/32; Age (mean +/− standard deviation): 26.72 +/− 12.41)

Two hundred seventy eight serum samples were used for the multiplex MRM assay. These included all the samples used for the ELISA assays described above, and included an additional 25 healthy control samples from Spain which had limiting volumes. The mass spectrometry data acquired was normalized using the appropriate regional control samples per cohort and the differential expression ratios were calculated for each candidate biomarker detected. Twenty of the biomarker candidates were reliably detected by the MRM assay. The biomarker candidates assessed by ELISA were not detected by the MRM assay. The ability of each biomarker candidate to classify the experimental and control sample groups was assessed individually (FIGS. 2-12) as well as in combination (Tables 3A-3D).

The candidate biomarkers that formed the best performing panels for brucellosis comparisons to Q fever, Lyme disease and to healthy controls have good individual performance but were also able to complement each other. Classification performance improved when these biomarkers were used in combination compared to when they were used individually.

TABLE 3A

Bru vs q-fever

|  | AUC |
|---|---|
| B4GALT1 | 0.876 |
| CALU | 0.883 |
| HIST3H3 | 0.897 |
| HIST4 | 0.999 |
| ICAM1 | 0.874 |
| LDHB | 0.964 |
| LYN | 0.504 |
| MAT2A | 0.954 |
| MDH1 | 0.972 |
| MMP9 | 0.776 |
| TPI1 | 0.875 |

| prot 1 | prot 2 | prot 3 | prot 4 | prot 5 | prot 6 | prot 7 | AUC 1 |
|---|---|---|---|---|---|---|---|
| LDHB | MDH1 | TPI1 | MAT2A |  |  |  | 0.980 |
| B4GALT1 | LDHB | MDH1 | MAT2A |  |  |  | 0.980 |
| B4GALT1 | LDHB | MAT2A |  |  |  |  | 0.977 |
| LDHB | MDH1 | MAT2A |  |  |  |  | 0.975 |
| CALU | MAT2A |  |  |  |  |  | 0.975 |
| LDHB | MDH1 |  |  |  |  |  | 0.974 |
| B4GALT1 | LDHB | MMP9 | MAT2A |  |  |  | 0.973 |
| CALU | LDHB | MDH1 | MAT2A |  |  |  | 0.973 |
| LDHB | MDH1 | MMP9 | MAT2A |  |  |  | 0.972 |
| ICAM1 | LDHB | MDH1 |  |  |  |  | 0.972 |
| LDHB | MDH1 | TPI1 |  |  |  |  | 0.971 |
| B4GALT1 | LDHB | TPI1 | MAT2A |  |  |  | 0.971 |
| CALU | MDH1 |  |  |  |  |  | 0.970 |
| B4GALT1 | LDHB | MDH1 |  |  |  |  | 0.970 |
| CALU | LDHB | MDH1 |  |  |  |  | 0.970 |
| ICAM1 | MDH1 |  |  |  |  |  | 0.970 |
| B4GALT1 | ICAM1 | LDHB | MAT2A |  |  |  | 0.970 |
| B4GALT1 | CALU | MAT2A |  |  |  |  | 0.969 |
| B4GALT1 | CALU | LDHB | MAT2A |  |  |  | 0.969 |
| LDHB | MDH1 | MMP9 |  |  |  |  | 0.968 |
| CALU | LDHB | MAT2A |  |  |  |  | 0.968 |
| B4GALT1 | CALU | LDHB | MDH1 |  |  |  | 0.968 |
| LDHB | MAT2A |  |  |  |  |  | 0.968 |
| B4GALT1 | LDHB | MDH1 | TPI1 |  |  |  | 0.968 |
| MDH1 | MAT2A |  |  |  |  |  | 0.968 |
| B4GALT1 | MDH1 |  |  |  |  |  | 0.967 |
| CALU | LDHB | MMP9 | MAT2A |  |  |  | 0.967 |
| B4GALT1 | ICAM1 | LDHB | MDH1 |  |  |  | 0.967 |
| ICAM1 | MAT2A |  |  |  |  |  | 0.967 |
| CALU | MDH1 | MAT2A |  |  |  |  | 0.967 |
| ICAM1 | MDH1 | MAT2A |  |  |  |  | 0.967 |
| ICAM1 | LDHB | MDH1 | MAT2A |  |  |  | 0.967 |
| CALU | LDHB | TPI1 | MAT2A |  |  |  | 0.967 |
| CALU | ICAM1 | MDH1 | MAT2A |  |  |  | 0.966 |
| CALU | LDHB | MDH1 | TPI1 |  |  |  | 0.966 |
| B4GALT1 | MDH1 | MAT2A |  |  |  |  | 0.966 |
| LDHB | MMP9 | MAT2A |  |  |  |  | 0.966 |
| B4GALT1 | LDHB | MDH1 | MMP9 |  |  |  | 0.966 |
| CALU | MMP9 | MAT2A |  |  |  |  | 0.966 |
| B4GALT1 | ICAM1 | MDH1 | MAT2A |  |  |  | 0.966 |
| CALU | ICAM1 | LDHB | MDH1 |  |  |  | 0.965 |
| ICAM1 | LDHB | MDH1 | TPI1 |  |  |  | 0.965 |
| LDHB | TPI1 | MAT2A |  |  |  |  | 0.965 |
| CALU | MDH1 | MMP9 | MAT2A |  |  |  | 0.965 |
| CALU | ICAM1 | MDH1 |  |  |  |  | 0.965 |
| ICAM1 | LDHB | MDH1 | MMP9 |  |  |  | 0.964 |
| B4GALT1 | CALU | MDH1 | MAT2A |  |  |  | 0.964 |
| ICAM1 | MMP9 | MAT2A |  |  |  |  | 0.964 |
| ICAM1 | LDHB | MAT2A |  |  |  |  | 0.964 |
| B4GALT1 | MDH1 | TPI1 | MAT2A |  |  |  | 0.964 |

TABLE 3A-continued

| | | Bru vs q-fever | | |
|---|---|---|---|---|
| CALU | LDHB | MDH1 | MMP9 | 0.964 |
| B4GALT1 | MDH1 | MMP9 | MAT2A | 0.963 |
| CALU | ICAM1 | LDHB | MAT2A | 0.963 |
| ICAM1 | MDH1 | MMP9 | MAT2A | 0.963 |
| ICAM1 | MDH1 | TPI1 | MAT2A | 0.963 |
| LDHB | TPI1 | | | 0.962 |
| LDHB | MMP9 | | | 0.962 |
| B4GALT1 | ICAM1 | MDH1 | | 0.962 |
| B4GALT1 | CALU | MDH1 | | 0.962 |
| B4GALT1 | CALU | MMP9 | MAT2A | 0.962 |
| ICAM1 | TPI1 | MAT2A | | 0.961 |
| B4GALT1 | CALU | ICAM1 | MAT2A | 0.961 |
| CALU | LDHB | | | 0.961 |
| LDHB | MDH1 | MMP9 | TPI1 | 0.961 |
| CALU | TPI1 | MAT2A | | 0.961 |
| B4GALT1 | LDHB | | | 0.960 |
| MDH1 | MMP9 | MAT2A | | 0.960 |
| MDH1 | TPI1 | MAT2A | | 0.960 |
| B4GALT1 | ICAM1 | MAT2A | | 0.960 |
| MDH1 | MMP9 | | | 0.960 |
| ICAM1 | LDHB | MMP9 | MAT2A | 0.960 |
| LDHB | MDH1 | LYN | | 0.960 |
| LDHB | MMP9 | TPI1 | | 0.960 |
| B4GALT1 | LDHB | TPI1 | | 0.959 |
| ICAM1 | LDHB | | | 0.959 |
| MDH1 | TPI1 | | | 0.959 |
| CALU | MDH1 | TPI1 | MAT2A | 0.959 |
| CALU | MDH1 | MMP9 | | 0.959 |
| ICAM1 | MDH1 | MMP9 | | 0.958 |
| ICAM1 | MDH1 | TPI1 | | 0.958 |
| LDHB | MDH1 | TPI1 | LYN | 0.958 |
| ICAM1 | LDHB | MMP9 | | 0.958 |
| CALU | ICAM1 | LDHB | | 0.958 |
| CALU | LDHB | TPI1 | | 0.958 |
| CALU | ICAM1 | MAT2A | | 0.957 |
| ICAM1 | LDHB | MDH1 | LYN | 0.957 |
| B4GALT1 | LDHB | LYN | MAT2A | 0.957 |
| ICAM1 | LDHB | TPI1 | | 0.957 |
| B4GALT1 | LDHB | MMP9 | | 0.956 |
| TPI1 | MAT2A | | | 0.956 |
| B4GALT1 | ICAM1 | MMP9 | MAT2A | 0.956 |
| B4GALT1 | MDH1 | TPI1 | | 0.956 |
| CALU | LDHB | MMP9 | | 0.956 |
| LDHB | MDH1 | LYN | MAT2A | 0.955 |
| B4GALT1 | ICAM1 | LDHB | | 0.955 |
| B4GALT1 | MDH1 | MMP9 | | 0.955 |
| ICAM1 | LDHB | TPI1 | MAT2A | 0.955 |
| MMP9 | TPI1 | MAT2A | | 0.954 |
| ICAM1 | MMP9 | TPI1 | MAT2A | 0.954 |
| B4GALT1 | CALU | TPI1 | MAT2A | 0.954 |
| CALU | MDH1 | TPI1 | | 0.954 |
| B4GALT1 | CALU | ICAM1 | MDH1 | 0.954 |
| B4GALT1 | LDHB | MMP9 | TPI1 | 0.954 |
| LDHB | MDH1 | MMP9 | LYN | 0.954 |
| MMP9 | MAT2A | | | 0.954 |
| B4GALT1 | CALU | LDHB | | 0.954 |
| CALU | ICAM1 | LDHB | TPI1 | 0.953 |
| ICAM1 | LDHB | MMP9 | TPI1 | 0.953 |
| B4GALT1 | ICAM1 | TPI1 | MAT2A | 0.953 |
| B4GALT1 | ICAM1 | LDHB | TPI1 | 0.952 |
| MDH1 | LYN | | | 0.952 |
| LDHB | MMP9 | TPI1 | MAT2A | 0.952 |
| B4GALT1 | ICAM1 | LDHB | MMP9 | 0.952 |
| CALU | ICAM1 | LDHB | MMP9 | 0.951 |
| MDH1 | MMP9 | TPI1 | MAT2A | 0.951 |
| CALU | LDHB | MMP9 | TPI1 | 0.951 |
| CALU | ICAM1 | MDH1 | MMP9 | 0.951 |
| CALU | ICAM1 | MMP9 | MAT2A | 0.951 |
| LDHB | MMP9 | LYN | MAT2A | 0.951 |
| B4GALT1 | CALU | LDHB | TPI1 | 0.951 |
| CALU | ICAM1 | TPI1 | MAT2A | 0.951 |
| MDH1 | MMP9 | TPI1 | | 0.950 |
| B4GALT1 | CALU | MDH1 | MMP9 | 0.950 |
| B4GALT1 | ICAM1 | MDH1 | TPI1 | 0.950 |
| B4GALT1 | CALU | LDHB | MMP9 | 0.950 |
| B4GALT1 | ICAM1 | MDH1 | MMP9 | 0.950 |
| ICAM1 | LDHB | LYN | MAT2A | 0.950 |
| B4GALT1 | CALU | ICAM1 | LDHB | 0.950 |

TABLE 3A-continued

| | | Bru vs q-fever | | |
|---|---|---|---|---|
| LDHB | TPI1 | LYN | MAT2A | 0.949 |
| B4GALT1 | TPI1 | MAT2A | | 0.949 |
| ICAM1 | MDH1 | LYN | | 0.949 |
| B4GALT1 | MMP9 | MAT2A | | 0.948 |
| CALU | MMP9 | TPI1 | MAT2A | 0.948 |
| CALU | LDHB | MDH1 | LYN | 0.948 |
| CALU | MDH1 | LYN | | 0.948 |
| LDHB | LYN | MAT2A | | 0.948 |
| B4GALT1 | MAT2A | | | 0.948 |
| CALU | ICAM1 | MDH1 | TPI1 | 0.947 |
| ICAM1 | MMP9 | TPI1 | | 0.947 |
| B4GALT1 | MMP9 | TPI1 | MAT2A | 0.947 |
| B4GALT1 | LDHB | MDH1 | LYN | 0.946 |
| LDHB | LYN | | | 0.946 |
| LDHB | TPI1 | LYN | | 0.945 |
| CALU | MDH1 | MMP9 | LYN | 0.945 |
| B4GALT1 | MDH1 | MMP9 | TPI1 | 0.945 |
| CALU | LYN | MAT2A | | 0.945 |
| CALU | MDH1 | LYN | MAT2A | 0.945 |
| CALU | LDHB | LYN | MAT2A | 0.944 |
| ICAM1 | LYN | MAT2A | | 0.944 |
| B4GALT1 | CALU | MDH1 | TPI1 | 0.943 |
| MDH1 | LYN | MAT2A | | 0.943 |
| CALU | MDH1 | MMP9 | TPI1 | 0.942 |
| B4GALT1 | MDH1 | LYN | | 0.942 |
| ICAM1 | MDH1 | LYN | MAT2A | 0.942 |
| MDH1 | MMP9 | LYN | | 0.942 |
| CALU | ICAM1 | MDH1 | LYN | 0.941 |
| MDH1 | TPI1 | LYN | | 0.941 |
| LDHB | MMP9 | LYN | | 0.941 |
| B4GALT1 | MDH1 | LYN | MAT2A | 0.940 |
| ICAM1 | MMP9 | LYN | MAT2A | 0.940 |
| CALU | MMP9 | LYN | MAT2A | 0.939 |
| ICAM1 | TPI1 | LYN | MAT2A | 0.938 |
| MDH1 | TPI1 | LYN | MAT2A | 0.938 |
| ICAM1 | MDH1 | MMP9 | LYN | 0.938 |
| ICAM1 | LDHB | LYN | | 0.938 |
| B4GALT1 | LDHB | LYN | | 0.938 |
| CALU | LDHB | TPI1 | LYN | 0.937 |
| B4GALT1 | CALU | LYN | MAT2A | 0.937 |
| LDHB | MMP9 | TPI1 | LYN | 0.937 |
| ICAM1 | MDH1 | TPI1 | LYN | 0.937 |
| CALU | ICAM1 | LYN | MAT2A | 0.937 |
| CALU | LDHB | LYN | | 0.936 |
| LYN | MAT2A | | | 0.935 |
| B4GALT1 | LDHB | TPI1 | LYN | 0.934 |
| ICAM1 | LDHB | MMP9 | LYN | 0.934 |
| CALU | TPI1 | LYN | MAT2A | 0.934 |
| MDH1 | MMP9 | TPI1 | LYN | 0.934 |
| CALU | MDH1 | TPI1 | LYN | 0.933 |
| B4GALT1 | LDHB | MMP9 | LYN | 0.933 |
| B4GALT1 | ICAM1 | MDH1 | LYN | 0.932 |
| B4GALT1 | MDH1 | MMP9 | LYN | 0.932 |
| TPI1 | LYN | MAT2A | | 0.932 |
| MDH1 | MMP9 | LYN | MAT2A | 0.932 |
| B4GALT1 | ICAM1 | LYN | MAT2A | 0.931 |
| B4GALT1 | ICAM1 | LDHB | LYN | 0.931 |
| MMP9 | TPI1 | LYN | MAT2A | 0.931 |
| CALU | LDHB | MMP9 | LYN | 0.931 |
| B4GALT1 | CALU | MDH1 | LYN | 0.930 |
| MMP9 | LYN | MAT2A | | 0.930 |
| CALU | ICAM1 | LDHB | LYN | 0.929 |
| B4GALT1 | MDH1 | TPI1 | LYN | 0.928 |
| ICAM1 | LDHB | TPI1 | LYN | 0.928 |
| B4GALT1 | CALU | LDHB | LYN | 0.926 |
| B4GALT1 | LYN | MAT2A | | 0.924 |
| B4GALT1 | TPI1 | LYN | MAT2A | 0.923 |
| B4GALT1 | MMP9 | LYN | MAT2A | 0.921 |
| B4GALT1 | CALU | | | 0.900 |
| B4GALT1 | CALU | TPI1 | | 0.899 |
| CALU | TPI1 | | | 0.898 |
| B4GALT1 | CALU | MMP9 | | 0.896 |
| B4GALT1 | CALU | MMP9 | TPI1 | 0.895 |
| B4GALT1 | ICAM1 | TPI1 | | 0.893 |
| CALU | MMP9 | TPI1 | | 0.893 |
| B4GALT1 | TPI1 | | | 0.893 |
| ICAM1 | TPI1 | | | 0.892 |
| CALU | ICAM1 | TPI1 | | 0.890 |

TABLE 3A-continued

| | | Bru vs q-fever | | | |
|---|---|---|---|---|---|
| B4GALT1 | CALU | ICAM1 | TPI1 | | 0.889 |
| B4GALT1 | CALU | ICAM1 | | | 0.888 |
| B4GALT1 | ICAM1 | | | | 0.886 |
| CALU | ICAM1 | MMP9 | TPI1 | | 0.886 |
| B4GALT1 | CALU | ICAM1 | MMP9 | | 0.885 |
| CALU | MMP9 | | | | 0.879 |
| ICAM1 | MMP9 | TPI1 | | | 0.879 |
| B4GALT1 | MMP9 | TPI1 | | | 0.878 |
| B4GALT1 | ICAM1 | MMP9 | TPI1 | | 0.878 |
| CALU | ICAM1 | | | | 0.877 |
| CALU | ICAM1 | MMP9 | | | 0.876 |
| B4GALT1 | ICAM1 | MMP9 | | | 0.872 |
| B4GALT1 | TPI1 | LYN | | | 0.866 |
| B4GALT1 | CALU | LYN | | | 0.864 |
| B4GALT1 | CALU | TPI1 | LYN | | 0.863 |
| MMP9 | TPI1 | | | | 0.863 |
| B4GALT1 | CALU | MMP9 | LYN | | 0.862 |
| ICAM1 | MMP9 | | | | 0.860 |
| CALU | TPI1 | LYN | | | 0.858 |
| B4GALT1 | MMP9 | | | | 0.858 |
| B4GALT1 | ICAM1 | TPI1 | LYN | | 0.853 |
| B4GALT1 | ICAM1 | LYN | | | 0.852 |
| ICAM1 | TPI1 | LYN | | | 0.852 |
| CALU | MMP9 | TPI1 | LYN | | 0.851 |
| B4GALT1 | LYN | | | | 0.851 |
| B4GALT1 | MMP9 | TPI1 | LYN | | 0.850 |
| B4GALT1 | CALU | ICAM1 | LYN | | 0.849 |
| CALU | ICAM1 | TPI1 | LYN | | 0.846 |
| ICAM1 | MMP9 | TPI1 | LYN | | 0.844 |
| B4GALT1 | ICAM1 | MMP9 | LYN | | 0.844 |
| B4GALT1 | MMP9 | LYN | | | 0.840 |
| TPI1 | LYN | | | | 0.839 |
| CALU | LYN | | | | 0.838 |
| CALU | MMP9 | LYN | | | 0.837 |
| CALU | ICAM1 | MMP9 | LYN | | 0.835 |
| ICAM1 | LYN | | | | 0.832 |
| CALU | ICAM1 | LYN | | | 0.832 |
| ICAM1 | MMP9 | LYN | | | 0.826 |
| MMP9 | TPI1 | LYN | | | 0.825 |
| MMP9 | LYN | | | | 0.746 |

TABLE 3B

| | Bru vs lyme | |
|---|---|---|
| | | AUC |
| | B4GALT1 | 0.842 |
| | CALU | 0.543 |
| | HIST3H3 | 0.753 |
| | HIST4 | 0.995 |
| | ICAM1 | 0.896 |
| | LDHB | 0.885 |
| | LYN | 0.841 |
| | MAT2A | 0.965 |
| | MDH1 | 0.946 |
| | MMP9 | 0.902 |
| | TPI1 | 0.652 |

| prot 1 | prot 2 | prot 3 | prot 4 | prot 5 | prot 6 | prot 7 | AUC 1 |
|---|---|---|---|---|---|---|---|
| B4GALT1 | HIST3H3 | LYN | | | | | 0.932 |
| B4GALT1 | CALU | ICAM1 | LDHB | TPI1 | MAT2A | | 0.931 |
| B4GALT1 | ICAM1 | LDHB | TPI1 | | | | 0.896 |
| CALU | HIST3H3 | HIST4 | MMP9 | LYN | | | 1.000 |
| CALU | HIST4 | ICAM1 | LDHB | MMP9 | LYN | | 1.000 |
| CALU | HIST4 | MMP9 | TPI1 | LYN | | | 1.000 |
| CALU | HIST4 | ICAM1 | MDH1 | MMP9 | TPI1 | | 1.000 |
| CALU | HIST3H3 | HIST4 | ICAM1 | | | | 1.000 |
| CALU | HIST3H3 | HIST4 | ICAM1 | MMP9 | | | 1.000 |
| CALU | HIST3H3 | HIST4 | TPI1 | LYN | | | 0.999 |
| CALU | HIST4 | ICAM1 | LDHB | MMP9 | | | 0.999 |
| CALU | HIST3H3 | HIST4 | LDHB | MDH1 | MMP9 | | 0.999 |
| CALU | HIST3H3 | HIST4 | ICAM1 | TPI1 | | | 0.999 |
| CALU | HIST4 | MDH1 | MMP9 | TPI1 | | | 0.999 |

TABLE 3B-continued

| | | Bru vs lyme | | | | |
|---|---|---|---|---|---|---|
| CALU | HIST3H3 | HIST4 | LDHB | MMP9 | TPI1 | 0.999 |
| CALU | HIST3H3 | HIST4 | ICAM1 | LDHB | | 0.999 |
| CALU | HIST3H3 | HIST4 | MMP9 | TPI1 | | 0.999 |
| CALU | HIST3H3 | HIST4 | MDH1 | MMP9 | TPI1 | 0.999 |
| CALU | HIST3H3 | HIST4 | MMP9 | | | 0.999 |
| CALU | HIST3H3 | HIST4 | MDH1 | TPI1 | LYN | 0.999 |
| CALU | HIST3H3 | ICAM1 | MDH1 | MMP9 | LYN | 0.999 |
| CALU | HIST3H3 | HIST4 | LDHB | TPI1 | | 0.998 |
| CALU | HIST3H3 | HIST4 | ICAM1 | MDH1 | | 0.998 |
| CALU | HIST4 | ICAM1 | | | | 0.998 |
| CALU | HIST3H3 | HIST4 | LDHB | MDH1 | TPI1 | 0.998 |
| CALU | HIST3H3 | HIST4 | ICAM1 | MDH1 | TPI1 | 0.998 |
| CALU | ICAM1 | MMP9 | LYN | | | 0.998 |
| CALU | HIST4 | ICAM1 | TPI1 | LYN | | 0.998 |
| CALU | HIST4 | ICAM1 | TPI1 | | | 0.998 |
| CALU | HIST3H3 | HIST4 | ICAM1 | LDHB | LYN | 0.998 |
| CALU | HIST4 | ICAM1 | MMP9 | TPI1 | MAT2A | 0.997 |
| CALU | HIST4 | LDHB | MMP9 | TPI1 | | 0.997 |
| CALU | HIST3H3 | MDH1 | LYN | | | 0.997 |
| CALU | HIST4 | LDHB | MMP9 | | | 0.997 |
| CALU | HIST4 | | | | | 0.997 |
| CALU | HIST4 | MDH1 | TPI1 | | | 0.997 |
| CALU | ICAM1 | MDH1 | MMP9 | LYN | | 0.997 |
| CALU | HIST3H3 | HIST4 | LDHB | MDH1 | LYN | 0.997 |
| CALU | HIST4 | LDHB | MMP9 | TPI1 | MAT2A | 0.997 |
| CALU | HIST4 | MDH1 | TPI1 | LYN | | 0.997 |
| CALU | HIST4 | MMP9 | TPI1 | | | 0.996 |
| CALU | HIST4 | ICAM1 | MDH1 | TPI1 | LYN | 0.996 |
| CALU | HIST4 | MDH1 | | | | 0.996 |
| CALU | HIST4 | LDHB | | | | 0.996 |
| CALU | HIST4 | ICAM1 | LDHB | LYN | | 0.995 |
| CALU | LDHB | MDH1 | MMP9 | LYN | | 0.995 |
| CALU | HIST4 | LDHB | MDH1 | TPI1 | | 0.995 |
| CALU | HIST4 | LDHB | MDH1 | | | 0.995 |
| CALU | ICAM1 | MMP9 | TPI1 | LYN | | 0.995 |
| CALU | MDH1 | MMP9 | LYN | | | 0.995 |
| CALU | HIST4 | ICAM1 | LDHB | MDH1 | | 0.995 |
| CALU | HIST4 | ICAM1 | LDHB | MDH1 | LYN | 0.993 |
| CALU | HIST4 | LDHB | MDH1 | LYN | | 0.993 |
| CALU | ICAM1 | LDHB | MDH1 | MMP9 | LYN | 0.993 |
| CALU | HIST3H3 | MDH1 | MMP9 | LYN | | 0.993 |
| CALU | HIST4 | ICAM1 | MMP9 | LYN | MAT2A | 0.992 |
| CALU | HIST4 | MDH1 | MMP9 | MAT2A | | 0.991 |
| CALU | LDHB | MDH1 | MMP9 | TPI1 | LYN | 0.991 |
| CALU | HIST4 | MMP9 | TPI1 | MAT2A | | 0.989 |
| CALU | HIST4 | ICAM1 | LDHB | MMP9 | MAT2A | 0.988 |
| CALU | ICAM1 | LDHB | MMP9 | MAT2A | | 0.987 |
| CALU | HIST3H3 | HIST4 | ICAM1 | MMP9 | MAT2A | 0.987 |
| CALU | LDHB | MMP9 | MAT2A | | | 0.986 |
| CALU | HIST3H3 | ICAM1 | LDHB | MMP9 | MAT2A | 0.986 |
| CALU | ICAM1 | MMP9 | LYN | MAT2A | | 0.984 |
| CALU | ICAM1 | MMP9 | TPI1 | LYN | MAT2A | 0.983 |
| CALU | HIST3H3 | HIST4 | MMP9 | MAT2A | | 0.983 |
| CALU | HIST3H3 | HIST4 | LDHB | MMP9 | MAT2A | 0.982 |
| CALU | HIST3H3 | ICAM1 | LDHB | MMP9 | | 0.982 |
| CALU | HIST3H3 | HIST4 | LDHB | TPI1 | MAT2A | 0.982 |
| CALU | ICAM1 | LDHB | MDH1 | MMP9 | MAT2A | 0.982 |
| CALU | MDH1 | MMP9 | MAT2A | | | 0.981 |
| CALU | LDHB | MMP9 | LYN | | | 0.980 |
| CALU | HIST3H3 | HIST4 | TPI1 | LYN | MAT2A | 0.979 |
| CALU | LDHB | MMP9 | TPI1 | MAT2A | | 0.979 |
| CALU | HIST4 | ICAM1 | LDHB | TPI1 | MAT2A | 0.978 |
| CALU | ICAM1 | MDH1 | MMP9 | TPI1 | | 0.978 |
| CALU | ICAM1 | LDHB | MMP9 | LYN | MAT2A | 0.978 |
| CALU | HIST3H3 | HIST4 | LDHB | MAT2A | | 0.977 |
| CALU | ICAM1 | MDH1 | MMP9 | LYN | MAT2A | 0.977 |
| CALU | MDH1 | MMP9 | TPI1 | LYN | MAT2A | 0.976 |
| CALU | HIST4 | ICAM1 | MDH1 | TPI1 | MAT2A | 0.976 |
| CALU | HIST3H3 | MMP9 | TPI1 | LYN | MAT2A | 0.976 |
| CALU | MMP9 | LYN | MAT2A | | | 0.975 |
| CALU | HIST3H3 | HIST4 | MAT2A | | | 0.975 |
| CALU | HIST4 | MDH1 | TPI1 | LYN | MAT2A | 0.974 |
| CALU | ICAM1 | MMP9 | MAT2A | | | 0.974 |
| CALU | LDHB | MMP9 | LYN | MAT2A | | 0.974 |
| CALU | MDH1 | MMP9 | LYN | MAT2A | | 0.973 |
| CALU | MMP9 | LYN | | | | 0.973 |
| CALU | MDH1 | MMP9 | | | | 0.973 |
| CALU | HIST3H3 | MMP9 | LYN | MAT2A | | 0.972 |

TABLE 3B-continued

| | | Bru vs lyme | | | | |
|---|---|---|---|---|---|---|
| CALU | HIST4 | LDHB | LYN | MAT2A | | 0.972 |
| CALU | ICAM1 | LDHB | MDH1 | | | 0.972 |
| CALU | HIST3H3 | MDH1 | MMP9 | LYN | MAT2A | 0.972 |
| CALU | HIST4 | MDH1 | LYN | MAT2A | | 0.971 |
| CALU | HIST4 | ICAM1 | MDH1 | MAT2A | | 0.970 |
| CALU | ICAM1 | LDHB | MMP9 | TPI1 | | 0.969 |
| CALU | HIST4 | ICAM1 | MAT2A | | | 0.969 |
| CALU | HIST4 | ICAM1 | LDHB | MAT2A | | 0.968 |
| CALU | HIST4 | ICAM1 | MDH1 | LYN | MAT2A | 0.968 |
| CALU | HIST4 | ICAM1 | LYN | MAT2A | | 0.966 |
| CALU | LDHB | MDH1 | MMP9 | | | 0.966 |
| CALU | HIST4 | ICAM1 | LDHB | MDH1 | MAT2A | 0.965 |
| CALU | MMP9 | TPI1 | MAT2A | | | 0.962 |
| CALU | HIST3H3 | MDH1 | MMP9 | TPI1 | | 0.962 |
| CALU | HIST3H3 | LDHB | MDH1 | | | 0.955 |
| CALU | ICAM1 | LDHB | MDH1 | TPI1 | LYN | 0.955 |
| CALU | LDHB | MDH1 | TPI1 | LYN | | 0.954 |
| CALU | HIST3H3 | ICAM1 | TPI1 | | | 0.953 |
| CALU | HIST3H3 | ICAM1 | LDHB | | | 0.950 |
| CALU | HIST3H3 | ICAM1 | LYN | | | 0.949 |
| CALU | ICAM1 | LYN | | | | 0.949 |
| CALU | ICAM1 | TPI1 | MAT2A | | | 0.948 |
| CALU | ICAM1 | MDH1 | TPI1 | MAT2A | | 0.944 |
| CALU | TPI1 | MAT2A | | | | 0.944 |
| CALU | ICAM1 | LDHB | MAT2A | | | 0.943 |
| CALU | ICAM1 | LDHB | LYN | | | 0.943 |
| CALU | HIST3H3 | MDH1 | MAT2A | | | 0.941 |
| CALU | ICAM1 | LDHB | TPI1 | MAT2A | | 0.941 |
| CALU | ICAM1 | LDHB | MDH1 | TPI1 | MAT2A | 0.941 |
| CALU | HIST3H3 | ICAM1 | MDH1 | TPI1 | MAT2A | 0.938 |
| CALU | ICAM1 | | | | | 0.938 |
| CALU | HIST3H3 | MAT2A | | | | 0.938 |
| CALU | LDHB | MDH1 | TPI1 | MAT2A | | 0.937 |
| CALU | LDHB | MDH1 | TPI1 | LYN | MAT2A | 0.937 |
| CALU | ICAM1 | LDHB | TPI1 | LYN | | 0.937 |
| CALU | HIST3H3 | TPI1 | MAT2A | | | 0.935 |
| CALU | HIST3H3 | LDHB | MDH1 | MAT2A | | 0.933 |
| CALU | ICAM1 | MDH1 | LYN | MAT2A | | 0.933 |
| CALU | HIST3H3 | MDH1 | LYN | MAT2A | | 0.931 |
| CALU | HIST3H3 | MDH1 | TPI1 | MAT2A | | 0.929 |
| CALU | HIST3H3 | MDH1 | TPI1 | LYN | | 0.928 |
| CALU | LDHB | MAT2A | | | | 0.928 |
| CALU | HIST3H3 | LDHB | MDH1 | LYN | MAT2A | 0.922 |
| CALU | HIST3H3 | LDHB | MDH1 | TPI1 | LYN | 0.922 |
| CALU | LDHB | TPI1 | MAT2A | | | 0.922 |
| CALU | LDHB | | | | | 0.903 |
| CALU | LDHB | TPI1 | LYN | | | 0.898 |
| CALU | LDHB | TPI1 | | | | 0.891 |
| CALU | HIST3H3 | LDHB | TPI1 | LYN | | 0.891 |
| HIST3H3 | HIST4 | MMP9 | TPI1 | LYN | | 1.000 |
| HIST3H3 | HIST4 | LDHB | MMP9 | LYN | | 1.000 |
| HIST3H3 | HIST4 | ICAM1 | MDH1 | MMP9 | TPI1 | 1.000 |
| HIST3H3 | HIST4 | ICAM1 | LDHB | MMP9 | TPI1 | 1.000 |
| HIST3H3 | HIST4 | ICAM1 | MDH1 | MMP9 | TPI1 | 1.000 |
| HIST3H3 | HIST4 | LYN | | | | 1.000 |
| HIST3H3 | HIST4 | LDHB | MMP9 | TPI1 | | 1.000 |
| HIST3H3 | HIST4 | ICAM1 | LDHB | TPI1 | LYN | 0.999 |
| HIST3H3 | HIST4 | LDHB | TPI1 | | | 0.998 |
| HIST3H3 | HIST4 | ICAM1 | TPI1 | | | 0.998 |
| HIST3H3 | HIST4 | LDHB | MDH1 | TPI1 | | 0.998 |
| HIST3H3 | HIST4 | ICAM1 | LDHB | | | 0.998 |
| HIST3H3 | ICAM1 | MDH1 | MMP9 | LYN | | 0.997 |
| HIST3H3 | HIST4 | ICAM1 | MDH1 | LYN | | 0.997 |
| HIST3H3 | ICAM1 | MMP9 | TPI1 | | | 0.994 |
| HIST3H3 | HIST4 | ICAM1 | MMP9 | LYN | MAT2A | 0.991 |
| HIST3H3 | LDHB | MDH1 | MMP9 | LYN | | 0.991 |
| HIST3H3 | ICAM1 | MMP9 | MAT2A | | | 0.990 |
| HIST3H3 | ICAM1 | MDH1 | MMP9 | TPI1 | | 0.990 |
| HIST3H3 | ICAM1 | LDHB | MMP9 | TPI1 | | 0.988 |
| HIST3H3 | HIST4 | LDHB | MDH1 | MMP9 | MAT2A | 0.986 |
| HIST3H3 | HIST4 | ICAM1 | LDHB | TPI1 | MAT2A | 0.985 |
| HIST3H3 | HIST4 | ICAM1 | MDH1 | MMP9 | MAT2A | 0.985 |
| HIST3H3 | ICAM1 | MDH1 | MMP9 | | | 0.985 |
| HIST3H3 | HIST4 | LDHB | MMP9 | LYN | MAT2A | 0.984 |
| HIST3H3 | ICAM1 | LDHB | MDH1 | MMP9 | TPI1 | 0.980 |
| HIST3H3 | MDH1 | MMP9 | | | | 0.980 |
| HIST3H3 | ICAM1 | MDH1 | MMP9 | MAT2A | | 0.979 |
| HIST3H3 | HIST4 | LDHB | MAT2A | | | 0.978 |

TABLE 3B-continued

| | | Bru vs lyme | | | |
|---|---|---|---|---|---|
| HIST3H3 | HIST4 | ICAM1 | LDHB | MAT2A | 0.977 |
| HIST3H3 | HIST4 | ICAM1 | LDHB | MDH1 | MAT2A | 0.976 |
| HIST3H3 | MMP9 | TPI1 | LYN | MAT2A | 0.970 |
| HIST3H3 | LDHB | MDH1 | MMP9 | TPI1 | MAT2A | 0.967 |
| HIST3H3 | MDH1 | MMP9 | TPI1 | MAT2A | 0.967 |
| HIST3H3 | LDHB | MMP9 | TPI1 | LYN | MAT2A | 0.965 |
| HIST3H3 | MMP9 | TPI1 | MAT2A | | 0.964 |
| HIST3H3 | MAT2A | | | | 0.944 |
| HIST3H3 | LDHB | MDH1 | | | 0.939 |
| HIST3H3 | ICAM1 | LDHB | MDH1 | MAT2A | 0.939 |
| HIST3H3 | MDH1 | TPI1 | LYN | MAT2A | 0.936 |
| HIST3H3 | ICAM1 | MDH1 | LYN | MAT2A | 0.936 |
| HIST3H3 | ICAM1 | LDHB | LYN | MAT2A | 0.934 |
| HIST3H3 | LDHB | MDH1 | TPI1 | | 0.932 |
| HIST3H3 | ICAM1 | LDHB | MDH1 | | 0.931 |
| HIST3H3 | ICAM1 | MDH1 | | | 0.931 |
| HIST3H3 | TPI1 | LYN | MAT2A | | 0.929 |
| HIST3H3 | LDHB | MDH1 | LYN | | 0.919 |
| HIST3H3 | LDHB | TPI1 | MAT2A | | 0.918 |
| HIST3H3 | ICAM1 | TPI1 | LYN | | 0.888 |
| HIST3H3 | LDHB | TPI1 | LYN | | 0.853 |
| HIST3H3 | TPI1 | LYN | | | 0.778 |
| HIST4 | ICAM1 | MDH1 | MMP9 | | 1.000 |
| HIST4 | MMP9 | | | | 0.999 |
| HIST4 | LDHB | MMP9 | TPI1 | | 0.999 |
| HIST4 | LDHB | MMP9 | TPI1 | MAT2A | 0.995 |
| HIST4 | ICAM1 | LDHB | MDH1 | LYN | MAT2A | 0.971 |
| HIST4 | ICAM1 | LDHB | MAT2A | | 0.971 |
| HIST4 | ICAM1 | MDH1 | MAT2A | | 0.970 |
| ICAM1 | LDHB | MMP9 | LYN | | 0.998 |
| ICAM1 | MMP9 | TPI1 | LYN | | 0.998 |
| ICAM1 | MDH1 | MMP9 | TPI1 | LYN | 0.996 |
| ICAM1 | LDHB | MMP9 | TPI1 | LYN | 0.994 |
| ICAM1 | MMP9 | LYN | MAT2A | | 0.985 |
| ICAM1 | MMP9 | TPI1 | LYN | MAT2A | 0.984 |
| ICAM1 | LDHB | MDH1 | MMP9 | TPI1 | 0.981 |
| ICAM1 | LDHB | MMP9 | MAT2A | | 0.977 |
| ICAM1 | MMP9 | MAT2A | | | 0.977 |
| ICAM1 | LDHB | MDH1 | MMP9 | LYN | MAT2A | 0.975 |
| ICAM1 | MDH1 | MMP9 | LYN | MAT2A | 0.975 |
| ICAM1 | LDHB | MMP9 | LYN | MAT2A | 0.974 |
| ICAM1 | MDH1 | TPI1 | LYN | MAT2A | 0.944 |
| ICAM1 | MDH1 | LYN | MAT2A | | 0.943 |
| ICAM1 | MDH1 | | | | 0.942 |
| ICAM1 | LDHB | LYN | MAT2A | | 0.942 |
| ICAM1 | MDH1 | TPI1 | | | 0.941 |
| ICAM1 | LDHB | TPI1 | LYN | MAT2A | 0.938 |
| ICAM1 | LDHB | LYN | | | 0.925 |
| ICAM1 | LDHB | MDH1 | TPI1 | LYN | 0.922 |
| ICAM1 | LDHB | LYN | | | 0.917 |
| ICAM1 | LYN | | | | 0.917 |
| ICAM1 | LDHB | TPI1 | LYN | | 0.915 |
| ICAM1 | TPI1 | LYN | | | 0.912 |
| ICAM1 | TPI1 | | | | 0.886 |
| LDHB | MDH1 | MMP9 | LYN | | 0.994 |
| LDHB | MDH1 | MMP9 | TPI1 | LYN | 0.992 |
| LDHB | MMP9 | MAT2A | | | 0.969 |
| LDHB | MDH1 | MMP9 | TPI1 | MAT2A | 0.969 |
| LDHB | MDH1 | MMP9 | TPI1 | | 0.968 |
| LDHB | MMP9 | | | | 0.962 |
| LDHB | MMP9 | LYN | MAT2A | | 0.957 |
| LDHB | MMP9 | TPI1 | | | 0.955 |
| LDHB | MMP9 | TPI1 | LYN | MAT2A | 0.953 |
| LDHB | LYN | MAT2A | | | 0.942 |
| LDHB | MAT2A | | | | 0.931 |
| LDHB | TPI1 | MAT2A | | | 0.927 |
| MDH1 | MMP9 | TPI1 | | | 0.973 |
| MDH1 | MMP9 | TPI1 | LYN | MAT2A | 0.970 |
| MDH1 | LYN | MAT2A | | | 0.948 |
| MDH1 | TPI1 | LYN | MAT2A | | 0.942 |
| MDH1 | TPI1 | LYN | | | 0.912 |
| MMP9 | LYN | | | | 0.976 |
| MMP9 | TPI1 | LYN | MAT2A | | 0.954 |
| MMP9 | TPI1 | | | | 0.939 |
| TPI1 | MAT2A | | | | 0.950 |
| TPI1 | LYN | | | | 0.809 |

TABLE 3C

| Bru vs control | |
|---|---|
| | AUC |
| B4GALT1 | 0.763 |
| CALU | 0.642 |
| HIST3H3 | 0.670 |
| HIST4 | 0.939 |
| ICAM1 | 0.862 |
| LDHB | 0.820 |
| LYN | 0.845 |
| MAT2A | 0.940 |
| MDH1 | 0.899 |
| MMP9 | 0.574 |
| TPI1 | 0.698 |

| prot 1 | prot 2 | prot 3 | prot 4 | prot 5 | prot 6 | prot 7 | AUC 1 |
|---|---|---|---|---|---|---|---|
| B4GALT1 | HIST3H3 | TPI1 | LYN | MAT2A | | | 0.934 |
| MMP9 | LYN | MAT2A | | | | | 0.934 |
| CALU | LYN | MAT2A | | | | | 0.936 |
| B4GALT1 | CALU | TPI1 | MAT2A | | | | 0.937 |
| HIST3H3 | LYN | MAT2A | | | | | 0.937 |
| B4GALT1 | CALU | ICAM1 | LDHB | TPI1 | MAT2A | | 0.937 |
| LDHB | MDH1 | MMP9 | TPI1 | LYN | MAT2A | | 0.937 |
| B4GALT1 | ICAM1 | LDHB | MAT2A | | | | 0.938 |
| HIST3H3 | MDH1 | LYN | MAT2A | | | | 0.938 |
| B4GALT1 | CALU | HIST3H3 | ICAM1 | MAT2A | | | 0.938 |
| B4GALT1 | ICAM1 | LDHB | MDH1 | MAT2A | | | 0.938 |
| B4GALT1 | ICAM1 | MDH1 | TPI1 | MAT2A | | | 0.938 |
| CALU | MDH1 | MMP9 | TPI1 | MAT2A | | | 0.938 |
| B4GALT1 | ICAM1 | LDHB | MDH1 | LYN | MAT2A | | 0.938 |
| CALU | HIST4 | LDHB | TPI1 | | | | 0.938 |
| B4GALT1 | CALU | HIST3H3 | HIST4 | | | | 0.938 |
| B4GALT1 | HIST3H3 | HIST4 | MMP9 | TPI1 | | | 0.938 |
| B4GALT1 | TPI1 | MAT2A | | | | | 0.938 |
| B4GALT1 | CALU | HIST3H3 | ICAM1 | LYN | MAT2A | | 0.938 |
| LDHB | MDH1 | TPI1 | LYN | MAT2A | | | 0.938 |
| CALU | LDHB | MDH1 | MMP9 | LYN | MAT2A | | 0.938 |
| B4GALT1 | CALU | ICAM1 | LDHB | LYN | MAT2A | | 0.939 |
| CALU | HIST3H3 | LDHB | MDH1 | TPI1 | MAT2A | | 0.939 |
| HIST3H3 | ICAM1 | MMP9 | TPI1 | LYN | MAT2A | | 0.939 |
| HIST3H3 | MMP9 | MAT2A | | | | | 0.939 |
| CALU | HIST3H3 | ICAM1 | TPI1 | MAT2A | | | 0.939 |
| B4GALT1 | CALU | HIST4 | ICAM1 | MMP9 | TPI1 | | 0.939 |
| B4GALT1 | HIST4 | TPI1 | | | | | 0.939 |
| B4GALT1 | HIST4 | MMP9 | TPI1 | | | | 0.939 |
| ICAM1 | LDHB | MDH1 | MMP9 | TPI1 | MAT2A | | 0.939 |
| HIST3H3 | ICAM1 | TPI1 | LYN | MAT2A | | | 0.939 |
| HIST3H3 | LDHB | MDH1 | LYN | MAT2A | | | 0.939 |
| ICAM1 | LDHB | MDH1 | MMP9 | LYN | MAT2A | | 0.940 |
| CALU | HIST4 | LDHB | | | | | 0.940 |
| HIST3H3 | LDHB | MAT2A | | | | | 0.940 |
| CALU | HIST3H3 | ICAM1 | MDH1 | TPI1 | MAT2A | | 0.940 |
| HIST3H3 | ICAM1 | MDH1 | MMP9 | TPI1 | MAT2A | | 0.940 |
| ICAM1 | MDH1 | MMP9 | TPI1 | LYN | MAT2A | | 0.940 |
| HIST3H3 | HIST4 | | | | | | 0.940 |
| CALU | LDHB | MDH1 | LYN | MAT2A | | | 0.940 |
| B4GALT1 | CALU | LDHB | MMP9 | LYN | MAT2A | | 0.940 |
| CALU | MMP9 | MAT2A | | | | | 0.940 |
| B4GALT1 | ICAM1 | LDHB | TPI1 | LYN | MAT2A | | 0.940 |
| B4GALT1 | MDH1 | TPI1 | MAT2A | | | | 0.940 |
| CALU | MDH1 | LYN | MAT2A | | | | 0.940 |
| MDH1 | LYN | MAT2A | | | | | 0.940 |
| B4GALT1 | HIST3H3 | HIST4 | ICAM1 | MMP9 | TPI1 | | 0.940 |
| HIST3H3 | LDHB | TPI1 | LYN | MAT2A | | | 0.940 |
| ICAM1 | LDHB | LYN | MAT2A | | | | 0.940 |
| LDHB | MMP9 | LYN | MAT2A | | | | 0.940 |
| B4GALT1 | TPI1 | LYN | MAT2A | | | | 0.940 |
| B4GALT1 | MDH1 | LYN | MAT2A | | | | 0.941 |
| B4GALT1 | HIST3H3 | HIST4 | LDHB | TPI1 | | | 0.941 |
| B4GALT1 | LDHB | TPI1 | MAT2A | | | | 0.941 |
| HIST3H3 | ICAM1 | MDH1 | LYN | MAT2A | | | 0.941 |
| B4GALT1 | CALU | TPI1 | LYN | MAT2A | | | 0.941 |
| B4GALT1 | CALU | MDH1 | LYN | MAT2A | | | 0.941 |
| B4GALT1 | HIST3H3 | ICAM1 | TPI1 | LYN | MAT2A | | 0.941 |
| B4GALT1 | ICAM1 | MMP9 | TPI1 | LYN | MAT2A | | 0.942 |
| CALU | HIST3H3 | LDHB | TPI1 | MAT2A | | | 0.942 |
| LDHB | MDH1 | MMP9 | TPI1 | MAT2A | | | 0.942 |
| CALU | HIST3H3 | MAT2A | | | | | 0.942 |

TABLE 3C-continued

| | | | | Bru vs control | | | |
|---|---|---|---|---|---|---|---|
| ICAM1 | LDHB | MMP9 | TPI1 | MAT2A | | | 0.942 |
| CALU | HIST3H3 | HIST4 | ICAM1 | LDHB | MMP9 | | 0.942 |
| HIST3H3 | ICAM1 | LDHB | MDH1 | MMP9 | MAT2A | | 0.942 |
| B4GALT1 | CALU | HIST4 | ICAM1 | MMP9 | | | 0.942 |
| HIST3H3 | MDH1 | MMP9 | MAT2A | | | | 0.942 |
| B4GALT1 | HIST4 | ICAM1 | LDHB | TPI1 | | | 0.943 |
| B4GALT1 | CALU | HIST4 | LDHB | | | | 0.943 |
| B4GALT1 | LYN | MAT2A | | | | | 0.943 |
| CALU | ICAM1 | MDH1 | TPI1 | LYN | MAT2A | | 0.943 |
| B4GALT1 | CALU | LDHB | LYN | MAT2A | | | 0.943 |
| HIST3H3 | ICAM1 | LDHB | MAT2A | | | | 0.943 |
| ICAM1 | MDH1 | TPI1 | LYN | MAT2A | | | 0.943 |
| B4GALT1 | HIST3H3 | HIST4 | ICAM1 | LDHB | | | 0.943 |
| B4GALT1 | HIST3H3 | ICAM1 | MMP9 | LYN | MAT2A | | 0.944 |
| LDHB | LYN | MAT2A | | | | | 0.944 |
| CALU | LDHB | MAT2A | | | | | 0.944 |
| B4GALT1 | CALU | ICAM1 | TPI1 | LYN | MAT2A | | 0.944 |
| CALU | LDHB | MDH1 | TPI1 | MAT2A | | | 0.944 |
| B4GALT1 | CALU | HIST4 | ICAM1 | LDHB | | | 0.945 |
| B4GALT1 | HIST3H3 | ICAM1 | LYN | MAT2A | | | 0.945 |
| B4GALT1 | HIST3H3 | HIST4 | LDHB | | | | 0.945 |
| CALU | HIST3H3 | HIST4 | ICAM1 | TPI1 | | | 0.945 |
| CALU | MDH1 | MMP9 | MAT2A | | | | 0.945 |
| B4GALT1 | HIST3H3 | HIST4 | ICAM1 | MMP9 | | | 0.946 |
| B4GALT1 | ICAM1 | MMP9 | LYN | MAT2A | | | 0.946 |
| CALU | HIST3H3 | HIST4 | TPI1 | LYN | MAT2A | | 0.946 |
| B4GALT1 | CALU | HIST4 | LDHB | MMP9 | MAT2A | | 0.946 |
| ICAM1 | MMP9 | MAT2A | | | | | 0.946 |
| CALU | HIST3H3 | TPI1 | MAT2A | | | | 0.946 |
| CALU | HIST3H3 | HIST4 | ICAM1 | LDHB | | | 0.946 |
| B4GALT1 | CALU | HIST4 | ICAM1 | MDH1 | LYN | | 0.946 |
| CALU | HIST4 | ICAM1 | MMP9 | TPI1 | | | 0.946 |
| HIST3H3 | LDHB | TPI1 | MAT2A | | | | 0.947 |
| B4GALT1 | HIST3H3 | HIST4 | | | | | 0.947 |
| HIST3H3 | ICAM1 | MDH1 | MMP9 | LYN | MAT2A | | 0.947 |
| CALU | ICAM1 | MMP9 | TPI1 | MAT2A | | | 0.947 |
| CALU | ICAM1 | LDHB | MDH1 | TPI1 | MAT2A | | 0.947 |
| CALU | ICAM1 | LDHB | MMP9 | TPI1 | MAT2A | | 0.948 |
| CALU | LDHB | MDH1 | MMP9 | MAT2A | | | 0.948 |
| HIST3H3 | ICAM1 | LYN | MAT2A | | | | 0.948 |
| B4GALT1 | CALU | HIST3H3 | HIST4 | MMP9 | MAT2A | | 0.948 |
| ICAM1 | MMP9 | LYN | MAT2A | | | | 0.948 |
| CALU | ICAM1 | LYN | MAT2A | | | | 0.948 |
| CALU | HIST3H3 | HIST4 | ICAM1 | LDHB | MMP9 | | 0.948 |
| B4GALT1 | CALU | HIST4 | ICAM1 | LDHB | LYN | | 0.949 |
| B4GALT1 | CALU | HIST3H3 | HIST4 | TPI1 | MAT2A | | 0.949 |
| HIST3H3 | HIST4 | ICAM1 | LDHB | MMP9 | | | 0.949 |
| HIST4 | ICAM1 | LDHB | | | | | 0.949 |
| HIST4 | ICAM1 | LDHB | TPI1 | | | | 0.950 |
| CALU | HIST4 | MDH1 | TPI1 | LYN | MAT2A | | 0.950 |
| B4GALT1 | HIST3H3 | HIST4 | ICAM1 | LDHB | MDH1 | | 0.950 |
| CALU | HIST3H3 | HIST4 | MMP9 | TPI1 | MAT2A | | 0.950 |
| B4GALT1 | CALU | HIST4 | ICAM1 | MDH1 | MMP9 | | 0.950 |
| B4GALT1 | CALU | HIST4 | ICAM1 | LDHB | MDH1 | | 0.950 |
| B4GALT1 | CALU | HIST3H3 | HIST4 | LDHB | MAT2A | | 0.951 |
| CALU | ICAM1 | LDHB | MAT2A | | | | 0.951 |
| CALU | HIST3H3 | ICAM1 | MDH1 | MMP9 | MAT2A | | 0.951 |
| HIST3H3 | ICAM1 | MDH1 | MAT2A | | | | 0.951 |
| HIST3H3 | TPI1 | MAT2A | | | | | 0.951 |
| B4GALT1 | CALU | HIST3H3 | HIST4 | LDHB | MDH1 | | 0.951 |
| CALU | HIST4 | ICAM1 | LDHB | MDH1 | TPI1 | | 0.951 |
| B4GALT1 | CALU | HIST4 | ICAM1 | MDH1 | TPI1 | | 0.951 |
| ICAM1 | LDHB | MDH1 | MAT2A | | | | 0.951 |
| CALU | ICAM1 | TPI1 | MAT2A | | | | 0.951 |
| CALU | HIST3H3 | HIST4 | ICAM1 | | | | 0.951 |
| ICAM1 | MDH1 | MMP9 | MAT2A | | | | 0.952 |
| HIST4 | LDHB | MMP9 | TPI1 | LYN | MAT2A | | 0.952 |
| CALU | HIST4 | LDHB | MDH1 | MMP9 | MAT2A | | 0.952 |
| HIST3H3 | HIST4 | ICAM1 | TPI1 | | | | 0.952 |
| ICAM1 | MDH1 | TPI1 | MAT2A | | | | 0.952 |
| B4GALT1 | HIST4 | ICAM1 | MDH1 | MMP9 | TPI1 | | 0.952 |
| B4GALT1 | CALU | HIST4 | LDHB | TPI1 | MAT2A | | 0.952 |
| CALU | ICAM1 | MDH1 | MMP9 | MAT2A | | | 0.953 |
| B4GALT1 | HIST3H3 | HIST4 | LDHB | MMP9 | MAT2A | | 0.953 |
| B4GALT1 | HIST4 | ICAM1 | LDHB | MDH1 | MMP9 | | 0.953 |
| MDH1 | TPI1 | MAT2A | | | | | 0.953 |
| B4GALT1 | HIST4 | LDHB | MDH1 | TPI1 | MAT2A | | 0.953 |
| CALU | HIST4 | LDHB | MDH1 | LYN | MAT2A | | 0.953 |

TABLE 3C-continued

| \multicolumn{7}{c}{Bru vs control} |
|---|---|---|---|---|---|---|
| B4GALT1 | HIST3H3 | HIST4 | LDHB | TPI1 | MAT2A | 0.953 |
| CALU | HIST4 | LDHB | LYN | MAT2A | | 0.954 |
| B4GALT1 | CALU | HIST4 | MDH1 | MMP9 | MAT2A | 0.954 |
| CALU | HIST3H3 | HIST4 | LDHB | TPI1 | LYN | 0.954 |
| CALU | HIST4 | ICAM1 | | | | 0.954 |
| B4GALT1 | HIST4 | ICAM1 | MDH1 | TPI1 | LYN | 0.954 |
| HIST4 | ICAM1 | LDHB | MMP9 | | | 0.954 |
| HIST3H3 | HIST4 | LDHB | MDH1 | MMP9 | TPI1 | 0.955 |
| HIST3H3 | HIST4 | ICAM1 | MDH1 | MMP9 | TPI1 | 0.955 |
| HIST4 | ICAM1 | MMP9 | | | | 0.956 |
| CALU | HIST4 | ICAM1 | MDH1 | MMP9 | TPI1 | 0.956 |
| B4GALT1 | HIST4 | ICAM1 | MDH1 | LYN | | 0.956 |
| HIST3H3 | HIST4 | MDH1 | MMP9 | TPI1 | MAT2A | 0.956 |
| B4GALT1 | HIST3H3 | HIST4 | ICAM1 | MMP9 | LYN | 0.956 |
| CALU | HIST4 | ICAM1 | TPI1 | LYN | MAT2A | 0.956 |
| B4GALT1 | HIST4 | ICAM1 | MMP9 | TPI1 | LYN | 0.957 |
| B4GALT1 | CALU | HIST3H3 | HIST4 | ICAM1 | MAT2A | 0.957 |
| CALU | HIST4 | LDHB | MMP9 | MAT2A | | 0.957 |
| B4GALT1 | HIST4 | MDH1 | MMP9 | TPI1 | MAT2A | 0.957 |
| B4GALT1 | HIST4 | ICAM1 | MDH1 | MMP9 | | 0.957 |
| B4GALT1 | HIST3H3 | HIST4 | ICAM1 | TPI1 | LYN | 0.957 |
| CALU | HIST3H3 | HIST4 | ICAM1 | MMP9 | LYN | 0.958 |
| B4GALT1 | CALU | HIST4 | MDH1 | MMP9 | LYN | 0.958 |
| CALU | HIST3H3 | HIST4 | ICAM1 | MDH1 | MAT2A | 0.958 |
| CALU | HIST4 | ICAM1 | MDH1 | MMP9 | | 0.958 |
| CALU | HIST4 | MDH1 | LYN | MAT2A | | 0.958 |
| HIST4 | ICAM1 | LDHB | MDH1 | MMP9 | | 0.958 |
| HIST3H3 | HIST4 | ICAM1 | LDHB | LYN | MAT2A | 0.958 |
| B4GALT1 | HIST4 | ICAM1 | LDHB | LYN | | 0.958 |
| HIST4 | ICAM1 | LDHB | MDH1 | TPI1 | LYN | 0.958 |
| B4GALT1 | HIST3H3 | HIST4 | TPI1 | MAT2A | | 0.958 |
| HIST3H3 | HIST4 | LDHB | MMP9 | MAT2A | | 0.959 |
| B4GALT1 | CALU | HIST4 | MDH1 | LYN | MAT2A | 0.959 |
| B4GALT1 | CALU | HIST4 | MMP9 | TPI1 | LYN | 0.959 |
| CALU | HIST3H3 | HIST4 | LDHB | TPI1 | MAT2A | 0.959 |
| HIST4 | ICAM1 | LDHB | TPI1 | LYN | MAT2A | 0.959 |
| HIST3H3 | HIST4 | LDHB | MMP9 | LYN | MAT2A | 0.959 |
| HIST4 | ICAM1 | MDH1 | | | | 0.960 |
| CALU | HIST3H3 | HIST4 | ICAM1 | LDHB | LYN | 0.960 |
| CALU | HIST4 | ICAM1 | MDH1 | TPI1 | MAT2A | 0.960 |
| HIST3H3 | HIST4 | ICAM1 | MMP9 | LYN | MAT2A | 0.960 |
| B4GALT1 | CALU | HIST4 | ICAM1 | MMP9 | MAT2A | 0.960 |
| CALU | HIST3H3 | HIST4 | ICAM1 | MAT2A | | 0.961 |
| B4GALT1 | HIST4 | TPI1 | MAT2A | | | 0.961 |
| HIST3H3 | HIST4 | ICAM1 | TPI1 | MAT2A | | 0.961 |
| CALU | HIST4 | MDH1 | TPI1 | | | 0.961 |
| B4GALT1 | HIST3H3 | HIST4 | MMP9 | TPI1 | LYN | 0.961 |
| B4GALT1 | HIST4 | ICAM1 | TPI1 | LYN | | 0.961 |
| B4GALT1 | HIST4 | LDHB | TPI1 | LYN | MAT2A | 0.961 |
| CALU | HIST4 | ICAM1 | LDHB | MMP9 | MAT2A | 0.961 |
| CALU | HIST3H3 | HIST4 | LDHB | MMP9 | LYN | 0.962 |
| CALU | HIST4 | ICAM1 | MMP9 | TPI1 | MAT2A | 0.962 |
| CALU | HIST3H3 | HIST4 | ICAM1 | LYN | | 0.963 |
| CALU | HIST4 | LDHB | MAT2A | | | 0.963 |
| HIST4 | LDHB | MDH1 | TPI1 | MAT2A | | 0.963 |
| HIST4 | ICAM1 | MDH1 | LYN | | | 0.964 |
| B4GALT1 | HIST4 | ICAM1 | TPI1 | MAT2A | | 0.967 |
| HIST4 | ICAM1 | LDHB | TPI1 | MAT2A | | 0.967 |
| HIST3H3 | HIST4 | MMP9 | LYN | MAT2A | | 0.967 |
| B4GALT1 | HIST4 | ICAM1 | MDH1 | MAT2A | | 0.967 |
| CALU | HIST4 | MDH1 | MMP9 | LYN | | 0.967 |
| HIST4 | TPI1 | MAT2A | | | | 0.967 |
| HIST3H3 | HIST4 | LDHB | TPI1 | LYN | | 0.967 |
| CALU | HIST3H3 | HIST4 | MMP9 | LYN | | 0.967 |
| CALU | HIST4 | LYN | | | | 0.967 |
| CALU | HIST4 | MMP9 | TPI1 | LYN | | 0.967 |
| HIST4 | MDH1 | LYN | MAT2A | | | 0.967 |
| CALU | HIST4 | LDHB | MDH1 | MMP9 | LYN | 0.967 |
| HIST4 | ICAM1 | MDH1 | LYN | MAT2A | | 0.967 |
| HIST4 | ICAM1 | TPI1 | MAT2A | | | 0.968 |
| HIST3H3 | HIST4 | ICAM1 | LDHB | MDH1 | MAT2A | 0.968 |
| B4GALT1 | HIST3H3 | HIST4 | TPI1 | LYN | | 0.968 |
| HIST4 | LDHB | MMP9 | MAT2A | | | 0.968 |
| HIST4 | ICAM1 | LDHB | MMP9 | LYN | | 0.969 |
| HIST4 | ICAM1 | MDH1 | MMP9 | LYN | MAT2A | 0.969 |
| HIST3H3 | HIST4 | MDH1 | MMP9 | MAT2A | | 0.969 |
| HIST4 | LDHB | MAT2A | | | | 0.969 |
| B4GALT1 | HIST4 | MMP9 | LYN | | | 0.969 |

TABLE 3C-continued

| | | | Bru vs control | | | |
|---|---|---|---|---|---|---|
| HIST4 | LDHB | MDH1 | MMP9 | LYN | MAT2A | 0.969 |
| B4GALT1 | HIST3H3 | HIST4 | ICAM1 | LYN | MAT2A | 0.969 |
| B4GALT1 | HIST4 | MMP9 | TPI1 | LYN | MAT2A | 0.969 |
| HIST3H3 | HIST4 | ICAM1 | LDHB | LYN | | 0.970 |
| B4GALT1 | HIST4 | ICAM1 | LDHB | LYN | MAT2A | 0.970 |
| HIST3H3 | HIST4 | MMP9 | LYN | | | 0.970 |
| HIST3H3 | HIST4 | MAT2A | | | | 0.970 |
| HIST4 | ICAM1 | LDHB | LYN | | | 0.970 |
| HIST3H3 | HIST4 | LDHB | MDH1 | MMP9 | LYN | 0.970 |
| B4GALT1 | HIST3H3 | HIST4 | LYN | MAT2A | | 0.970 |
| HIST3H3 | HIST4 | LYN | MAT2A | | | 0.970 |
| HIST4 | LDHB | LYN | | | | 0.970 |
| HIST3H3 | HIST4 | ICAM1 | MDH1 | MMP9 | MAT2A | 0.971 |
| HIST4 | LDHB | MDH1 | MMP9 | TPI1 | LYN | 0.971 |
| B4GALT1 | HIST3H3 | HIST4 | LYN | | | 0.971 |
| HIST3H3 | HIST4 | TPI1 | LYN | | | 0.971 |
| HIST3H3 | HIST4 | MDH1 | | | | 0.971 |
| HIST4 | LDHB | MDH1 | LYN | | | 0.971 |
| B4GALT1 | HIST4 | ICAM1 | MMP9 | LYN | MAT2A | 0.973 |
| HIST4 | ICAM1 | LYN | MAT2A | | | 0.973 |
| HIST4 | MDH1 | MAT2A | | | | 0.974 |
| HIST3H3 | HIST4 | LDHB | LYN | | | 0.974 |
| HIST3H3 | HIST4 | LDHB | MDH1 | MAT2A | | 0.975 |
| HIST3H3 | HIST4 | LYN | | | | 0.975 |
| HIST4 | MMP9 | LYN | | | | 0.975 |
| B4GALT1 | HIST4 | LDHB | MMP9 | LYN | MAT2A | 0.976 |
| HIST3H3 | HIST4 | LDHB | MDH1 | LYN | | 0.976 |
| HIST3H3 | HIST4 | MDH1 | MAT2A | | | 0.978 |

TABLE 3D

| | Bru vs *salmonella* | |
|---|---|---|
| | | AUC |
| | B4GALT1 | 1.000 |
| | CALU | 0.920 |
| | HIST3H3 | 0.845 |
| | HIST4 | 1.000 |
| | ICAM1 | 0.934 |
| | LDHB | 0.953 |
| | LYN | 0.887 |
| | MAT2A | 0.958 |
| | MDH1 | 0.997 |
| | MMP9 | 0.732 |
| | TPI1 | 0.965 |

| prot 1 | prot 2 | prot 3 | prot 4 | prot 5 | prot 6 | prot 7 | AUC 1 |
|---|---|---|---|---|---|---|---|
| B4GALT1 | LDHB | MDH1 | MMP9 | MAT2A | | | 0.997 |
| B4GALT1 | HIST3H3 | HIST4 | MDH1 | LYN | MAT2A | | 0.997 |
| B4GALT1 | MDH1 | LYN | MAT2A | | | | 0.997 |
| B4GALT1 | HIST3H3 | ICAM1 | MDH1 | MAT2A | | | 0.997 |
| B4GALT1 | MDH1 | TPI1 | LYN | MAT2A | | | 0.997 |
| B4GALT1 | LDHB | MDH1 | LYN | MAT2A | | | 0.996 |
| CALU | HIST4 | LYN | | | | | 0.996 |
| CALU | HIST4 | MMP9 | | | | | 0.996 |
| B4GALT1 | HIST4 | MDH1 | MMP9 | TPI1 | LYN | | 0.996 |
| B4GALT1 | HIST3H3 | ICAM1 | MDH1 | MMP9 | MAT2A | | 0.996 |
| B4GALT1 | CALU | HIST3H3 | LDHB | MAT2A | | | 0.996 |
| B4GALT1 | HIST4 | ICAM1 | TPI1 | MAT2A | | | 0.996 |
| B4GALT1 | HIST3H3 | HIST4 | LDHB | TPI1 | LYN | | 0.996 |
| B4GALT1 | HIST4 | TPI1 | MAT2A | | | | 0.996 |
| HIST4 | ICAM1 | MDH1 | TPI1 | LYN | | | 0.996 |
| CALU | HIST4 | MDH1 | LYN | | | | 0.996 |
| HIST4 | ICAM1 | MMP9 | TPI1 | | | | 0.996 |
| B4GALT1 | HIST3H3 | ICAM1 | MMP9 | TPI1 | LYN | | 0.996 |
| B4GALT1 | CALU | ICAM1 | MAT2A | | | | 0.996 |
| CALU | HIST4 | LDHB | MDH1 | MMP9 | LYN | | 0.996 |
| B4GALT1 | HIST4 | MDH1 | MMP9 | MAT2A | | | 0.996 |
| B4GALT1 | LDHB | MDH1 | TPI1 | MAT2A | | | 0.995 |
| B4GALT1 | HIST4 | MDH1 | MAT2A | | | | 0.995 |
| B4GALT1 | HIST4 | MDH1 | TPI1 | LYN | MAT2A | | 0.995 |
| HIST3H3 | HIST4 | MDH1 | TPI1 | MAT2A | | | 0.995 |
| B4GALT1 | HIST3H3 | ICAM1 | LDHB | MAT2A | | | 0.995 |

TABLE 3D-continued

| | | Bru vs *salmonella* | | | | |
|---|---|---|---|---|---|---|
| B4GALT1 | HIST3H3 | LDHB | MDH1 | MMP9 | MAT2A | 0.995 |
| CALU | HIST4 | LDHB | LYN | | | 0.995 |
| CALU | HIST4 | ICAM1 | TPI1 | | | 0.995 |
| HIST4 | ICAM1 | LDHB | TPI1 | | | 0.995 |
| CALU | HIST4 | MDH1 | MMP9 | TPI1 | LYN | 0.995 |
| B4GALT1 | LDHB | MDH1 | MAT2A | | | 0.995 |
| HIST3H3 | HIST4 | ICAM1 | MDH1 | MMP9 | MAT2A | 0.995 |
| B4GALT1 | LDHB | MDH1 | MMP9 | TPI1 | MAT2A | 0.995 |
| B4GALT1 | CALU | HIST3H3 | TPI1 | LYN | MAT2A | 0.995 |
| HIST3H3 | HIST4 | ICAM1 | LDHB | MDH1 | MAT2A | 0.995 |
| B4GALT1 | ICAM1 | LDHB | MAT2A | | | 0.995 |
| B4GALT1 | CALU | LDHB | MDH1 | MMP9 | MAT2A | 0.995 |
| B4GALT1 | CALU | HIST3H3 | HIST4 | LDHB | MAT2A | 0.995 |
| MDH1 | MMP9 | | | | | 0.995 |
| B4GALT1 | CALU | LDHB | TPI1 | LYN | MAT2A | 0.995 |
| ICAM1 | MDH1 | TPI1 | | | | 0.995 |
| CALU | HIST4 | LDHB | MMP9 | | | 0.995 |
| B4GALT1 | CALU | HIST3H3 | HIST4 | MDH1 | MAT2A | 0.995 |
| CALU | HIST4 | ICAM1 | MMP9 | | | 0.995 |
| B4GALT1 | CALU | HIST4 | LDHB | MDH1 | LYN | 0.995 |
| HIST4 | LYN | | | | | 0.995 |
| B4GALT1 | CALU | HIST3H3 | MDH1 | MMP9 | MAT2A | 0.995 |
| HIST3H3 | ICAM1 | MDH1 | | | | 0.995 |
| B4GALT1 | MDH1 | MAT2A | | | | 0.995 |
| HIST3H3 | HIST4 | LDHB | MDH1 | MMP9 | MAT2A | 0.995 |
| B4GALT1 | CALU | HIST4 | MDH1 | LYN | MAT2A | 0.994 |
| CALU | MDH1 | LYN | | | | 0.994 |
| HIST4 | TPI1 | LYN | | | | 0.994 |
| B4GALT1 | HIST4 | MMP9 | TPI1 | MAT2A | | 0.994 |
| B4GALT1 | HIST3H3 | MDH1 | MMP9 | MAT2A | | 0.994 |
| B4GALT1 | HIST3H3 | MDH1 | TPI1 | LYN | MAT2A | 0.994 |
| B4GALT1 | HIST3H3 | ICAM1 | MMP9 | MAT2A | | 0.994 |
| B4GALT1 | ICAM1 | MAT2A | | | | 0.994 |
| HIST3H3 | LDHB | MDH1 | LYN | | | 0.994 |
| CALU | HIST3H3 | ICAM1 | MDH1 | | | 0.994 |
| B4GALT1 | CALU | HIST3H3 | ICAM1 | LDHB | MAT2A | 0.994 |
| HIST4 | ICAM1 | LDHB | MDH1 | TPI1 | LYN | 0.994 |
| B4GALT1 | HIST3H3 | LDHB | TPI1 | MAT2A | | 0.994 |
| B4GALT1 | ICAM1 | LDHB | MMP9 | TPI1 | MAT2A | 0.993 |
| ICAM1 | MDH1 | MMP9 | | | | 0.993 |
| CALU | ICAM1 | MDH1 | TPI1 | | | 0.993 |
| CALU | HIST3H3 | MDH1 | TPI1 | | | 0.993 |
| CALU | HIST4 | LDHB | MMP9 | TPI1 | | 0.993 |
| HIST3H3 | LDHB | MDH1 | | | | 0.993 |
| CALU | HIST3H3 | MDH1 | LYN | | | 0.993 |
| ICAM1 | LDHB | MDH1 | | | | 0.993 |
| HIST4 | MDH1 | MMP9 | TPI1 | LYN | | 0.993 |
| CALU | HIST3H3 | MDH1 | MMP9 | | | 0.993 |
| MDH1 | MMP9 | TPI1 | | | | 0.993 |
| HIST4 | ICAM1 | LDHB | MDH1 | MAT2A | | 0.993 |
| B4GALT1 | ICAM1 | LDHB | MDH1 | MAT2A | | 0.993 |
| CALU | HIST4 | ICAM1 | LDHB | MMP9 | | 0.993 |
| HIST3H3 | HIST4 | TPI1 | MAT2A | | | 0.992 |
| B4GALT1 | HIST3H3 | LDHB | MDH1 | MAT2A | | 0.992 |
| CALU | ICAM1 | MDH1 | MMP9 | | | 0.992 |
| CALU | ICAM1 | LDHB | MDH1 | LYN | | 0.992 |
| HIST3H3 | HIST4 | ICAM1 | TPI1 | MAT2A | | 0.992 |
| B4GALT1 | HIST3H3 | ICAM1 | LDHB | TPI1 | MAT2A | 0.992 |
| HIST3H3 | HIST4 | ICAM1 | LDHB | MAT2A | | 0.992 |
| CALU | LDHB | MDH1 | MMP9 | | | 0.991 |
| LDHB | MDH1 | MMP9 | | | | 0.991 |
| CALU | HIST4 | LDHB | MMP9 | TPI1 | LYN | 0.991 |
| HIST3H3 | ICAM1 | LDHB | MDH1 | | | 0.991 |
| CALU | HIST3H3 | ICAM1 | MDH1 | TPI1 | | 0.991 |
| B4GALT1 | CALU | HIST4 | ICAM1 | MAT2A | | 0.991 |
| B4GALT1 | CALU | HIST4 | MDH1 | MAT2A | | 0.991 |
| B4GALT1 | CALU | HIST3H3 | ICAM1 | MDH1 | MAT2A | 0.991 |
| LDHB | MDH1 | TPI1 | | | | 0.991 |
| HIST3H3 | HIST4 | MMP9 | LYN | MAT2A | | 0.991 |
| CALU | HIST3H3 | LDHB | MDH1 | LYN | | 0.991 |
| HIST3H3 | MDH1 | MMP9 | TPI1 | | | 0.990 |
| CALU | HIST4 | ICAM1 | LDHB | MMP9 | TPI1 | 0.990 |
| HIST3H3 | HIST4 | MMP9 | MAT2A | | | 0.990 |
| HIST3H3 | HIST4 | MDH1 | LYN | MAT2A | | 0.990 |
| HIST3H3 | HIST4 | MAT2A | | | | 0.990 |
| HIST3H3 | HIST4 | MDH1 | TPI1 | LYN | MAT2A | 0.990 |
| HIST4 | MDH1 | MMP9 | MAT2A | | | 0.990 |
| CALU | ICAM1 | LDHB | MDH1 | MMP9 | LYN | 0.990 |

TABLE 3D-continued

| | | Bru vs *salmonella* | | | | |
|---|---|---|---|---|---|---|
| MDH1 | LYN | | | | | 0.990 |
| HIST4 | ICAM1 | LDHB | TPI1 | MAT2A | | 0.989 |
| HIST3H3 | HIST4 | ICAM1 | MMP9 | MAT2A | | 0.989 |
| HIST3H3 | HIST4 | ICAM1 | LDHB | LYN | MAT2A | 0.989 |
| CALU | HIST3H3 | MDH1 | TPI1 | LYN | | 0.989 |
| B4GALT1 | CALU | MDH1 | TPI1 | LYN | MAT2A | 0.988 |
| CALU | HIST3H3 | HIST4 | MDH1 | MAT2A | | 0.988 |
| HIST4 | MDH1 | TPI1 | MAT2A | | | 0.988 |
| LDHB | MDH1 | TPI1 | LYN | | | 0.988 |
| CALU | ICAM1 | MDH1 | TPI1 | LYN | | 0.988 |
| HIST3H3 | ICAM1 | LDHB | MDH1 | MMP9 | | 0.988 |
| MDH1 | TPI1 | LYN | | | | 0.988 |
| HIST4 | MMP9 | MAT2A | | | | 0.988 |
| CALU | HIST3H3 | HIST4 | LDHB | MDH1 | MAT2A | 0.987 |
| HIST3H3 | HIST4 | ICAM1 | TPI1 | LYN | MAT2A | 0.987 |
| B4GALT1 | HIST3H3 | TPI1 | MAT2A | | | 0.987 |
| CALU | HIST4 | ICAM1 | LYN | | | 0.987 |
| ICAM1 | MDH1 | TPI1 | LYN | | | 0.987 |
| HIST4 | TPI1 | MAT2A | | | | 0.987 |
| CALU | LDHB | MDH1 | TPI1 | LYN | | 0.987 |
| LDHB | MDH1 | MAT2A | | | | 0.987 |
| HIST3H3 | MDH1 | MAT2A | | | | 0.987 |
| ICAM1 | LDHB | MDH1 | MMP9 | LYN | | 0.987 |
| HIST3H3 | LDHB | MDH1 | MMP9 | | | 0.986 |
| HIST3H3 | HIST4 | MMP9 | LYN | MAT2A | | 0.986 |
| CALU | HIST3H3 | HIST4 | MDH1 | MMP9 | MAT2A | 0.986 |
| CALU | HIST4 | LDHB | MDH1 | MMP9 | MAT2A | 0.986 |
| CALU | HIST3H3 | LDHB | MDH1 | MMP9 | LYN | 0.986 |
| B4GALT1 | CALU | ICAM1 | LDHB | MDH1 | MAT2A | 0.986 |
| B4GALT1 | CALU | LDHB | MDH1 | MAT2A | | 0.986 |
| HIST4 | ICAM1 | LDHB | TPI1 | LYN | | 0.985 |
| HIST4 | LDHB | MMP9 | TPI1 | MAT2A | | 0.985 |
| CALU | ICAM1 | MDH1 | MMP9 | MAT2A | | 0.985 |
| B4GALT1 | HIST3H3 | MMP9 | TPI1 | MAT2A | | 0.985 |
| CALU | HIST3H3 | HIST4 | LDHB | MMP9 | MAT2A | 0.985 |
| CALU | HIST4 | MDH1 | MAT2A | | | 0.985 |
| B4GALT1 | CALU | HIST4 | ICAM1 | TPI1 | MAT2A | 0.984 |
| CALU | HIST3H3 | HIST4 | LDHB | MAT2A | | 0.984 |
| HIST3H3 | HIST4 | LYN | MAT2A | | | 0.984 |
| B4GALT1 | CALU | TPI1 | MAT2A | | | 0.984 |
| HIST4 | ICAM1 | TPI1 | MAT2A | | | 0.984 |
| CALU | MDH1 | MMP9 | MAT2A | | | 0.984 |
| HIST3H3 | HIST4 | TPI1 | LYN | MAT2A | | 0.983 |
| B4GALT1 | CALU | HIST4 | MDH1 | TPI1 | MAT2A | 0.983 |
| CALU | HIST3H3 | HIST4 | MDH1 | LYN | MAT2A | 0.982 |
| HIST3H3 | MDH1 | MMP9 | MAT2A | | | 0.982 |
| LDHB | MDH1 | MMP9 | TPI1 | LYN | | 0.981 |
| CALU | LDHB | MDH1 | MMP9 | TPI1 | | 0.981 |
| B4GALT1 | CALU | LDHB | MDH1 | TPI1 | MAT2A | 0.981 |
| B4GALT1 | CALU | ICAM1 | MDH1 | TPI1 | MAT2A | 0.981 |
| CALU | HIST3H3 | HIST4 | ICAM1 | MAT2A | | 0.981 |
| LDHB | MDH1 | MMP9 | TPI1 | LYN | MAT2A | 0.980 |
| CALU | HIST3H3 | ICAM1 | MDH1 | MAT2A | | 0.980 |
| B4GALT1 | CALU | HIST3H3 | MDH1 | TPI1 | MAT2A | 0.980 |
| HIST4 | LDHB | MDH1 | MMP9 | LYN | MAT2A | 0.980 |
| HIST3H3 | LDHB | MDH1 | MMP9 | TPI1 | LYN | 0.980 |
| LDHB | TPI1 | | | | | 0.979 |
| LDHB | MDH1 | MMP9 | LYN | MAT2A | | 0.979 |
| CALU | HIST4 | ICAM1 | MAT2A | | | 0.979 |
| LDHB | MDH1 | MMP9 | TPI1 | MAT2A | | 0.979 |
| HIST3H3 | MDH1 | TPI1 | MAT2A | | | 0.979 |
| MDH1 | MMP9 | TPI1 | LYN | MAT2A | | 0.978 |
| CALU | HIST4 | ICAM1 | MDH1 | TPI1 | MAT2A | 0.978 |
| HIST4 | ICAM1 | LDHB | MMP9 | TPI1 | LYN | 0.978 |
| CALU | LDHB | MAT2A | | | | 0.978 |
| HIST4 | ICAM1 | LDHB | TPI1 | LYN | MAT2A | 0.978 |
| MDH1 | TPI1 | LYN | MAT2A | | | 0.978 |
| ICAM1 | LDHB | MDH1 | MMP9 | TPI1 | MAT2A | 0.978 |
| ICAM1 | LDHB | MDH1 | TPI1 | LYN | | 0.977 |
| MDH1 | LYN | MAT2A | | | | 0.976 |
| CALU | HIST3H3 | HIST4 | LYN | MAT2A | | 0.976 |
| HIST3H3 | ICAM1 | LDHB | MDH1 | MAT2A | | 0.976 |
| CALU | HIST3H3 | LDHB | MDH1 | MAT2A | | 0.976 |
| ICAM1 | LDHB | MDH1 | MMP9 | LYN | MAT2A | 0.975 |
| CALU | HIST3H3 | ICAM1 | LDHB | MDH1 | MAT2A | 0.975 |
| HIST4 | MDH1 | MMP9 | TPI1 | LYN | MAT2A | 0.975 |
| ICAM1 | LDHB | MDH1 | TPI1 | LYN | MAT2A | 0.974 |
| CALU | ICAM1 | TPI1 | LYN | | | 0.974 |

TABLE 3D-continued

Bru vs *salmonella*

| | | | | | | |
|---|---|---|---|---|---|---|
| HIST4 | LYN | MAT2A | | | | 0.974 |
| ICAM1 | MMP9 | TPI1 | LYN | | | 0.974 |
| HIST4 | LDHB | LYN | MAT2A | | | 0.974 |
| CALU | LDHB | MDH1 | LYN | MAT2A | | 0.973 |
| ICAM1 | MDH1 | MMP9 | TPI1 | LYN | MAT2A | 0.973 |
| CALU | HIST4 | ICAM1 | MMP9 | LYN | MAT2A | 0.973 |
| HIST4 | ICAM1 | LDHB | MMP9 | LYN | MAT2A | 0.973 |
| LDHB | MMP9 | LYN | | | | 0.971 |
| ICAM1 | LDHB | MMP9 | LYN | | | 0.971 |
| HIST3H3 | ICAM1 | LDHB | TPI1 | | | 0.971 |
| CALU | ICAM1 | LDHB | MAT2A | | | 0.969 |
| CALU | HIST3H3 | MDH1 | LYN | MAT2A | | 0.968 |
| ICAM1 | TPI1 | MAT2A | | | | 0.968 |
| CALU | LDHB | MMP9 | LYN | | | 0.967 |
| CALU | HIST3H3 | ICAM1 | LDHB | TPI1 | LYN | 0.962 |
| CALU | HIST3H3 | ICAM1 | LDHB | LYN | | 0.962 |
| CALU | ICAM1 | LDHB | TPI1 | LYN | MAT2A | 0.962 |
| CALU | HIST3H3 | ICAM1 | TPI1 | LYN | | 0.962 |
| ICAM1 | LDHB | MMP9 | TPI1 | MAT2A | | 0.962 |
| CALU | HIST3H3 | ICAM1 | LDHB | | | 0.962 |
| HIST3H3 | ICAM1 | MMP9 | TPI1 | | | 0.962 |
| CALU | HIST3H3 | MMP9 | TPI1 | LYN | MAT2A | 0.961 |
| CALU | LDHB | TPI1 | MAT2A | | | 0.961 |
| CALU | LDHB | LYN | MAT2A | | | 0.961 |
| CALU | HIST4 | TPI1 | LYN | MAT2A | | 0.960 |
| CALU | ICAM1 | MMP9 | TPI1 | LYN | | 0.960 |
| CALU | HIST3H3 | LDHB | TPI1 | LYN | MAT2A | 0.960 |
| HIST3H3 | ICAM1 | MMP9 | TPI1 | LYN | | 0.960 |
| HIST3H3 | ICAM1 | MAT2A | | | | 0.960 |
| CALU | HIST3H3 | ICAM1 | TPI1 | MAT2A | | 0.958 |
| HIST3H3 | ICAM1 | LDHB | MMP9 | TPI1 | MAT2A | 0.958 |
| HIST3H3 | LDHB | | | | | 0.958 |
| ICAM1 | LDHB | MMP9 | LYN | MAT2A | | 0.958 |
| CALU | HIST3H3 | ICAM1 | TPI1 | | | 0.958 |
| MMP9 | TPI1 | MAT2A | | | | 0.958 |
| HIST3H3 | LDHB | MMP9 | MAT2A | | | 0.957 |
| CALU | HIST3H3 | TPI1 | LYN | MAT2A | | 0.957 |
| CALU | ICAM1 | MMP9 | LYN | MAT2A | | 0.957 |
| CALU | ICAM1 | LYN | | | | 0.957 |
| CALU | LYN | | | | | 0.957 |
| ICAM1 | MMP9 | MAT2A | | | | 0.957 |
| HIST3H3 | LDHB | LYN | MAT2A | | | 0.956 |
| CALU | HIST3H3 | MMP9 | LYN | | | 0.956 |
| ICAM1 | MMP9 | TPI1 | LYN | MAT2A | | 0.956 |
| CALU | HIST3H3 | ICAM1 | MMP9 | TPI1 | LYN | 0.954 |
| CALU | LDHB | MMP9 | | | | 0.954 |
| CALU | HIST3H3 | LDHB | | | | 0.954 |
| HIST3H3 | ICAM1 | LYN | | | | 0.954 |
| LDHB | MMP9 | LYN | MAT2A | | | 0.954 |
| HIST3H3 | ICAM1 | TPI1 | LYN | MAT2A | | 0.954 |
| CALU | ICAM1 | LYN | MAT2A | | | 0.953 |
| CALU | HIST3H3 | ICAM1 | LDHB | MMP9 | LYN | 0.952 |
| CALU | HIST3H3 | LYN | | | | 0.950 |
| HIST3H3 | ICAM1 | MMP9 | TPI1 | LYN | MAT2A | 0.950 |
| CALU | HIST3H3 | ICAM1 | LYN | | | 0.947 |
| HIST3H3 | MMP9 | LYN | MAT2A | | | 0.945 |
| HIST3H3 | ICAM1 | MMP9 | LYN | MAT2A | | 0.943 |
| CALU | ICAM1 | | | | | 0.933 |
| ICAM1 | MMP9 | | | | | 0.930 |
| HIST3H3 | ICAM1 | MMP9 | | | | 0.924 |
| CALU | HIST3H3 | ICAM1 | MMP9 | | | 0.923 |
| CALU | HIST3H3 | | | | | 0.908 |
| HIST3H3 | MMP9 | LYN | | | | 0.906 |
| HIST3H3 | MMP9 | | | | | 0.832 |

Further analysis of the markers identified the best performing markers and panels of markers for Q-fever comparisons to Brucellosis, Lyme disease and to healthy controls that have good individual performance and that were also able to complement each other. Similarly, the best performing markers and panels of markers for Lyme Disease comparisons to Brucellosis, Q-Fever and to healthy controls that have good individual performance and that were also able to complement each other were identified. (Tables 4A-4G).

TABLE 4A

| Protein | Transition | Disease Group | Reference Group | DI |
|---|---|---|---|---|
| B4GALT1 | 186 | Q-fever | Healthy Control | 0.67 |
| CALU | 249 | Q-fever | Healthy Control | 0.42 |
| HIST3H3 | 470 | Q-fever | Healthy Control | 0.50 |
| HIST4 | 475 | Q-fever | Healthy Control | 0.13 |
| ICAM1 | 541 | Q-fever | Healthy Control | 0.82 |
| LDHB | 599 | Q-fever | Healthy Control | 0.66 |

TABLE 4A-continued

| Protein | Transition | Disease Group | Reference Group | DI |
|---|---|---|---|---|
| LYN | — | Q-fever | Healthy Control | 5.08 |
| MAT2A | — | Q-fever | Healthy Control | 1.25 |
| MDH1 | 652 | Q-fever | Healthy Control | 0.64 |
| MMP9 | 654 | Q-fever | Healthy Control | 0.54 |
| TPI1 | 1056 | Q-fever | Healthy Control | 0.56 |
| B4GALT1 | 186 | Healthy Control | Q-fever | 1.49 |
| CALU | 249 | Healthy Control | Q-fever | 2.37 |
| HIST3H3 | 470 | Healthy Control | Q-fever | 1.99 |
| HIST4 | 475 | Healthy Control | Q-fever | 7.95 |
| ICAM1 | 541 | Healthy Control | Q-fever | 1.21 |
| LDHB | 599 | Healthy Control | Q-fever | 1.52 |
| LYN | — | Healthy Control | Q-fever | 0.20 |
| MAT2A | — | Healthy Control | Q-fever | 0.80 |
| MDH1 | 652 | Healthy Control | Q-fever | 1.55 |
| MMP9 | 654 | Healthy Control | Q-fever | 1.85 |
| TPI1 | 1056 | Healthy Control | Q-fever | 1.78 |

TABLE 4B

| Protein | Transition | Disease Group | Reference Group | DI |
|---|---|---|---|---|
| B4GALT1 | 186 | Brucellosis | Q-Fever | 2.73 |
| CALU | 249 | Brucellosis | Q-Fever | 3.17 |
| HIST3H3 | 470 | Brucellosis | Q-Fever | 4.56 |
| HIST4 | 475 | Brucellosis | Q-Fever | 130.92 |
| ICAM1 | 541 | Brucellosis | Q-Fever | 3.18 |
| LDHB | 599 | Brucellosis | Q-Fever | 3.94 |
| LYN | — | Brucellosis | Q-Fever | 1.14 |
| MAT2A | — | Brucellosis | Q-Fever | 0.19 |
| MDH1 | 652 | Brucellosis | Q-Fever | 4.28 |
| MMP9 | 654 | Brucellosis | Q-Fever | 2.59 |
| TPI1 | 1056 | Brucellosis | Q-Fever | 3.15 |
| B4GALT1 | 186 | Q-Fever | Brucellosis | 0.37 |
| CALU | 249 | Q-Fever | Brucellosis | 0.32 |
| HIST3H3 | 470 | Q-Fever | Brucellosis | 0.22 |
| HIST4 | 475 | Q-Fever | Brucellosis | 0.01 |
| ICAM1 | 541 | Q-Fever | Brucellosis | 0.31 |
| LDHB | 599 | Q-Fever | Brucellosis | 0.25 |
| LYN | — | Q-Fever | Brucellosis | 0.87 |
| MAT2A | — | Q-Fever | Brucellosis | 5.29 |
| MDH1 | 652 | Q-Fever | Brucellosis | 0.23 |
| MMP9 | 654 | Q-Fever | Brucellosis | 0.39 |
| TPI1 | 1056 | Q-Fever | Brucellosis | 0.32 |

TABLE 4C

| Protein | Transition | Disease Group | Reference Group | DI |
|---|---|---|---|---|
| B4GALT1 | 186 | Lyme disease | Healthy Control | 0.70 |
| CALU | 249 | Lyme disease | Healthy Control | 1.54 |
| HIST3H3 | 470 | Lyme disease | Healthy Control | 0.95 |
| HIST4 | 475 | Lyme disease | Healthy Control | 0.29 |
| ICAM1 | 541 | Lyme disease | Healthy Control | 0.90 |
| LDHB | 599 | Lyme disease | Healthy Control | 0.98 |
| LYN | — | Lyme disease | Healthy Control | 1.25 |
| MAT2A | — | Lyme disease | Healthy Control | 1.18 |
| MDH1 | 652 | Lyme disease | Healthy Control | 0.84 |
| MMP9 | 654 | Lyme disease | Healthy Control | 4.48 |
| TPI1 | 1056 | Lyme disease | Healthy Control | 0.96 |
| B4GALT1 | 186 | Healthy Control | Lyme disease | 1.43 |
| CALU | 249 | Healthy Control | Lyme disease | 0.65 |
| HIST3H3 | 470 | Healthy Control | Lyme disease | 1.05 |
| HIST4 | 475 | Healthy Control | Lyme disease | 3.41 |
| ICAM1 | 541 | Healthy Control | Lyme disease | 1.12 |
| LDHB | 599 | Healthy Control | Lyme disease | 1.02 |
| LYN | — | Healthy Control | Lyme disease | 0.80 |
| MAT2A | — | Healthy Control | Lyme disease | 0.85 |
| MDH1 | 652 | Healthy Control | Lyme disease | 1.19 |
| MMP9 | 654 | Healthy Control | Lyme disease | 0.22 |
| TPI1 | 1056 | Healthy Control | Lyme disease | 1.04 |

TABLE 4D

| Protein | Transition | Disease Group | Reference Group | DI |
|---|---|---|---|---|
| B4GALT1 | 186 | Brucellosis | Lyme | 2.62 |
| CALU | 249 | Brucellosis | Lyme | 0.87 |
| HIST3H3 | 470 | Brucellosis | Lyme | 2.41 |
| HIST4 | 475 | Brucellosis | Lyme | 56.14 |
| ICAM1 | 541 | Brucellosis | Lyme | 2.92 |
| LDHB | 599 | Brucellosis | Lyme | 2.65 |
| LYN | — | Brucellosis | Lyme | 4.66 |
| MAT2A | — | Brucellosis | Lyme | 0.20 |
| MDH1 | 652 | Brucellosis | Lyme | 3.26 |
| MMP9 | 654 | Brucellosis | Lyme | 0.31 |
| TPI1 | 1056 | Brucellosis | Lyme | 1.84 |
| B4GALT1 | 186 | Lyme | Brucellosis | 0.38 |
| CALU | 249 | Lyme | Brucellosis | 1.15 |
| HIST3H3 | 470 | Lyme | Brucellosis | 0.42 |
| HIST4 | 475 | Lyme | Brucellosis | 0.02 |
| ICAM1 | 541 | Lyme | Brucellosis | 0.34 |
| LDHB | 599 | Lyme | Brucellosis | 0.38 |
| LYN | — | Lyme | Brucellosis | 0.21 |
| MAT2A | — | Lyme | Brucellosis | 5.02 |
| MDH1 | 652 | Lyme | Brucellosiso | 0.31 |
| MMP9 | 654 | Lyme | Brucellosis | 3.19 |
| TPI1 | 1056 | Lyme | Brucellosis | 0.54 |

TABLE 4E

| Protein | Transition | Disease Group | Reference Group | DI |
|---|---|---|---|---|
| B4GALT1 | 186 | Lyme disease | Q-Fever | 1.04 |
| CALU | 249 | Lyme disease | Q-Fever | 3.65 |
| HIST3H3 | 470 | Lyme disease | Q-Fever | 1.89 |
| HIST4 | 475 | Lyme disease | Q-Fever | 2.33 |
| ICAM1 | 541 | Lyme disease | Q-Fever | 1.09 |
| LDHB | 599 | Lyme disease | Q-Fever | 1.49 |
| LYN | — | Lyme disease | Q-Fever | 0.25 |
| MAT2A | — | Lyme disease | Q-Fever | 0.95 |
| MDH1 | 652 | Lyme disease | Q-Fever | 1.31 |
| MMP9 | 654 | Lyme disease | Q-Fever | 8.29 |
| TPI1 | 1056 | Lyme disease | Q-Fever | 1.71 |
| B4GALT1 | 186 | Q-Fever | Lyme disease | 0.96 |
| CALU | 249 | Q-Fever | Lyme disease | 0.27 |
| HIST3H3 | 470 | Q-Fever | Lyme disease | 0.53 |
| HIST4 | 475 | Q-Fever | Lyme disease | 0.43 |
| ICAM1 | 541 | Q-Fever | Lyme disease | 0.92 |
| LDHB | 599 | Q-Fever | Lyme disease | 0.67 |
| LYN | — | Q-Fever | Lyme disease | 4.07 |
| MAT2A | — | Q-Fever | Lyme disease | 1.05 |
| MDH1 | 652 | Q-Fever | Lyme disease | 0.76 |
| MMP9 | 654 | Q-Fever | Lyme disease | 0.12 |
| TPI1 | 1056 | Q-Fever | Lyme disease | 0.58 |

TABLE 4F

| Minimal optimal panel | | Brucellosis vs | | |
|---|---|---|---|---|
| | | Control | Q-fever | Lyme |
| HIST4 | LYN | 0.974 | | 1.000 |
| HIST4 | MAT2A | 0.974 | 0.992 | |
| HIST4 | MDH1 | | 0.998 | |
| HIST4 | LDHB | | 0.996 | |
| HIST4 | MMP9 | | | 0.999 |
| HIST4 | ICAM1 | | | 0.998 |

TABLE 4G

| Minimal optimal panel | | Lyme vs | | |
|---|---|---|---|---|
| | | Control | Q-fever | Brucella |
| MMP9 | | 0.950 | | |
| MMP9 | MDH1 | 0.964 | | |

TABLE 4G-continued

| | | Lyme vs | | |
|---|---|---|---|---|
| Minimal optimal panel | | Control | Q-fever | Brucella |
| CALU | B4GALT1 | | 0.961 | |
| HIST4 | | | | 0.995 |
| HIST4 | LYN | | | 1.000 |
| HIST4 | MMP9 | | | 0.999 |

TABLE 4H

| | | Q fever vs | | |
|---|---|---|---|---|
| Minimal optimal panel | | Control | Lyme | Brucella |
| LYN | LDHB | 0.908 | | |
| CALU | | | 0.941 | |
| CALU | B4GALT1 | | 0.961 | |
| HIST4 | | | | 0.999 |
| HIST4 | LDHB | | | 0.996 |
| HIST4 | MDH1 | | | 0.998 |

Discussion

A rational approach for identification of a new class of candidate biomarkers of the zoonosis, brucellosis, has been described herein. Currently brucellosis can be diagnosed either by recovering viable bacteria from patient cultures or, more typically, by measuring the relative reactivity of anti-*Brucella* immunoglobulin from patient sera. Perturbations to the secretome and secretome-associated compartments of infected host cells were focused on and identified the and then many of those changes were followed into the periphery.

Proteomic analysis to the secretome 24 hours after infection was focused on. By that time the *Brucella* bacteria that survived the early stages of infection have established their intracellular niche, and have begun to significantly impact the host cell physiology as they begin to expand their numbers (Celli J, et al. (2003) *J Exp Med* 198: 545-556; Lamontagne J, et al. (2009) *J Proteome Res* 8: 1594-1609). To reflect *Brucella* cell tropism in vivo both macrophage and trophoblast cell lines were used as infection models. The bone marrow-derived and cell line macrophage infection models of *Brucella* infection have been extensively described. Epithelial placental trophoblasts, which are in direct contact with the fetus, also constitute an important *Brucella abortus* target. *Brucella* can attain significant numbers within trophoblasts without damaging the chorionic layer. When infected trophoblasts separate from the basal membrane and die, they can release large amounts of bacteria into the fetal layers (Anderson T D, et al. (1986) *Vet Pathol* 23: 227-239; Anderson T D, et al. (1986) *Vet Pathol* 23: 219-226; Ushizawa K, et al. (2005) *J Reprod Dev* 51: 211-220). Thus, *Brucella* infected trophoblast cell lines are a physiologically relevant complement to macrophage infections and given the secretory functions of these cells, they are an excellent source for identifying candidate secreted protein biomarkers. Bovine (Miyazaki H, et al. (2002) *Placenta* 23: 613-630) caprine (Ramsoondar J, et al. (1993) *Biol Reprod* 49: 681-694), porcine (Halwachs-Baumann G, et al. (2006) *J Clin Virol* 37: 91-97) as well as a few human trophoblastic cell lines derived from placental tumors have been used as in vitro infection models (Pfaff E W, et al. (2005) *Int J Parasitol* 35: 1569-1576; Vidricaire G, et al. (2003) *J Biol Chem* 278: 15832-15844; Gross A, et al. (2004) *Microb Pathog* 36: 75-82), although these models are not as well characterized as the macrophage models. The response of professional phagocytes and epithelial cells to *Brucella* infection appeared to differ, and using both cell models a rich dataset of differentially expressed proteins was identified. The vast majority appeared to be potentially secreted, reflecting the multiple mechanisms available to mammalian cells for protein secretion (Chua C E, et al. (2012) *J Cell Physiol* 227: 3722-3730; Glebov K, Walter J (2012) *Neurodegener Dis* 10: 309-312; Giuliani F, et al. (2011) *Curr Opin Cell Biol* 23: 498-504).

Biomarkers

The incubation period for *Brucella* infection in humans may last several weeks. During this period the bacteria distribute mainly in regional lymphatics close to the site of infection, typically the oropharyngeal, tonsils, cervical or retro orbital lymphatics (Sauret J M, Vilissova N (2002) *J Am Board Fam Med* 15(5); Spink W W (1956) The Nature of Brucellosis. University of Minnesota Press. pp. 114-115). A transient local inflammation may be observed. Symptoms generally manifest 3-8 weeks after infection, when the bacteria have dispersed through the reticuloendothelial system to the liver and spleen (Rodriguez-Zapata M, et al. (2010) *Infect Immun* 78: 3272-3279). The symptoms appear to be related more to the host Th1 response and chronic inflammatory reactions than to toxic effects mediated directly by bacterial proteins or components, such as exotoxins or LPS. The sera that was tested were most likely collected when the subjects had reached this latter stage of disease progression, after the manifestation of symptoms and likely after major organs such as the liver and spleen had become infected. Biomarker discovery using the cell line models, however, was done at 24 hours of infection. A subset of the secreted proteins we observed after a 24 hour infection of macrophages and trophoblasts appeared specifically associated with acute brucellosis in these presumably later stage subjects. This indicates that the changes to the secretory pathways of infected host cells at the onset of infection remained relevant at the later stages as well.

Brucellosis presents clinically as recurring fever typically with joint and abdominal pain. Lyme disease has a similar clinical presentation and epidemiology as brucellosis, but a dissimilar infection mechanism. Q-fever also has a similar presentation and epidemiology as brucellosis, and a similar infection mechanism. *Salmonellosis*, in contrast, has a different clinical presentation and epidemiology than brucellosis but a similar infection mechanism. These three additional diseases, therefore, would be useful in assessing the specificity of the candidate biomarkers as well as their physiological relevance.

Host proteins defined panels able to distinguish sera from subjects with brucellosis from those infected with Lyme disease, Q-fever, or *salmonellosis*. They represented various biological functions identified in the secretome of the *Brucella*-infected cells that seemed to complement each other in the panel calculations.

EQUIVALENTS

In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes a plurality of system elements or method steps, those elements or steps may be replaced with a single element or step. Likewise, a single element or step may be replaced with a plurality of elements or steps that serve the same purpose. Further, where parameters for various properties are specified herein for exemplary embodiments, those parameters may be adjusted up or down by ¹/20th, ¹/10th, ¹/5th, ¹/3rd, ½, etc., or by rounded-off approximations thereof, unless otherwise specified. Moreover, while exemplary embodiments have been shown and described with references to particular embodiments thereof, those of ordinary skill in the art will understand that various substitutions and alterations in form and details may be made therein without departing from the scope of the invention. Further still, other aspects, functions and advantages are also within the scope of the invention.

Exemplary flowcharts are provided herein for illustrative purposes and are non-limiting examples of methods. One of ordinary skill in the art will recognize that exemplary methods may include more or fewer steps than those illustrated in the exemplary flowcharts, and that the steps in the exemplary flowcharts may be performed in a different order than shown.

INCORPORATION BY REFERENCE

The contents of all references, including patents and patent applications, cited throughout this application are hereby incorporated herein by reference in their entirety. The appropriate components and methods of those references may be selected for the invention and embodiments thereof. Still further, the components and methods identified in the Background section are integral to this disclosure and can be used in conjunction with or substituted for components and methods described elsewhere in the disclosure within the scope of the invention.

We claim:

1. A method for detecting HISTH4, LDHB, and MDH1 in a subject,
   obtaining a fluid sample(s) from a subject suspected of having Brucellosis,
   detecting whether HISTH4, LDHB, and MDH1 are present in the fluid sample(s) by ionizing the fluid sample(s) and detecting charged particles corresponding to HISTH4, LDHB, and MDH1;
   thereby detecting HISTH4, LDHB, and MDH1 in a subject suspected of having Brucellosis.

2. The method of claim 1, further comprising detecting whether one or more markers selected from the group consisting of LYN, MAT2A, B4GALT1, HIST3H3, ICAM1, CALU, COROIA, ENO1, EPB41L3, FLNA, GSTP1, H6PD, HISTH2BE, HIST4H4, ITGAM, MMP9, PRKCSH, RPSA, TKT, and TPI1 is present in the fluid sample(s).

3. The method of claim 1, further comprising detecting whether one or more markers selected from the group consisting of SLC3A2, GOT1, GOT2, ACADVL, DBI, ACOX1, AHNAK, AIMP1, AKRIBI, ANPEP, ANXA2, ANXA5, ANXA6, AKR7A2, ARPC3, ASAH1, B4GALT1, BCAM, BLOC1S5, CALU, CAPG, CAPZB, CAPZA2, CBX1, CDC37, HSPE1, CHMP1A, CHMP1B, CHMP2A, CHMP4A, CHMP4B, CHMP5, CLIO, CNDP2, CNPY2, COP A, COPB2, COROIA, COROIB, COROIC, CPVL, C19orf10, CXorf26, CXCL10, CACYBP, DSP, HSD17B4, DLG1, DNASE2, DDT, DYNLL1, EPB41L3, EEF1A1, EEF1B2, EEF1D, EEF2, ENG, EHD1, ELAVL1, EMC2, EMR2, ENO1, EN03, HSP90B1, EROIL, ESYT2, EVL, ST13, F5, FKBP4, FLNA, FH, H6PD, GPI, GDI2, ARHG-DIA, GGH, GBA, PRKCSH, GNS, HSPA9, HSPA5, GSTP1, GLT25D1, HIST1H1D, HIST1H1B, HIST3H2A, H2AFY, HIST2H2BE, HIST2H2BF, HIST3H3, HIST1H4A, HSD17B10, HEXA, HMGB3, HNRNPC, HNRNPD, HNRNPK, HNRNPR, HNRNPU, HSP90AA1, HSP90AB1, HSPAIA, HSPA8, ICAM1, EIF5A2, ILIB, IMPDH2, ISYNA1, ISOC1, ITGA5, ITGAM, ITPR1, KRT9, KRT7, KRT8, CAMK2D, PKM, LASP1, LIMA1, LMNA, LMNB1, LMNB2, LRCH1, GAA, LYN, MDH2, MESDC2, MAT2A, MYL12A, MMP9, RABIF, MYH10, MYH9, MY01E, MY06, PPP1R12A, NAGA, POR, NME1, NME2, NDRG1, NDUFA2, NAP1L1, NPM1, NUTF2, NCL, NUDC, OAS2, PAFAH1B2, PA2G4, PARK7, PARP1, PRCP, PDCD6IP, P4HB, PDIA5, PEBP1, PECAM1, PFDN1, PFDN2, PGAM1, PGK1, PIP4K2A, PIP5K1A, PLEKH02, PLEC, PLOD3, LCP1, PNP, ALPP, PPIA, PPIB, PRDX1, PRDX2, PRDX3, PRDX6, PRPF19, PSMC6, PSMC3, PSMC2, PRSS8, NPEPPS, PSMA7, PSMB5, PSMDIO, PSMD11, PSMD14, PSMD1, PSMD2, PSMD4, PTBP3, PAICS, ATIC, PXMP2, RAB6A, RANGAP1, RAI14, RAN, RANBP1, RBBP4, RAD23B, RPL14, RPL23A, RPL24, RPL26, RPL29, RPL3, RPL31, RPL7A, RPL8, RPLP2, MRPL39, HNRNPA1, HNRNPA2B1, RPS23, RPS8, RSAD2, RPSA, RUVBL1, RUVBL2, S100P, S100A6, S100A11, SEC61B, SEPT11, SEPT2, SEPT6, SEPT7, SEPT9, PHGDH, SF3B3, SFPQ, SIAE, SNRPD3, NAPA, SOD2, SORT1, SGSH, SPRED1, SPTBN1, SPG11, SPTAN1, SRSF3, SRSF8, STIP1, STMN1, STRAP, STX11, SUM03, EPRS, IARS2, TAGLN2, TALDO1, TUBA4A, TUBB4B, TUBB, TBL2, CCT4, CCT8, TDRD6, VCP, TKT, TLN1, TMOD3, TPI1, TRA2B, TXNRD1, USP14, UGGT1, ATP6V1A, ATP6V1B2, ATP6V1D, ATP6V1E1, ATP6V1F, ATP6V1G1, VPS4A, XRCC6, and YBX1 is present in the fluid sample(s).

4. The method of claim 1, further comprising detecting whether one or more markers selected from the group consisting of LYN, MAT2A, ICAM1, MMP9, CALU, and B4GALT1 is present in the fluid sample(s).

5. The method of claim 1, further comprising detecting whether one or more markers selected from the group consisting of HIST3H3, ICAM1, FLNA, H6PD, and MMP9 is present in the fluid sample(s).

6. The method of claim 1, wherein the fluid sample(s) is a blood sample(s) or a urine sample(s).

7. The method of claim 1, wherein the subject is a veterinary subject.

8. The method of claim 1, wherein the subject is human.

9. The method of claim 1, further comprising detecting whether one or more markers selected from the group consisting of HIST3H3, ICAM1, H6PD, and MMP9 is present in the fluid sample(s).

10. The method of claim 1, further comprising detecting whether two or more markers selected from the group consisting of HIST3H3, ICAM1, H6PD, and MMP9 are present in the fluid sample(s).

11. The method of claim 1, further comprising detecting whether three or more markers selected from the group consisting of HIST3H3, ICAM1, H6PD, and MMP9 are present in the fluid sample(s).

12. The method of claim 1, further comprising detecting whether HIST3H3, ICAM1, H6PD, and MMP9 are present in the fluid sample(s).

* * * * *